United States Patent
Singh et al.

(10) Patent No.: US 9,149,475 B2
(45) Date of Patent: Oct. 6, 2015

(54) PROTEIN KINASE C INHIBITORS AND USES THEREOF

(71) Applicant: Rigel Pharmaceuticals, Inc., South San Francisco, CA (US)

(72) Inventors: Rajinder Singh, Belmont, CA (US); Hui Li, Santa Clara, CA (US); Haoran Zhao, Foster City, CA (US); Rao Kolluri, Foster City, CA (US); Kin Tso, San Francisco, CA (US); John Ramphal, Union City, CA (US); Shihai Gu, Union City, CA (US); Carlos Valdez, San Ramon, CA (US); Jing Zhang, Mercer Island, WA (US); Emily Stauffer, San Francisco, CA (US); Matthew Duncton, San Bruno, CA (US); Salvador Alvarez, Fremont, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 163 days.

(21) Appl. No.: 13/718,632

(22) Filed: Dec. 18, 2012

(65) Prior Publication Data
US 2013/0210810 A1    Aug. 15, 2013

Related U.S. Application Data

(63) Continuation of application No. 12/691,607, filed on Jan. 21, 2010, now Pat. No. 8,377,924.

(60) Provisional application No. 61/146,273, filed on Jan. 21, 2009, provisional application No. 61/264,165, filed on Nov. 24, 2009.

(51) Int. Cl.
| | |
|---|---|
| *A61K 31/506* | (2006.01) |
| *A61K 31/55* | (2006.01) |
| *A61K 31/538* | (2006.01) |
| *A61K 31/5377* | (2006.01) |
| *C07D 401/12* | (2006.01) |
| *C07D 401/14* | (2006.01) |
| *C07D 413/12* | (2006.01) |

(52) U.S. Cl.
CPC ............. *A61K 31/506* (2013.01); *A61K 31/538* (2013.01); *A61K 31/5377* (2013.01); *A61K 31/55* (2013.01); *C07D 401/12* (2013.01); *C07D 401/14* (2013.01); *C07D 413/12* (2013.01)

(58) Field of Classification Search
CPC ... A61K 31/506; A61K 31/55; A61K 31/538; A61K 31/5377
USPC ........... 514/217.06, 230.5, 233.8, 235.8, 275; 544/105, 122, 323, 324; 540/601; 435/184
See application file for complete search history.

(56) References Cited

U.S. PATENT DOCUMENTS

| | | | |
|---|---|---|---|
| 2003/0171359 A1 | 9/2003 | Dahmann et al. | |
| 2005/0234049 A1 * | 10/2005 | Singh et al. | ................ 514/224.2 |
| 2006/0270694 A1 | 11/2006 | Wong | |
| 2012/0022092 A1 | 1/2012 | Holland et al. | |

FOREIGN PATENT DOCUMENTS

| | | |
|---|---|---|
| JP | 2006515298 | 5/2006 |
| JP | 2008540436 | 11/2008 |
| JP | 2010533733 | 10/2010 |
| WO | 2003032997 | 4/2003 |
| WO | 2005013996 | 2/2005 |
| WO | 2005097108 | * 10/2005 |
| WO | 2009158571 | 12/2009 |

OTHER PUBLICATIONS

Database Caplus [online] chemical abstract service, Columbus, Ohio, US; 2003, XP002590095, database accession No. 138:321292 abstract.

* cited by examiner

*Primary Examiner* — James O. Wilson
*Assistant Examiner* — Ebenezer O Sackey
(74) *Attorney, Agent, or Firm* — Rudy J. Ng; Carol L. Francis; Bozicevic, Field & Francis LLP

(57) ABSTRACT

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

21 Claims, No Drawings

PROTEIN KINASE C INHIBITORS AND USES THEREOF

CROSS-REFERENCE TO RELATED APPLICATIONS

This application is a continuation of U.S. application Ser. No. 12/691,607, filed on Jan. 21, 2010, which claims priority benefit under 35 U.S.C. §119(e) to U.S. Provisional Patent Application No. 61/146,273, filed on Jan. 21, 2009 and U.S. Provisional Patent Application No. 61/264,165, filed on Nov. 24, 2009, all of which are incorporated by reference in their entireties.

BACKGROUND

Protein kinase C ("PKC") is a key enzyme in signal transduction involved in a variety of cellular functions, including cell growth, regulation of gene expression, and ion channel activity. The PKC family of isozymes includes at least 11 different protein kinases that can be divided into at least three subfamilies based on their homology and sensitivity to activators. Each isozyme includes a number of homologous ("conserved" or "C") domains interspersed with isozyme-unique ("variable" or "V") domains. Members of the "classical" or "cPKC" subfamily, PKC α, $β_i$, $β_{ii}$ and γ, contain four homologous domains (C1, C2, C3 and C4) and require calcium, phosphatidylserine, and diacylglycerol or phorbol esters for activation. Members of the "novel" or "nPKC" subfamily, PKC δ, ε, η and θ, lack the C2 homologous domain and do not require calcium for activation. Finally, members of the "atypical" or "αPKC" subfamily, PKC ζ and λ/ι, lack both the C2 and one-half of the C1 homologous domains and are insensitive to diacylglycerol, phorbol esters and calcium.

SUMMARY

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

Exemplary chemical structures are provided throughout the disclosure. By way of example, such compounds are represented by the following formula:

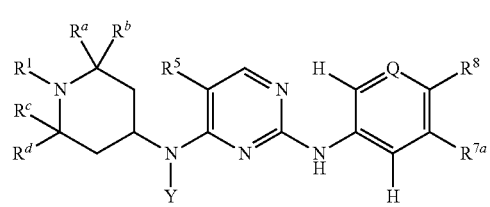

(I)

wherein $R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$;

$R^{7a}$, $R^{7b}$, and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk, if present, is alkyl or substituted alkyl;

A is selected from aryl, cycloalkyl, heteroaryl, and heterocyclyl;

wherein the A ring can be substituted or unsubstituted; or wherein two of $R^{7a}$, $R^{7b}$, and $R^8$ together with the carbon atom to which they are attached form a carbocyclic or heterocyclic 4 to 8-membered ring, wherein the carbocyclic or heterocyclic 4 to 8-membered ring is unsubstituted or substituted; or a salt or stereoisomer thereof.

DEFINITIONS

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "substituted alkyl" refers to an alkyl group as defined herein wherein one or more carbon atoms in the alkyl chain have been optionally replaced with a heteroatom such as —O—, —N—, —S—, $S(O)_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —$NR^aR^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —$NR^{10}$—, —$NR^{10}$C(O)—, —C(O)$NR^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"—where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-5-alkyl, alkylene-S-substituted alkyl, substituted alkylene-5-alkyl and substituted alkylene-5-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O) substituted alkyl, NR$^{20}$C(O)cycloalkyl, —NR$^{20}$C(O) substituted cycloalkyl, —NR$^{20}$C(O)cycloalkenyl, —NR$^{20}$C(O) substituted cycloalkenyl, —NR$^{20}$C(O) alkenyl, —NR$^{20}$C(O) substituted alkenyl, —NR$^{20}$C(O)alkynyl, —NR$^{20}$C(O) substituted alkynyl, —NR$^{20}$C(O)aryl, —NR$^{20}$C(O) substituted aryl, —NR$^{20}$C(O)heteroaryl, —NR$^{20}$C(O) substituted heteroaryl, —NR$^{20}$C(O)heterocyclic, and —NR$^{20}$C(O) substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —$SO_2NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —$NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like), provided that the point of attachment is through an atom of the aromatic aryl group. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —$NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —$N_3$.

"Carboxyl," "carboxy" or "carboxylate" refers to —$CO_2H$ or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl, imidazolyl or furyl) or multiple condensed rings (e.g., indolizinyl, quinolinyl, benzimidazolyl or benzothienyl), wherein the condensed rings may or may not be aromatic and/or contain a heteroatom, provided that the point of attachment is through an atom of the aromatic heteroaryl group. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cylcoalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cylcoalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the disclosure herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a compound of the invention and the other a typical counter ion such as chloride, or two ionized compounds of the invention can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the disclosure herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$R$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like.

The term "salt thereof" means a compound formed when the hydrogen of an acid is replaced by a cation, such as a metal cation or an organic cation and the like. Where applicable, the salt is a pharmaceutically acceptable salt, although this is not required for salts of intermediate compounds that are not intended for administration to a patient.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human animals, especially mammals.

The term "treating" or "treatment" as used herein means the treating or treatment of a disease or medical condition in a patient, such as a mammal (particularly a human) that includes: (a) preventing the disease or medical condition from occurring, i.e., prophylactic treatment of a patient; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient.

DETAILED DESCRIPTION

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

The nomenclature used herein to name the subject compounds is illustrated in the Examples herein. This nomenclature has generally been derived using the commercially-available AutoNom software (MDL, San Leandro, Calif.).

Representative Embodiments

The following substituents and values are intended to provide representative examples of various aspects and embodiments. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

The compositions of the present disclosure include compounds of formulae I-XIII, shown below. Pharmaceutical compositions and methods of the present disclosure also contemplate compounds of formulae I-XIII.

Formula I

In one of its composition aspects, the present embodiments provide a compound of formula (I):

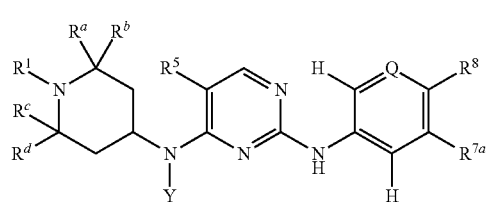

wherein $R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$;

$R^{7a}$, $R^{7b}$, and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk, if present, is alkyl or substituted alkyl;

A is selected from aryl, cycloalkyl, heteroaryl, and heterocyclyl;

wherein the A ring can be substituted or unsubstituted; or wherein two of $R^{7a}$, $R^{7b}$, and $R^8$ together with the carbon atom to which they are attached form a carbocyclic or heterocyclic 4 to 8-membered ring, wherein the carbocyclic or heterocyclic 4 to 8-membered ring is unsubstituted or substituted;

or a salt or stereoisomer thereof.

In certain embodiments, in formula I, the compound is not

N2-[3-Chloro-4-(4-methylpiperazino)carbonyl]phenyl-5-fluoro-N4-(1,2,2,6,6-pentamethylpiperidin-4-yl)-2,4-pyrimidinediamine;

5-Fluoro-N2-[4-(4-methylpiperazino)carbonyl-3-trifluoromethyl]phenyl-N4-(1,2,2,6,6-pentamethylpiperidin-4-yl)-2,4-pyrimidinediamine;

N2-[3-Chloro-4-(pyrimin-2-yl)oxy]phenyl-5-fluoro-N4-(1,2,2,6,6-pentamethylpiperidin-4-yl)-2,4-pyrimidinediamine;

N2-{3-Chloro-4-[2-(4-morpholino)ethoxy]}phenyl-5-fluoro-N4-(1,2,2,6,6-pentamethylpiperidin-4-yl)-2,4-pyrimidinediamine;

5-Cyano-N2-{3-chloro-4-[2-(4-morpholino)ethoxy]}phenyl-N4-(1,2,2,6,6-pentamethylpiperidin-4-yl)-2,4-pyrimidinediamine;

N2-[3-(cyclopropylaminocarbonylmethoxy)-4-methoxy]phenyl-5-fluoro-N4-(1,2,2,6,6-pentamethylpiperidin-4-yl)-2,4-pyrimidinediamine;

5-fluoro-N2-[4-methoxy-3-(pyridin-4-ylmethoxy)]phenyl-N4-(1,2,2,6,6-pentamethylpiperidin-4-yl)-2,4-pyrimidinediamine;

5-fluoro-N2-[4-methoxy-3-(pyridin-3-ylmethoxy)]phenyl-N4-(1,2,2,6,6-pentamethylpiperidin-4-yl)-2,4-pyrimidinediamine;

5-fluoro-N2-(3-methoxy-5-(2-morpholinoethoxy)phenyl)-N4-(1,2,2,6,6-pentamethylpiperidin-4-yl)pyrimidine-2,4-diamine;

5-fluoro-N2-(3-methoxy-5-(2-morpholinoethoxy)phenyl)-N4-(2,2,6,6-tetramethylpiperidin-4-yl)pyrimidine-2,4-diamine;

5-fluoro-N2-(3-methoxy-5-(2-(pyrrolidin-1-yl)ethoxy)phenyl)-N4-(1,2,2,6,6-pentamethylpiperidin-4-yl)pyrimidine-2,4-diamine;

5-fluoro-N2-(3-methoxy-5-(2-(pyrrolidin-1-yl)ethoxy)phenyl)-N4-(2,2,6,6-tetramethylpiperidin-4-yl)pyrimidine-2,4-diamine;

N2-(3-(2-(1H-pyrrol-1-yl)ethoxy)-5-methoxyphenyl)-5-fluoro-N4-(1,2,2,6,6-pentamethylpiperidin-4-yl)pyrimidine-2,4-diamine;

N2-(3-(2-(1H-pyrrol-1-yl)ethoxy)-5-methoxyphenyl)-5-fluoro-N4-(2,2,6,6-tetramethylpiperidin-4-yl)pyrimidine-2,4-diamine;

N2-(3-(2,5-dimethyl-1H-pyrrol-1-yl)-4-(2-morpholinoethoxy)phenyl)-5-fluoro-N4-(1,2,2,6,6-pentamethylpiperidin-4-yl)pyrimidine-2,4-diamine;

N2-(3-(2,5-dimethyl-1H-pyrrol-1-yl)-4-(2-(pyrrolidin-1-yl)ethoxy)phenyl)-5-fluoro-N4-(1,2,2,6,6-pentamethylpiperidin-4-yl)pyrimidine-2,4-diamine;

N2-(3-(2,5-dimethyl-1H-pyrrol-1-yl)-4-(2-morpholinoethoxy)phenyl)-5-fluoro-N4-(2,2,6,6-tetramethylpiperidin-4-yl)pyrimidine-2,4-diamine;

N2-(3-(2,5-dimethyl-1H-pyrrol-1-yl)-4-(2-(pyrrolidin-1-yl)ethoxy)phenyl)-5-fluoro-N4-(2,2,6,6-tetramethylpiperidin-4-yl)pyrimidine-2,4-diamine; or N2-{3-Chloro-4-[2-(4-morpholino)ethoxy]}phenyl-5-cyano-N4-(2,2,6,6-tetramethylpiperidin-4-yl)-2,4-pyrimidinediamine.

Formula Ia

In one of its composition aspects, the present embodiments provide a compound of formula (Ia):

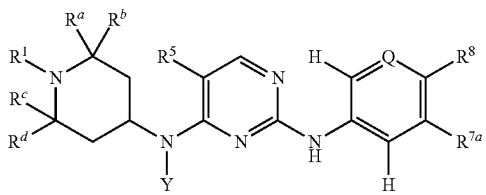

(Ia)

wherein:

R⁵ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

R¹ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$ $R^{7a}$, $R^{7b}$, and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

wherein at least one of $R^{7a}$, $R^{7b}$, and $R^8$ is —O-alk-A;

alk, if present, is alkyl or substituted alkyl;

A is selected from aryl, cycloalkyl, heteroaryl, and heterocyclyl;

wherein the A ring can be substituted or unsubstituted;

or a salt or stereoisomer thereof;

provided that, the compound is not

N2-[3-Chloro-4-(4-methylpiperazino)carbonyl]phenyl-5-fluoro-N4-(1,2,2,6,6-pentamethylpiperidin-4-yl)-2,4-pyrimidinediamine;

5-Fluoro-N2-[4-(4-methylpiperazino)carbonyl-3-trifluoromethyl]phenyl-N4-(1,2,2,6,6-pentamethylpiperidin-4-yl)-2,4-pyrimidinediamine;

N2-[3-Chloro-4-(pyrimin-2-yl)oxy]phenyl-5-fluoro-N4-(1,2,2,6,6-pentamethylpiperidin-4-yl)-2,4-pyrimidinediamine;

N2-{3-Chloro-4-[2-(4-morpholino)ethoxy]}phenyl-5-fluoro-N4-(1,2,2,6,6-pentamethylpiperidin-4-yl)-2,4-pyrimidinediamine;

5-Cyano-N2-{3-chloro-4-[2-(4-morpholino)ethoxy]}phenyl-N4-(1,2,2,6,6-pentamethylpiperidin-4-yl)-2,4-pyrimidinediamine;

N2-[3-(cyclopropylaminocarbonylmethoxy)-4-methoxy]phenyl-5-fluoro-N4-(1,2,2,6,6-pentamethylpiperidin-4-yl)-2,4-pyrimidinediamine;

5-fluoro-N2-[4-methoxy-3-(pyridin-4-ylmethoxy)]phenyl-N4-(1,2,2,6,6-pentamethylpiperidin-4-yl)-2,4-pyrimidinediamine;

5-fluoro-N2-[4-methoxy-3-(pyridin-3-ylmethoxy)]phenyl-N4-(1,2,2,6,6-pentamethylpiperidin-4-yl)-2,4-pyrimidinediamine;

5-fluoro-N2-(3-methoxy-5-(2-morpholinoethoxy)phenyl)-N4-(1,2,2,6,6-pentamethylpiperidin-4-yl)pyrimidine-2,4-diamine;

5-fluoro-N2-(3-methoxy-5-(2-morpholinoethoxy)phenyl)-N4-(2,2,6,6-tetramethylpiperidin-4-yl)pyrimidine-2,4-diamine;

5-fluoro-N2-(3-methoxy-5-(2-(pyrrolidin-1-yl)ethoxy)phenyl)-N4-(1,2,2,6,6-pentamethylpiperidin-4-yl)pyrimidine-2,4-diamine;

5-fluoro-N2-(3-methoxy-5-(2-(pyrrolidin-1-yl)ethoxy)phenyl)-N4-(2,2,6,6-tetramethylpiperidin-4-yl)pyrimidine-2,4-diamine;

N2-(3-(2-(1H-pyrrol-1-yl)ethoxy)-5-methoxyphenyl)-5-fluoro-N4-(1,2,2,6,6-pentamethylpiperidin-4-yl)pyrimidine-2,4-diamine;

N2-(3-(2-(1H-pyrrol-1-yl)ethoxy)-5-methoxyphenyl)-5-fluoro-N4-(2,2,6,6-tetramethylpiperidin-4-yl)pyrimidine-2,4-diamine;

N2-(3-(2,5-dimethyl-1H-pyrrol-1-yl)-4-(2-morpholinoethoxy)phenyl)-5-fluoro-N4-(1,2,2,6,6-pentamethylpiperidin-4-yl)pyrimidine-2,4-diamine;

N2-(3-(2,5-dimethyl-1H-pyrrol-1-yl)-4-(2-(pyrrolidin-1-yl)ethoxy)phenyl)-5-fluoro-N4-(1,2,2,6,6-pentamethylpiperidin-4-yl)pyrimidine-2,4-diamine;

N2-(3-(2,5-dimethyl-1H-pyrrol-1-yl)-4-(2-morpholinoethoxy)phenyl)-5-fluoro-N4-(2,2,6,6-tetramethylpiperidin-4-yl)pyrimidine-2,4-diamine;

N2-(3-(2,5-dimethyl-1H-pyrrol-1-yl)-4-(2-(pyrrolidin-1-yl)ethoxy)phenyl)-5-fluoro-N4-(2,2,6,6-tetramethylpiperidin-4-yl)pyrimidine-2,4-diamine; or N2-{3-Chloro-4-[2-(4-morpholino)ethoxy]}phenyl-5-cyano-N4-(2,2,6,6-tetramethylpiperidin-4-yl)-2,4-pyrimidinediamine.

In formula Ia, R⁵ can be selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl. In certain instances, R⁵ is cyano, halogen, acyl, aminoacyl, or nitro. In certain instances, R⁵ is halogen. In certain instances, R⁵ is fluoro. In certain instances, R⁵ is fluoro, cyano, or aminoacyl. In certain instances, R⁵ is cyano, or aminoacyl.

In formula Ia, Y can be selected from hydrogen and alkyl. In certain instances, Y is hydrogen. In certain instances, Y is alkyl.

In formula Ia, R¹ can be selected from hydrogen, alkyl, substituted alkyl, cycloalkyl, acyl, and oxy radical. In certain instances, R¹ is hydrogen or alkyl. In certain instances, R¹ is hydrogen. In certain instances, R¹ is alkyl. In certain instances, R¹ is methyl. In certain instances, R¹ is hydrogen, alkyl, substituted alkyl, or oxy radical. In certain instances, R¹ is hydrogen, alkyl, substituted alkyl, acyl, or cycloalkyl.

In formula Ia, $R^a$ and $R^b$ can be independently selected from hydrogen and alkyl. In certain instances, $R^a$ and $R^b$ are both alkyl. In certain instances, $R^a$ and $R^b$ are both methyl. In certain instances, at least one of $R^a$ and $R^b$ is alkyl.

In formula Ia, $R^c$ and $R^d$ can be independently selected from hydrogen and alkyl. In certain instances, $R^c$ and $R^d$ are both alkyl. In certain instances, $R^c$ and $R^d$ are both methyl. In certain instances, at least one of $R^c$ and $R^d$ is alkyl.

In formula Ia, Q can be selected from N and $CR^{7b}$. In certain instances, Q is $CR^{7b}$. In certain instances, Q is N.

In formula Ia, $R^{7a}$, $R^{7b}$, and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, heterocyclyl, alkenyl, substituted alkenyl, alkynyl, substituted alkynyl, cycloalkyl, substituted cycloalkyl, aryl, alkoxycarbonylamino, aminocarbonylamino, acyl, carboxyl, carboxyl ester, aminoacyl, sulfonyl, sulfonylamino, aminosulfonyl, and —O-alk-A; wherein at least one of $R^{7a}$, $R^{7b}$, and $R^8$ is —O-alk-A.

In certain instances, in formula Ia, $R^{7a}$, $R^{7b}$, and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, heterocyclyl, and —O-alk-A, wherein at least one of $R^{7a}$, $R^{7b}$, and $R^8$ is —O-alk-A.

In formula Ia, for "—O-alk-A," alk can be present or not present and is alkyl or substituted alkyl. In certain instances, alk is not present. In certain instances, alk is present and is alkyl. In certain instances, alk is present and is ethylene or propylene. In certain instances, alk is present and is substituted alkyl. In certain instances, alk is present and is substituted ethylene or substituted propylene.

In certain instances, in formula Ia, for "—O-alk-A," alk is not present or alk is present and is ethylene, substituted ethylene, propylene, or —C(CH$_3$)$_2$CH$_2$—. In certain instances, in formula I, for "—O-alk-A," alk is not present or alk is present and is substituted propylene, —C(CH$_3$)$_2$CH$_2$CH$_2$—, or —C(CH$_3$)$_2$CH$_2$C(O)—.

In formula Ia, A can be selected from aryl, cycloalkyl, heteroaryl, and heterocyclyl; wherein the A ring can be substituted or unsubstituted. In certain instances, A is aryl or substituted aryl. In certain instances, A is cycloalkyl or substituted cycloalkyl. In certain instances, A is heteroaryl or substituted heteroaryl. In certain instances, A is heterocyclyl or substituted heterocyclyl. In certain instances, A is heteroaryl, substituted heteroaryl, heterocyclyl, or substituted heterocyclyl.

In certain instances, in formula Ia, A is selected from azetidine, imidazole, pyrazole, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, pteridine, carbazole, carboline, isothiazole, phenazine, isoxazole, imidazolidine, imidazoline, oxazole, oxazolidine, piperidine, piperazine, indoline, phthalimide, 1,2,3,4-tetrahydroisoquinoline, tetrazole, triazole, thiazole, thiazolidine, thiophene, thiomorpholinyl, 1,1-dioxothiomorpholinyl, piperidinyl, 3-pyrrolidine; wherein the A ring can be substituted or unsubstituted.

In certain instances, in formula Ia, A is selected from 1-triazole, 3-pyrrolidine, 4-piperidine, and 1-imidazolidine; wherein the A ring can be substituted or unsubstituted.

In certain instances, in formula Ia, A is selected from piperidine, tetrahydropyranyl, tetrahydrothiopyranyl, azetidinyl, azepanyl, and furanyl; wherein the A ring can be substituted or unsubstituted.

Formula Ib

In one of its composition aspects, the present embodiments provide a compound of formula (Ib):

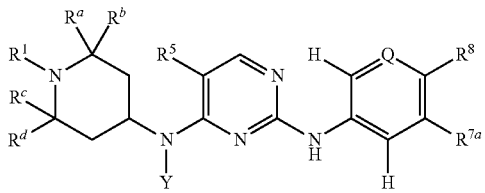

(Ib)

wherein:
$R^5$ is selected from alkyl, substituted alkyl, hydroxy, alkoxy, substituted alkoxy, amino, substituted amino, cyano, fluoro, iodo, acyl, aminoacyl, and nitro;
Y is selected from hydrogen and alkyl;
$R^1$ is selected from hydrogen, alkyl, substituted alkyl, cycloalkyl, acyl, and oxy radical;
$R^a$ and $R^b$ are independently selected from hydrogen and alkyl;
$R^c$ and $R^d$ are independently selected from hydrogen and alkyl;
Q is selected from N and $CR^{7b}$;
$R^{7a}$, $R^{7b}$, and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;
wherein at least one of $R^{7a}$, $R^{7b}$, and $R^8$ is —O-alk-A;
alk, if present, is alkyl or substituted alkyl;
A is selected from aryl, cycloalkyl, heteroaryl, and heterocyclyl, provided that $R^9$ is not 4-morpholinyl, 3-pyridinyl, 4-pyridinyl, 1-pyrrolidinyl, and 1-pyrrolyl;
wherein the A ring can be substituted or unsubstituted;
or a salt or stereoisomer thereof.

In formula Ib, $R^5$ can be selected from alkyl, substituted alkyl, hydroxy, alkoxy, substituted alkoxy, amino, substituted amino, cyano, fluoro, iodo, acyl, aminoacyl, and nitro. In certain instances, $R^5$ is cyano, fluoro, iodo, acyl, aminoacyl, or nitro. In certain instances, $R^5$ is fluoro. In certain instances, $R^5$ is fluoro, cyano, or aminoacyl. In certain instances, $R^5$ is cyano, or aminoacyl.

In formula Ib, Y can be selected from hydrogen and alkyl. In certain instances, Y is hydrogen. In certain instances, Y is alkyl.

In formula Ib, $R^1$ can be selected from hydrogen, alkyl, substituted alkyl, cycloalkyl, acyl, and oxy radical. In certain instances, $R^1$ is hydrogen or alkyl. In certain instances, $R^1$ is hydrogen. In certain instances, $R^1$ is alkyl. In certain instances, $R^1$ is methyl. In certain instances, $R^1$ is hydrogen, alkyl, substituted alkyl, or oxy radical. In certain instances, $R^1$ is hydrogen, alkyl, substituted alkyl, acyl, or cycloalkyl.

In formula Ib, $R^a$ and $R^b$ can be independently selected from hydrogen and alkyl. In certain instances, $R^a$ and $R^b$ are both alkyl. In certain instances, $R^a$ and $R^b$ are both methyl. In certain instances, at least one of $R^a$ and $R^b$ is alkyl.

In formula Ib, $R^c$ and $R^d$ can be independently selected from hydrogen and alkyl. In certain instances, $R^c$ and $R^d$ are both alkyl. In certain instances, $R^c$ and $R^d$ are both methyl. In certain instances, at least one of $R^c$ and $R^d$ is alkyl.

In formula Ib, Q can be selected from N and $CR^{7b}$. In certain instances, Q is $CR^{7b}$. In certain instances, Q is N.

In formula Ib, $R^{7a}$, $R^{7b}$, and $R^8$ can be independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A; wherein at least one of $R^{7a}$, $R^{7b}$, and $R^8$ is —O-alk-A.

In certain instances, in formula Ib, $R^{7a}$, $R^{7b}$, and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, and —O-alk-A; wherein at least one of $R^{7a}$, $R^{7b}$, and $R^8$ is —O-alk-A.

In formula Ib, for "—O-alk-A," alk can be present or not present and is alkyl or substituted alkyl. In certain instances, alk is not present. In certain instances, alk is present and is alkyl. In certain instances, alk is present and is ethylene or propylene. In certain instances, alk is present and is substituted alkyl. In certain instances, alk is present and is substituted ethylene or substituted propylene.

In certain instances, in formula Ib, for "—O-alk-A," alk is not present or alk is present and is ethylene, substituted ethylene, propylene, or —C(CH$_3$)$_2$CH$_2$—. In certain instances, in formula I, for "—O-alk-A," alk is not present or alk is present and is substituted propylene, —C(CH$_3$)$_2$CH$_2$CH$_2$—, or —C(CH$_3$)$_2$CH$_2$C(O)—.

In formula Ib, A can be selected from aryl, cycloalkyl, heteroaryl, and heterocyclyl, provided that A is not 4-morpholinyl, 3-pyridinyl, 4-pyridinyl, 1-pyrrolidinyl, and 1-pyrrolyl; wherein the A ring can be substituted or unsubstituted. In certain instances, A is aryl or substituted aryl. In certain instances, A is cycloalkyl or substituted cycloalkyl. In certain instances, A is heteroaryl or substituted heteroaryl. In certain instances, A is heterocyclyl or substituted heterocyclyl. In certain instances, A is heteroaryl, substituted heteroaryl, heterocyclyl, or substituted heterocyclyl.

In certain instances, in formula Ib, A is selected from azetidine, imidazole, pyrazole, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, pteridine, carbazole, carboline, isothiazole, phenazine, isoxazole, imidazolidine, imidazoline, oxazole, oxazolidine, piperidine, piperazine, indoline, phthalimide, 1,2,3,4-tetrahydroisoquinoline, tetrazole, triazole, thiazole, thiazolidine, thiophene, thiomorpholinyl, 1,1-dioxothiomorpholinyl, piperidinyl, 3-pyrrolidine; wherein the A ring can be substituted or unsubstituted.

In certain instances, in formula Ib, A is selected from 1-triazole, 3-pyrrolidine, 4-piperidine, and 1-imidazolidine; wherein the A ring can be substituted or unsubstituted.

In certain instances, in formula Ib, A is selected from piperidine, tetrahydropyranyl, tetrahydrothiopyranyl, azetidinyl, azepanyl, and furanyl; wherein the A ring can be substituted or unsubstituted.

Formula IIa

In one of its composition aspects, the present embodiments provide a compound of formula (IIa):

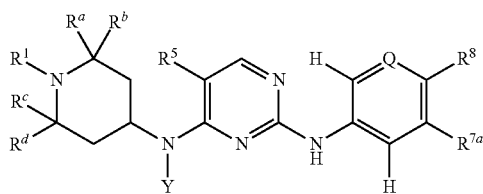

(IIa)

wherein:

$R^5$ is selected from alkyl, substituted alkyl, hydroxy, alkoxy, substituted alkoxy, amino, substituted amino, cyano, fluoro, iodo, acyl, aminoacyl, and nitro;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$ $R^{7a}$, $R^{7b}$, and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

wherein at least one of $R^{7a}$, $R^{7b}$, and $R^8$ is fluoro, difluoromethoxy, and trifluoromethyl; and wherein at least one of $R^{7a}$, $R^{7b}$, and $R^8$ is selected from $C_2$-$C_{10}$ alkoxy and —O-alk-A;

alk, if present, is alkyl or substituted alkyl;

A is selected from aryl, cycloalkyl, heteroaryl, and heterocyclyl;

wherein the A ring can be substituted or unsubstituted;

or a salt or stereoisomer thereof.

In formula IIa, $R^5$ can be selected from alkyl, substituted alkyl, hydroxy, alkoxy, substituted alkoxy, amino, substituted amino, cyano, fluoro, iodo, acyl, aminoacyl, and nitro. In certain instances, $R^5$ is cyano, fluoro, iodo, acyl, aminoacyl, or nitro. In certain instances, $R^5$ is fluoro. In certain instances, $R^5$ is fluoro, cyano, or aminoacyl. In certain instances, $R^5$ is cyano, or aminoacyl.

In formula IIa, Y can be selected from hydrogen and alkyl. In certain instances, Y is hydrogen. In certain instances, Y is alkyl.

In formula IIa, $R^1$ can be selected from hydrogen, alkyl, substituted alkyl, cycloalkyl, acyl, and oxy radical. In certain instances, $R^1$ is hydrogen or alkyl. In certain instances, $R^1$ is hydrogen. In certain instances, $R^1$ is alkyl. In certain instances, $R^1$ is methyl. In certain instances, $R^1$ is hydrogen, alkyl, substituted alkyl, or oxy radical. In certain instances, $R^1$ is hydrogen, alkyl, substituted alkyl, acyl, or cycloalkyl.

In formula IIa, $R^a$ and $R^b$ can be independently selected from hydrogen and alkyl. In certain instances, $R^a$ and $R^b$ are both alkyl. In certain instances, $R^a$ and $R^b$ are both methyl. In certain instances, at least one of $R^a$ and $R^b$ is alkyl.

In formula IIa, $R^c$ and $R^d$ can be independently selected from hydrogen and alkyl. In certain instances, $R^c$ and $R^d$ are both alkyl. In certain instances, $R^c$ and $R^d$ are both methyl. In certain instances, at least one of $R^c$ and $R^d$ is alkyl.

In formula IIa, Q can be selected from N and $CR^{7b}$. In certain instances, Q is $CR^{7b}$. In certain instances, Q is N.

In formula IIa, $R^{7a}$, $R^{7b}$, and $R^8$ can be independently selected from hydrogen, alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A; wherein at least one of $R^{7a}$, $R^{7b}$, and $R^8$ is fluoro, difluoromethoxy, and trifluoromethyl; and wherein at least one of $R^{7a}$, $R^{7b}$, and $R^8$ is selected from $C_2$-$C_{10}$ alkoxy and —O-alk-A.

In certain instances, in formula IIa, $R^{7a}$, $R^{7b}$, and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, and —O-alk-A; wherein at least one of $R^{7a}$, $R^{7b}$, and $R^8$ is fluoro, difluoromethoxy, and trifluoromethyl; and wherein at least one of $R^{7a}$, $R^{7b}$, and $R^8$ is selected from $C_2$-$C_{10}$ alkoxy and —O-alk-A.

In formula IIa, at least one of $R^{7a}$, $R^{7b}$, and $R^8$ is fluoro, difluoromethoxy, and trifluoromethyl. In certain instances, at least one of $R^{7a}$, $R^{7b}$, and $R^8$ is difluoromethoxy. In certain instances, at least one of $R^{7a}$, $R^{7b}$, and $R^8$ is fluoro. In certain instances, at least one of $R^{7a}$, $R^{7b}$, and $R^8$ is trifluoromethyl.

In formula IIa, at least one of $R^{7a}$, $R^{7b}$, and $R^8$ is selected from $C_2$-$C_{10}$ alkoxy and —O-alk-A. In certain instances, at least one of $R^{7a}$, $R^{7b}$, and $R^8$ is —O-alk-A. In certain instances, at least one of $R^{7a}$, $R^{7b}$, and $R^8$ is $C_2$-$C_{10}$ alkoxy. In certain instances, at least one of $R^{7a}$, $R^{7b}$, and $R^8$ is ethoxy or isopropoxy.

In certain instances, in formula IIa, at least one of $R^{7a}$, $R^{7b}$, and $R^8$ is difluoromethoxy and at least one of $R^{7a}$, $R^{7b}$, and $R^8$ is —O-alk-A. In certain instances, in formula IIa, at least one of $R^{7a}$, $R^{7b}$, and $R^8$ is difluoromethoxy and at least one of $R^{7a}$, $R^{7b}$, and $R^8$ is $C_2$-$C_{10}$ alkoxy.

In certain instances, in formula IIa, at least one of $R^{7a}$, $R^{7b}$, and $R^8$ is difluoromethoxy or fluoro, and at least one of $R^{7a}$, $R^{7b}$, and $R^8$ is —O-alk-A.

In formula IIa, for "—O-alk-A," alk can be present or not present and is alkyl or substituted alkyl. In certain instances, alk is not present. In certain instances, alk is present and is alkyl. In certain instances, alk is present and is ethylene or propylene. In certain instances, alk is present and is substituted alkyl.

In certain instances, in formula IIa, for "—O-alk-A," alk is not present or alk is present and is ethylene, substituted ethylene, propylene, or —C(CH$_3$)$_2$CH$_2$—. In certain instances, in formula I, for "—O-alk-A," alk is not present or alk is present and is substituted propylene, —C(CH$_3$)$_2$CH$_2$CH$_2$—, or —C(CH$_3$)$_2$CH$_2$C(O)—.

In formula IIa, A can be selected from aryl, cycloalkyl, heteroaryl, and heterocyclyl, wherein the A ring can be substituted or unsubstituted. In certain instances, A is aryl or substituted aryl. In certain instances, A is cycloalkyl or substituted cycloalkyl. In certain instances, A is heteroaryl or substituted heteroaryl. In certain instances, A is heterocyclyl or substituted heterocyclyl. In certain instances, A is heteroaryl, substituted heteroaryl, heterocyclyl, or substituted heterocyclyl.

In certain instances, in formula IIa, A is selected from azetidine, imidazole, pyrazole, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, pteridine, carbazole, carboline, isothiazole, phenazine, isoxazole, imidazolidine, imidazoline, oxazole, oxazolidine, piperidine, piperazine, indoline, phthalimide, 1,2,3,4-tetrahydroisoquinoline, tetrazole, triazole, thiazole, thiazolidine, thiophene, thiomorpholinyl, 1,1-dioxothiomorpholinyl, piperidinyl, 3-pyrrolidine; wherein the A ring can be substituted or unsubstituted.

In certain instances, in formula IIa, A is selected from 1-triazole, 3-pyrrolidine, 4-piperidine, and 1-imidazolidine; wherein the A ring can be substituted or unsubstituted.

In certain instances, in formula IIa, A is selected from piperidine, tetrahydropyranyl, tetrahydrothiopyranyl, azetidinyl, azepanyl, and furanyl; wherein the A ring can be substituted or unsubstituted.

Formula IIb

In one of its composition aspects, the present embodiments provide a compound of formula (IIb):

(IIb)

wherein:

$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and CR$^{7b}$;

$R^{7a}$, $R^{7b}$, and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

wherein at least one of $R^{7a}$, $R^{7b}$, and $R^8$ is difluoromethoxy; and wherein at least one of $R^{7a}$, $R^{7b}$, and $R^8$ is selected from alkyl, substituted alkyl, $C_2$-$C_{10}$ alkoxy, —O-alk-A, heterocyclyl, substituted heterocyclyl, heteroaryl, and substituted heteroaryl; provided that the heterocyclyl and heteroaryl are not 4-morpholinyl, 1-piperizinyl, or 1-pyrrolidinyl;

alk, if present, is alkyl or substituted alkyl;

A is selected from aryl, cycloalkyl, heteroaryl, and heterocyclyl;

wherein the A ring can be substituted or unsubstituted;

or a salt or stereoisomer thereof.

In formula IIb, $R^5$ can be selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl. In certain instances, $R^5$ is cyano, halogen, acyl, aminoacyl, or nitro. In certain instances, $R^5$ is halogen. In certain instances, $R^5$ is fluoro. In certain instances, $R^5$ is fluoro, cyano, or aminoacyl. In certain instances, $R^5$ is cyano, or aminoacyl.

In formula IIb, Y can be selected from hydrogen and alkyl. In certain instances, Y is hydrogen. In certain instances, Y is alkyl.

In formula IIb, $R^1$ can be selected from hydrogen, alkyl, substituted alkyl, cycloalkyl, acyl, and oxy radical. In certain instances, $R^1$ is hydrogen or alkyl. In certain instances, $R^1$ is hydrogen. In certain instances, $R^1$ is alkyl. In certain instances, $R^1$ is methyl. In certain instances, $R^1$ is hydrogen, alkyl, substituted alkyl, or oxy radical. In certain instances, $R^1$ is hydrogen, alkyl, substituted alkyl, acyl, or cycloalkyl.

In formula IIb, $R^a$ and $R^b$ can be independently selected from hydrogen and alkyl. In certain instances, $R^a$ and $R^b$ are both alkyl. In certain instances, $R^a$ and $R^b$ are both methyl. In certain instances, at least one of $R^a$ and $R^b$ is alkyl.

In formula IIb, $R^c$ and $R^d$ can be independently selected from hydrogen and alkyl. In certain instances, $R^c$ and $R^d$ are both alkyl. In certain instances, $R^c$ and $R^d$ are both methyl. In certain instances, at least one of $R^c$ and $R^d$ is alkyl.

In formula IIb, Q can be selected from N and $CR^{7b}$. In certain instances, Q is $CR^{7b}$. In certain instances, Q is N.

In formula IIb, $R^{7a}$, $R^{7b}$, and $R^8$ can be independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A; wherein at least one of $R^{7a}$, $R^{7b}$, and $R^8$ is difluoromethoxy; and wherein at least one of $R^{7a}$, $R^{7b}$, and $R^8$ is selected from alkyl, substituted alkyl, $C_2$-$C_{10}$ alkoxy, —O-alk-A, heterocyclyl, substituted heterocyclyl, heteroaryl, and substituted heteoaryl; provided that the heterocyclyl and heteroaryl are not 1-morpholinyl, 1-piperizinyl, or 1-pyrrolidinyl.

In certain instances, in formula IIb, $R^{7a}$, $R^{7b}$, and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, and —O-alk-A; wherein at least one of $R^{7a}$, $R^{7b}$, and $R^8$ is difluoromethoxy; and wherein at least one of $R^{7a}$, $R^{7b}$, and $R^8$ is selected from alkyl, substituted alkyl, $C_2$-$C_{10}$ alkoxy, —O-alk-A, heterocyclyl, substituted heterocyclyl, heteroaryl, and substituted heteoaryl; provided that the heterocyclyl and heteroaryl are not 4-morpholinyl, 1-piperizinyl, or 1-pyrrolidinyl.

In formula IIb, at least one of $R^{7a}$, $R^{7b}$, and $R^8$ is difluoromethoxy.

In formula IIb, wherein at least one of $R^{7a}$, $R^{7b}$, and $R^8$ is selected from alkyl, substituted alkyl, $C_2$-$C_{10}$ alkoxy, —O-alk-A, heterocyclyl, substituted heterocyclyl, heteroaryl, and substituted heteoaryl. In certain instances, at least one of $R^{7a}$, $R^{7b}$, and $R^8$ is alkyl. In certain instances, at least one of $R^{7a}$, $R^{7b}$, and $R^8$ is substituted alkyl. In certain instances, at least one of $R^{7a}$, $R^{7b}$, and $R^8$ is trifluoromethyl. In certain instances, at least one of $R^{7a}$, $R^{7b}$, and $R^8$ is $C_2$-$C_{10}$ alkoxy. In certain instances, at least one of $R^{7a}$, $R^{7b}$, and $R^8$ is ethoxy. In certain instances, at least one of $R^{7a}$, $R^{7b}$, and $R^8$ is —O-alk-A. In certain instances, $R^{7a}$, $R^{7b}$, and $R^8$ is selected from heterocyclyl, substituted heterocyclyl, heteroaryl, and substituted heteoaryl.

In certain instances, in formula IIb, at least one of $R^{7a}$, $R^{7b}$, and $R^8$ is difluoromethoxy and at least one of $R^{7a}$, $R^{7b}$, and $R^8$ is substituted alkyl. In certain instances, at least one of $R^{7a}$, $R^{7b}$, and $R^8$ is difluoromethoxy and at least one of $R^{7a}$, $R^{7b}$, and $R^8$ is trifluoromethyl.

In formula IIb, for "—O-alk-A," alk can be present or not present and is alkyl or substituted alkyl. In certain instances, alk is not present. In certain instances, alk is present and is alkyl. In certain instances, alk is present and is ethylene or propylene. In certain instances, alk is present and is substituted alkyl.

In certain instances, in formula IIb, for "—O-alk-A," alk is not present or alk is present and is ethylene, substituted ethylene, propylene, or —C(CH$_3$)$_2$CH$_2$—. In certain instances, in formula I, for "—O-alk-A," alk is not present or alk is present and is substituted propylene, —C(CH$_3$)$_2$CH$_2$CH$_2$—, or —C(CH$_3$)$_2$CH$_2$C(O)—.

In formula IIb, A can be selected from aryl, cycloalkyl, heteroaryl, and heterocyclyl, wherein the A ring can be substituted or unsubstituted. In certain instances, A is aryl or substituted aryl. In certain instances, A is cycloalkyl or substituted cycloalkyl. In certain instances, A is heteroaryl or substituted heteroaryl. In certain instances, A is heterocyclyl or substituted heterocyclyl. In certain instances, A is heteroaryl, substituted heteroaryl, heterocyclyl, or substituted heterocyclyl.

In certain instances, in formula IIb, A is selected from azetidine, imidazole, pyrazole, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, pteridine, carbazole, carboline, isothiazole, phenazine, isoxazole, imidazolidine, imidazoline, oxazole, oxazolidine, piperidine, piperazine, indoline, phthalimide, 1,2,3,4-tetrahydroisoquinoline, tetrazole, triazole, thiazole, thiazolidine, thiophene, thiomorpholinyl, 1,1-dioxothiomorpholinyl, piperidinyl, 3-pyrrolidine; wherein the A ring can be substituted or unsubstituted.

In certain instances, in formula IIb, A is selected from 1-triazole, 3-pyrrolidine, 4-piperidine, and 1-imidazolidine; wherein the A ring can be substituted or unsubstituted.

In certain instances, in formula IIb, A is selected from piperidine, tetrahydropyranyl, tetrahydrothiopyranyl, azetidinyl, azepanyl, and furanyl; wherein the A ring can be substituted or unsubstituted.

Formula III

In one of its composition aspects, the present embodiments provide a compound of formula (III):

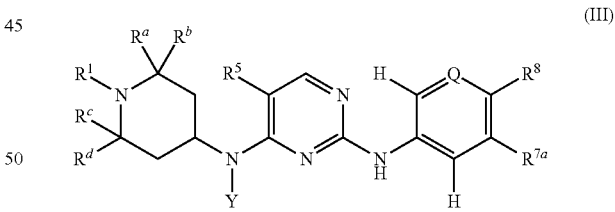

wherein:
$R^5$ is selected from halogen, cyano, acyl, and aminoacyl;
Y is selected from hydrogen and alkyl;
$R^1$ is selected from hydrogen, alkyl, substituted alkyl, cycloalkyl, acyl, and O$^-$;
$R^a$ and $R^b$ are independently selected from hydrogen and alkyl;
$R^c$ and $R^d$ are independently selected from hydrogen and alkyl;
Q is selected from N and $CR^{7b}$
$R^{7a}$ is selected from amino, substituted amino, and acylamino;
$R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk, if present, is alky or substituted alkyl;

A is selected from aryl, cycloalkyl, heteroaryl, and heterocyclyl;

wherein the A ring can be substituted or unsubstituted;

or a salt or stereoisomer thereof.

In formula III, $R^5$ is selected from halogen, cyano, acyl, and aminoacyl. In certain instances, $R^5$ is halogen. In certain instances, $R^5$ is fluoro. In certain instances, $R^5$ is cyano. In certain instances, $R^5$ is acyl. In certain instances, $R^5$ is aminoacyl.

In formula III, Y can be selected from hydrogen and alkyl. In certain instances, Y is hydrogen. In certain instances, Y is alkyl.

In formula III, $R^1$ can be selected from hydrogen, alkyl, substituted alkyl, cycloalkyl, acyl, and oxy radical. In certain instances, $R^1$ is hydrogen or alkyl. In certain instances, $R^1$ is hydrogen. In certain instances, $R^1$ is alkyl. In certain instances, $R^1$ is methyl. In certain instances, $R^1$ is hydrogen, alkyl, substituted alkyl, or oxy radical. In certain instances, $R^1$ is hydrogen, alkyl, substituted alkyl, acyl, or cycloalkyl.

In formula III, $R^a$ and $R^b$ can be independently selected from hydrogen and alkyl. In certain instances, $R^a$ and $R^b$ are both alkyl. In certain instances, $R^a$ and $R^b$ are both methyl. In certain instances, at least one of $R^a$ and $R^b$ is alkyl.

In formula III, $R^c$ and $R^d$ can be independently selected from hydrogen and alkyl. In certain instances, $R^c$ and $R^d$ are both alkyl. In certain instances, $R^c$ and $R^d$ are both methyl. In certain instances, at least one of $R^c$ and $R^d$ is alkyl.

In formula III, Q can be selected from N and $CR^{7b}$. In certain instances, Q is $CR^{7b}$. In certain instances, Q is N.

In formula III, $R^{7a}$ is selected from amino and substituted amino. In certain instances, $R^{7a}$ is amino. $R^{7a}$ is substituted amino. $R^{7a}$ is isopropylamino or methyl isopropylamino.

In formula III, $R^{7b}$ and $R^8$ can be independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A.

In certain instances, in formula III, $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, and —O-alk-A.

In formula III, for "—O-alk-A," alk can be present or not present and is alkyl or substituted alkyl. In certain instances, alk is not present. In certain instances, alk is present and is alkyl. In certain instances, alk is present and is ethylene or propylene. In certain instances, alk is present and is substituted alkyl. In certain instances, alk is present and is substituted ethylene or substituted propylene.

In certain instances, in formula III, for "—O-alk-A," alk is not present or alk is present and is ethylene, substituted ethylene, propylene, or —C(CH$_3$)$_2$CH$_2$—. In certain instances,
in formula I, for "—O-alk-A," alk is not present or alk is present and is substituted propylene, —C(CH$_3$)$_2$CH$_2$CH$_2$—, or —C(CH$_3$)$_2$CH$_2$C(O)—.

In formula III, A can be selected from aryl, cycloalkyl, heteroaryl, and heterocyclyl, wherein the A ring can be substituted or unsubstituted. In certain instances, A is aryl or substituted aryl. In certain instances, A is cycloalkyl or substituted cycloalkyl. In certain instances, A is heteroaryl or substituted heteroaryl. In certain instances, A is heterocyclyl or substituted heterocyclyl. In certain instances, A is heteroaryl, substituted heteroaryl, heterocyclyl, or substituted heterocyclyl.

In certain instances, in formula III, A is selected from azetidine, imidazole, pyrazole, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, pteridine, carbazole, carboline, isothiazole, phenazine, isoxazole, imidazolidine, imidazoline, oxazole, oxazolidine, piperidine, piperazine, indoline, phthalimide, 1,2,3,4-tetrahydroisoquinoline, tetrazole, triazole, thiazole, thiazolidine, thiophene, thiomorpholinyl, 1,1-dioxothiomorpholinyl, piperidinyl, 3-pyrrolidine; wherein the A ring can be substituted or unsubstituted.

In certain instances, in formula III, A is selected from 1-triazole, 3-pyrrolidine, 4-piperidine, and 1-imidazolidine; wherein the A ring can be substituted or unsubstituted.

In certain instances, in formula III, A is selected from piperidine, tetrahydropyranyl, tetrahydrothiopyranyl, azetidinyl, azepanyl, and furanyl; wherein the A ring can be substituted or unsubstituted.

Formula IV

In one of its composition aspects, the present embodiments provide a compound of formula (IV):

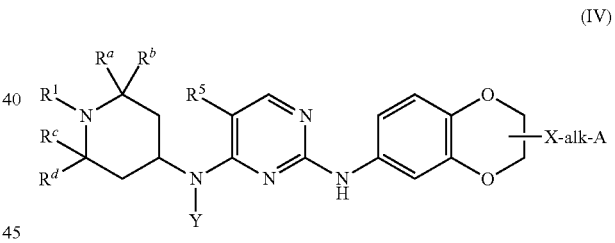

wherein:

$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

X, if present, is O or C=O, alk, if present, is alkyl or substituted alkyl;

A is selected from aryl, cycloalkyl, heteroaryl, and heterocyclyl, wherein A is not piperazinyl;

wherein the A ring can be substituted or unsubstituted;

or a salt or stereoisomer thereof.

In formula IV, $R^5$ can be selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl. In certain instances, $R^5$ is cyano, halogen, acyl, aminoacyl, or nitro. In certain instances, $R^5$ is halogen. In certain instances, $R^5$ is fluoro. In certain instances, $R^5$ is fluoro, cyano, or aminoacyl. In certain instances, $R^5$ is cyano, or aminoacyl.

In formula IV, Y can be selected from hydrogen and alkyl. In certain instances, Y is hydrogen. In certain instances, Y is alkyl.

In formula IV, $R^1$ can be selected from hydrogen, alkyl, substituted alkyl, cycloalkyl, acyl, and oxy radical. In certain instances, $R^1$ is hydrogen or alkyl. In certain instances, $R^1$ is hydrogen. In certain instances, $R^1$ is alkyl. In certain instances, $R^1$ is methyl. In certain instances, $R^1$ is hydrogen, alkyl, substituted alkyl, or oxy radical. In certain instances, $R^1$ is hydrogen, alkyl, substituted alkyl, acyl, or cycloalkyl.

In formula IV, $R^a$ and $R^b$ can be independently selected from hydrogen and alkyl. In certain instances, $R^a$ and $R^b$ are both alkyl. In certain instances, $R^a$ and $R^b$ are both methyl. In certain instances, at least one of $R^a$ and $R^b$ is alkyl.

In formula IV, $R^c$ and $R^d$ can be independently selected from hydrogen and alkyl. In certain instances, $R^c$ and $R^d$ are both alkyl. In certain instances, $R^c$ and $R^d$ are both methyl. In certain instances, at least one of $R^c$ and $R^d$ is alkyl.

In formula IV, X can be present or not present and is O or C=O. In certain instances, X is not present. In certain instances, X is present and is O. In certain instances, X is present and is C=O.

In formula IV, alk can be present or not present and is alkyl or substituted alkyl. In certain instances, alk is not present. In certain instances, alk is present and is alkyl. In certain instances, alk is present and is methylene. In certain instances, alk is present and is substituted alkyl.

In formula IV, A can be selected from aryl, cycloalkyl, heteroaryl, and heterocyclyl, provided that A is not piperazinyl; wherein the A ring can be substituted or unsubstituted. In certain instances, A is aryl or substituted aryl. In certain instances, A is cycloalkyl or substituted cycloalkyl. In certain instances, A is heteroaryl or substituted heteroaryl. In certain instances, A is heterocyclyl or substituted heterocyclyl. In certain instances, A is heteroaryl, substituted heteroaryl, heterocyclyl, or substituted heterocyclyl.

In certain instances, in formula IV, A is piperidinyl or morpholinyl. In certain instances, in formula IV, A is 1-piperidinyl or 4-morpholinyl.

Formula Va

In one of its composition aspects, the present embodiments provide a compound of formula (Va):

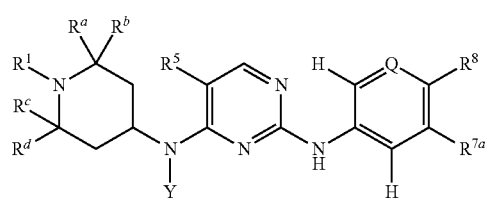

(Va)

wherein:
$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
Y is selected from hydrogen and alkyl;
$R^1$ is selected from hydrogen, alkyl, substituted alkyl, cycloalkyl, acyl, and oxy radical;
$R^a$ and $R^b$ are independently selected from hydrogen and alkyl;
$R^c$ and $R^d$ are independently selected from hydrogen and alkyl;
Q is selected from N and $CR^{7b}$;
$R^{7a}$ is selected from 1-pyrazolyl, substituted 1-pyrazolyl, 1-triazolyl, substituted 1-triazolyl, 5-tetrazolyl and substituted 5-tetrazolyl;
$R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;
alk, if present, is alkyl or substituted alkyl;
A is selected from aryl, cycloalkyl, heteroaryl, and heterocyclyl;
wherein the A ring can be substituted or unsubstituted;
or a salt or stereoisomer thereof.

In formula Va, $R^5$ can be selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl. In certain instances, $R^5$ is cyano, halogen, acyl, aminoacyl, or nitro. In certain instances, $R^5$ is halogen. In certain instances, $R^5$ is fluoro. In certain instances, $R^5$ is fluoro, cyano, or aminoacyl. In certain instances, $R^5$ is cyano, or aminoacyl.

In formula Va, Y can be selected from hydrogen and alkyl. In certain instances, Y is hydrogen. In certain instances, Y is alkyl.

In formula Va, $R^1$ can be selected from hydrogen, alkyl, substituted alkyl, cycloalkyl, acyl, and oxy radical. In certain instances, $R^1$ is hydrogen or alkyl. In certain instances, $R^1$ is hydrogen. In certain instances, $R^1$ is alkyl. In certain instances, $R^1$ is methyl. In certain instances, $R^1$ is hydrogen, alkyl, substituted alkyl, or oxy radical. In certain instances, $R^1$ is hydrogen, alkyl, substituted alkyl, acyl, or cycloalkyl.

In formula Va, $R^a$ and $R^b$ can be independently selected from hydrogen and alkyl. In certain instances, $R^a$ and $R^b$ are both alkyl. In certain instances, $R^a$ and $R^b$ are both methyl. In certain instances, at least one of $R^a$ and $R^b$ is alkyl.

In formula Va, $R^c$ and $R^d$ can be independently selected from hydrogen and alkyl. In certain instances, $R^c$ and $R^d$ are both alkyl. In certain instances, $R^c$ and $R^d$ are both methyl. In certain instances, at least one of $R^c$ and $R^d$ is alkyl.

In formula Va, Q can be selected from N and $CR^{7b}$. In certain instances, Q is $CR^{7b}$. In certain instances, Q is N.

In formula Va, $R^{7a}$ can be selected from 1-pyrazolyl, 1-triazolyl, and 5-tetrazolyl. In certain instances, $R^{7a}$ is 1-pyrazolyl or substituted 1-pyrazolyl. In certain instances, $R^{7a}$ is 1-triazolyl or substituted 1-triazolyl. In certain instances, $R^{7a}$ is 5-tetrazolyl or substituted 5-tetrazolyl.

In formula Va, $R^{7b}$ and $R^8$ can be independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A.

In certain instances, in formula V, $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, and —O-alk-A.

In formula Va, for "—O-alk-A," alk can be present or not present and is alkyl or substituted alkyl. In certain instances, alk is not present. In certain instances, alk is present and is alkyl. In certain instances, alk is present and is ethylene or propylene. In certain instances, alk is present and is substituted alkyl. In certain instances, alk is present and is substituted ethylene or substituted propylene.

In certain instances, in formula Va, for "—O-alk-A," alk is not present or alk is present and is ethylene, substituted ethylene, propylene, or —C(CH$_3$)$_2$CH$_2$—. In certain instances, in formula I, for "—O-alk-A," alk is not present or alk is present and is substituted propylene, —C(CH$_3$)$_2$CH$_2$CH$_2$—, or —C(CH$_3$)$_2$CH$_2$C(O)—.

In formula Va, A can be selected from aryl, cycloalkyl, heteroaryl, and heterocyclyl; wherein the A ring can be substituted or unsubstituted. In certain instances, A is aryl or substituted aryl. In certain instances, A is cycloalkyl or substituted cycloalkyl. In certain instances, A is heteroaryl or substituted heteroaryl. In certain instances, A is heterocyclyl or substituted heterocyclyl. In certain instances, A is heteroaryl, substituted heteroaryl, heterocyclyl, or substituted heterocyclyl.

In certain instances, in formula Va, A is selected from azetidine, imidazole, pyrazole, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, pteridine, carbazole, carboline, isothiazole, phenazine, isoxazole, imidazolidine, imidazoline, oxazole, oxazolidine, piperidine, piperazine, indoline, phthalimide, 1,2,3,4-tetrahydroisoquinoline, tetrazole, triazole, thiazole, thiazolidine, thiophene, thiomorpholinyl, 1,1-dioxothiomorpholinyl, piperidinyl, 3-pyrrolidine; wherein the A ring can be substituted or unsubstituted.

In certain instances, in formula Va, A is selected from 1-triazole, 3-pyrrolidine, 4-piperidine, and 1-imidazolidine; wherein the A ring can be substituted or unsubstituted.

In certain instances, in formula Va, A is selected from piperidine, tetrahydropyranyl, tetrahydrothiopyranyl, azetidinyl, azepanyl, and furanyl; wherein the A ring can be substituted or unsubstituted.

Formula Vb

In one of its composition aspects, the present embodiments provide a compound of formula (Vb):

(Vb)

wherein
$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
Y is selected from hydrogen and alkyl;
$R^1$ is selected from hydrogen, alkyl, substituted alkyl, cycloalkyl, acyl, and oxy radical;
$R^a$ and $R^b$ are independently selected from hydrogen and alkyl;
$R^c$ and $R^d$ are independently selected from hydrogen and alkyl;
Q is selected from N and $CR^{7b}$;
$R^{7b}$ is selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;
alk, if present, is alkyl or substituted alkyl;
A is selected from aryl, cycloalkyl, heteroaryl, and heterocyclyl;
wherein the A ring can be substituted or unsubstituted;
$R^8$ is selected from fluoro, trifluoromethyl, difluoromethoxy, hydroxyl, and isopropoxy;
$R^{7x}$ is selected from alkyl, alkylthio, and substituted alkylthio;
$R^{7y}$ is selected from hydrogen and alkyl;
the dashed line can be single bond or double bond;
or a salt or stereoisomer thereof.

Formula Vc

In one of its composition aspects, the present embodiments provide a compound of formula (Vc):

(Vc)

wherein
$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
Y is selected from hydrogen and alkyl;
$R^1$ is selected from hydrogen, alkyl, substituted alkyl, cycloalkyl, acyl, and oxy radical;
$R^a$ and $R^b$ are independently selected from hydrogen and alkyl;
$R^c$ and $R^d$ are independently selected from hydrogen and alkyl;
Q is selected from N and $CR^{7b}$;
$R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk, if present, is alkyl or substituted alkyl;

A is selected from aryl, cycloalkyl, heteroaryl, and heterocyclyl;

wherein the A ring can be substituted or unsubstituted;

$R^{7x}$ is 2,2,2-trifluoroethylthio;

$R^{7y}$ is selected from hydrogen and alkyl; the dashed line can be single bond or double bond; or a salt or stereoisomer thereof.

Formula Vd

In one of its composition aspects, the present embodiments provide a compound of formula (Vd):

(Vd)

wherein $R^5$ is —CONH$_2$ or cyano;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$;

$R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk, if present, is alkyl or substituted alkyl;

A is selected from aryl, cycloalkyl, heteroaryl, and heterocyclyl;

wherein the A ring can be substituted or unsubstituted;

$R^{7x}$ is propyl;

$R^{7y}$ is selected from hydrogen and alkyl;

the dashed line can be single bond or double bond;

or a salt or stereoisomer thereof.

Formula Ve

In one of its composition aspects, the present embodiments provide a compound of formula (Ve):

(Ve)

wherein:

$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$ $R^{7b}$ is selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk, if present, is alkyl or substituted alkyl;

A is selected from aryl, cycloalkyl, heteroaryl, and heterocyclyl;

wherein the A ring can be substituted or unsubstituted;

$R^8$ are independently selected from hydrogen, alkyl, halogen, cyano, hydroxyl, $C_{2-10}$ alkoxy, substituted alkoxy, and aminocarbonyloxy;

or a salt or stereoisomer thereof.

Formula Vf

In one of its composition aspects, the present embodiments provide a compound of formula (Vf):

(Vf)

$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$;

$R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk, if present, is alkyl or substituted alkyl;

A is selected from aryl, cycloalkyl, heteroaryl, and heterocyclyl;

wherein the A ring can be substituted or unsubstituted;

$R^{7x}$ is selected from alkyl, substituted alkyl, cycloalkyl, and substituted cycloalkyl;

or a salt or stereoisomer thereof.

Formula Vg

In one of its composition aspects, the present embodiments provide a compound of formula (Vg):

(Vg)

$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$;

$R^{7a}$ and $R^{7b}$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk, if present, is alkyl or substituted alkyl;

A is selected from aryl, cycloalkyl, heteroaryl, and heterocyclyl;

wherein the A ring can be substituted or unsubstituted;

$R^8$ is selected from hydrogen, alkyl, substituted alkyl, acyl, aminoacyl, and sulfonyl;

or a salt or stereoisomer thereof.

Formula Vh

In one of its composition aspects, the present embodiments provide a compound of formula (Vh):

(Vh)

$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$;

$R^{7b}$ and $R^{7b}$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk, if present, is alkyl or substituted alkyl;

A is selected from aryl, cycloalkyl, heteroaryl, and heterocyclyl;

wherein the A ring can be substituted or unsubstituted;

$R^8$ is selected from hydrogen, alkyl, substituted alkyl, acyl, aminoacyl, and sulfonyl;

or a salt or stereoisomer thereof.

Formula Vi

In one of its composition aspects, the present embodiments provide a compound of formula (Vi):

(Vi)

wherein $R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$;

$R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, and aminosulfonyl;

wherein at least one of $R^{7b}$ and $R^8$ is cycloalkyl;

$R^{7x}$ and $R^{7y}$ are independently selected from hydrogen and alkyl;

the dashed line can be single bond or double bond;
or a salt or stereoisomer thereof.

In certain embodiments of a compound of formula (Vi), at least one of $R^{7b}$ and $R^8$ is cyclopropyl or cyclobutyl. In certain embodiments of a compound of formula (Vi), at least one of $R^{7b}$ and $R^8$ is cyclopropyl.

Formula Vj

In one of its composition aspects, the present embodiments provide a compound of formula (Vj):

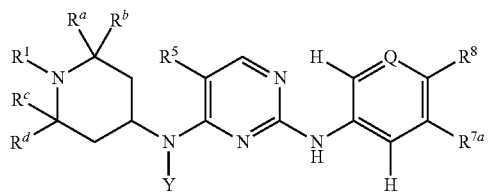

(Vj)

wherein:

$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$;

$R^{7a}$, $R^{7b}$, and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

wherein at least one of $R^{7a}$, $R^{7b}$, and $R^8$ is selected from cycloalkyl or —O—$C_{3-10}$ heterocyclyl group having one oxygen ring atom;

alk, if present, is alkyl or substituted alkyl;

A is selected from aryl, cycloalkyl, heteroaryl, and heterocyclyl;

wherein the A ring can be substituted or unsubstituted;

or a salt or stereoisomer thereof.

In certain embodiments of a compound of formula (Vj), at least one of $R^{7a}$, $R^{7b}$, and $R^8$ is cyclopropyl or cyclobutyl. In certain embodiments of a compound of formula (Vj), at least one of $R^{7a}$, $R^{7b}$, and $R^8$ is cyclopropyl. In certain embodiments of a compound of formula (Vj), at least one of $R^{7a}$, $R^{7b}$, and $R^8$ is O-oxetanyl, O-oxolanyl (tetrahydrofuranyl), or O-oxanyl (tetrahydropyranyl). In certain embodiments of a compound of formula (Vj), at least one of $R^{7a}$, $R^{7b}$, and $R^8$ is

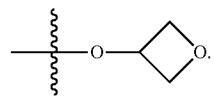

Formula Vk

In one of its composition aspects, the present embodiments provide a compound of formula (Vk):

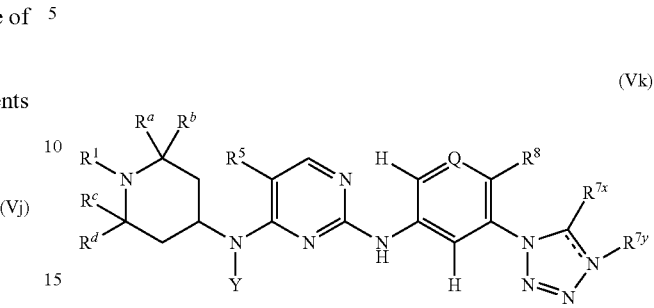

(Vk)

wherein $R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$;

$R^{7b}$ is selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk, if present, is alkyl or substituted alkyl;

A is selected from aryl, cycloalkyl, heteroaryl, and heterocyclyl;

wherein the A ring can be substituted or unsubstituted;

$R^8$ is selected from fluoro, trifluoromethyl, difluoromethoxy, hydroxyl, and isopropoxy;

$R^{7x}$ is selected from hydrogen, alkyl, substituted alkyl, alkylthio, and substituted alkylthio;

$R^{7y}$ is selected from hydrogen, alkyl, and substituted alkyl;

the dashed line can be single bond or double bond;

or a salt or stereoisomer thereof.

In certain embodiments of a compound of formula (Vk), $R^{7x}$ is selected from alkyl, alkylthio, and substituted alkylthio. In certain embodiments of a compound of formula (Vk), $R^{7x}$ is 2,2,2-trifluoroethylthio. In certain embodiments of a compound of formula (Vk), $R^{7x}$ is propyl. In certain embodiments of a compound of formula (Vk), at least one of $R^{7b}$ and $R^8$ is cycloalkyl. In certain embodiments of a compound of formula (Vk), at least one of $R^{7a}$, $R^{7b}$, and $R^8$ is selected from cycloalkyl or —O—$C_{3-10}$ heterocyclyl group having one oxygen ring atom.

Formulae VI-XIII

In one of its composition aspects, the present embodiments provide a compound of formula (VI):

$$(VI)$$

or a pharmaceutically acceptable salt thereof, wherein:

$R^1$ is selected from hydrogen, an oxy radical, lower alkyl, and substituted lower alkyl;

$R^a$, $R^b$, $R^c$ and $R^d$ independently are selected from hydrogen and alkyl;

m is an integer from one to four;

n is zero, one or two;

$R^2$, for each occurrence, independently is selected from alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, substituted aminocarbonyl, sulfonyl, sulfonylamino, and aminosulfonyl;

$R^3$, for each occurrence, independently represents oxo, lower alkyl, substituted lower alkyl, alkoxy, substituted alkoxy, alkylthio, substituted alkylthio, cycloalkyl, substituted cycloalkyl, heterocyclyl or substituted heterocyclyl;

$R^5$ is selected from alkyl, substituted alkyl, hydroxy, alkoxy, substituted alkoxy, amino, substituted amino, aminocarbonyl, carboxyl, carboxyl ester, cyano, halo, nitro, alkenyl, substituted alkenyl, alkynyl, substituted alkynyl, and trihalomethyl;

Q represents a nitrogen or an optionally substituted carbon atom;

X represents O or C(=O);

Alk represents an optional alkylene group;

A represents an aryl, heteroaryl, cycloalkyl or heterocyclyl group;

p is 1, 2 or 3; and q is 0, 1, 2, 3 or 4;

provided that, the compound is not

N2-[3-Chloro-4-(4-methylpiperazino)carbonyl]phenyl-5-fluoro-N4-(1,2,2,6,6-pentamethylpiperidin-4-yl)-2,4-pyrimidinediamine;

5-Fluoro-N2-[4-(4-methylpiperazino)carbonyl-3-trifluoromethyl]phenyl-N4-(1,2,2,6,6-pentamethylpiperidin-4-yl)-2,4-pyrimidinediamine;

N2-[3-Chloro-4-(pyrimin-2-yl)oxy]phenyl-5-fluoro-N4-(1,2,2,6,6-pentamethylpiperidin-4-yl)-2,4-pyrimidinediamine;

N2-{3-Chloro-4-[2-(4-morpholino)ethoxy]}phenyl-5-fluoro-N4-(1,2,2,6,6-pentamethylpiperidin-4-yl)-2,4-pyrimidinediamine;

5-Cyano-N2-{3-chloro-4-[2-(4-morpholino)ethoxy]}phenyl-N4-(1,2,2,6,6-pentamethylpiperidin-4-yl)-2,4-pyrimidinediamine;

N2-[3-(cyclopropylaminocarbonylmethoxy)-4-methoxy]phenyl-5-fluoro-N4-(1,2,2,6,6-pentamethylpiperidin-4-yl)-2,4-pyrimidinediamine;

5-fluoro-N2-[4-methoxy-3-(pyridin-4-ylmethoxy)]phenyl-N4-(1,2,2,6,6-pentamethylpiperidin-4-yl)-2,4-pyrimidinediamine;

5-fluoro-N2-[4-methoxy-3-(pyridin-3-ylmethoxy)]phenyl-N4-(1,2,2,6,6-pentamethylpiperidin-4-yl)-2,4-pyrimidinediamine;

5-fluoro-N2-(3-methoxy-5-(2-morpholinoethoxy)phenyl)-N4-(1,2,2,6,6-pentamethylpiperidin-4-yl)pyrimidine-2,4-diamine;

5-fluoro-N2-(3-methoxy-5-(2-morpholinoethoxy)phenyl)-N4-(2,2,6,6-tetramethylpiperidin-4-yl)pyrimidine-2,4-diamine;

5-fluoro-N2-(3-methoxy-5-(2-(pyrrolidin-1-yl)ethoxy)phenyl)-N4-(1,2,2,6,6-pentamethylpiperidin-4-yl)pyrimidine-2,4-diamine;

5-fluoro-N2-(3-methoxy-5-(2-(pyrrolidin-1-yl)ethoxy)phenyl)-N4-(2,2,6,6-tetramethylpiperidin-4-yl)pyrimidine-2,4-diamine;

N2-(3-(2-(1H-pyrrol-1-yl)ethoxy)-5-methoxyphenyl)-5-fluoro-N4-(1,2,2,6,6-pentamethylpiperidin-4-yl)pyrimidine-2,4-diamine;

N2-(3-(2-(1H-pyrrol-1-yl)ethoxy)-5-methoxyphenyl)-5-fluoro-N4-(2,2,6,6-tetramethylpiperidin-4-yl)pyrimidine-2,4-diamine;

N2-(3-(2,5-dimethyl-1H-pyrrol-1-yl)-4-(2-morpholinoethoxy)phenyl)-5-fluoro-N4-(1,2,2,6,6-pentamethylpiperidin-4-yl)pyrimidine-2,4-diamine;

N2-(3-(2,5-dimethyl-1H-pyrrol-1-yl)-4-(2-(pyrrolidin-1-yl)ethoxy)phenyl)-5-fluoro-N4-(1,2,2,6,6-pentamethylpiperidin-4-yl)pyrimidine-2,4-diamine;

N2-(3-(2,5-dimethyl-1H-pyrrol-1-yl)-4-(2-morpholinoethoxy)phenyl)-5-fluoro-N4-(2,2,6,6-tetramethylpiperidin-4-yl)pyrimidine-2,4-diamine;

N2-(3-(2,5-dimethyl-1H-pyrrol-1-yl)-4-(2-(pyrrolidin-1-yl)ethoxy)phenyl)-5-fluoro-N4-(2,2,6,6-tetramethylpiperidin-4-yl)pyrimidine-2,4-diamine; or N2-{3-Chloro-4-[2-(4-morpholino)ethoxy]}phenyl-5-cyano-N4-(2,2,6,6-tetramethylpiperidin-4-yl)-2,4-pyrimidinediamine.

In a certain embodiment, the compound is not a compound disclosed in U.S. patent application Ser. No. 12/175,441, filed 17 Jul. 2008, which is incorporated by reference in its entirety.

Certain compounds of interest have the formulae above wherein at least one or two of $R^a$, $R^b$, $R^c$, and $R^d$ are lower alkyl. In certain instances, at least two of $R^a$, $R^b$, $R^c$, and $R^d$ represent methyl groups. Particular examples of such compounds include those wherein $R^a$, $R^b$, $R^c$ and $R^d$ are methyl groups.

In one aspect the disclosed compounds have the formula $$(VII)$$

wherein $R^1$ is selected from hydrogen, an oxy radical, lower alkyl, and substituted lower alkyl;

Q is N, N→O, or $CR^7$;

$R^2$ is selected from alkyl, substituted alkyl, substituted alkyl, alkoxy other than methoxy, alkenyl, substituted alkenyl, alkynyl, substituted alkynyl, cycloalkyl, substituted cycloalkyl, heterocyclyl, substituted heterocyclyl, aryl, substituted aryl, heteroaryl other than 2,5-dimethyl-1H-pyrrol-1-yl, acylamino, alkoxycarbonylamino, aminocarbonylamino, acyl, fluoro, hydroxyl, carboxyl, carboxy ester, cyano, aminocarbonyl, substituted aminocarbonyl, sulfonyl, sulfonylamino and aminosulfonyl;

R⁷ is selected from hydrogen, alkyl, substituted alkyl, substituted alkyl, alkoxy other than methoxy, alkenyl, substituted alkenyl, alkynyl, substituted alkynyl, cycloalkyl, substituted cycloalkyl, heterocyclyl, substituted heterocyclyl, aryl, substituted aryl, heteroaryl other than 2,5-dimethyl-1H-pyrrol-1-yl, acylamino, alkoxycarbonylamino, aminocarbonylamino, acyl, fluoro, hydroxyl, carboxyl, carboxy ester, cyano, aminocarbonyl, substituted aminocarbonyl, sulfonyl, sulfonylamino and aminosulfonyl;

X represents O;

alk represents an optional alkylene group;

A represents an aryl, heteroaryl, cycloalkyl or heterocyclyl group;

p is 1, 2 or 3;

q is 0, 1, 2, 3 or 4.

With reference to the formulae above, typically, X is in the 3 or 4 position. Exemplary compounds disclosed herein having X in the 4 position can be represented by the formula:

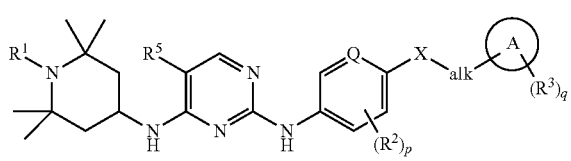
(VIII)

Exemplary compounds are represented by the formula

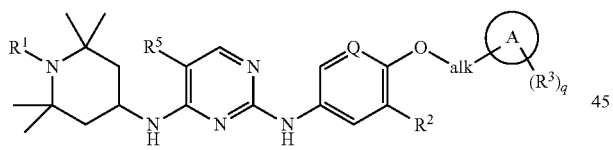
(IX)

In certain embodiments R² represents a lower alkyl group, in particular substituted lower alkyl, such as haloalkyl. By way of example, in certain embodiments R² is the haloalkyl group trifluoromethyl. In other embodiments, R² is a halo group, such as a fluoro group, or is an alkoxy group, in particular substituted alkoxy, such as a haloalkoxy group. Examples of such haloalkoxy R² groups in the presently disclosed compounds include, without limitation, difluoromethoxy groups.

Typically, R¹ is hydrogen, lower alkyl, such as methyl or ethyl, or substituted lower alkyl, such as cyclopropylmethyl, and including haloalkykl, such as trifluoroethyl. More typically, R¹ is selected from hydrogen, methyl, cyclopropyl methyl and trifluoroethyl.

In certain embodiments of the formulas described above, R⁵ is selected from fluoro, cyano and —C(O)NH₂.

In certain examples, the presently disclosed compounds have the formula

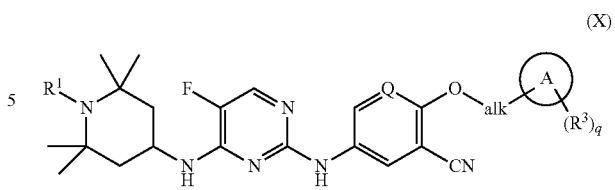
(X)

In certain embodiments, "alk" represents an optionally substituted ethylene or propylene moiety, including, without limitation, —CH₂CH₂—, —CH₂CH₂CH₂—, —C(CH₃)₂CH₂CH₂—, —C(CH₃)₂CH₂—, —C(CH₃)₂CH₂C(O)—.

In certain embodiments "alk" is absent. Such compounds can be represented by the formula:

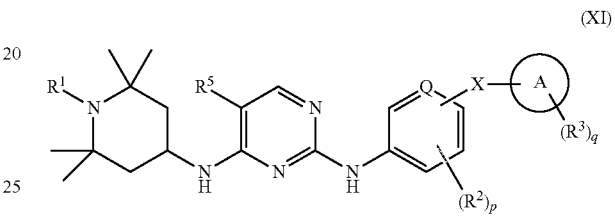
(XI)

Certain examples of such compounds can be represented by the formula

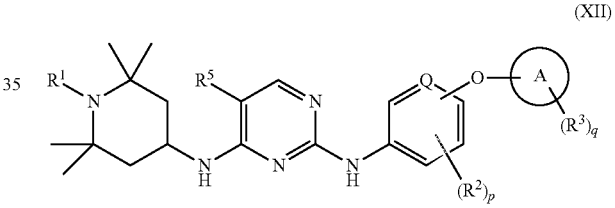
(XII)

More particularly, certain examples of such compounds have the formula:

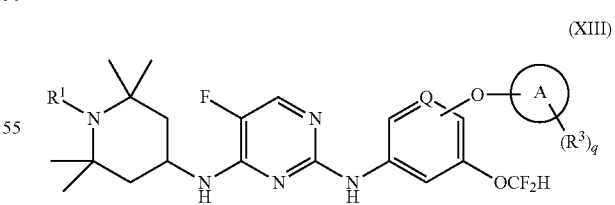
(XIII)

In certain embodiments Q represents N. In certain embodiments Q represents CH.

In another aspect in conjunction with the above and below described formulas A is a heterocyclic group. Examples of such heterocyclic groups include saturated and unsaturated groups having a single ring or multiple rings, including fused, bridged and spiro ring systems, and having from 3 to 15 ring atoms, including 1 to 4 heteroatoms. These ring heteroatoms are selected from nitrogen, sulfur and oxygen. In fused and spiro ring systems, one or more of the rings can be cycloalkyl or aryl so long as the A ring system is bonded to X through an atom in the heterocyclic ring. In one embodiment suitable A heterocyclic groups are selected from five- and six-membered nitrogen-containing heterocycles. By way of example such five- and six-membered nitrogen-containing heterocycles include, without limitation, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, pteridine, carbazole, carboline, isothiazole, phenazine, isoxazole, imidazolidine, imidazoline, oxazole, oxazolidine, piperidine, piperazine, indoline, phthalimide, 1,2,3,4-tetrahydroisoquinoline, tetrazole, triazole, thiazole, thiazolidine, thiophene, morpholinyl, thiomorpholinyl, 1,1-dioxothiomorpholinyl, piperidinyl, pyrrolidine, and the like.

In certain embodiments, in formulae VI-XIII, p can be zero.

In certain embodiments, in formulae VI-XIII, X is not present.

In certain embodiments, in formulae VI-XIII, $R^1$ is hydrogen or alkyl; $R^5$ is halo, cyano, or aminocarbonyl; p is zero; Q is C; Q is optionally substituted carbon atom; X is not present; alk is not present; A is a heteroaryl or heterocyclyl group. In certain instances, A is pyrazolyl, tetrazolyl, or triazolyl.

In certain embodiments, in formulae VI-XIII, $R^1$ is hydrogen or alkyl; $R^5$ is halo, cyano, or aminocarbonyl; p is 1, 2, or 3; Q is C; Q is optionally substituted carbon atom; X is not present; alk is not present; A is a heteroaryl or heterocyclyl group. In certain instances, A is pyrazolyl, tetrazolyl, or triazolyl.

In certain embodiments, in formulae VI-XIII, $R^1$ is hydrogen or alkyl; $R^5$ is halo, cyano, or aminocarbonyl; p is 1, 2, or 3; Q is N; Q is optionally substituted carbon atom; X is not present; alk is not present; A is a heteroaryl or heterocyclyl group. In certain instances, A is pyrazolyl, tetrazolyl, or triazolyl.

In certain embodiments, in formulae VI-XIII, $R^1$ is hydrogen or alkyl; $R^5$ is halo, cyano, or aminocarbonyl; p is 1, 2, or 3; Q is C; Q is optionally substituted carbon atom; X is not present; alk is not present; A is not present.

In certain embodiments, in formulae VI-XIII, $R^1$ is hydrogen or alkyl; $R^5$ is halo, cyano, or aminocarbonyl; p is 1, 2, or 3; Q is N; Q is optionally substituted carbon atom; X is not present; alk is not present; A is not present.

Particular compounds of interest are shown in the following tables.

TABLE 1

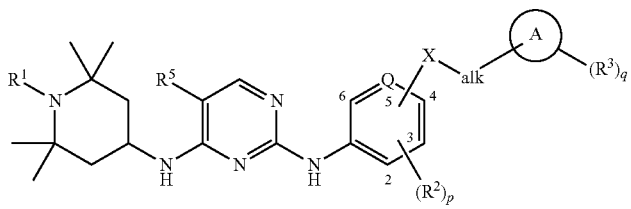

| cmpd | $R^1$ | $R^5$ | $(R^2)_p$ | Q | X | alk | A | $(R^3)_q$ |
|---|---|---|---|---|---|---|---|---|
| I-1 | Me | F | — | C | — | — | 3-1H-pyrazol-1-yl | 3-methyl |
| I-2 | Me | F | — | C | — | — | 3-1H-pyrazol-1-yl | 3-trifluoromethyl |
| I-3 | H | F | — | C | — | — | 3-1H-pyrazol-1-yl | 3-trifluoromethyl |
| I-4 | Me | F | 4-difluoromethoxy | C | — | — | 3-1H-pyrrol-1-yl | 2,5-dimethyl |
| I-5 | H | F | 4-difluoromethoxy | C | — | — | 3-1H-pyrrol-1-yl | 2,5-dimethyl |
| I-6 | Me | F | 5-fluoro | C | 3-O | ethylene | 1,2,3-triazol-1-yl | — |
| I-7 | H | F | — | C | — | — | 3-1H-pyrazol-1-yl | 3-methyl |
| I-8 | H | F | 5-fluoro | C | 3-O | ethylene | 1,2,3-triazol-1-yl | — |
| I-9 | Me | F | 4-fluoro | C | — | — | 3-(1H-tetrazol-1-yl) | 5-methyl |
| I-10 | H | F | 4-fluoro | C | — | — | 3-(1H-tetrazol-1-yl) | 5-methyl |
| I-11 | cyclopropyl methyl | F | 4-fluoro | C | — | — | 3-(1H-tetrazol-1-yl) | 5-methyl |
| I-12 | Me | F | — | C | — | — | 3-(1H-1,2,4-triazol-1-yl) | — |
| I-13 | Me | F | 4-ethoxy | C | — | — | 3-(1H-pyrrol-1-yl) | 2,5-dimethyl |
| I-14 | H | F | 4-ethoxy | C | — | — | 3-(1H-pyrrol-1-yl) | 2,5-dimethyl |
| I-15 | Me | F | 4-isopropoxy | C | — | — | 3-(1H-pyrrol-1-yl) | 2,5-dimethyl |
| I-16 | H | F | 4-isopropoxy | C | — | — | 3-(1H-pyrrol-1-yl) | 2,5-dimethyl |
| I-17 | H | cyano | 5-fluoro | C | 3-O | ethylene | 1,2,3-triazol-1-yl | — |
| I-18 | H | cyano | 4-fluoro | C | — | — | 3-(1H-tetrazol-1-yl) | 5-methyl |
| I-19 | H | F | — | C | — | — | 3-(1,2,4-triazol-1-yl) | — |
| I-20 | Me | F | 4-trifluoromethoxy | C | — | — | 3-(1H-tetrazol-1-yl) | 5-methyl |
| I-21 | H | F | 4-trifluoromethoxy | C | — | — | 3-(1H-tetrazol-1-yl) | 5-methyl |
| I-22 | Me | F | — | C | — | — | 3-(1H-pyrazol-1-yl) | — |
| I-23 | H | F | — | C | — | — | 3-(1H-pyrazol-1-yl) | — |
| I-24 | H | F | 3-difluoromethoxy | C | 4-O | ethylene | 1,2,3-triazol-1-yl | — |
| I-25 | H | F | 3-difluoromethoxy | C | 4-O | ethylene | 1,2,4-triazol-1-yl | — |
| I-26 | Me | F | 3-difluoromethoxy | C | 4-O | ethylene | 1,2,3-triazol-1-yl | — |
| I-27 | Me | F | 3-difluoromethoxy | C | 4-O | ethylene | 1,2,4-triazol-1-yl | — |

TABLE 1-continued

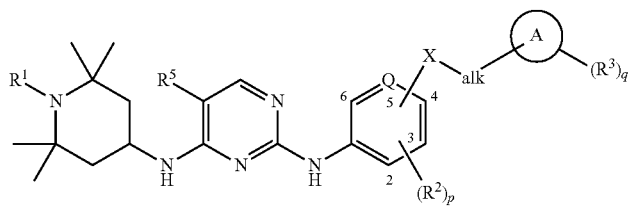

| cmpd | R¹ | R⁵ | (R²)ₚ | Q | X | alk | A | (R³)q |
|---|---|---|---|---|---|---|---|---|
| I-28 | H | F | 5-trifluoromethyl | C | 3-O | ethylene | 1,2,4-triazol-1-yl | — |
| I-29 | Me | F | 5-trifluoromethyl | C | 3-O | ethylene | 1,2,4-triazol-1-yl | — |
| I-30 | H | F | 3-difluoromethoxy | C | 4-O | ethylene | pyrolidin-1-yl | 2-oxo |
| I-31 | Me | F | 3-difluoromethoxy | C | 4-O | ethylene | pyrolidin-1-yl | 2-oxo |
| I-32 | H | F | 5-trifluoromethyl | C | 3-O | ethylene | 1,2,3-triazol-1-yl | — |
| I-33 | Me | F | 5-trifluoromethyl | C | 3-O | ethylene | 1,2,3-triazol-1-yl | — |
| I-34 | H | cyano | 3-difluoromethoxy | C | 4-O | ethylene | 1,2,3-triazol-1-yl | — |
| I-35 | H | F | 5-F | C | 3-O | propylene | 1H-pyrrol-1-yl | — |
| I-36 | Me | F | 5-F | C | 3-O | propylene | 1H-pyrrol-1-yl | — |
| I-37 | H | F | 5-fluoro | C | 3-O | ethylene | pyrolidin-1-yl | 2-oxo |
| I-38 | Me | F | 5-fluoro | C | 3-O | ethylene | pyrolidin-1-yl | 2-oxo |
| I-39 | H | F | 5-fluoro | C | 3-O | ethylene | 1,2,4-triazol-1-yl | — |
| I-40 | Me | F | 5-fluoro | C | 3-O | ethylene | 1,2,4-triazol-1-yl | — |
| I-41 | Me | F | 3-difluoromethoxy | C | 4-O | propylene | 1H-pyrrol-1-yl | — |
| I-42 | H | F | 3-difluoromethoxy | C | 4-O | propylene | 1H-pyrrol-1-yl | — |
| I-43 | Me | F | 3-difluoromethoxy | C | 4-O | — | pyridin-4-yl | — |
| I-44 | Me | F | 3-difluoromethoxy | C | 4-O | — | pyridin-3-yl | — |
| I-45 | H | F | 3-difluoromethoxy | C | 4-O | — | pyridin-3-yl | — |
| I-46 | Me | F | 3-difluoromethoxy | C | 4-O | ethylene | pyrolidin-1-yl | — |
| I-47 | H | F | 3-difluoromethoxy | C | 4-O | propylene | 4-morpholine | — |
| I-48 | Me | F | 3-difluoromethoxy | C | 4-O | propylene | 4-morpholine | — |
| I-49 | Me | F | 5-trifluoromethyl | C | 3-O | propylene | 1H-pyrrol-1-yl | — |
| I-50 | H | F | 3-difluoromethoxy | C | 4-O | ethylene | imidazolidin-1-yl | 2-oxo |
| I-51 | Me | F | 3-difluoromethoxy | C | 4-O | ethylene | imidazolidin-1-yl | 2-oxo |
| I-52 | Me | cyano | 3-difluoromethoxy | C | 4-O | — | pyridin-3-yl | — |
| I-53 | Me | cyano | 3-difluoromethoxy | C | 4-O | — | pyridin-4-yl | — |
| I-54 | Me | cyano | 3-difluoromethoxy | C | 4-O | ethylene | 1,2,4-triazol-1-yl | — |
| I-55 | Me | cyano | 3-difluoromethoxy | C | 4-O | ethylene | 1,2,3-triazol-1-yl | — |
| I-56 | Me | F | 3-trifluoromethyl | C | 4-O | ethylene | pyrolidin-1-yl | 2-oxo |
| I-57 | H | F | 3-trifluoromethyl | C | 4-O | ethylene | pyrolidin-1-yl | 2-oxo |
| I-58 | H | cyano | 3-difluoromethoxy | C | 4-O | — | pyridin-4-yl | — |
| I-59 | H | F | 3-trifluoromethyl | C | 4-O | — | pyridin-3-yl | — |
| I-60 | H | F | 3-trifluoromethyl | C | 4-O | ethylene | pyrolindin-1-yl | — |
| I-61 | Me | F | 3-trifluoromethyl | C | 4-O | — | pyridin-3-yl | — |
| I-62 | Me | F | 3-trifluoromethyl | C | 4-O | — | pyridin-4-yl | — |
| I-63 | H | F | 3-difluoromethoxy | C | — | — | pyridin-3-yl | — |

TABLE 1-continued

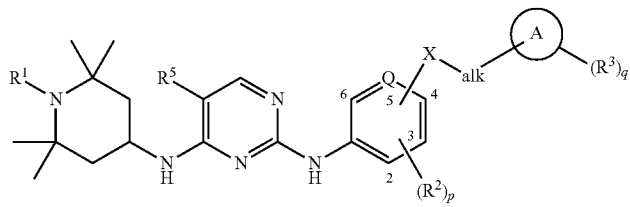

| cmpd | R¹ | R⁵ | (R²)ₚ | Q | X | alk | A | (R³)_q |
|---|---|---|---|---|---|---|---|---|
| I-64 | Me | F | 3-difluoromethoxy | C | — | — | pyridin-3-yl | — |
| I-65 | H | F | 3-trifluoromethyl | C | 4-O | ethylene | 4-morpholine | — |
| I-66 | 2,2,2-trifluoroethyl | F | 3-difluoromethoxy | C | 4-O | propylene | 4-morpholine | — |
| I-67 | H | C(O)NH₂ | 4-fluoro | C | — | — | 3-(1H-tetrazol-1-yl) | — |
| I-68 | H | C(O)NH₂ | 4-ethoxy | C | — | — | 3-(1H-tetrazol-1-yl) | 5-ethyl |
| I-69 | Me | F | — | C | — | — | 3-(1H-tetrazol-1-yl) | 5-(2,2,2-trifluoroethylthio) |
| I-70 | H | F | — | C | — | — | 3-(1H-tetrazol-1-yl) | 5-(2,2,2-trifluoroethylthio) |
| I-71 | Me | C(O)NH₂ | — | C | — | — | 3-(1H-tetrazol-1-yl) | 5-(2,2,2-trifluoroethylthio) |
| I-72 | H | C(O)NH₂ | — | C | — | — | 3-(1H-tetrazol-1-yl) | 5-(2,2,2-trifluoroethylthio) |
| I-73 | Me | cyano | 4-fluoro | C | — | — | 3-(1H-tetrazol-1-yl) | — |
| I-74 | H | F | 4-methoxy | C | — | — | 3-(1H-tetrazol-1-yl) | 5-propyl |
| I-75 | Me | C(O)NH₂ | 4-methoxy | C | — | — | 3-(1H-tetrazol-1-yl) | 5-propyl |
| I-76 | H | C(O)NH₂ | 4-methoxy | C | — | — | 3-(1H-tetrazol-1-yl) | 5-propyl |
| I-77 | H | cyano | 4-fluoro | C | — | — | 3-(1H-tetrazol-1-yl) | — |
| I-78 | Me | cyano | — | C | — | — | 3-(1H-tetrazol-1-yl) | 5-(2,2,2-trifluoroethylthio) |
| I-79 | H | cyano | — | C | — | — | 3-(1H-tetrazol-1-yl) | 5-(2,2,2-trifluoroethylthio) |
| I-80 | Me | cyano | 4-methoxy | C | — | — | 3-(1H-tetrazol-1-yl) | 5-propyl |
| I-81 | H | cyano | 4-methoxy | C | — | — | 3-(1H-tetrazol-1-yl) | 5-propyl |
| I-82 | H | F | 4-difluoromethoxy | C | — | — | 3-(1H-tetrazol-1-yl) | 5-ethyl |
| I-83 | H | C(O)NH₂ | 4-difluoromethoxy | C | — | — | 3-(1H-tetrazol-1-yl) | 5-ethyl |
| I-84 | H | cyano | 4-difluoromethoxy | C | — | — | 3-(1H-tetrazol-1-yl) | 5-ethyl |
| I-85 | H | cyano | — | C | — | — | 3-(2H-tetrazol-5-yl) | — |
| I-86 | Me | F | — | C | — | — | 3-(1H-tetrazol-5-yl) | 1-isopropyl |
| I-87 | H | F | — | C | — | — | 3-(1H-tetrazol-5-yl) | 1-isopropyl |
| I-88 | Me | cyano | — | C | — | — | 3-(1H-tetrazol-5-yl) | 1-isopropyl |
| I-89 | Me | F | — | C | — | — | 3-(1H-tetrazol-5-yl) | 1-cyclopropyl |
| I-90 | H | F | — | C | — | — | 3-(1H-tetrazol-5-yl) | 1-cyclopropyl |
| I-91 | Me | F | — | C | — | — | 3-(1H-tetrazol-5-yl) | 1-(2-fluoroethyl) |
| I-92 | H | F | — | C | — | — | 3-(1H-tetrazol-5-yl) | 1-(2-fluoroethyl) |
| I-93 | H | F | 4-methoxy | C | — | — | 3-(1H-pyrrol-1-yl) | 2,5-dimethyl |
| I-94 | Me | cyano | — | C | — | — | 3-(1H-tetrazol-5-yl) | 1-cyclopropyl |
| I-95 | H | cyano | — | C | — | — | 3-(1H-tetrazol-5-yl) | 1-cyclopropyl |
| I-96 | Me | cyano | — | C | — | — | 3-(1H-tetrazol-5-yl) | 1-(2-fluoroethyl) |
| I-97 | H | cyano | — | C | — | — | 3-(1H-tetrazol-5-yl) | 1-(2-fluoroethyl) |
| I-98 | Me | F | — | C | — | — | 3-(1H-tetrazol-5-yl) | 4-ethylmorpholine |
| I-99 | H | F | — | C | — | — | 3-(1H-tetrazol-5-yl) | 4-ethylmorpholine |
| I-100 | Me | F | 4-fluoro | C | — | — | 3-(1H-pyrrol-1-yl) | 2,5-dimethyl |
| I-101 | H | F | 4-fluoro | C | — | — | 3-(1H-pyrrol-1-yl) | 2,5-dimethyl |
| I-102 | Me | F | 4-cyano | C | — | — | 3-(1H-pyrrol-1-yl) | 2,5-dimethyl |
| I-103 | Me | F | 4-CO(O)NHCH(CH₃)₂ | C | — | — | 3-(1H-pyrrol-1-yl) | 2,5-dimethyl |
| I-104 | H | F | 3-difluoromethoxy | C | 4-O | — | piperidin-4-yl | 1-isopropyl |
| I-105 | Me | F | 3-difluoromethoxy | C | 4-O | — | piperidin-4-yl | 1-isopropyl |
| I-106 | H | F | 3-difluoromethoxy; 5-trifluoromethyl | C | — | — | — | — |
| I-107 | Me | F | 3-difluoromethoxy; 5-trifluoromethyl | C | — | — | — | — |
| I-108 | H | F | 3-difluoromethoxy; 4-ethoxy | C | — | — | — | — |
| I-109 | Me | F | 3-difluoromethoxy; 4-ethoxy | C | — | — | — | — |
| I-110 | Me | F | 3-methoxy; 5-acetamido | C | — | — | — | — |

TABLE 1-continued

| cmpd | R¹ | R⁵ | (R²)$_p$ | Q | X | alk | A | (R³)$_q$ |
|---|---|---|---|---|---|---|---|---|
| I-111 | O• | F | 3,5-di,ethoxy | C | — | — | — | — |
| I-112 | Me | F | 4-hydroxyl | N | — | — | 3-(1H-tetrazol-1-y) | 5-methyl |
| I-113 | Me | F | 4-isopropoxy | N | — | — | 3-(1H-tetrazol-1-y) | 5-methyl |
| I-114 | H | F | 4-isopropoxy | N | — | — | 3-(1H-tetrazol-1-y) | 5-methyl |
| I-115 | Me | F | 4-isopropoxy | N | — | — | 3-(1H-pyrrol-1-yl) | 2,5-dimethyl |
| I-116 | H | F | 4-isopropoxy | N | — | — | 3-(1H-pyrrol-1-yl) | 2,5-dimethyl |
| I-117 | Me | F | 3-difluoromethoxy; 4-ethoxy | N | — | — | — | — |
| I-118 | H | F | 3-difluoromethoxy; 4-ethoxy | N | — | — | — | — |
| I-119 | Me | F | 3-trifluoromethyl | C | 4-O | ethylene | 4-morpholine | — |
| I-120 | H | F | 3-difluoromethoxy | C | 4-O | ethylene | 4-morpholine | — |
| I-121 | Me | F | 3-difluoromethoxy | C | 4-O | ethylene | 4-morpholine | — |
| I-122 | H | F | 3-difluoromethoxy | C | 4-O | —C(CH$_3$)$_2$CH$_2$— | 4-morpholine | — |
| I-123 | Me | F | 3-difluoromethoxy | C | 4-O | —C(CH$_3$)$_2$CH$_2$— | 4-morpholine | — |
| I-124 | H | F | 3-difluoromethoxy | C | 4-O | —C(CH$_3$)$_2$CH$_2$— | pyrrolidin-1-yl | — |
| I-125 | Me | F | 3-difluoromethoxy | C | 4-O | —C(CH$_3$)$_2$CH$_2$— | pyrrolidin-1-yl | — |
| I-126 | Me | F | 4-isopropoxy | N | — | — | 3-1H-tetrazol-5-yl | 1-methyl |
| I-127 | H | F | 4-isopropoxy | N | — | — | 3-1H-tetrazol-5-yl | 1-methyl |
| I-128 | Me | —C(O)NH$_2$ | 4-isopropoxy | N | — | — | 3-1H-tetrazol-5-yl | 1-methyl |
| I-129 | Me | cyano | 4-isopropoxy | N | — | — | 3-1H-tetrazol-5-yl | 1-methyl |
| I-130 | H | cyano | 4-isopropoxy | N | — | — | 3-1H-tetrazol-5-yl | 1-methyl |
| I-131 | Me | F | 4-isopropoxy | N | — | — | 3-1H-tetrazol-5-yl | 1-isopropyl |
| I-132 | H | F | 4-isopropoxy | N | — | — | 3-1H-tetrazol-5-yl | 1-isopropyl |
| I-133 | Me | —C(O)NH$_2$ | 4-isopropoxy | N | — | — | 3-1H-tetrazol-5-yl | 1-isopropyl |
| I-134 | H | —C(O)NH$_2$ | 4-isopropoxy | N | — | — | 3-1H-tetrazol-5-yl | 1-isopropyl |
| I-135 | Me | cyano | 4-isopropoxy | N | — | — | 3-1H-tetrazol-5-yl | 1-isopropyl |
| I-136 | H | cyano | 4-isopropoxy | N | — | — | 3-1H-tetrazol-5-yl | 1-isopropyl |
| I-137 | Me | F | 4-isopropoxy | N | — | — | 3-1H-tetrazol-5-yl | 1-cyclopropyl |
| I-138 | H | F | 4-isopropoxy | N | — | — | 3-1H-tetrazol-5-yl | 1-cyclopropyl |
| I-139 | Me | cyano | 4-isopropoxy | N | — | — | 3-1H-tetrazol-5-yl | 1-cyclopropyl |
| I-140 | H | cyano | 4-isopropoxy | N | — | — | 3-1H-tetrazol-5-yl | 1-cyclopropyl |
| I-141 | H | F | 3-difluoromethoxy | N | 4-O | ethylene | pyrrolidin-1-yl | 2-oxo |
| I-142 | Me | F | 3-difluoromethoxy | N | 4-O | ethylene | pyrrolidin-1-yl | — |
| I-143 | H | F | 3-difluoromethoxy | N | 4-O | ethylene | pyrrolidin-1-yl | — |
| I-144 | H | F | 3-difluoromethoxy | C | 4-O | — | piperidin-4-yl | 1-(2,2,2-trifluoroethyl) |
| I-145 | Me | F | 3-difluoromethoxy | C | 4-O | — | piperidin-4-yl | 1-(2,2,2-trifluoroethyl) |
| I-146 | H | F | 3-difluoromethoxy | C | 4-O | — | (R)-pyrrolidin-3-yl | 1-isopropyl |
| I-147 | Me | F | 3-difluoromethoxy | C | 4-O | — | (R)-pyrrolidin-3-yl | 1-isopropyl |
| I-148 | H | F | 3-difluoromethoxy | C | 4-O | — | (S)-pyrrolidin-3-yl | 1-isopropyl |
| I-149 | Me | F | 3-difluoromethoxy | C | 4-O | — | (S)-pyrrolidin-3-yl | 1-isopropyl |
| I-150 | H | F | 3-cyano | C | 4-O | — | piperidin-4-yl | 1-isopropyl |
| I-151 | Me | F | 3-cyano | C | 4-O | — | piperidin-4-yl | 1-isopropyl |

TABLE 2

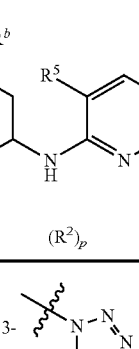

| cmpd | R¹ | (R²)$_p$ | Y¹ | Y² | X | n | A |
|---|---|---|---|---|---|---|---|
| II-1 | Me | — | O | O | C(=O) | 0 | piperidin-1-yl |
| II-2 | Me | — | O | O | C(=O) | 0 | 4-morpholine |
| II-3 | H | — | O | O | C(=O) | 0 | piperidin-1-yl |
| II-4 | H | — | O | O | C(=O) | 0 | 4-morpholine |
| II-5 | Me | — | O | O | — | 1 | piperidin-1-yl |
| II-6 | Me | — | O | O | — | 1 | 4-morpholine |

TABLE 2-continued

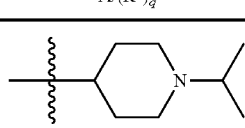

| cmpd | R¹ | (R²)$_p$ | Y¹ | Y² | X | n | A |
|---|---|---|---|---|---|---|---|
| II-7 | H | — | O | O | — | 1 | piperidin-1-yl |
| II-8 | H | — | O | O | — | 1 | 4-morpholine |
| II-9 | H | 3,3-dimethyl; 2-oxo | N(CH₂)₂F | O | — | 0 | — |
| II-10 | H | — | O | O | — | 0 | — |

TABLE 3

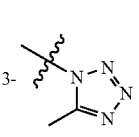

| cmpd | R¹ | R$^a$/R$^b$ | R$^c$/R$^d$ | R⁵ | (R²)$_p$ | Q | X | alk | A/(R³)$_q$ |
|---|---|---|---|---|---|---|---|---|---|
| III-1 | —CH₃ | CH₃/CH₃ | CH₃/CH₃ | F | 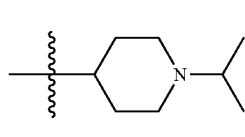 3- | C | 4-O | — | 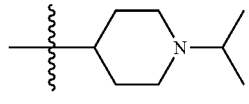 [SMILES: *C1CCN(C(C)C)CC1] |
| III-2 | H | CH₃/CH₃ | CH₃/CH₃ | F | 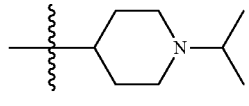 3- | C | 4-O | — | 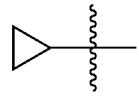 [SMILES: *C1CC1] |
| III-3 | CF₃CH₂— | CH₃/CH₃ | CH₃/CH₃ | F | 3-OCF₂H | C | 4-O | — | 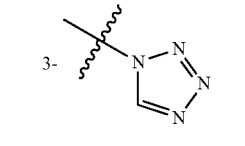 |
| III-4 | CH₃CO— | CH₃/CH₃ | CH₃/CH₃ | F | 3-OCF₂H | C | 4-O | — | 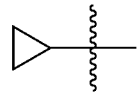 [SMILES: *C1CC1] |
| III-5 | 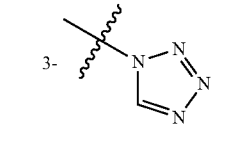 [SMILES: *n1cnnn1] | CH₃/H | CH₃/H | F | — | C | — | — | 3- 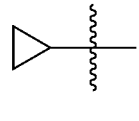 |
| III-6 | 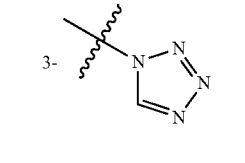 [SMILES: *n1cnnn1] | CH₃/H | CH₃/H | F | 4-CH₃ | C | — | — | 3- |
| III-7 | | CH₃/H | CH₃/H | F | 5-OCH₃ | C | — | — | 3- |

TABLE 3-continued

| cmpd | R¹ | Rᵃ/Rᵇ | Rᶜ/Rᵈ | R⁵ | (R²)ₚ | Q | X | alk | A/(R³)_q |
|---|---|---|---|---|---|---|---|---|---|
| III-8 | cyclopropyl | CH₃/H | CH₃/H | F | — | C | — | — | 3-(1-tetrazolyl) |
| III-9 | cyclopropyl | CH₃/H | CH₃/H | F | — | C | — | — | 3-(5-(SCH₂CF₃)-1-tetrazolyl) |
| III-10 | cyclopropyl | CH₃/H | CH₃/H | F | — | C | — | — | 3-(5-(SCH₃)-1-tetrazolyl) |
| III-11 | cyclopropyl | CH₃/H | CH₃/H | F | 4-F | C | — | — | 3-(1-tetrazolyl) |
| III-12 | —CH₃ | CH₃/CH₃ | CH₃/CH₃ | F | 3-F | C | 4-O | — | 1-acetylpiperidin-4-yl |
| III-13 | —H | CH₃/CH₃ | CH₃/CH₃ | F | 3-F | C | 4-O | — | 1-acetylpiperidin-4-yl |
| III-14 | —CH₃ | CH₃/CH₃ | CH₃/CH₃ | F | 3-F | C | 4-O | — | 1-methanesulfonylpiperidin-4-yl |
| III-15 | —H | CH₃/CH₃ | CH₃/CH₃ | F | 3-F | C | 4-O | — | 1-methanesulfonylpiperidin-4-yl |
| III-16 | —CH₃ | CH₃/CH₃ | CH₃/CH₃ | F | 3-F | C | 4-O | — | 1-(ethylcarbamoyl)piperidin-4-yl |
| III-17 | —H | CH₃/CH₃ | CH₃/CH₃ | F | 3-F | C | 4-O | — | 1-(ethylcarbamoyl)piperidin-4-yl |

TABLE 3-continued

| cmpd | R¹ | Rᵃ/Rᵇ | Rᶜ/Rᵈ | R⁵ | (R²)ₚ | Q | X | alk | A/(R³)_q |
|---|---|---|---|---|---|---|---|---|---|
| III-18 | —CH₃ | CH₃/CH₃ | CH₃/CH₃ | F | 3-F | C | 4-O | — | 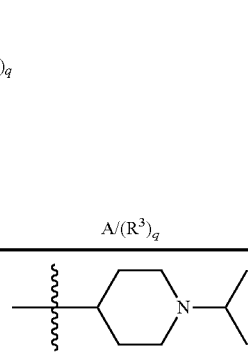 |
| III-19 | —H | CH₃/CH₃ | CH₃/CH₃ | F | 3-F | C | 4-O | — | 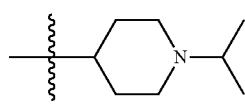 |
| III-20 | —CH₃ | CH₃/CH₃ | CH₃/CH₃ | F | 3-OCF₂H | C | 4-O | — | 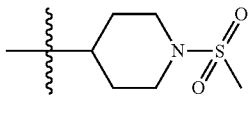 |
| III-21 | —H | CH₃/CH₃ | CH₃/CH₃ | F | 3-OCF₂H | C | 4-O | — | 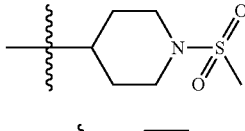 |
| III-22 | —CH₃ | CH₃/CH₃ | CH₃/CH₃ | F | 3-OCF₂H | C | 4-O | — | 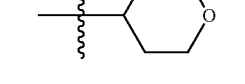 |
| III-23 | —H | CH₃/CH₃ | CH₃/CH₃ | F | 3-OCF₂H | C | 4-O | — | 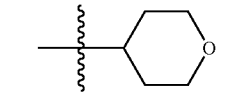 [SMILES: *C1CCOCC1] |
| III-24 | —CH₃ | CH₃/CH₃ | CH₃/CH₃ | F | 3-F | C | 4-O | — | 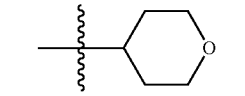 [SMILES: *C1CCOCC1] |
| III-25 | —CH₃ | CH₃/CH₃ | CH₃/CH₃ | F | 3-F, 5-F | C | 4-O | — | 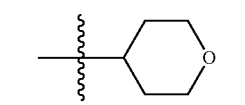 |
| III-26 | —H | CH₃/CH₃ | CH₃/CH₃ | F | 3-F, 5-F | C | 4-O | — | 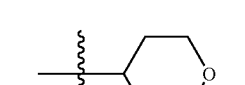 |
| III-27 | —CH₃ | CH₃/CH₃ | CH₃/CH₃ | F | 3-OCF₂H | C | 4-O | — | 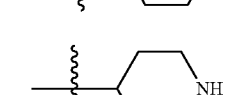 |
| III-28 | —H | CH₃/CH₃ | CH₃/CH₃ | F | 3-OCF₂H | C | 4-O | — | 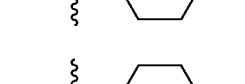 |
| III-29 | —CH₃ | CH₃/CH₃ | CH₃/CH₃ | F | 3-F | C | 4-O | — | 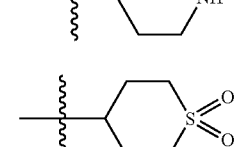 |

TABLE 3-continued

| cmpd | R¹ | Rᵃ/Rᵇ | Rᶜ/Rᵈ | R⁵ | (R²)ₚ | Q | X | alk | A/(R³)_q |
|---|---|---|---|---|---|---|---|---|---|
| III-30 | —H | CH₃/CH₃ | CH₃/CH₃ | F | 3-F | C | 4-O | — | 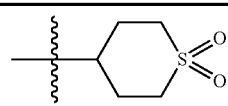 |
| III-31 | —CH₃ | CH₃/CH₃ | CH₃/CH₃ | F | 3-OCF₂H | C | 4-O | — | 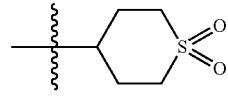 [SMILES: *C1CCS(=O)(=O)CC1] |
| III-32 | —H | CH₃/CH₃ | CH₃/CH₃ | F | 3-OCF₂H | C | 4-O | — | 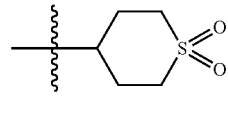 [SMILES: *C1CCS(=O)(=O)CC1] |
| III-33 | —CH₃ | CH₃/CH₃ | CH₃/CH₃ | F | 3-F | C | 4-O | — | 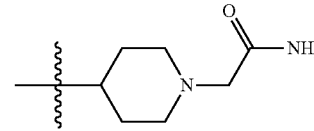 |
| III-34 | —H | CH₃/CH₃ | CH₃/CH₃ | F | 3-F | C | 4-O | — | 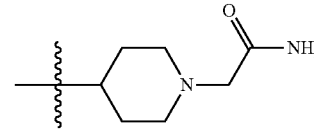 |
| III-35 | —CH₃ | CH₃/CH₃ | CH₃/CH₃ | F | 3-OCF₂H | C | 4-O | — | 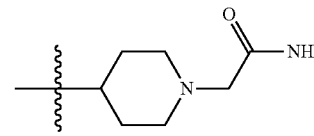 |
| III-36 | —H | CH₃/CH₃ | CH₃/CH₃ | F | 3-OCF₂H | C | 4-O | — | 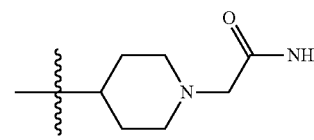 |
| III-37 | —CH₃ | CH₃/CH₃ | CH₃/CH₃ | F | 3-OCF₂H | C | 4-O | — | 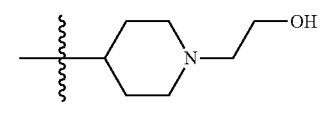 [SMILES: *C1CCN(CCO)CC1] |
| III-38 | —H | CH₃/CH₃ | CH₃/CH₃ | F | 3-OCF₂H | C | 4-O | — | 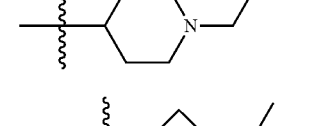 |
| III-39 | —H | CH₃/CH₃ | CH₃/CH₃ | F | 3-OCF₂H | C | 4-O | — | 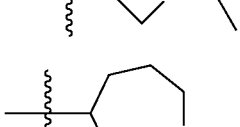 |
| III-40 | —H | CH₃/CH₃ | CH₃/CH₃ | F | 3-OCF₂H | C | 4-O | — | 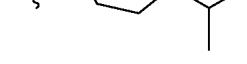 |

TABLE 3-continued

| cmpd | R¹ | Rᵃ/Rᵇ | Rᶜ/Rᵈ | R⁵ | (R²)ₚ | Q | X | alk | A/(R³)_q |
|---|---|---|---|---|---|---|---|---|---|
| III-41 | —CH₃ | CH₃/CH₃ | CH₃/CH₃ | F | 3-OCF₂H | C | 4-O | — | azepane-N-isopropyl |
| III-42 | —H | CH₃/CH₃ | CH₃/CH₃ | F | 3-OCF₂H | C | 4-O | — | N-acetyl azepane |
| III-43 | —CH₃ | CH₃/CH₃ | CH₃/CH₃ | F | 3-OCF₂H | C | 4-O | — | N-acetyl azepane |
| III-44 | —H | CH₃/CH₃ | CH₃/CH₃ | F | 3-OCF₂H | C | 4-O | — | N-acetyl piperidine |
| III-45 | —CH₃ | CH₃/CH₃ | CH₃/CH₃ | F | 3-OCF₂H | C | 4-O | — | N-acetyl piperidine |
| III-46 | —H | CH₃/CH₃ | CH₃/CH₃ | F | 3-F | C | 4-O | —C(CH₃)₂CH₂C(CH₃)₂— | pyrrolidine |
| III-47 | —CH₃ | CH₃/CH₃ | CH₃/CH₃ | F | 3-F | C | 4-O | —C(CH₃)₂CH₂C(CH₃)₂— | pyrrolidine |
| III-48 | —H | CH₃/CH₃ | CH₃/CH₃ | F | 3-F, 5-F | C | 4-O | —C(CH₃)₂C(O)C(CH₃)₂— | pyrrolidine |
| III-49 | —CH₃ | CH₃/CH₃ | CH₃/CH₃ | F | 3-F, 5-F | C | 4-O | —C(CH₃)₂C(O)C(CH₃)₂— | pyrrolidine |
| III-50 | —H | CH₃/CH₃ | CH₃/CH₃ | F | 3-OCF₂H | C | 4-O | — | N-(2-fluoroethyl) piperidine |

TABLE 3-continued

| cmpd | R¹ | Rᵃ/Rᵇ | Rᶜ/Rᵈ | R⁵ | (R²)ₚ | Q | X | alk | A/(R³)q |
|---|---|---|---|---|---|---|---|---|---|
| III-51 | —CH₃ | CH₃/CH₃ | CH₃/CH₃ | F | 3-OCF₂H | C | 4-O | — | 4-(1-(2-fluoroethyl)piperidinyl) |
| III-52 | —CH₃ | CH₃/CH₃ | CH₃/CH₃ | F | 3-OCF₂H | C | 4-O | — | 4-(1-benzylpiperidinyl) |
| III-53 | —H | CH₃/CH₃ | CH₃/CH₃ | F | 3-F | C | 4-O | — | 4-(1-(2-(benzyloxy)ethyl)piperidinyl) |
| III-54 | —CH₃ | CH₃/CH₃ | CH₃/CH₃ | F | 3-F | C | 4-O | — | 4-(1-(2-(benzyloxy)ethyl)piperidinyl) |
| III-55 | —H | CH₃/CH₃ | CH₃/CH₃ | F | 3-F, 5-F | C | 4-O | — | 4-(1-(2-(benzyloxy)ethyl)piperidinyl) |
| III-56 | —CH₃ | CH₃/CH₃ | CH₃/CH₃ | F | 3-F, 5-F | C | 4-O | — | 4-(1-(2-(benzyloxy)ethyl)piperidinyl) |
| III-57 | —H | CH₃/CH₃ | CH₃/CH₃ | F | 3-F | C | 4-O | — | 4-(1-(2-hydroxyethyl)piperidinyl) |
| III-58 | —CH₃ | CH₃/CH₃ | CH₃/CH₃ | F | 3-F | C | 4-O | — | 4-(1-(2-hydroxyethyl)piperidinyl) |
| III-59 | —H | CH₃/CH₃ | CH₃/CH₃ | F | 3-F, 5-F | C | 4-O | — | 4-(1-(2-hydroxyethyl)piperidinyl) |
| III-60 | —CH₃ | CH₃/CH₃ | CH₃/CH₃ | F | 3-F, 5-F | C | 4-O | — | 4-(1-(2-hydroxyethyl)piperidinyl) |
| III-61 | —H | CH₃/CH₃ | CH₃/CH₃ | F | 3-NH(CH(CH₃)₂), 4-O(CH(CH₃)₂) | C | — | — | — |
| III-62 | —CH₃ | CH₃/CH₃ | CH₃/CH₃ | F | 3-NH(CH(CH₃)₂), 4-O(CH(CH₃)₂) | C | — | — | — |
| III-63 | —H | CH₃/CH₃ | CH₃/CH₃ | F | 4-CH₃ | C | — | — | 3-(1-methyl-1H-tetrazol-5-yl) |

TABLE 3-continued
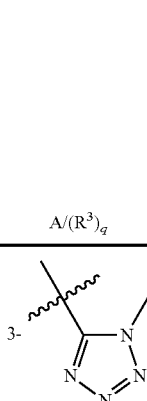
| cmpd | R¹ | Rᵃ/Rᵇ | Rᶜ/Rᵈ | R⁵ | (R²)ₚ | Q | X | alk | A/(R³)_q |
|---|---|---|---|---|---|---|---|---|---|
| III-64 | —CH₃ | CH₃/CH₃ | CH₃/CH₃ | F | 4-CH₃ | C | — | — | 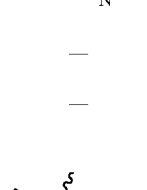 3- |
| III-65 | —H | CH₃/CH₃ | CH₃/CH₃ | F | 3-N(CH₃(CH(CH₃)₂), 4-O(CH(CH₃)₂) | C | — | — | — |
| III-66 | —CH₃ | CH₃/CH₃ | CH₃/CH₃ | F | 3-N(CH₃(CH(CH₃)₂), 4-O(CH(CH₃)₂) | C | — | — | — |
| III-67 | —H | CH₃/CH₃ | CH₃/CH₃ | F | 4-OCF₂H | C | — | — | 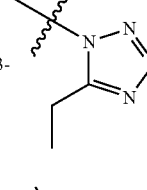 3- |
| III-68 | —CH₃ | CH₃/CH₃ | CH₃/CH₃ | F | — | C | — | — | 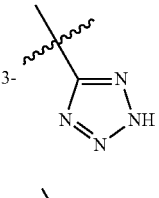 3- |
| III-69 | —H | CH₃/CH₃ | CH₃/CH₃ | F | — | C | — | — | 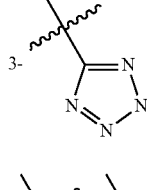 3- |
| III-70 | —CH₃ | CH₃/CH₃ | CH₃/CH₃ | F | — | C | — | — | 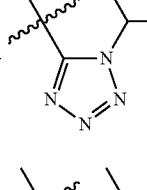 3- |
| III-71 | —H | CH₃/CH₃ | CH₃/CH₃ | F | — | C | — | — | 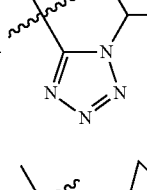 3- |
| III-72 | —CH₃ | CH₃/CH₃ | CH₃/CH₃ | F | — | C | — | — | 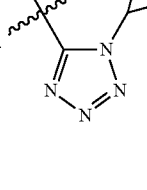 3- |

TABLE 3-continued

| cmpd | R¹ | Rᵃ/Rᵇ | Rᶜ/Rᵈ | R⁵ | (R²)ₚ | Q | X | alk | A/(R³)_q |
|---|---|---|---|---|---|---|---|---|---|
| III-73 | —H | CH₃/CH₃ | CH₃/CH₃ | F | — | C | — | — | 3-(1-cyclopropyl-tetrazol-5-yl) |
| III-74 | —CH₃ | CH₃/CH₃ | CH₃/CH₃ | F | — | C | — | — | 3-(1-(2-fluoroethyl)-tetrazol-5-yl) |
| III-75 | —H | CH₃/CH₃ | CH₃/CH₃ | F | — | C | — | — | 3-(1-(2-fluoroethyl)-tetrazol-5-yl) |
| III-76 | —CH₃ | CH₃/CH₃ | CH₃/CH₃ | F | — | C | — | — | 3-(1-(2-morpholinoethyl)-tetrazol-5-yl) |
| III-77 | —H | CH₃/CH₃ | CH₃/CH₃ | F | — | C | — | — | 3-(1-(2-morpholinoethyl)-tetrazol-5-yl) |
| III-78 | —CH₃ | CH₃/CH₃ | CH₃/CH₃ | F | 3-F, 5-F | C | 4-O | — | 4-(methylsulfonyl)piperidin-4-yl |
| III-79 | —CH₃ | CH₃/CH₃ | CH₃/CH₃ | F | 3-F, 5-F | C | 4-O | — | 1-(methylsulfonyl)azepan-4-yl |

TABLE 3-continued

| cmpd | R¹ | Rᵃ/Rᵇ | Rᶜ/Rᵈ | R⁵ | (R²)ₚ | Q | X | alk | A/(R³)q |
|---|---|---|---|---|---|---|---|---|---|
| III-80 | —H | CH₃/CH₃ | CH₃/CH₃ | F | 3-F, 5-F | C | 4-O | — | 4-(N-methylsulfonyl)azepan-1-yl |
| III-81 | —CH₃ | CH₃/CH₃ | CH₃/CH₃ | F | 3-F, 5-F | C | 4-O | — | 4-(N-acetyl)azepan-1-yl |
| III-82 | —H | CH₃/CH₃ | CH₃/CH₃ | F | 3-F, 5-F | C | 4-O | — | 4-(N-acetyl)azepan-1-yl |
| III-83 | —CH₃ | CH₃/CH₃ | CH₃/CH₃ | F | 3-F, 5-F | C | 4-O | — | 4-(N-ethylcarbamoyl)azepan-1-yl |
| III-84 | —H | CH₃/CH₃ | CH₃/CH₃ | F | 3-F, 5-F | C | 4-O | — | 4-(N-methylsulfonyl)piperidin-1-yl |
| III-85 | —H | CH₃/CH₃ | CH₃/CH₃ | F | 3-F, 5-F | C | 4-O | — | 4-(N-ethylcarbamoyl)azepan-1-yl |
| III-86 | —H | CH₃/CH₃ | CH₃/CH₃ | F | 3-OCF₂H | C | 4-O | — | 4-(N-ethylcarbamoyl)piperidin-1-yl |
| III-87 | —CH₃ | CH₃/CH₃ | CH₃/CH₃ | F | 3-OCF₂H | C | 4-O | — | 4-(N-ethylcarbamoyl)azepan-1-yl |
| III-88 | —H | CH₃/CH₃ | CH₃/CH₃ | F | 3-OCF₂H | C | 4-O | — | 4-(N-ethylcarbamoyl)azepan-1-yl |

TABLE 3-continued

| cmpd | R¹ | Rᵃ/Rᵇ | Rᶜ/Rᵈ | R⁵ | (R²)ₚ | Q | X | alk | A/(R³)_q |
|---|---|---|---|---|---|---|---|---|---|
| III-89 | —CH₃ | CH₃/CH₃ | CH₃/CH₃ | F | 3-OCF₂H | C | 4-O | — | 4-(N-methylsulfonyl)azepan-4-yl |
| III-90 | —H | CH₃/CH₃ | CH₃/CH₃ | F | 3-OCF₂H | C | 4-O | — | 4-(N-methylsulfonyl)azepan-4-yl |
| III-91 | —CH₃ | CH₃/CH₃ | CH₃/CH₃ | F | 3-F, 5-F | C | 4-O | — | 1-acetylpiperidin-4-yl |
| III-92 | —H | CH₃/CH₃ | CH₃/CH₃ | F | 3-F, 5-F | C | 4-O | — | 1-acetylpiperidin-4-yl |
| III-95 | —CH₃ | CH₃/CH₃ | CH₃/CH₃ | F | 3-Cl | C | 4-O | — | 1-isopropylpiperidin-4-yl |
| III-96 | —H | CH₃/CH₃ | CH₃/CH₃ | F | 3-Cl | C | 4-O | — | 1-(2-fluoroethyl)piperidin-4-yl |
| III-97 | —CH₃ | CH₃/CH₃ | CH₃/CH₃ | F | 3-Cl | C | 4-O | — | 1-(2-fluoroethyl)piperidin-4-yl |
| III-98 | —H | CH₃/CH₃ | CH₃/CH₃ | F | 3-Cl | C | 4-O | — | 1-isopropylpiperidin-4-yl |
| III-99 | —CH₃ | CH₃/CH₃ | CH₃/CH₃ | F | 3-OCF₂H | C | 4-O | — | tetrahydrofuran-3-yl |
| III-100 | —H | CH₃/CH₃ | CH₃/CH₃ | F | 3-OCF₂H | C | 4-O | — | tetrahydrofuran-3-yl |
| III-101 | —CH₃ | CH₃/CH₃ | CH₃/CH₃ | F | 3-CF₃ | C | 4-O | — | 1-isopropylpiperidin-4-yl |

TABLE 3-continued

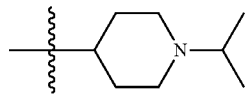

| cmpd | R$^1$ | R$^a$/R$^b$ | R$^c$/R$^d$ | R$^5$ | (R$^2$)$_p$ | Q | X | alk | A/(R$^3$)$_q$ |
|---|---|---|---|---|---|---|---|---|---|
| III-102 | —H | CH$_3$/CH$_3$ | CH$_3$/CH$_3$ | F | 3-CF$_3$ | C | 4-O | — |  |
| III-103 (TFA salt) | —CH$_3$ | CH$_3$/CH$_3$ | CH$_3$/CH$_3$ | F | 3-OCF$_2$H | C | 4-O | — | 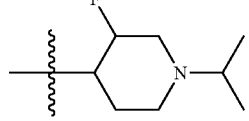 |
| III-104 (TFA salt) | —H | CH$_3$/CH$_3$ | CH$_3$/CH$_3$ | F | 3-OCF$_2$H | C | 4-O | — |  |
| III-105 | —CH$_3$ | CH$_3$/CH$_3$ | CH$_3$/CH$_3$ | F | 3-OCF$_2$H | C | 4-O | — | 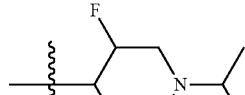 |
| III-106 | —H | CH$_3$/CH$_3$ | CH$_3$/CH$_3$ | F | 3-OCF$_2$H | C | 4-O | — |  |
| III-107 | —CH$_3$ | CH$_3$/CH$_3$ | CH$_3$/CH$_3$ | F | 3-OCF$_2$H | C | 4-O | — | 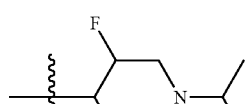 |
| III-108 | —H | CH$_3$/CH$_3$ | CH$_3$/CH$_3$ | F | 3-OCF$_2$H | C | 4-O | — |  |
| III-109 | —H | CH$_3$/CH$_3$ | CH$_3$/CH$_3$ | F | 3-F | C | 4-O | — | 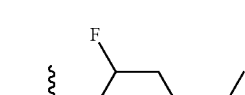 |
| III-110 | —CD$_3$ | CH$_3$/CH$_3$ | CH$_3$/CH$_3$ | F | 3-OCHF$_2$ | C | 4-O | — |  |
| III-111 | —CD$_3$ | CH$_3$/CH$_3$ | CH$_3$/CH$_3$ | F | 3-Cl | C | 4-O | — | 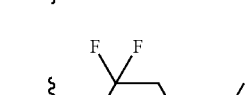 |

TABLE 3-continued

| cmpd | R[1] | R[a]/R[b] | R[c]/R[d] | R[5] | (R[2])[p] | Q | X | alk | A/(R[3])[q] |
|---|---|---|---|---|---|---|---|---|---|
| III-112 | —CD$_3$ | CH$_3$/CH$_3$ | CH$_3$/CH$_3$ | F | 3-OCHF$_2$ | C | 4-O | — | 3-fluoro-1-isopropylpiperidin-4-yl |
| III-113 | —CD$_3$ | CH$_3$/CH$_3$ | CH$_3$/CH$_3$ | F | 4-CH$_3$ | C | — | — | 3-(1H-tetrazol-1-yl) |
| III-114 | —CD$_3$ | CH$_3$/CH$_3$ | CH$_3$/CH$_3$ | F | — | C | — | — | 3-(1H-tetrazol-1-yl) |
| III-115 | —CD$_3$ | CH$_3$/CH$_3$ | CH$_3$/CH$_3$ | F | — | C | — | — | 3-(5-methyl-1H-tetrazol-1-yl) |
| III-116 | —H | CH$_3$/CH$_3$ | CH$_3$/CH$_3$ | —F | 5-cyclopropyl | C | — | — | 3-(1H-tetrazol-1-yl) |
| III-117 | —CH$_3$ | CH$_3$/CH$_3$ | CH$_3$/CH$_3$ | —F | 5-cyclopropyl | C | — | — | 3-(1H-tetrazol-1-yl) |
| III-118 | —H | CH$_3$/CH$_3$ | CH$_3$/CH$_3$ | —F | 4-cyclopropyl | C | — | — | 3-(1H-tetrazol-1-yl) |
| III-119 | —CH$_3$ | CH$_3$/CH$_3$ | CH$_3$/CH$_3$ | —F | 4-cyclopropyl | C | — | — | 3-(1H-1,2,3-triazol-1-yl) |
| III-120 | —H | CH$_3$/CH$_3$ | CH$_3$/CH$_3$ | —F | 4-F | C | — | — | 3-(1-methyl-1H-tetrazol-5-yl) |

TABLE 3-continued
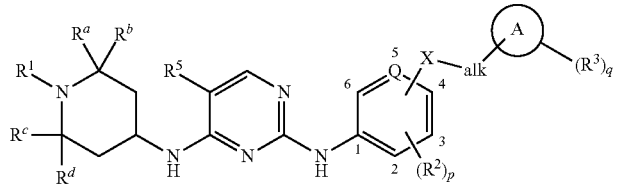
| cmpd | R¹ | Rᵃ/Rᵇ | Rᶜ/Rᵈ | R⁵ | (R²)ₚ | Q | X | alk | A/(R³)_q |
|---|---|---|---|---|---|---|---|---|---|
| III-121 | —CH₃ | CH₃/CH₃ | CH₃/CH₃ | —F | 4-F | C | — | — | 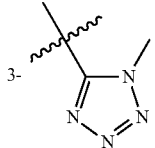 [SMILES: *c1nnnn1C] |
| III-122 | —H | CH₃/CH₃ | CH₃/CH₃ | —F | 4-O(CH(CH₃)₂) | C | — | — | 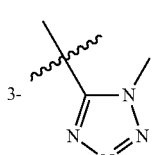 |
| III-123 | —CH₃ | CH₃/CH₃ | CH₃/CH₃ | —F | 4-O(CH(CH₃)₂) | C | — | — | 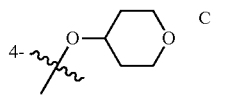 |
| III-124 | —H | CH₃/CH₃ | CH₃/CH₃ | —F | 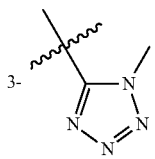 [SMILES: *c1nnnn1C] | C | — | — | 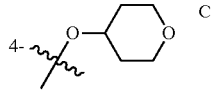 |
| III-125 | —CH₃ | CH₃/CH₃ | CH₃/CH₃ | —F | 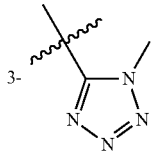 [SMILES: *c1nnnn1C] | C | — | — | 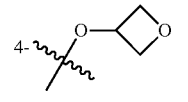 [SMILES: *OC1COC1] |
| III-126 | —H | CH₃/CH₃ | CH₃/CH₃ | —F | 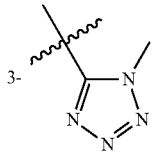 [SMILES: *c1nnnn1C] | C | — | — | 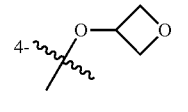 |
| III-127 | —CH₃ | CH₃/CH₃ | CH₃/CH₃ | —F | 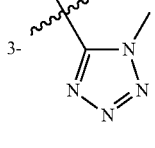 | C | — | — | 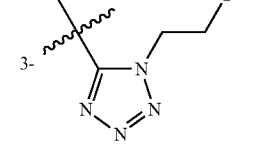 |
| III-128 | —CH₃ | CH₃/CH₃ | CH₃/CH₃ | —F | 4-F | C | — | — |  |

TABLE 3-continued
| cmpd | R¹ | Rᵃ/Rᵇ | Rᶜ/Rᵈ | R⁵ | (R²)ₚ | Q | X | alk | A/(R³)_q |
|---|---|---|---|---|---|---|---|---|---|
| III-129 | —H | CH₃/CH₃ | CH₃/CH₃ | —F | 4-F | C | — | — | 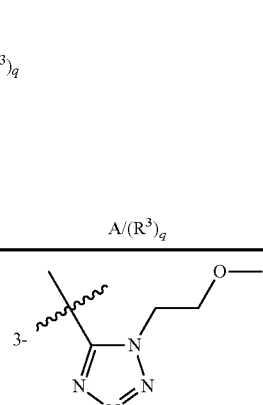 |
| III-130 | —H | CH₃/CH₃ | CH₃/CH₃ | —F | 4-Cl | C | — | — | 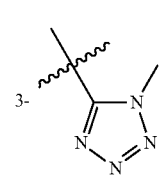 [SMILES: *c1nnnn1C] |
| III-131 | —CH₃ | CH₃/CH₃ | CH₃/CH₃ | —F | 4-Cl | C | — | — | 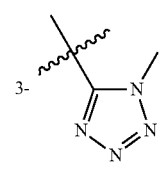 [SMILES: *c1nnnn1C] |
| III-132 | —H | CH₃/CH₃ | CH₃/CH₃ | —F | 5-CH₃ | C | — | — | 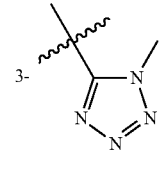 [SMILES: *c1nnnn1C] |
| III-133 | —CH₃ | CH₃/CH₃ | CH₃/CH₃ | —F | 5-CH₃ | C | — | — | 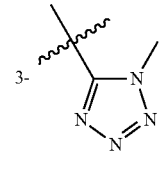 [SMILES: *c1nnnn1C] |
| III-134 | —H | CH₃/CH₃ | CH₃/CH₃ | —F | 5-Cl | C | — | — | 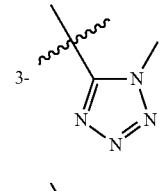 |
| III-135 | —CH₃ | CH₃/CH₃ | CH₃/CH₃ | —F | 5-Cl | C | — | — | 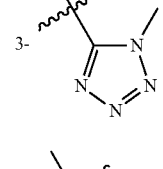 |
| III-136 | —H | CH₃/CH₃ | CH₃/CH₃ | —F | 4-F; 5-F | C | — | — | 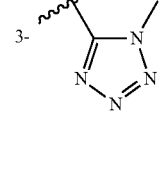 |

TABLE 3-continued

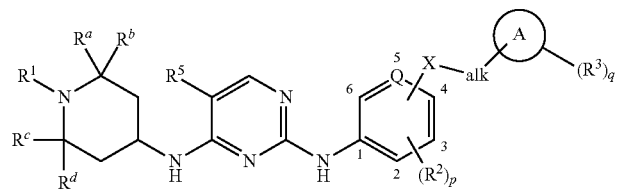

| cmpd | R¹ | Rᵃ/Rᵇ | Rᶜ/Rᵈ | R⁵ | (R²)ₚ | Q | X | alk | A/(R³)q |
|---|---|---|---|---|---|---|---|---|---|
| III-137 | —CH₃ | CH₃/CH₃ | CH₃/CH₃ | —F | 4-F; 5-F | C | — | — | 3- tetrazole |
| III-138 | —H | CH₃/CH₃ | CH₃/CH₃ | —F | 5-F | C | — | — | 3- tetrazole |
| III-139 | —CH₃ | CH₃/CH₃ | CH₃/CH₃ | —F | 5-F | C | — | — | 3- tetrazole |
| III-140 | —H | CH₃/CH₃ | CH₃/CH₃ | —F | 5-CF₃ | C | — | — | 3- tetrazole |
| III-141 | —CH₃ | CH₃/CH₃ | CH₃/CH₃ | —F | 5-CF₃ | C | — | — | 3- tetrazole |
| III-142 | —H | CH₃/CH₃ | CH₃/CH₃ | —F | 4-O(CH(CH₃)₂); 5-F | C | — | — | 3- tetrazole |
| III-143 | —H | CH₃/CH₃ | CH₃/CH₃ | —F | 5-CN | C | — | — | 3- tetrazole |
| III-144 | —CH₃ | CH₃/CH₃ | CH₃/CH₃ | —F | 5-CN | C | — | — | 3- tetrazole |

TABLE 3-continued

| cmpd | R¹ | Rᵃ/Rᵇ | Rᶜ/Rᵈ | R⁵ | (R²)ₚ | Q | X | alk | A/(R³)ᵩ |
|---|---|---|---|---|---|---|---|---|---|
| III-145 | —H | CH₃/CH₃ | CH₃/CH₃ | —F | 5- (oxetane) | C | — | — | 3- (1-methyl-tetrazol-5-yl) |
| III-146 | —CH₃ | CH₃/CH₃ | CH₃/CH₃ | —F | 5- (oxetane) | C | — | — | 3- (1-methyl-tetrazol-5-yl) |
| III-147 | —H | CH₃/CH₃ | CH₃/CH₃ | —F | 5- (cyclopropyl) | C | — | — | 3- (1-methyl-tetrazol-5-yl) |
| III-148 | —H | CH₃/CH₃ | CH₃/CH₃ | —F | 4- (cyclopropyl) | C | — | — | 3- (1-methyl-tetrazol-5-yl) |

Particular compounds of interest, and salts or solvates or stereoisomers thereof, include:

I-1: 5-fluoro-N2-(3-(3-methyl-1H-pyrazol-1-yl)phenyl)-N4-(1,2,2,6,6-pentamethylpiperidin-4-yl)pyrimidine-2,4-diamine I-2: 5-fluoro-N2-(3-(3-(trifluoromethyl)-1H-pyrazol-1-yl)phenyl)-N4-(1,2,2,6,6-pentamethylpiperidin-4-yl)pyrimidine-2,4-diamine I-3: 5-fluoro-N2-(3-(3-(trifluoromethyl)-1H-pyrazol-1-yl)phenyl)-N4-(2,2,6,6-tetramethylpiperidin-4-yl)pyrimidine-2,4-diamine I-4: N2-(4-(difluoromethoxy)-3-(2,5-dimethyl-1H-pyrrol-1-yl)phenyl)-5-fluoro-N4-(1,2,2,6,6-pentamethylpiperidin-4-yl)pyrimidine-2,4-diamine I-5: N2-(4-(difluoromethoxy)-3-(2,5-dimethyl-1H-pyrrol-1-yl)phenyl)-5-fluoro-N4-(2,2,6,6-tetramethylpiperidin-4-yl)pyrimidine-2,4-diamine I-6: N2-(3-(2-(1H-1,2,3-triazol-1-yl)ethoxy)-5-fluorophenyl)-5-fluoro-N4-(1,2,2,6,6-pentamethylpiperidin-4-yl)pyrimidine-2,4-diamine I-7: 5-fluoro-N2-(3-(3-methyl-1H-pyrazol-1-yl)phenyl)-N4-(2,2,6,6-tetramethylpiperidin-4-yl)pyrimidine-2,4-diamine I-8: N2-(3-(2-(1H-1,2,3-triazol-1-yl)ethoxy)-5-fluorophenyl)-5-fluoro-N4-(2,2,6,6-tetramethylpiperidin-4-yl)pyrimidine-2,4-diamine I-9: 5-fluoro-N2-(4-fluoro-3-(5-methyl-1H-tetrazol-1-yl)phenyl)-N4-(1,2,2,6,6-pentamethylpiperidin-4-yl)pyrimidine-2,4-diamine I-10: 5-fluoro-N2-(4-fluoro-3-(5-methyl-1H-tetrazol-1-yl)phenyl)-N4-(2,2,6,6-tetramethylpiperidin-4-yl)pyrimidine-2,4-diamine I-11: N4-(1-(cyclopropylmethyl)-2,2,6,6-tetramethylpiperidin-4-yl)-5-fluoro-N2-(4-fluoro-3-(5-methyl-1H-tetrazol-1-yl)phenyl)pyrimidine-2,4-diamine I-12: N2-(3-(1H-1,2,4-triazol-1-yl)phenyl)-5-fluoro-N4-(1,2,2,6,6-pentamethylpiperidin-4-yl)pyrimidine-2,4-diamine I-13: N2-(4-ethoxy-3-(2,5-dimethyl-1H-pyrrol-1-yl)phenyl)-5-fluoro-N4-(1,2,2,6,6-pentamethylpiperidin-4-yl)pyrimidine-2,4-diamine I-14: N2-(4-ethoxy-3-(2,5-dimethyl-1H-pyrrol-1-yl)phenyl)-5-fluoro-N4-(2,2,6,6-tetramethylpiperidin-4-yl)pyrimidine-2,4-diamine I-15: N2-(4-isopropyloxy-3-(2,5-dimethyl-1H-pyrrol-1-yl)phenyl)-5-fluoro-N4-(1,2,2,6,6-pentamethylpiperidin-4-yl)pyrimidine-2,4-diamine I-16: N2-(4-isopropyloxy-3-(2,5-dimethyl-1H-pyrrol-1-yl)phenyl)-5-fluoro-N4-(2,2,6,6-tetramethylpiperidin-4-yl)pyrimidine-2,4-diamine I-17: 4-(2,2,6,6-tetramethylpiperidin-4-ylamino)-2-(3-(2-(1H-1,2,3-triazol-1-yl)ethoxy)-5-fluorophenylamino)pyrimidine-5-carbonitrile I-18: 4-(2,2,6,6-tetramethylpiperidin-4-ylamino)-2-(4-fluoro-3-(5-methyl-1H-tetrazol-1-yl)phenylamino)pyrimidine-5-carbonitrile I-19: N2-(3-(1H-1,2,4-triazol-1-yl)phenyl)-5-fluoro-N4-(2,2,6,6-tetramethylpiperidin-4-yl)pyrimidine-2,4-diamine I-20: 5-fluoro-N2-(3-(5-methyl-1H-tetrazol-1-yl)-4-(trifluoromethoxy)phenyl)-N4-(1,2,2,6,6-pentamethylpiperidin-4-yl)pyrimidine-2,4-diamine I-21: 5-fluoro-N2-(3-(5-methyl-1H-tetrazol-1-yl)-4-(trifluoromethoxy)phenyl)-N4-(2,2,6,6-tetramethylpiperidin-4-yl)pyrimidine-2,4-diamine I-22: N2-(3-(1H-pyrazol-1-yl)phenyl)-5-fluoro-N4-(1,2,2,6,6-pentamethylpiperidin-4-yl)pyrimidine-2,4-diamine I-23: N2-(3-(1H-pyrazol-1-yl)phenyl)-5-fluoro-N4-(2,2,6,6-tetramethylpiperidin-4-yl)pyrimidine-2,4-diamine I-24: N2-(4-(2-(1H-1,2,3-triazol-1-yl)ethoxy)-3-(difluoromethoxy)phenyl)-5-fluoro-N4-(2,2,6,6-tetramethylpiperidin-4-yl)pyrimidine-2,4-diamine I-25: N2-(4-(2-(1H-1,2,4-triazol-1-yl)ethoxy)-3-(difluoromethoxy)phenyl)-5-fluoro-N4-(2,2,6,6-tetramethylpiperidin-4-yl)pyrimidine-2,4-diamine I-26: N2-(4-(2-(1H-1,2,3-triazol-1-yl)ethoxy)-3-(difluoromethoxy)phenyl)-5-fluoro-N4-(1,2,2,6,6-pentamethylpiperidin-4-yl)pyrimidine-2,4-diamine I-27: N2-(4-(2-(1H-1,2,4-triazol-1-yl)ethoxy)-3-(difluoromethoxy)phenyl)-5-fluoro-N4-(1,2,2,6,6-pentamethylpiperidin-4-yl)pyrimidine-2,4-diamine I-28: N2-(3-(2-(1H-1,2,4-triazol-1-yl)ethoxy)-5-(trifluoromethyl)phenyl)-5-fluoro-N4-(2,2,6,6-tetramethylpiperidin-4-yl)pyrimidine-2,4-diamine I-29: N2-(3-(2-(1H-1,2,4-triazol-1-yl)ethoxy)-5-(trifluoromethyl)phenyl)-5-fluoro-N4-(1,2,2,6,6-pentamethylpiperidin-4-yl)pyrimidine-2,4-diamine I-30: 1-(2-(4-(4-(2,2,6,6-tetramethylpiperidin-4-ylamino)-5-fluoropyrimidin-2-ylamino)-2-(difluoromethoxy)phenoxy)ethyl)pyrrolidin-2-one I-31: 1-(2-(4-(4-(1,2,2,6,6-pentamethylpiperidin-4-ylamino)-5-fluoropyrimidin-2-ylamino)-2-(difluoromethoxy)phenoxy)ethyl)pyrrolidin-2-one I-32: N2-(3-(2-(1H-1,2,3-triazol-1-yl)ethoxy)-5-(trifluoromethyl)phenyl)-5-fluoro-N4-(2,2,6,6-tetramethylpiperidin-4-yl)pyrimidine-2,4-diamine I-33: N2-(3-(2-(1H-1,2,3-triazol-1-yl)ethoxy)-5-(trifluoromethyl)phenyl)-5-fluoro-N4-(1,2,2,6,6-pentamethylpiperidin-4-yl)pyrimidine-2,4-diamine I-34: 4-(2,2,6,6-tetramethylpiperidin-4-ylamino)-2-(4-(2-(1H-1,2,3-triazol-1-yl)ethoxy)-3-(difluoromethoxy)phenylamino)pyrimidine-5-carbonitrile I-35: N2-(3-(3-(1H-pyrrol-1-yl)propoxy)-5-fluorophenyl)-5-fluoro-N4-(2,2,6,6-tetramethylpiperidin-4-yl)pyrimidine-2,4-diamine I-36: N2-(3-(3-(1H-pyrrol-1-yl)propoxy)-5-fluorophenyl)-5-fluoro-N4-(1,2,2,6,6-pentamethylpiperidin-4-yl)pyrimidine-2,4-diamine I-37: 1-(2-(3-(4-(2,2,6,6-tetramethylpiperidin-4-ylamino)-5-fluoropyrimidin-2-ylamino)-5-fluorophenoxy)ethyl)pyrrolidin-2-one I-38: 1-(2-(3-(4-(1,2,2,6,6-pentamethylpiperidin-4-ylamino)-5-fluoropyrimidin-2-ylamino)-5-fluorophenoxy)ethyl)pyrrolidin-2-one I-39: N2-(3-(2-(1H-1,2,4-triazol-1-yl)ethoxy)-5-fluorophenyl)-5-fluoro-N4-(2,2,6,6-tetramethylpiperidin-4-yl)pyrimidine-2,4-diamine I-40: N2-(3-(2-(1H-1,2,4-triazol-1-yl)ethoxy)-5-fluorophenyl)-5-fluoro-N4-(1,2,2,6,6-pentamethylpiperidin-4-yl)pyrimidine-2,4-diamine I-41: N2-(4-(3-(1H-pyrrol-1-yl)propoxy)-3-(difluoromethoxy)phenyl)-5-fluoro-N4-(1,2,2,6,6-pentamethylpiperidin-4-yl)pyrimidine-2,4-diamine I-42: N2-(4-(3-(1H-pyrrol-1-yl)propoxy)-3-(difluoromethoxy)phenyl)-5-fluoro-N4-(2,2,6,6-tetramethylpiperidin-4-yl)pyrimidine-2,4-diamine I-43: N2-(3-(difluoromethoxy)-4-(pyridin-4-yloxy)phenyl)-5-fluoro-N4-(1,2,2,6,6-pentamethylpiperidin-4-yl)pyrimidine-2,4-diamine I-44: N2-(3-(difluoromethoxy)-4-(pyridin-3-yloxy)phenyl)-5-fluoro-N4-(1,2,2,6,6-pentamethylpiperidin-4-yl)pyrimidine-2,4-diamine I-45: N2-(3-(difluoromethoxy)-4-(pyridin-3-yloxy)phenyl)-5-fluoro-N4-(2,2,6,6-tetramethylpiperidin-4-yl)pyrimidine-2,4-diamine I-46: N2-(4-(2-(pyrrolidin-1-yl)ethoxy)-3-(difluoromethoxy)phenyl)-5-fluoro-N4-(1,2,2,6,6-pentamethylpiperidin-4-yl)pyrimidine-2,4-diamine I-47: N2-(4-(3-morpholinopropoxy)-3-(difluoromethoxy)phenyl)-5-fluoro-N4-(2,2,6,6-tetramethylpiperidin-4-yl)pyrimidine-2,4-diamine I-48: N2-(4-(3-morpholinopropoxy)-3-(difluoromethoxy)phenyl)-5-fluoro-N4-(1,2,2,6,6-pentamethylpiperidin-4-yl)pyrimidine-2,4-diamine I-49: N2-(3-(3-(1H-pyrrol-1-yl)propoxy)-5-(trifluoromethyl)phenyl)-5-fluoro-N4-(1,2,2,6,6-pentamethylpiperidin-4-yl)pyrimidine-2,4-diamine I-50: 1-(2-(4-(4-(2,2,6,6-tetramethylpiperidin-4-ylamino)-5-fluoropyrimidin-2-ylamino)-2-(difluoromethoxy)phenoxy)ethyl)imidazolidin-2-one I-51: 1-(2-(4-(4-(1,2,2,6,6-pentamethylpiperidin-4-ylamino)-5-fluoropyrimidin-2-ylamino)-2-(difluoromethoxy)phenoxy)ethyl)imidazolidin-2-one I-52: 4-(1,2,2,6,6-pentamethylpiperidin-4-ylamino)-2-(3-(difluoromethoxy)-4-(pyridin-3-yloxy)phenylamino)pyrimidine-5-carbonitrile I-53: 4-(1,2,2,6,6-pentamethylpiperidin-4-ylamino)-2-(3-(difluoromethoxy)-4-(pyridin-4-yloxy)phenylamino)pyrimidine-5-carbonitrile I-54: 4-(1,2,2,6,6-pentamethylpiperidin-4-ylamino)-2-(4-(2-(1H-1,2,4-triazol-1-yl)ethoxy)-3-(difluoromethoxy)phenylamino)pyrimidine-5-carbonitrile I-55: 4-(1,2,2,6,6-pentamethylpiperidin-4-ylamino)-2-(4-(2-(1H-1,2,3-triazol-1-yl)ethoxy)-3-(difluoromethoxy)phenylamino)pyrimidine-5-carbonitrile I-56: 1-(2-(4-(4-(1,2,2,6,6-pentamethylpiperidin-4-ylamino)-5-fluoropyrimidin-2-ylamino)-2-(trifluoromethyl)phenoxy)ethyl)pyrrolidin-2-one I-57: 1-(2-(4-(4-(2,2,6,6-tetramethylpiperidin-4-ylamino)-5-fluoropyrimidin-2-ylamino)-2-(trifluoromethyl)phenoxy)ethyl)pyrrolidin-2-one I-58: 4-(2,2,6,6-tetramethylpiperidin-4-ylamino)-2-(3-(difluoromethoxy)-4-(pyridin-4-yloxy)phenylamino)pyrimidine-5-carbonitrile I-59: 5-fluoro-N2-(3-(trifluoromethyl)-4-(pyridin-3-yloxy)phenyl)-N4-(2,2,6,6-tetramethylpiperidin-4-yl)pyrimidine-2,4-diamine I-60: N2-(4-(2-(pyrrolidin-1-yl)ethoxy)-3-(difluoromethoxy)phenyl)-5-fluoro-N4-(2,2,6,6-tetramethylpiperidin-4-yl)pyrimidine-2,4-diamine I-61: 5-fluoro-N2-(3-(trifluoromethyl)-4-(pyridin-3-yloxy)phenyl)-N4-(1,2,2,6,6-pentamethylpiperidin-4-yl)pyrimidine-2,4-diamine I-62: 5-fluoro-N2-(3-(trifluoromethyl)-4-(pyridin-4-yloxy)phenyl)-N4-(1,2,2,6,6-pentamethylpiperidin-4-yl)pyrimidine-2,4-diamine I-63: N2-(3-(difluoromethoxy)-4-(pyridin-3-yl)phenyl)-5-fluoro-N4-(2,2,6,6-tetramethylpiperidin-4-yl)pyrimidine-2,4-diamine I-64: N2-(3-(difluoromethoxy)-4-(pyridin-3-yl)phenyl)-5-fluoro-N4-(1,2,2,6,6-pentamethylpiperidin-4-yl)pyrimidine-2,4-diamine I-65: N2-(4-(2-morpholinoethoxy)-3-(trifluoromethyl)phenyl)-5-fluoro-N4-(2,2,6,6-tetramethylpiperidin-4-yl)pyrimidine-2,4-diamine I-66: N2-(4-(3-morpholinopropoxy)-3-(difluoromethoxy)phenyl)-5-fluoro-N4-(1-(2,2,2-trifluoroethyl)-2,2,6,6-tetramethylpiperidin-4-yl)pyrimidine-2,4-diamine I-67: 5-aminocarbonyl-N2-[4-fluoro-3-(1H-tetrazol-1-yl)]phenyl-N4-(2,2,6,6-tetramethylpiperidin-4-yl)-2,4-pyrimidinediamine I-68: 5-aminocarbonyl-N2-[4-ethoxy-3-(5-ethyl-1H-tetrazol-1-yl)]phenyl-N4-(2,2,6,6-tetramethylpiperidin-4-yl)-2,4-pyrimidinediamine I-69: 5-fluoro-N4-(1,2,2,6,6-pentamethylpiperidin-4-yl)-N2-{3-[5-(2,2,2-trifluoroethyl)thio]-1H-tetrazol-1-yl}phenyl-2,4-pyrimidinediamine I-70: 5-fluoro-N4-(2,2,6,6-tetramethylpiperidin-4-yl)-N2-{3-[5-(2,2,2-trifluoroethyl)thio]-1H-tetrazol-1-yl}phenyl-2,4-pyrimidinediamine I-71: 5-aminocarbonyl-N4-(1,2,2,6,6-pentamethylpiperidin-4-yl)-N2-{3-[5-(2,2,2-trifluoroethyl)thio]-1H-tetrazol-1-yl}phenyl-2,4-pyrimidinediamine I-72: 5-aminocarbonyl-N4-(2,2,6,6-tetramethylpiperidin-4-yl)-N2-{3-[5-(2,2,2-trifluoroethyl)thio]-1H-tetrazol-1-yl}phenyl-2,4-pyrimidinediamine I-73: 5-cyano-N2-[4-fluoro-3-(1H-tetrazol-1-yl)]phenyl-N4-(1,2,2,6,6-pentamethylpiperidin-4-yl)-2,4-pyrimidinediamine I-74: 5-fluoro-N2-[4-methoxy-3-(5-propyl-1H-tetrazol-1-yl)]phenyl-N4-(2,2,6,6-tetramethylpiperidin-4-yl)-2,4-pyrimidinediamine I-75: 5-aminocarbonyl-N2-[4-methoxy-3-(5-propyl-1H-tetrazol-1-yl)]phenyl-N4-(1,2,2,6,6-pentamethylpiperidin-4-yl)-2,4-pyrimidinediamine I-76: 5-aminocarbonyl-N2-[4-methoxy-3-(5-propyl-1H-tetrazol-1-yl)]phenyl-N4-(2,2,6,6-tetramethylpiperidin-4-yl)-2,4-pyrimidinediamine I-77: 5-cyano-N2-[4-fluoro-3-(1H-tetrazol-1-yl)]phenyl-N4-(2,2,6,6-tetramethylpiperidin-4-yl)-2,4-pyrimidinediamine I-78: 5-cyano-N4-(1,2,2,6,6-pentamethylpiperidin-4-yl)-N2-{3-[5-(2,2,2-trifluoroethyl)thio]-1H-tetrazol-1-yl}phenyl-2,4-pyrimidinediamine I-79: 5-cyano-N4-(2,2,6,6-tetramethylpiperidin-4-yl)-N2-{3-[5-(2,2,2-trifluoroethyl)thio]-1H-tetrazol-1-yl}phenyl-2,4-pyrimidinediamine I-80: 5-cyano-N2-[4-methoxy-3-(5-propyl-1H-tetrazol-1-yl)]phenyl-N4-(1,2,2,6,6-pentamethylpiperidin-4-yl)-2,4-pyrimidinediamine I-81: 5-cyano-N2-[4-methoxy-3-(5-propyl-1H-tetrazol-1-yl)]phenyl-N4-(2,2,6,6-tetramethylpiperidin-4-yl)-2,4-pyrimidinediamine I-82: N2-[4-difluoromethoxy-3-(5-ethyl-1H-tetrazol-1-yl)]phenyl-5-fluoro-N4-(2,2,6,6-tetramethylpiperidin-4-yl)-2,4-pyrimidinediamine I-83: 5-aminocarbonyl-N2-[4-difluoromethoxy-3-(5-ethyl-1H-tetrazol-1-yl)]phenyl-N4-(2,2,6,6-tetramethylpiperidin-4-yl)-2,4-pyrimidinediamine I-84: 5-cyano-N2-[4-difluoromethoxy-3-(5-ethyl-1H-tetrazol-1-yl)]phenyl-N4-(2,2,6,6-tetramethylpiperidin-4-yl)-2,4-pyrimidinediamine I-85: 5-Cyano-N4-(2,2,6,6-tetramethylpiperidin-4-yl)-N2-[3-(tetrazol-5-yl)]phenyl-2,4-pyrimidinediamine I-86: 5-Fluoro-N2-{3-[1-N-isopropyl-(tetrazol-5-yl)]}phenyl-N4-(1,2,2,6,6-pentamethylpiperidin-4-yl)-2,4-pyrimidinediamine I-87: 5-Fluoro-N2-{3-[1-N-isopropyl-(tetrazol-5-yl)]}phenyl-N4-(2,2,6,6-tetramethylpiperidin-4-yl)-2,4-pyrimidinediamine I-88: 5-Cyano-N2-{3-[1-N-isopropyl-(tetrazol-5-yl)]}phenyl-N4-(1,2,2,6,6-pentamethylpiperidin-4-yl)-2,4-pyrimidinediamine I-89: N2-{3-[1-N-Cyclopropyl-(tetrazol-5-yl)]}phenyl-5-fluoro-N4-(1,2,2,6,6-pentamethylpiperidin-4-yl)-2,4-pyrimidinediamine I-90: N2-{3-[1-N-Cyclopropyl-(tetrazol-5-yl)]}phenyl-5-fluoro-N4-(2,2,6,6-tetramethylpiperidin-4-yl)-2,4-pyrimidinediamine I-91: N2-{3-[1-N-(2-Fluoroethyl)-(tetrazol-5-yl)]}phenyl-5-fluoro-N4-(1,2,2,6,6-pentamethylpiperidin-4-yl)-2,4-pyrimidinediamine I-92: N2-{3-[1-N-(2-Fluoroethyl)-(tetrazol-5-yl)]}phenyl-5-fluoro-N4-(2,2,6,6-tetramethylpiperidin-4-yl)-2,4-pyrimidinediamine I-93: N2-[3-(2,5-Dimethyl-pyrrol-1-yl)-4-methoxy]phenyl-5-fluoro-N4-(2,2,6,6-tetramethylpiperidin-4-yl)-2,4-pyrimidinediamine I-94: 5-Cyano-N2-{3-[1-N-cyclopropyl-(tetrazol-5-yl)]}phenyl-N4-(1,2,2,6,6-pentamethylpiperidin-4-yl)-2,4-pyrimidinediamine I-95: 5-Cyano-N2-{3-[1-N-cyclopropyl-(tetrazol-5-yl)]}phenyl-N4-(2,2,6,6-tetramethylpiperidin-4-yl)-2,4-pyrimidinediamine I-96: 5-Cyano-N2-{3-[1-N-(2-fluoroethyl)-(tetrazol-5-yl)]}phenyl-N4-(1,2,2,6,6-pentamethylpiperidin-4-yl)-2,4-pyrimidinediamine I-97: 5-Cyano-N2-{3-[1-N-(2-fluoroethyl)-(tetrazol-5-yl)]}phenyl-N4-(2,2,6,6-tetramethylpiperidin-4-yl)-2,4-pyrimidinediamine I-98: 5-Fluoro-N2-{3-[1-N-(2-morpholinoethyl)-(tetrazol-5-yl)]}phenyl-N4-(1,2,2,6,6-pentamethylpiperidin-4-yl)-2,4-pyrimidinediamine I-99: 5-Fluoro-N2-{3-[1-N-(2-morpholinoethyl)-(tetrazol-5-yl)]}phenyl-N4-(2,2,6,6-tetramethylpiperidin-4-yl)-2,4-pyrimidinediamine I-100: N2-[3-(2,5-Dimethyl-pyrrol-1-yl)-4-fluoro]phenyl-5-fluoro-N4-(1,2,2,6,6-pentamethylpiperidin-4-yl)-2,4-pyrimidinediamine I-101: N2-[3-(2,5-Dimethyl-pyrrol-1-yl)-4-fluoro]phenyl-5-fluoro-N4-(2,2,6,6-tetramethylpiperidin-4-yl)-2,4-pyrimidinediamine I-102: N2-[4-Cyano-3-(2,5-dimethyl-pyrrol-1-yl)]phenyl-5-fluoro-N4-(1,2,2,6,6-pentamethylpiperidin-4-yl)-2,4-pyrimidinediamine I-103: N2-[3-(2,5-Dimethyl-pyrrol-1-yl)-4-(isopropylaminocarboxyloxy)]phenyl-5-fluoro-N4-(1,2,2,6,6-pentamethylpiperidin-4-yl)-2,4-pyrimidinediamine I-104: N2-(4-(1-isopropylpiperidin-4-yloxy)-3-(difluoromethoxy)phenyl)-5-fluoro-N4-(2,2,6,6-tetramethylpiperidin-4-yl)pyrimidine-2,4-diamine I-105: N2-(4-(1-isopropylpiperidin-4-yloxy)-3-(difluoromethoxy)phenyl)-5-fluoro-N4-(1,2,2,6,6-pentamethylpiperidin-4-yl)pyrimidine-2,4-diamine I-106: N2-(3-(difluoromethoxy)-5-(trifluoromethyl)phenyl)-5-fluoro-N4-(2,2,6,6-tetramethylpiperidin-4-yl)pyrimidine-2,4-diamine I-107: N2-(3-(difluoromethoxy)-5-(trifluoromethyl)phenyl)-5-fluoro-N4-(1,2,2,6,6-pentamethylpiperidin-4-yl)pyrimidine-2,4-diamine I-108: N2-(3-(difluoromethoxy)-4-ethoxyphenyl)-5-fluoro-N4-(2,2,6,6-tetramethylpiperidin-4-yl)pyrimidine-2,4-diamine I-109: N2-(3-(difluoromethoxy)-4-ethoxyphenyl)-5-fluoro-N4-(1,2,2,6,6-pentamethylpiperidin-4-yl)pyrimidine-2,4-diamine I-110: N2-(3-Acetylamino-5-methoxyphenyl)-5-fluoro-N4-(1,2,2,6,6-pentamethylpiperidin-4-yl)-2,4-pyrimidinediamine I-111: N2-(3,5-Dimethoxyphenyl)-5-fluoro-N4-(1-N-oxide-2,2,6,6-pentamethylpiperidin-4-yl)-2,4-pyrimidinediamine I-112: 5-(4-(1,2,2,6,6-pentamethylpiperidin-4-ylamino)-5-fluoropyrimidin-2-ylamino)-3-(5-methyl-1H-tetrazol-1-yl)pyridin-2-ol I-113: 5-fluoro-N2-(6-isopropoxy-5-(5-methyl-1H-tetrazol-1-yl)pyridin-3-yl)-N4-(1,2,2,6,6-pentamethylpiperidin-4-yl)pyrimidine-2,4-diamine I-114: 5-fluoro-N2-(6-isopropoxy-5-(5-methyl-1H-tetrazol-1-yl)pyridin-3-yl)-N4-(2,2,6,6-tetramethylpiperidin-4-yl)pyrimidine-2,4-diamine I-115: 5-fluoro-N2-(6-isopropoxy-5-(2,5-dimethyl-1H-pyrrol-1-yl)pyridin-3-yl)-N4-(1,2,2,6,6-pentamethylpiperidin-4-yl)pyrimidine-2,4-diamine I-116: 5-fluoro-N2-(6-isopropoxy-5-(2,5-dimethyl-1H-pyrrol-1-yl)pyridin-3-yl)-N4-(2,2,6,6-tetramethylpiperidin-4-yl)pyrimidine-2,4-diamine I-117: N2-(5-(difluoromethoxy)-6-ethoxypyridin-3-yl)-5-fluoro-N4-(1,2,2,6,6-pentamethylpiperidin-4-yl)pyrimidine-2,4-diamine I-118: N2-(5-(difluoromethoxy)-6-ethoxypyridin-3-yl)-5-fluoro-N4-(2,2,6,6-tetramethylpiperidin-4-yl)pyrimidine-2,4-diamine I-119: N2-(4-(2-morpholinoethoxy)-3-(trifluoromethyl)phenyl)-5-fluoro-N4-(1,2,2,6,6-pentamethylpiperidin-4-yl)pyrimidine-2,4-diamine I-120: N2-(4-(2-morpholinoethoxy)-3-(difluoromethoxy)phenyl)-5-fluoro-N4-(2,2,6,6-tetramethylpiperidin-4-yl)pyrimidine-2,4-diamine I-121: N2-(4-(2-morpholinoethoxy)-3-(difluoromethoxy)phenyl)-5-fluoro-N4-(1,2,2,6,6-pentamethylpiperidin-4-yl)pyrimidine-2,4-diamine I-122: N2-(4-(2-methyl-1-morpholinopropan-2-yloxy)-3-(difluoromethoxy)phenyl)-5-fluoro-N4-(2,2,6,6-tetramethylpiperidin-4-yl)pyrimidine-2,4-diamine I-123: N2-(4-(2-methyl-1-morpholinopropan-2-yloxy)-3-(difluoromethoxy)phenyl)-5-fluoro-N4-(1,2,2,6,6-pentamethylpiperidin-4-yl)pyrimidine-2,4-diamine I-124: N2-(4-(2-methyl-1-(pyrrolidin-1-yl)propan-2-yloxy)-3-(difluoromethoxy)phenyl)-5-fluoro-N4-(2,2,6,6-tetramethylpiperidin-4-yl)pyrimidine-2,4-diamine I-125: 5-aminocarbonyl-N2-[4-fluoro-3-(1H-tetrazol-1-yl)]phenyl-N4-(2,2,6,6-tetramethylpiperidin-4-yl)-2,4-pyrimidinediamine I-126: 5-fluoro-N2-(6-isopropoxy-5-(1-methyl-1H-tetrazol-5-yl)pyridin-3-yl)-N4-(1,2,2,6,6-pentamethylpiperidin-4-yl)pyrimidine-2,4-diamine I-127: 5-fluoro-N2-(6-isopropoxy-5-(1-methyl-1H-tetrazol-5-yl)pyridin-3-yl)-N4-(2,2,6,6-tetramethylpiperidin-4-yl)pyrimidine-2,4-diamine I-128: 2-(6-isopropoxy-5-(1-methyl-1H-tetrazol-5-yl)pyridin-3-ylamino)-4-(1,2,2,6,6-pentamethylpiperidin-4-ylamino)pyrimidine-5-carboxamide I-129: 2-(6-isopropoxy-5-(1-methyl-1H-tetrazol-5-yl)pyridin-3-ylamino)-4-(1,2,2,6,6-pentamethylpiperidin-4-ylamino)pyrimidine-5-carbonitrile I-130: 2-(6-isopropoxy-5-(1-methyl-1H-tetrazol-5-yl)pyridin-3-ylamino)-4-(2,2,6,6-tetramethylpiperidin-4-ylamino)pyrimidine-5-carbonitrile I-131: 5-fluoro-N2-(6-isopropoxy-5-(1-isopropyl-1H-tetrazol-5-yl)pyridin-3-yl)-N4-(1,2,2,6,6-pentamethylpiperidin-4-yl)pyrimidine-2,4-diamine I-132: 5-fluoro-N2-(6-isopropoxy-5-(1-isopropyl-1H-tetrazol-5-yl)pyridin-3-yl)-N4-(2,2,6,6-tetramethylpiperidin-4-yl)pyrimidine-2,4-diamine I-133: 2-(6-isopropoxy-5-(1-isopropyl-1H-tetrazol-5-yl)pyridin-3-ylamino)-4-(1,2,2,6,6-pentamethylpiperidin-4-ylamino)pyrimidine-5-carboxamide I-134: 2-(6-isopropoxy-5-(1-isopropyl-1H-tetrazol-5-yl)pyridin-3-ylamino)-4-(2,2,6,6-tetramethylpiperidin-4-ylamino)pyrimidine-5-carboxamide I-135: 2-(6-isopropoxy-5-(1-isopropyl-1H-tetrazol-5-yl)pyridin-3-ylamino)-4-(1,2,2,6,6-pentamethylpiperidin-4-ylamino)pyrimidine-5-carbonitrile I-136: 2-(6-isopropoxy-5-(1-isopropyl-1H-tetrazol-5-yl)pyridin-3-ylamino)-4-(2,2,6,6-tetramethylpiperidin-4-ylamino)pyrimidine-5-carbonitrile I-137: N2-(5-(1-cyclopropyl-1H-tetrazol-5-yl)-6-isopropoxypyridin-3-yl)-5-fluoro-N4-(1,2,2,6,6-pentamethylpiperidin-4-yl)pyrimidine-2,4-diamine I-138: N2-(5-(1-cyclopropyl-1H-tetrazol-5-yl)-6-isopropoxypyridin-3-yl)-5-fluoro-N4-(2,2,6,6-tetramethylpiperidin-4-yl)pyrimidine-2,4-diamine I-139: 2-(5-(1-cyclopropyl-1H-tetrazol-5-yl)-6-isopropoxypyridin-3-ylamino)-4-(1,2,2,6,6-pentamethylpiperidin-4-ylamino)pyrimidine-5-carbonitrile I-140: 2-(5-(1-cyclopropyl-1H-tetrazol-5-yl)-6-isopropoxypyridin-3-ylamino)-4-(2,2,6,6-tetramethylpiperidin-4-ylamino)pyrimidine-5-carbonitrile I-141: 1-(2-(3-(difluoromethoxy)-5-(5-fluoro-4-(2,2,6,6-tetramethylpiperidin-4-ylamino)pyrimidin-2-ylamino)pyridin-2-yloxy)ethyl)pyrrolidin-2-one I-142: N2-(5-(difluoromethoxy)-6-(2-(pyrrolidin-1-yl)ethoxy)pyridin-3-yl)-5-fluoro-N4-(1,2,2,6,6-pentamethylpiperidin-4-yl)pyrimidine-2,4-diamine I-143: N2-(5-(difluoromethoxy)-6-(2-(pyrrolidin-1-yl)ethoxy)pyridin-3-yl)-5-fluoro-N4-(2,2,6,6-tetramethylpiperidin-4-yl)pyrimidine-2,4-diamine I-144: N2-(4-(1-(2,2,2-trifluoroethyl)piperidin-4-yloxy)-3-(difluoromethoxy)phenyl)-5-fluoro-N4-(2,2,6,6-tetramethylpiperidin-4-yl)pyrimidine-2,4-diamine I-145: N2-(4-(1-(2,2,2-trifluoroethyl)piperidin-4-yloxy)-3-(difluoromethoxy)phenyl)-5-fluoro-N4-(1,2,2,6,6-pentamethylpiperidin-4-yl)pyrimidine-2,4-diamine I-146: N2-(4-((R)-1-isopropylpyrrolidin-3-yloxy)-3-(difluoromethoxy)phenyl)-5-fluoro-N4-(2,2,6,6-tetramethylpiperidin-4-yl)pyrimidine-2,4-diamine I-147: N2-(4-((R)-1-isopropylpyrrolidin-3-yloxy)-3-(difluoromethoxy)phenyl)-5-fluoro-N4-(1,2,2,6,6-pentamethylpiperidin-4-yl)pyrimidine-2,4-diamine I-148: N2-(4-((S)-1-isopropylpyrrolidin-3-yloxy)-3-(difluoromethoxy)phenyl)-5-fluoro-N4-(2,2,6,6-tetramethylpiperidin-4-yl)pyrimidine-2,4-diamine I-149: N2-(4-((S)-1-isopropylpyrrolidin-3-yloxy)-3-(difluoromethoxy)phenyl)-5-fluoro-N4-(1,2,2,6,6-pentamethylpiperidin-4-yl)pyrimidine-2,4-diamine I-150: 2-(1-isopropylpiperidin-4-yloxy)-5-(4-(2,2,6,6-tetramethylpiperidin-4-ylamino)-5-fluoropyrimidin-2-ylamino)benzonitrile I-151: 2-(1-isopropylpiperidin-4-yloxy)-5-(4-(1,2,2,6,6-pentamethylpiperidin-4-ylamino)-5-fluoropyrimidin-2-ylamino)benzonitrile II-1: (6-(4-(1,2,2,6,6-pentamethylpiperidin-4-ylamino)-5-fluoropyrimidin-2-ylamino)-2,3-dihydrobenzo[b][1,4]dioxin-2-yl)(piperidin-1-yl)methanone II-2: (6-(4-(1,2,2,6,6-pentamethylpiperidin-4-ylamino)-5-fluoropyrimidin-2-ylamino)-2,3-dihydrobenzo[b][1,4]dioxin-2-yl)(morpholino)methanone II-3: (6-(4-(2,2,6,6-tetramethylpiperidin-4-ylamino)-5-fluoropyrimidin-2-ylamino)-2,3-dihydrobenzo[b][1,4]dioxin-2-yl)(piperidin-1-yl)methanone II-4: (6-(4-(2,2,6,6-tetramethylpiperidin-4-ylamino)-5-fluoropyrimidin-2-ylamino)-2,3-dihydrobenzo[b][1,4]dioxin-2-yl)(morpholino)methanone II-5: 5-fluoro-N2-(2,3-dihydro-2-((piperidin-1-yl)methyl)benzo[b][1,4]dioxin-6-yl)-N4-(1,2,2,6,6-pentamethylpiperidin-4-yl)pyrimidine-2,4-diamine II-6: 5-fluoro-N2-(2,3-dihydro-2-(morpholinomethyl)benzo[b][1,4]dioxin-6-yl)-N4-(1,2,2,6,6-pentamethylpiperidin-4-yl)pyrimidine-2,4-diamine II-7: 5-fluoro-N2-(2,3-dihydro-2-((piperidin-1-yl)methyl)benzo[b][1,4]dioxin-6-yl)-N4-(2,2,6,6-tetramethylpiperidin-4-yl)pyrimidine-2,4-diamine II-8: 5-fluoro-N2-(2,3-dihydro-2-(morpholinomethyl)benzo[b][1,4]dioxin-6-yl)-N4-(2,2,6,6-tetramethylpiperidin-4-yl)pyrimidine-2,4-diamine II-9: N2-[2,2-Dimethyl-4-(2-fluoroethyl)-1,4-benzoxazin-3-one-7-yl]-5-fluoro-N4-(2,2,6,6-tetramethylpiperidin-4-yl)-2,4-pyrimidinediamine II-10: N2-(3,4-Ethylenedioxy)phenyl-5-fluoro-N4-(2,2,6,6-tetramethylpiperidin-4-yl)-2,4-pyrimidinediamine or a solvate, prodrug, or a pharmaceutically acceptable salt thereof.

Particular compounds of interest, and salts or solvates or stereoisomers thereof, include:

III-1: 5-fluoro-N2-(4-(1-isopropylpiperidin-4-yloxy)-3-(5-methyl-1H-tetrazol-1-yl)phenyl)-N4-(1,2,2,6,6-pentamethylpiperidin-4-yl)pyrimidine-2,4-diamine III-2: 5-fluoro-N2-(4-(1-isopropylpiperidin-4-yloxy)-3-(5-methyl-1H-tetrazol-1-yl)phenyl)-N4-(2,2,6,6-tetramethylpiperidin-4-yl)pyrimidine-2,4-diamine III-3: N2-(3-(Difluoromethoxy)-4-(1-isopropylpiperidin-4-yloxy)phenyl)-5-fluoro-N4-(2,2,6,6-tetramethyl-1-(2,2,2-trifluoroethyl)piperidin-4-yl)pyrimidine-2,4-diamine III-4: 1-(4-(2-(3-(Difluoromethoxy)-4-(1-isopropylpiperidin-4-yloxy)phenylamino)-5-fluoropyrimidin-4-ylamino)-2,2,6,6-tetramethylpiperidin-1-yl)ethanone III-5: $N^2$-(3-(1H-tetrazol-1-yl)phenyl)-N4-(1-cyclopropyl-2,6-dimethylpiperidin-4-yl)-5-fluoropyrimidine-2,4-diamine III-6: $N^4$-(1-cyclopropyl-2,6-dimethylpiperidin-4-yl)-5-fluoro-N2-(4-methyl-3-(1H-tetrazol-1-yl)phenyl)pyrimidine-2,4-diamine III-7: $N^4$-(1-cyclopropyl-2,6-dimethylpiperidin-4-yl)-5-fluoro-N2-(3-methoxy-5-(1H-tetrazol-1-yl)phenyl)pyrimidine-2,4-diamine III-8: $N^4$-(1-cyclopropyl-2,6-dimethylpiperidin-4-yl)-5-fluoro-N2-(3-(5-methyl-1H-tetrazol-1-yl)phenyl)pyrimidine-2,4-diamine III-9: $N^4$-(1-cyclopropyl-2,6-dimethylpiperidin-4-yl)-5-fluoro-N2-(3-(5-(2,2,2-trifluoroethylthio)-1H-tetrazol-1-yl)phenyl)pyrimidine-2,4-diamine III-10: $N^4$-(1-cyclopropyl-2,6-dimethylpiperidin-4-yl)-5-fluoro-N2-(3-(5-(methylthio)-1H-tetrazol-1-yl)phenyl)pyrimidine-2,4-diamine III-11: $N^4$-(1-cyclopropyl-2,6-dimethylpiperidin-4-yl)-5-fluoro-$N^2$-(4-fluoro-3-(1H-tetrazol-1-yl)phenyl)pyrimidine-2,4-diamine III-12: 1-(4-(2-fluoro-4-(5-fluoro-4-(1,2,2,6,6-pentamethylpiperidin-4-ylamino)pyrimidin-2-ylamino)phenoxy)piperidin-1-yl)ethanone III-13: 1-(4-(2-fluoro-4-(5-fluoro-4-(2,2,6,6-tetramethylpiperidin-4-ylamino)pyrimidin-2-ylamino)phenoxy)piperidin-1-yl)ethanone III-14: 5-fluoro-N2-(3-fluoro-4-(1-(methylsulfonyl)piperidin-4-yloxy)phenyl)-N4-(1,2,2,6,6-pentamethylpiperidin-4-yl)pyrimidine-2,4-diamine III-15: 5-fluoro-N2-(3-fluoro-4-(1-(methylsulfonyl)piperidin-4-yloxy)phenyl)-N4-(2,2,6,6-tetramethylpiperidin-4-yl)pyrimidine-2,4-diamine III-16: N-ethyl-4-(2-fluoro-4-(5-fluoro-4-(1,2,2,6,6-pentamethylpiperidin-4-ylamino)pyrimidin-2-ylamino)phenoxy)piperidine-1-carboxamide III-17: N-ethyl-4-(2-fluoro-4-(5-fluoro-4-(2,2,6,6-tetramethylpiperidin-4-ylamino)pyrimidin-2-ylamino)phenoxy)piperidine-1-carboxamide III-18: 5-fluoro-N2-(3-fluoro-4-(1-isopropylpiperidin-4-yloxy)phenyl)-N4-(1,2,2,6,6-pentamethylpiperidin-4-yl)pyrimidine-2,4-diamine III-19: 5-fluoro-N2-(3-fluoro-4-(1-isopropylpiperidin-4-yloxy)phenyl)-N4-(2,2,6,6-tetramethylpiperidin-4-yl)pyrimidine-2,4-diamine III-20: N2-(3-(difluoromethoxy)-4-(1-(methylsulfonyl)piperidin-4-yloxy)phenyl)-5-fluoro-N4-(1,2,2,6,6-pentamethylpiperidin-4-yl)pyrimidine-2,4-diamine III-21: N2-(3-(difluoromethoxy)-4-(1-(methylsulfonyl)piperidin-4-yloxy)phenyl)-5-fluoro-N4-(2,2,6,6-tetramethylpiperidin-4-yl)pyrimidine-2,4-diamine III-22: N2-(3-(difluoromethoxy)-4-(tetrahydro-2H-pyran-4-yloxy)phenyl)-5-fluoro-N4-(1,2,2,6,6-pentamethylpiperidin-4-yl)pyrimidine-2,4-diamine III-23: N2-(3-(difluoromethoxy)-4-(tetrahydro-2H-pyran-4-yloxy)phenyl)-5-fluoro-N4-(2,2,6,6-tetramethylpiperidin-4-yl)pyrimidine-2,4-diamine III-24: 5-fluoro-N2-(3-fluoro-4-(tetrahydro-2H-pyran-4-yloxy)phenyl)-N4-(1,2,2,6,6-pentamethylpiperidin-4-yl)pyrimidine-2,4-diamine III-25: N2-(3,5-difluoro-4-(tetrahydro-2H-pyran-4-yloxy)phenyl)-5-fluoro-N4-(1,2,2,6,6-pentamethylpiperidin-4-yl)pyrimidine-2,4-diamine III-26: N2-(3,5-difluoro-4-(tetrahydro-2H-pyran-4-yloxy)phenyl)-5-fluoro-N4-(2,2,6,6-tetramethylpiperidin-4-yl)pyrimidine-2,4-diamine III-27: N2-(3-(difluoromethoxy)-4-(piperidin-4-yloxy)phenyl)-5-fluoro-N4-(1,2,2,6,6-pentamethylpiperidin-4-yl)pyrimidine-2,4-diamine III-28: N2-(3-(difluoromethoxy)-4-(piperidin-4-yloxy)phenyl)-5-fluoro-N4-(2,2,6,6-tetramethylpiperidin-4-yl)pyrimidine-2,4-diamine III-29: N2-[4-(1,1-Dioxo-hexahydro-1λ6-thiopyran-4-yloxy)-3-fluoro-phenyl]-5-fluoro-N4-(1,2,2,6,6-pentamethyl-piperidin-4-yl)-pyrimidine-2,4-diamine III-30: N2-[4-(1,1-Dioxo-hexahydro-1λ6-thiopyran-4-yloxy)-3-fluoro-phenyl]-5-fluoro-N4-(2,2,6,6-tetramethyl-piperidin-4-yl)-pyrimidine-2,4-diamine III-31: N2-[3-Difluoromethoxy-4-(1,1-dioxo-hexahydro-1λ6-thiopyran-4-yloxy)-phenyl]-5-fluoro-N4-(1,2,2,6,6-pentamethyl-piperidin-4-yl)-pyrimidine-2,4-diamine III-32: N2-[3-Difluoromethoxy-4-(1,1-dioxo-hexahydro-1λ6-thiopyran-4-yloxy)-phenyl]-5-fluoro-N4-(2,2,6,6-tetramethyl-piperidin-4-yl)-pyrimidine-2,4-diamine III-33: 2-(4-(2-Fluoro-4-(5-fluoro-4-(1,2,2,6,6-pentamethylpiperidin-4-ylamino)pyrimidin-2-ylamino)phenoxy)piperidin-1-yl)acetamide III-34: 2-(4-(2-Fluoro-4-(5-fluoro-4-(2,2,6,6-tetramethylpiperidin-4-ylamino)pyrimidin-2-ylamino)phenoxy)piperidin-1-yl)acetamide III-35: 2-(4-(2-(Difluoromethoxy)-4-(5-fluoro-4-(1,2,2,6,6-pentamethylpiperidin-4-ylamino)pyrimidin-2-ylamino)phenoxy)piperidin-1-yl)acetamide III-36: 2-(4-(2-(Difluoromethoxy)-4-(5-fluoro-4-(2,2,6,6-tetramethylpiperidin-4-ylamino)pyrimidin-2-ylamino)phenoxy)piperidin-1-yl)acetamide III-37: 2-(4-(2-(Difluoromethoxy)-4-(5-fluoro-4-(1,2,2,6,6-pentamethylpiperidin-4-ylamino)pyrimidin-2-ylamino)phenoxy)piperidin-1-yl)ethanol III-38: 2-(4-(2-(Difluoromethoxy)-4-(5-fluoro-4-(2,2,6,6-tetramethylpiperidin-4-ylamino)pyrimidin-2-ylamino)phenoxy)piperidin-1-yl)ethanol III-39: N2-(3-(Difluoromethoxy)-4-(1-isopropylazetidin-3-yloxy)phenyl)-5-fluoro-N4-(2,2,6,6-tetramethylpiperidin-4-yl)pyrimidine-2,4-diamine III-40: N2-(3-(difluoromethoxy)-4-(1-isopropylazepan-4-yloxy)phenyl)-5-fluoro-N4-(2,2,6,6-tetramethylpiperidin-4-yl)pyrimidine-2,4-diamine III-41: N2-(3-(difluoromethoxy)-4-(1-isopropylazepan-4-yloxy)phenyl)-5-fluoro-N4-(1,2,2,6,6-pentamethylpiperidin-4-yl)pyrimidine-2,4-diamine III-42: 1-(4-(2-(difluoromethoxy)-4-(5-fluoro-4-(2,2,6,6-tetramethylpiperidin-4-ylamino)pyrimidin-2-ylamino)phenoxy)azepan-1-yl)ethanone III-43: 1-(4-(2-(difluoromethoxy)-4-(5-fluoro-4-(1,2,2,6,6-pentamethylpiperidin-4-ylamino)pyrimidin-2-ylamino)phenoxy)azepan-1-yl)ethanone III-44: 1-(4-(2-(difluoromethoxy)-4-(5-fluoro-4-(2,2,6,6-tetramethylpiperidin-4-ylamino)pyrimidin-2-ylamino)phenoxy)piperidin-1-yl)ethanone III-45: 1-(4-(2-(difluoromethoxy)-4-(5-fluoro-4-(1,2,2,6,6-pentamethylpiperidin-4-ylamino)pyrimidin-2-ylamino)phenoxy)piperidin-1-yl)ethanone III-46: 5-fluoro-N2-(3-fluoro-4-(2-methyl-4-(pyrrolidin-1-yl)butan-2-yloxy)phenyl)-N4-(2,2,6,6-tetramethylpiperidin-4-yl)pyrimidine-2,4-diamine III-47: 5-fluoro-N2-(3-fluoro-4-(2-methyl-4-(pyrrolidin-1-yl)butan-2-yloxy)phenyl)-N4-(1,2,2,6,6-pentamethylpiperidin-4-yl)pyrimidine-2,4-diamine III-48: N2-(3,5-difluoro-4-(2-methyl-4-(pyrrolidin-1-yl)butan-2-yloxy)phenyl)-5-fluoro-N4-(2,2,6,6-tetramethylpiperidin-4-yl)pyrimidine-2,4-diamine III-49: N2-(3,5-difluoro-4-(2-methyl-4-(pyrrolidin-1-yl)butan-2-yloxy)phenyl)-5-fluoro-N4-(1,2,2,6,6-pentamethylpiperidin-4-yl)pyrimidine-2,4-diamine III-50: N2-(3-(difluoromethoxy)-4-(1-(2-fluoroethyl)piperidin-4-yloxy)phenyl)-5-fluoro-N4-(2,2,6,6-tetramethylpiperidin-4-yl)pyrimidine-2,4-diamine III-51: N2-(3-(difluoromethoxy)-4-(1-(2-fluoroethyl)piperidin-4-yloxy)phenyl)-5-fluoro-N4-(1,2,2,6,6-pentamethylpiperidin-4-yl)pyrimidine-2,4-diamine III-52: N2-(4-(1-benzylpiperidin-4-yloxy)-3-(difluoromethoxy)phenyl)-5-fluoro-N4-(1,2,2,6,6-pentamethylpiperidin-4-yl)pyrimidine-2,4-diamine III-53: N2-(4-(1-(2-(benzyloxy)ethyl)piperidin-4-yloxy)-3-fluorophenyl)-5-fluoro-N4-(2,2,6,6-tetramethylpiperidin-4-yl)pyrimidine-2,4-diamine III-54: N2-(4-(1-(2-(benzyloxy)ethyl)piperidin-4-yloxy)-3-fluorophenyl)-5-fluoro-N4-(1,2,2,6,6-pentamethylpiperidin-4-yl)pyrimidine-2,4-diamine III-55: N2-(4-(1-(2-(benzyloxy)ethyl)piperidin-4-yloxy)-3,5-difluorophenyl)-5-fluoro-N4-(2,2,6,6-tetramethylpiperidin-4-yl)pyrimidine-2,4-diamine III-56: N2-(4-(1-(2-(benzyloxy)ethyl)piperidin-4-yloxy)-3,5-difluorophenyl)-5-fluoro-N4-(1,2,2,6,6-pentamethylpiperidin-4-yl)pyrimidine-2,4-diamine III-57: 2-(4-(2-fluoro-4-(5-fluoro-4-(2,2,6,6-tetramethylpiperidin-4-ylamino)pyrimidin-2-ylamino)phenoxy)piperidin-1-yl)ethanol III-58: 2-(4-(2-fluoro-4-(5-fluoro-4-(1,2,2,6,6-pentamethylpiperidin-4-ylamino)pyrimidin-2-ylamino)phenoxy)piperidin-1-yl)ethanol III-59: 2-(4-(2,6-difluoro-4-(5-fluoro-4-(2,2,6,6-tetramethylpiperidin-4-ylamino)pyrimidin-2-ylamino)phenoxy)piperidin-1-yl)ethanol III-60: 2-(4-(2,6-difluoro-4-(5-fluoro-4-(1,2,2,6,6-pentamethylpiperidin-4-ylamino)pyrimidin-2-ylamino)phenoxy)piperidin-1-yl)ethanol III-61: 5-fluoro-N2-(4-isopropoxy-3-(isopropylamino)phenyl)-N4-(2,2,6,6-tetramethylpiperidin-4-yl)pyrimidine-2,4-diamine III-62: 5-fluoro-N2-(4-isopropoxy-3-(isopropylamino)phenyl)-N4-(1,2,2,6,6-pentamethylpiperidin-4-yl)pyrimidine-2,4-diamine III-63: 5-fluoro-N2-(4-methyl-3-(1-methyl-1H-tetrazol-5-yl)phenyl)-N4-(2,2,6,6-tetramethylpiperidin-4-yl)pyrimidine-2,4-diamine III-64: 5-fluoro-N2-(4-methyl-3-(1-methyl-1H-tetrazol-5-yl)phenyl)-N4-(1,2,2,6,6-pentamethylpiperidin-4-yl)pyrimidine-2,4-diamine III-65: 5-fluoro-N2-(4-isopropoxy-3-(isopropyl(methyl)amino)phenyl)-N4-(2,2,6,6-tetramethylpiperidin-4-yl)pyrimidine-2,4-diamine III-66: 5-fluoro-N2-(4-isopropoxy-3-(isopropyl(methyl)amino)phenyl)-N4-(1,2,2,6,6-pentamethylpiperidin-4-yl)pyrimidine-2,4-diamine III-67: N2-(4-(difluoromethoxy)-3-(5-ethyl-1H-tetrazol-1-yl)phenyl)-5-fluoro-N4-(2,2,6,6-tetramethylpiperidin-4-yl)pyrimidine-2,4-diamine III-68: N2-(3-(2H-tetrazol-5-yl)phenyl)-5-fluoro-N4-(1,2,2,6,6-pentamethylpiperidin-4-yl)pyrimidine-2,4-diamine III-69: N2-(3-(2H-tetrazol-5-yl)phenyl)-5-fluoro-N4-(2,2,6,6-tetramethylpiperidin-4-yl)pyrimidine-2,4-diamine III-70: 5-fluoro-N2-(3-(1-isopropyl-1H-tetrazol-5-yl)phenyl)-N4-(1,2,2,6,6-pentamethylpiperidin-4-yl)pyrimidine-2,4-diamine III-71: 5-fluoro-N2-(3-(1-isopropyl-1H-tetrazol-5-yl)phenyl)-N4-(2,2,6,6-tetramethylpiperidin-4-yl)pyrimidine-2,4-diamine III-72: N2-(3-(1-cyclopropyl-1H-tetrazol-5-yl)phenyl)-5-fluoro-N4-(1,2,2,6,6-pentamethylpiperidin-4-yl)pyrimidine-2,4-diamine III-73: N2-(3-(1-cyclopropyl-1H-tetrazol-5-yl)phenyl)-5-fluoro-N4-(2,2,6,6-tetramethylpiperidin-4-yl)pyrimidine-2,4-diamine III-74: 5-fluoro-N2-(3-(1-(2-fluoroethyl)-1H-tetrazol-5-yl)phenyl)-N4-(1,2,2,6,6-pentamethylpiperidin-4-yl)pyrimidine-2,4-diamine III-75: 5-fluoro-N2-(3-(1-(2-fluoroethyl)-1H-tetrazol-5-yl)phenyl)-N4-(2,2,6,6-tetramethylpiperidin-4-yl)pyrimidine-2,4-diamine III-76: 5-fluoro-N2-(3-(1-(2-morpholinoethyl)-1H-tetrazol-5-yl)phenyl)-N4-(1,2,2,6,6-pentamethylpiperidin-4-yl)pyrimidine-2,4-diamine III-77: 5-fluoro-N2-(3-(1-(2-morpholinoethyl)-1H-tetrazol-5-yl)phenyl)-N4-(2,2,6,6-tetramethylpiperidin-4-yl)pyrimidine-2,4-diamine III-78: N2-(3,5-difluoro-4-(1-(methylsulfonyl)piperidin-4-yloxy)phenyl)-5-fluoro-N4-(1,2,2,6,6-pentamethylpiperidin-4-yl)pyrimidine-2,4-diamine III-79: N2-(3,5-difluoro-4-(1-(methylsulfonyl)azepan-4-yloxy)phenyl)-5-fluoro-N4-(1,2,2,6,6-pentamethylpiperidin-4-yl)pyrimidine-2,4-diamine III-80: N2-(3,5-difluoro-4-(1-(methylsulfonyl)azepan-4-yloxy)phenyl)-5-fluoro-N4-(2,2,6,6-tetramethylpiperidin-4-yl)pyrimidine-2,4-diamine III-81: 1-(4-(2,6-difluoro-4-(5-fluoro-4-(1,2,2,6,6-pentamethylpiperidin-4-ylamino)pyrimidin-2-ylamino)phenoxy)azepan-1-yl)ethanone III-82: 1-(4-(2,6-difluoro-4-(5-fluoro-4-(2,2,6,6-tetramethylpiperidin-4-ylamino)pyrimidin-2-ylamino)phenoxy)azepan-1-yl)ethanone III-83: 4-(2,6-difluoro-4-(5-fluoro-4-(1,2,2,6,6-pentamethylpiperidin-4-ylamino)pyrimidin-2-ylamino)phenoxy)-N-ethylazepane-1-carboxamide III-84: N2-(3,5-difluoro-4-(1-(methylsulfonyl)piperidin-4-yloxy)phenyl)-5-fluoro-N4-(2,2,6,6-tetramethylpiperidin-4-yl)pyrimidine-2,4-diamine III-85: 4-(2,6-difluoro-4-(5-fluoro-4-(2,2,6,6-tetramethylpiperidin-4-ylamino)pyrimidin-2-ylamino)phenoxy)-N-ethylazepane-1-carboxamide III-86: 4-(2-(difluoromethoxy)-4-(5-fluoro-4-(2,2,6,6-tetramethylpiperidin-4-ylamino)pyrimidin-2-ylamino)phenoxy)-N-ethylpiperidine-1-carboxamide III-87: 4-(2-(difluoromethoxy)-4-(5-fluoro-4-(1,2,2,6,6-pentamethylpiperidin-4-ylamino)pyrimidin-2-ylamino)phenoxy)-N-ethylazepane-1-carboxamide III-88: 4-(2-(difluoromethoxy)-4-(5-fluoro-4-(2,2,6,6-tetramethylpiperidin-4-ylamino)pyrimidin-2-ylamino)phenoxy)-N-ethylazepane-1-carboxamide III-89: N2-(3-(difluoromethoxy)-4-(1-(methylsulfonyl)azepan-4-yloxy)phenyl)-5-fluoro-N4-(1,2,2,6,6-pentamethylpiperidin-4-yl)pyrimidine-2,4-diamine III-90: N2-(3-(difluoromethoxy)-4-(1-(methylsulfonyl)azepan-4-yloxy)phenyl)-5-fluoro-N4-(2,2,6,6-tetramethylpiperidin-4-yl)pyrimidine-2,4-diamine III-91: 1-(4-(2,6-difluoro-4-(5-fluoro-4-(1,2,2,6,6-pentamethylpiperidin-4-ylamino)pyrimidin-2-ylamino)phenoxy)piperidin-1-yl)ethanone III-92: 1-(4-(2,6-difluoro-4-(5-fluoro-4-(2,2,6,6-tetramethylpiperidin-4-ylamino)pyrimidin-2-ylamino)phenoxy)piperidin-1-yl)ethanone III-95: N2-(3-chloro-4-(1-isopropylpiperidin-4-yloxy)phenyl)-5-fluoro-N4-(1,2,2,6,6-pentamethylpiperidin-4-yl)pyrimidine-2,4-diamine III-96: N2-(3-chloro-4-(1-(2-fluoroethyl)piperidin-4-yloxy)phenyl)-5-fluoro-N4-(2,2,6,6-tetramethylpiperidin-4-yl)pyrimidine-2,4-diamine III-97: N2-(3-chloro-4-(1-(2-fluoroethyl)piperidin-4-yloxy)phenyl)-5-fluoro-N4-(1,2,2,6,6-pentamethylpiperidin-4-yl)pyrimidine-2,4-diamine III-98: N2-(3-chloro-4-(1-isopropylpiperidin-4-yloxy)phenyl)-5-fluoro-N4-(2,2,6,6-tetramethylpiperidin-4-yl)pyrimidine-2,4-diamine III-99: (S)—N2-(3-(difluoromethoxy)-4-(tetrahydrofuran-3-yloxy)phenyl)-5-fluoro-N4-(1,2,2,6,6-pentamethylpiperidin-4-yl)pyrimidine-2,4-diamine III-100: (S)—N2-(3-(difluoromethoxy)-4-(tetrahydrofuran-3-yloxy)phenyl)-5-fluoro-N4-(2,2,6,6-tetramethylpiperidin-4-yl)pyrimidine-2,4-diamine III-101: 5-fluoro-N2-(4-(1-isopropylpiperidin-4-yloxy)-3-(trifluoromethyl)phenyl)-N4-(1,2,2,6,6-pentamethylpiperidin-4-yl)pyrimidine-2,4-diamine III-102: 5-fluoro-N2-(4-(1-isopropylpiperidin-4-yloxy)-3-(trifluoromethyl)phenyl)-N4-(2,2,6,6-tetramethylpiperidin-4-yl)pyrimidine-2,4-diamine III-103: N2-(3-(difluoromethoxy)-4-(3-fluoro-1-isopropylpiperidin-4-yloxy)phenyl)-5-fluoro-N4-(1,2,2,6,6-pentamethylpiperidin-4-yl)pyrimidine-2,4-diamine trifluoroacetate salt III-104: N2-(3-(difluoromethoxy)-4-(3-fluoro-1-isopropylpiperidin-4-yloxy)phenyl)-5-fluoro-N4-(2,2,6,6-tetramethylpiperidin-4-yl)pyrimidine-2,4-diamine trifluoroacetate salt III-105: N2-(3-(difluoromethoxy)-4-(3-fluoro-1-isopropylpiperidin-4-yloxy)phenyl)-5-fluoro-N4-(1,2,2,6,6-pentamethylpiperidin-4-yl)pyrimidine-2,4-diamine III-106: N2-(3-(difluoromethoxy)-4-(3-fluoro-1-isopropylpiperidin-4-yloxy)phenyl)-5-fluoro-N4-(2,2,6,6-tetramethylpiperidin-4-yl)pyrimidine-2,4-diamine III-107: N2-(4-(3,3-difluoro-1-isopropylpiperidin-4-yloxy)-3-(difluoromethoxy)phenyl)-5-fluoro-N4-(1,2,2,6,6-pentamethylpiperidin-4-yl)pyrimidine-2,4-diamine III-108: N2-(4-(3,3-difluoro-1-isopropylpiperidin-4-yloxy)-3-(difluoromethoxy)phenyl)-5-fluoro-N4-(2,2,6,6-tetramethylpiperidin-4-yl)pyrimidine-2,4-diamine III-109: 5-fluoro-N2-(3-fluoro-4-(tetrahydro-2H-pyran-4-yloxy)phenyl)-N4-(2,2,6,6-tetramethylpiperidin-4-yl)pyrimidine-2,4-diamine III-110: N2-(3-(difluoromethoxy)-4-(1-isopropylpiperidin-4-yloxy)phenyl)-5-fluoro-N4-(1-trideuteromethyl-2,2,6,6-tetramethylpiperidin-4-yl)pyrimidine-2,4-diamine III-111: N2-(3-(chloro)-4-(1-isopropylpiperidin-4-yloxy)phenyl)-5-fluoro-N4-(1-trideuteromethyl-2,2,6,6-tetramethylpiperidin-4-yl)pyrimidine-2,4-diamine III-112: N2-(3-(difluoromethoxy)-4-(3-fluoro-1-isopropylpiperidin-4-yloxy)phenyl)-5-fluoro-N4-(1-trideuteromethyl-2,2,6,6-tetramethylpiperidin-4-yl)pyrimidine-2,4-diamine III-113: 5-fluoro-N2-(4-methyl-3-(1H-tetrazol-1-yl)phenyl)-N4-(1-trideuteromethyl-2,2,6,6-tetramethylpiperidin-4-yl)pyrimidine-2,4-diamine III-114: 5-fluoro-N2-(3-(1H-tetrazol-1-yl)phenyl)-N4-(1-trideuteromethyl-2,2,6,6-tetramethylpiperidin-4-yl)pyrimidine-2,4-diamine III-115: 5-fluoro-N2-(3-(5-methyl-1H-tetrazol-1-yl)phenyl)-N4-(1-trideuteromethyl-2,2,6,6-tetramethylpiperidin-4-yl)pyrimidine-2,4-diamine III-116: $N^2$-(3-cyclopropyl-5-(1H-tetrazol-1-yl)phenyl)-5-fluoro-$N^4$(2,2,6,6-tetramethylpiperidin-4-yl)pyrimidine-2,4-diamine III-117: $N^2$-(3-cyclopropyl-5-(1H-tetrazol-1-yl)phenyl)-5-fluoro-$N^4$(1,2,2,6,6-pentamethylpiperidin-4-yl)pyrimidine-2,4-diamine III-118: $N^2$-(4-cyclopropyl-3-(1H-tetrazol-1-yl)phenyl)-5-fluoro-$N^4$(2,2,6,6-tetramethylpiperidin-4-yl)pyrimidine-2,4-diamine III-119: $N^2$-(4-cyclopropyl-3-(1H-tetrazol-1-yl)phenyl)-5-fluoro-$N^4$(1,2,2,6,6-pentamethylpiperidin-4-yl)pyrimidine-2,4-diamine III-120: 5-fluoro-N2-(4-fluoro-3-(1-methyl-1H-tetrazol-5-yl)phenyl)-N4-(2,2,6,6-tetramethylpiperidin-4-yl)pyrimidine-2,4-diamine;

III-121: 5-fluoro-N2-(4-fluoro-3-(1-methyl-1H-tetrazol-5-yl)phenyl)-N4-(1,2,2,6,6-pentamethylpiperidin-4-yl)pyrimidine-2,4-diamine III-122: 5-fluoro-N2-(4-isopropoxy-3-(1-methyl-1H-tetrazol-5-yl)phenyl)-N4-(2,2,6,6-tetramethylpiperidin-4-yl)pyrimidine-2,4-diamine III-123: 5-fluoro-N2-(4-isopropoxy-3-(1-methyl-1H-tetrazol-5-yl)phenyl)-N4-(1,2,2,6,6-pentamethylpiperidin-4-yl)pyrimidine-2,4-diamine III-124: 5-fluoro-N2-(3-(1-methyl-1H-tetrazol-5-yl)-4-(tetrahydro-2H-pyran-4-yloxy)phenyl)-N4-(2,2,6,6-tetramethylpiperidin-4-yl)pyrimidine-2,4-diamine III-125: 5-fluoro-N2-(3-(1-methyl-1H-tetrazol-5-yl)-4-(tetrahydro-2H-pyran-4-yloxy)phenyl)-N4-(1,2,2,6,6-pentamethylpiperidin-4-yl)pyrimidine-2,4-diamine III-126: 5-fluoro-N2-(3-(1-methyl-1H-tetrazol-5-yl)-4-(oxetan-3-yloxy)phenyl)-N4-(2,2,6,6-tetramethylpiperidin-4-yl)pyrimidine-2,4-diamine III-127: 5-fluoro-N2-(3-(1-methyl-1H-tetrazol-5-yl)-4-(oxetan-3-yloxy)phenyl)-N4-(1,2,2,6,6-pentamethylpiperidin-4-yl)pyrimidine-2,4-diamine III-128: 5-fluoro-N2-(4-fluoro-3-(1-(2-methoxyethyl)-1H-tetrazol-5-yl)phenyl)-N4-(1,2,2,6,6-pentamethylpiperidin-4-yl)pyrimidine-2,4-diamine III-129: 5-fluoro-N2-(4-fluoro-3-(1-(2-methoxyethyl)-1H-tetrazol-5-yl)phenyl)-N4-(2,2,6,6-tetramethylpiperidin-4-yl)pyrimidine-2,4-diamine III-130: N2-(4-chloro-3-(1-methyl-1H-tetrazol-5-yl)phenyl)-5-fluoro-N4-(2,2,6,6-tetramethylpiperidin-4-yl)pyrimidine-2,4-diamine III-131: N2-(4-chloro-3-(1-methyl-1H-tetrazol-5-yl)phenyl)-5-fluoro-N4-(1,2,2,6,6-pentamethylpiperidin-4-yl)pyrimidine-2,4-diamine III-132: 5-fluoro-N2-(3-methyl-5-(1-methyl-1H-tetrazol-5-yl)phenyl)-N4-(2,2,6,6-tetramethylpiperidin-4-yl)pyrimidine-2,4-diamine III-133: 5-fluoro-N2-(3-methyl-5-(1-methyl-1H-tetrazol-5-yl)phenyl)-N4-(1,2,2,6,6-pentamethylpiperidin-4-yl)pyrimidine-2,4-diamine III-134: N2-(3-chloro-5-(1-methyl-1H-tetrazol-5-yl)phenyl)-5-fluoro-N4-(2,2,6,6-tetramethylpiperidin-4-yl)pyrimidine-2,4-diamine III-135: N2-(3-chloro-5-(1-methyl-1H-tetrazol-5-yl)phenyl)-5-fluoro-N4-(1,2,2,6,6-pentamethylpiperidin-4-yl)pyrimidine-2,4-diamine III-136: N2-(3,4-difluoro-5-(1-methyl-1H-tetrazol-5-yl)phenyl)-5-fluoro-N4-(2,2,6,6-tetramethylpiperidin-4-yl)pyrimidine-2,4-diamine III-137: N2-(3,4-difluoro-5-(1-methyl-1H-tetrazol-5-yl)phenyl)-5-fluoro-N4-(1,2,2,6,6-pentamethylpiperidin-4-yl)pyrimidine-2,4-diamine III-138: 5-fluoro-N2-(3-fluoro-5-(1-methyl-1H-tetrazol-5-yl)phenyl)-N4-(2,2,6,6-tetramethylpiperidin-4-yl)pyrimidine-2,4-diamine III-139: 5-fluoro-N2-(3-fluoro-5-(1-methyl-1H-tetrazol-5-yl)phenyl)-N4-(1,2,2,6,6-pentamethylpiperidin-4-yl)pyrimidine-2,4-diamine III-140: 5-fluoro-N2-(3-(1-methyl-1H-tetrazol-5-yl)-5-(trifluoromethyl)phenyl)-N4-(2,2,6,6-tetramethylpiperidin-4-yl)pyrimidine-2,4-diamine III-141: 5-fluoro-N2-(3-(1-methyl-1H-tetrazol-5-yl)-5-(trifluoromethyl)phenyl)-N4-(1,2,2,6,6-pentamethylpiperidin-4-yl)pyrimidine-2,4-diamine III-142: 5-fluoro-N2-(3-fluoro-4-isopropoxy-5-(1-methyl-1H-tetrazol-5-yl)phenyl)-N4-(2,2,6,6-tetramethylpiperidin-4-yl)pyrimidine-2,4-diamine III-143: 3-(5-fluoro-4-(2,2,6,6-tetramethylpiperidin-4-ylamino)pyrimidin-2-ylamino)-5-(1-methyl-1H-tetrazol-5-yl)benzonitrile III-144: 3-(5-fluoro-4-(1,2,2,6,6-pentamethylpiperidin-4-ylamino)pyrimidin-2-ylamino)-5-(1-methyl-1H-tetrazol-5-yl)benzonitrile III-145: 5-fluoro-N2-(3-(1-methyl-1H-tetrazol-5-yl)-5-(oxetan-3-yloxy)phenyl)-N4-(2,2,6,6-tetramethylpiperidin-4-yl)pyrimidine-2,4-diamine III-146: 5-fluoro-N2-(3-(1-methyl-1H-tetrazol-5-yl)-5-(oxetan-3-yloxy)phenyl)-N4-(1,2,2,6,6-pentamethylpiperidin-4-yl)pyrimidine-2,4-diamine III-147: N2-(3-cyclopropyl-5-(1-methyl-1H-tetrazol-5-yl)phenyl)-5-fluoro-N4-(2,2,6,6-tetramethylpiperidin-4-yl)pyrimidine-2,4-diamine III-148: N2-(4-cyclopropyl-3-(1-methyl-1H-tetrazol-5-yl)phenyl)-5-fluoro-N4-(2,2,6,6-tetramethylpiperidin-4-yl)pyrimidine-2,4-diamine or a solvate, prodrug, or a pharmaceutically acceptable salt thereof.

Particular compounds of interest, and salts or solvates or stereoisomers thereof, include:

I-67: 5-aminocarbonyl-N2-[4-fluoro-3-(1H-tetrazol-1-yl)]phenyl-N4-(2,2,6,6-tetramethylpiperidin-4-yl)-2,4-pyrimidinediamine I-68: 5-aminocarbonyl-N2-[4-ethoxy-3-(5-ethyl-1H-tetrazol-1-yl)]phenyl-N4-(2,2,6,6-tetramethylpiperidin-4-yl)-2,4-pyrimidinediamine I-74: 5-fluoro-N2-[4-methoxy-3-(5-propyl-1H-tetrazol-1-yl)]phenyl-N4-(2,2,6,6-tetramethylpiperidin-4-yl)-2,4-pyrimidinediamine I-77: 5-cyano-N2-[4-fluoro-3-(1H-tetrazol-1-yl)]phenyl-N4-(2,2,6,6-tetramethylpiperidin-4-yl)-2,4-pyrimidinediamine I-93: N2-[3-(2,5-Dimethyl-pyrrol-1-yl)-4-methoxy]phenyl-5-fluoro-N4-(2,2,6,6-tetramethylpiperidin-4-yl)-2,4-pyrimidinediamine I-111: N2-(3,5-Dimethoxyphenyl)-5-fluoro-N4-(1-N-oxide-2,2,6,6-pentamethylpiperidin-4-yl)-2,4-pyrimidinediamine II-9: N2-[2,2-Dimethyl-4-(2-fluoroethyl)-1,4-benzoxazin-3-one-7-yl]-5-fluoro-N4-(2,2,6,6-tetramethylpiperidin-4-yl)-2,4-pyrimidinediamine II-10: N2-(3,4-Ethylenedioxy)phenyl-5-fluoro-N4-(2,2,6,6-tetramethylpiperidin-4-yl)-2,4-pyrimidinediamine or a solvate, prodrug, or a pharmaceutically acceptable salt thereof.

The compounds described also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present disclosure.

The present disclosure also provides pharmaceutical compositions comprising a pharmaceutically acceptable carrier and a therapeutically effective amount of a compound of formulae I-XIII or a pharmaceutically acceptable salt or solvate or stereoisomer thereof.

A disclosed compound can be administered alone, as the sole active pharmaceutical agent, or in combination with one or more additional compounds of formulae I-XIII or in conjunction with other agents. When administered as a combination, the therapeutic agents can be formulated as separate compositions that are administered simultaneously or at different times, or the therapeutic agents can be administered together as a single composition combining two or more therapeutic agents. Thus, the pharmaceutical compositions disclosed herein containing a compound of formulae I-XIII optionally contain other therapeutic agents. Accordingly, certain embodiments are directed to such pharmaceutical composition, wherein the composition further comprises a therapeutically effective amount of an agent selected as is known to those of skill in the art.

The subject compounds can inhibit a protein kinase C activity. Accordingly, the compounds are useful for treating a disease or disorder that is mediated through the activity of a PKC activity in a subject. Also, the compounds are useful for treating a disease or disorder that is associated with the activation of T-cells in a subject.

The present disclosure provides a method of treating an inflammatory disease in a subject, the method comprising administering to the subject with a compound of formulae I-XIII or a salt or solvate or stereoisomer thereof.

The present disclosure also provides a method of treating an autoimmune disease in a subject, the method comprising administering to the subject with a compound of formulae I-XIII or a salt or solvate or stereoisomer thereof.

The present disclosure also provides a method of treating an ocular disease or disorder involving inflammatory and/or neovascular events.

The present disclosure also provides a method of treating diseases or conditions of interest including, but are not limited to, atherosclerosis, vascular occlusion due to vascular injury, angioplasty, restenosis, obesity, syndrome X, impaired glucose tolerance, polycystic ovary syndrome, hypertension, heart failure, chronic obstructive pulmonary disease, CNS diseases, Alzheimer disease, amyotrophic lateral sclerosis, cancer, infectious disease, AIDS, septic shock, adult respiratory distress syndrome, ischemia/reperfusion injury, myocardial infarction, stroke, gut ischemia, renal failure, hemorrhage shock, and traumatic shock, and traumatic brain injury.

The present disclosure also provides a method of treating diseases or conditions of interest including, but are not limited to, T-cell mediated acute or chronic inflammatory diseases or disorders or autoimmune diseases, rheumatoid arthritis, osteoarthritis, systemic lupus erythematosus, Hashimoto's thyroidis, multiple sclerosis, myasthenia gravis, diabetes type I or II and the disorders associated therewith, transplant rejection, graft versus host disease, respiratory diseases, asthma, inflammatory lung injury, inflammatory liver injury, inflammatory glomerular injury, cutaneous manifestations of immunologically-mediated disorders or illnesses, inflammatory and hyperproliferative skin diseases, psoriasis, atopic dermatitis, allergic contact dermatitis, irritant contact dermatitis and further eczematous dermatitises, seborrhoeic dermatitis, inflammatory eye diseases, Sjoegren's syndrome, keratoconjunctivitis, uveitis, inflammatory bowel disease, Crohn's disease or ulcerative colitis, Guillain-Barre syndrome, and allergies.

The subject compounds can be used for treating a cell proliferative disorder. The present disclosure also provides a method of treating diseases or conditions of interest including, but are not limited to, hematopoietic neoplasm, lymphoid neoplasm, T cell neoplasm, T lymphoblastic leukemia, B cell neoplasm, B-lymphoblastic leukemia, Burkitt's lymphoma, myeloid neoplasm, myeloproferative disease, chronic myelogenous leukemia (CML), myelodysplastic disease, chronic myelomonocytic leukemia, myelodysplastic syndrome, and acute myeloid leukemia.

Since subject compounds possess PKC inhibitory properties, such compounds are also useful as research tools. Accordingly, the disclosure also provides for a method for using a compound of formulae I-XIII or a salt or solvate or stereoisomer thereof as a research tool for studying a biological system or sample, or for discovering new chemical compounds having PKC inhibitory properties.

The embodiments are also directed to processes and novel intermediates useful for preparing compounds of formulae I-XIII or a salt or solvate or stereoisomer thereof.

In one embodiment, the above process further comprises the step of forming a salt of a compound of formulae I-XIII. Embodiments are directed to the other processes described herein; and to the product prepared by any of the processes described herein.

The embodiments are also directed to a compound of formulae I-XIII or a salt or solvate or stereoisomer thereof, for use in therapy or as a medicament.

Additionally, the embodiments are directed to the use of a compound of formulae I-XIII or a salt or solvate or stereoisomer thereof, for the manufacture of a medicament; especially for the manufacture of a medicament for the inhibition of protein kinase C (PKC) activity. The embodiments are also directed to the use of a compound of formulae I-XIII or a salt or solvate or stereoisomer thereof for the manufacture of a medicament for the treatment of a disease or disorder mediated or sustained through the activity of PKC activity. The embodiments are also directed to the use of a compound of formulae I-XIII or a salt or solvate or stereoisomer thereof for the manufacture of a medicament for the treatment of a disease or disorder associated with the activation of T-cells. Diseases or conditions of interest include, but are not limited to, an inflammatory disease, an immunological disorder, an autoimmune disease, an ocular disease or disorder involving inflammatory and/or neovascular events, organ and bone marrow transplant rejection, acute or chronic inflammation, allergies, contact dermatitis, psoriasis, rheumatoid arthritis, multiple sclerosis, type I diabetes, type II diabetes, inflammatory bowel disease, Guillain-Barre syndrome, Crohn's disease, ulcerative colitis, graft versus host disease, and lupus erythematosus.

The embodiments are also directed to the use of a compound of formulae I-XIII or a salt or solvate or stereoisomer thereof for the manufacture of a medicament for the treatment of a cell proliferative disorder. Diseases or conditions of interest include, but are not limited to, hematopoietic neoplasm, lymphoid neoplasm, T cell neoplasm, T lymphoblastic leukemia, B cell neoplasm, B-lymphoblastic leukemia, Burkitt's lymphoma, myeloid neoplasm, myeloproferative disease, chronic myelogenous leukemia (CML), myelodysplastic disease, chronic myelomonocytic leukemia, myelodysplastic syndrome, acute myeloid leukemia.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. Suitable exemplary methods that can be routinely adapted to synthesize the 2,4-pyrimidinediamine compounds and prodrugs of the invention are found in U.S. Pat. No. 5,958,935, the disclosure of which is incorporated herein by reference. Specific examples describing the synthesis of numerous 2,4-pyrimidinediamine compounds and prodrugs, as well as intermediates therefore, are described in the U.S. publication No. US2004/0029902A1, the contents of which are incorporated herein by reference. Suitable exemplary methods that can be routinely used and/or adapted to synthesize active 2,4-pyrimidinediamine compounds can also be found in WO 03/063794, U.S. application Ser. No. 10/631,029 filed Jul. 29, 2003, WO2004/014382, U.S. publication No. 2005-0234049 A1, and WO005/016893, the disclosures of which are incorporated herein by reference. All of the compounds described herein (including prodrugs) can be prepared by routine adaptation of these methods.

Exemplary synthetic methods for the 2,4-substituted pyrimidinediamines described herein are described below. Those of skill in the art will also be able to readily adapt these methods for the synthesis of specific 2,4-substituted pyrimidinediamines as described herein.

A variety of exemplary synthetic routes that can be used to synthesize the 2,4-pyrimidinediamine compounds of the invention are described in schemes below. These methods can be routinely adapted to synthesize the 2,4-pyrimidinediamine compounds and prodrugs described herein.

Synthesis of Formulae I-V

In a certain embodiment, the compounds can be synthesized from substituted or unsubstituted uracils as illustrated in Scheme 1, below:

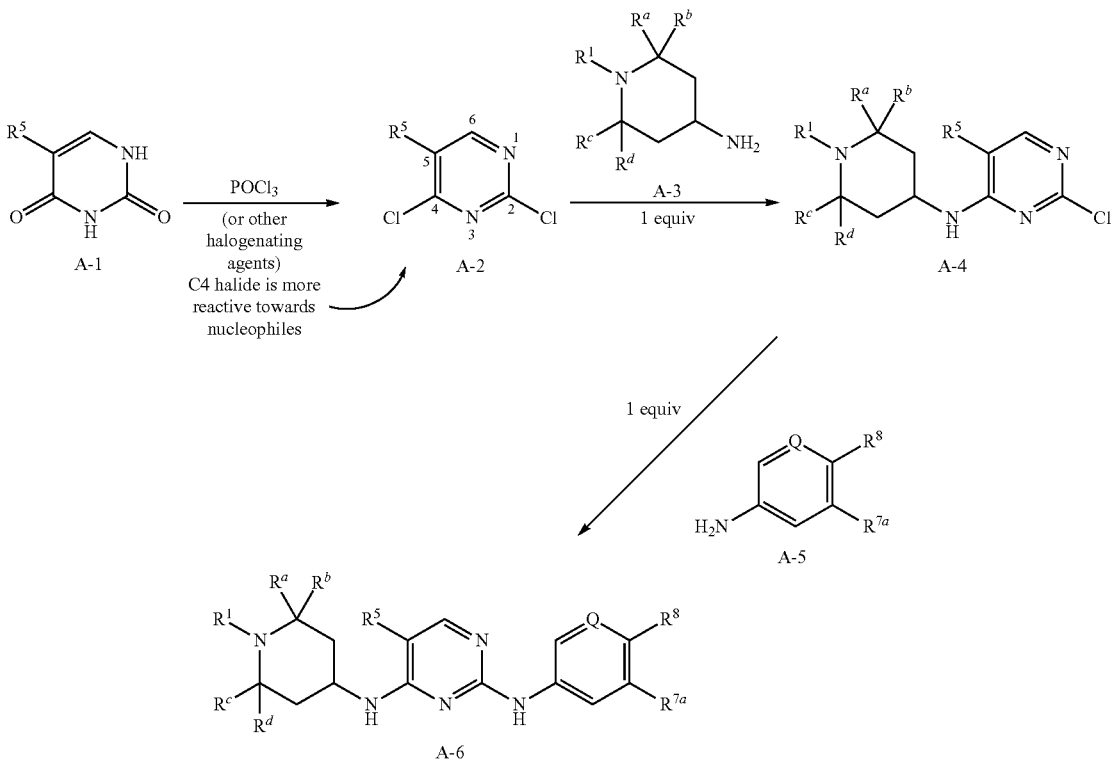

In Scheme 1, $R^1$, $R^a$, $R^b$, $R^c$, $R^d$, $R^5$, $R^8$, $R^{7a}$, and Q are as set forth hereinbefore.

According to Scheme 1, uracil A-1 is dihalogenated at the 2- and 4-positions using a standard dehydrating-halogenating agent such as POCl$_3$ (phosphorus oxychloride) (or other standard halogenating agent) under standard conditions to yield 2,4 dichloropyrimidine A-2. Depending upon the substituents in pyrimidinediamine A-2, the chloride at the C4 position is more reactive towards nucleophiles than the chloride at the C2 position. This differential reactivity can be exploited by first reacting 2,4 dichloropyrimidine A-2 with one equivalent of amine A-3, yielding 4N-substituted-2-chloro-4-pyrimidineamine A-4, followed by amine A-5 to yield a 2,4-pyrimidinediamine derivative A-6.

Typically, the C4 halide is more reactive towards nucleophiles, as illustrated in the scheme. However, as will be recognized by skilled artisans, the identity of the substituent may alter this reactivity. For example, when the substituent is trifluoromethyl, a 50:50 mixture of 4N-substituted-4-pyrimidineamine A-4 and the corresponding 2N-substituted-2-pyrimidineamine is obtained. The regioselectivity of the reaction can also be controlled by adjusting the solvent and other synthetic conditions (such as temperature), as is well-known in the art.

In a certain embodiment, to couple compounds with an electrophilic leaving group, such as halides or pseudohalides, and compounds with an amino group, nucleophilic aromatic substitution can be used. For example, a halogen substituent on Compound A-2 and the amino group on Compound A-3 can react. Also for example, a halogen substituent on Compound A-4 and the amino group on Compound A-5 can react. Conditions for nucleophilic aromatic substitution include the compounds reacting in a polar aprotic solvent or polar protic solvent. Suitable solvents include alcohols (such as isopropanol, methanol, ethanol), formic acid, dimethylsulfoxide, dimethylformamide, dioxane, and tetrahydrofuran. The reaction can be run at room temperature or can be heated.

In a certain embodiment, to couple compounds with an electrophilic leaving group, such as halides or pseudohalides, and aryl compounds with an amino group, a coupling reaction, such as a Buchwald coupling reaction, can be used. The Buchwald coupling reaction involves palladium-catalyzed synthesis of aryl amines. Starting materials are aryl halides or pseudohalides (for example, triflates) and primary or secondary amines. Such reaction can be performed using a variety of methods well known in the art and specific examples can be had by reference to the Examples hereunder described.

The reactions depicted in Scheme 1 may proceed more quickly when the reaction mixtures are heated via microwave. When heating in this fashion, the following conditions can be used: heat to 175° C. in ethanol for 5-20 min. in a Smith Reactor (Personal Chemistry, Uppsala, Sweden) in a sealed tube (at 20 bar pressure).

A specific embodiment of Scheme 1 utilizing 5-fluorouracil (Aldrich #32, 937-1) as a starting material is illustrated in Scheme 2, below.

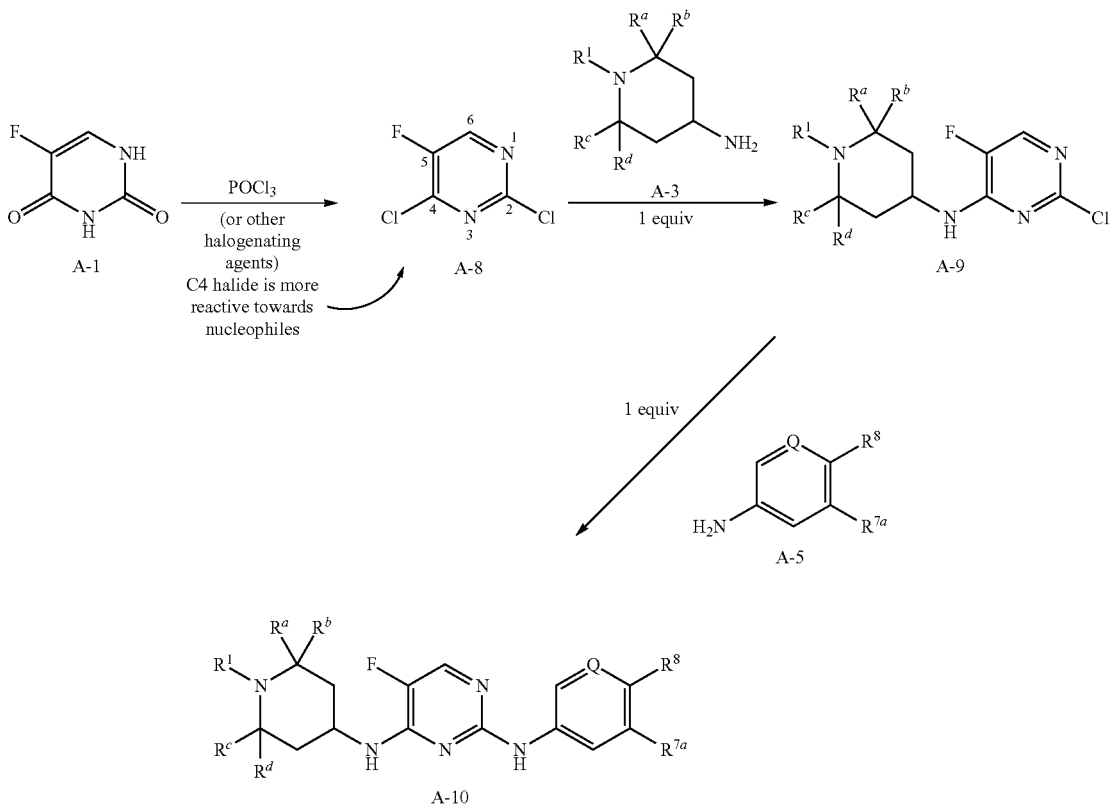

Scheme 2

In Scheme 2, $R^1$, $R^a$, $R^b$, $R^c$, $R^d$, $R^8$, $R^{7a}$, and Q are as set forth hereinbefore.

Asymmetric 2N,4N-disubstituted-5-fluoro-2,4-pyrimidinediamine A-10 can be obtained by reacting 2,4-dichloro-5-fluoropyrimidine A-8 with one equivalent of amine A-3 (to yield 2-chloro-N4-substituted-5-fluoro-4-pyrimidineamine A-9) followed by one or more equivalents of amine A-5.

Synthesis of Formulae VI-XIII

In a certain embodiment, the compounds can be synthesized from substituted or unsubstituted uracils as illustrated in Scheme 3, below:

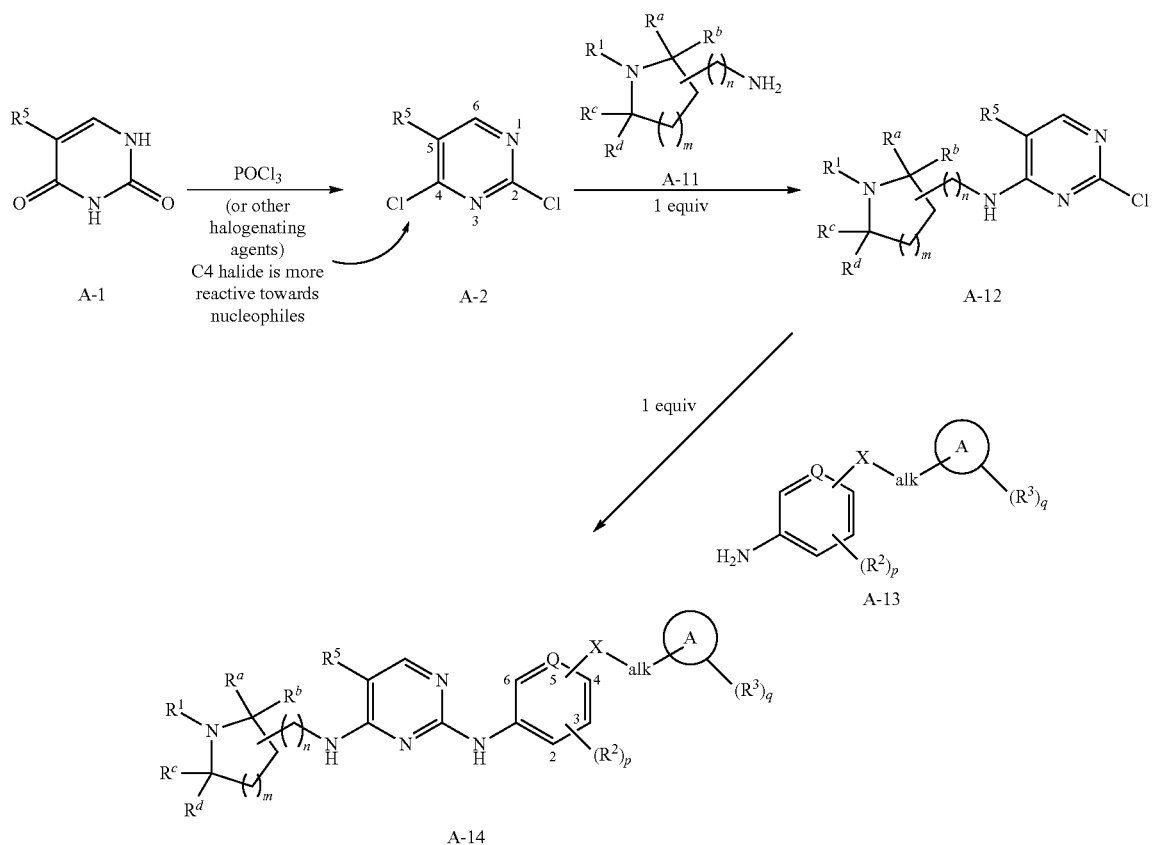

In Scheme 3, $R^1$, $R^a$, $R^b$, $R^c$, $R^d$, $R^2$, $R^3$, $R^5$, A, Q, X, m, n, p, q and alk are as set forth hereinbefore.

Similar to Scheme 1, according to Scheme 3, uracil A-1 is dihalogenated at the 2- and 4-positions using a standard dehydrating-halogenating agent such as $POCl_3$ (phosphorus oxychloride) (or other standard halogenating agent) under standard conditions to yield 2,4 dichloropyrimidine A-2. Depending upon the substituents in pyrimidinediamine A-2, the chloride at the C4 position is more reactive towards nucleophiles than the chloride at the C2 position. This differential reactivity can be exploited by first reacting 2,4 dichloropyrimidine A-2 with one equivalent of amine A-11, yielding 4N-substituted-2-chloro-4-pyrimidineamine A-12, followed by amine A-13 to yield a 2,4-pyrimidinediamine derivative A-14.

Typically, the C4 halide is more reactive towards nucleophiles, as illustrated in the scheme. However, as will be recognized by skilled artisans, the identity of the substituent may alter this reactivity. For example, when the substituent is trifluoromethyl, a 50:50 mixture of 4N-substituted-4-pyrimidineamine A-4 and the corresponding 2N-substituted-2-pyrimidineamine is obtained. The regioselectivity of the reaction can also be controlled by adjusting the solvent and other synthetic conditions (such as temperature), as is well-known in the art.

In a certain embodiment, to couple compounds with an electrophilic leaving group, such as halides or pseudohalides, and compounds with an amino group, nucleophilic aromatic substitution can be used. For example, a halogen substituent on Compound A-2 and the amino group on Compound A-11 can react. Also for example, a halogen substituent on Compound A-12 and the amino group on Compound A-13 can react. Conditions for nucleophilic aromatic substitution include the compounds reacting in a polar aprotic solvent or polar protic solvent. Suitable solvents include alcohols (such as isopropanol, methanol, ethanol), formic acid, dimethylsulfoxide, dimethylformamide, dioxane, and tetrahydrofuran. The reaction can be run at room temperature or can be heated.

In a certain embodiment, to couple compounds with an electrophilic leaving group, such as halides or pseudohalides, and aryl compounds with an amino group, a coupling reaction, such as a Buchwald coupling reaction, can be used. The Buchwald coupling reaction involves palladium-catalyzed synthesis of aryl amines. Starting materials are aryl halides or pseudohalides (for example, triflates) and primary or secondary amines. Such reaction can be performed using a variety of methods well known in the art and specific examples can be had by reference to the Examples hereunder described.

The reactions depicted in Scheme 3 may proceed more quickly when the reaction mixtures are heated via microwave. When heating in this fashion, the following conditions can be used: heat to 175° C. in ethanol for 5-20 min. in a Smith Reactor (Personal Chemistry, Uppsala, Sweden) in a sealed tube (at 20 bar pressure).

A specific embodiment of Scheme 3 utilizing 5-fluorouracil (Aldrich #32, 937-1) as a starting material is illustrated in Scheme 4, below.

Scheme 4

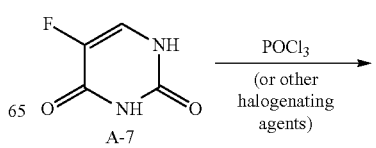

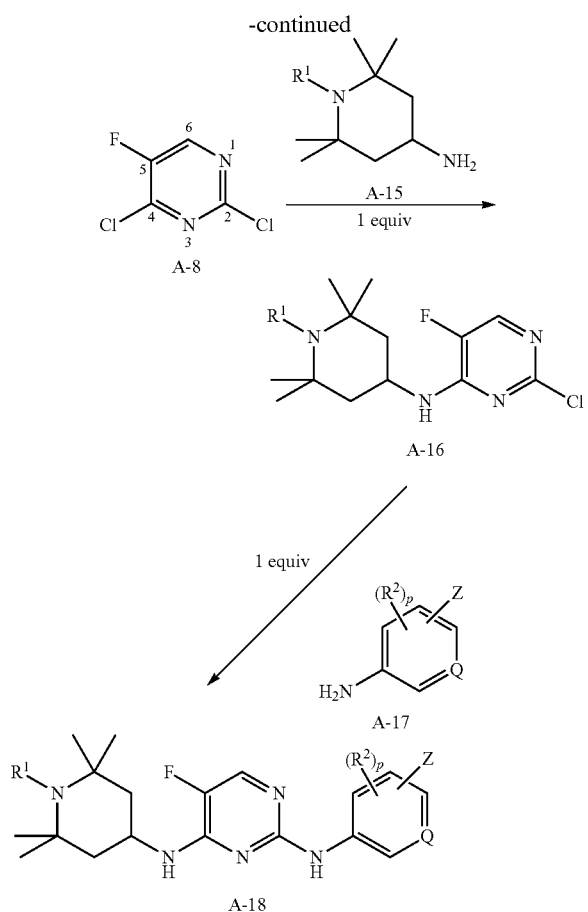

In Scheme 4, Z represents —X-alk-A-$(R^3)_q$, $R^1$, $(R^2)_p$, $(R^3)_q$, A, Q, X, p, and alk are as previously defined.

Asymmetric 2N,4N-disubstituted-5-fluoro-2,4-pyrimidinediamine A-18 can be obtained by reacting 2,4-dichloro-5-fluoropyrimidine A-8 with one equivalent of amine A-15 (to yield 2-chloro-N4-substituted-5-fluoro-4-pyrimidineamine A-16) followed by one or more equivalents of amine A-17.

Skilled artisans will recognize that in some instances, the compounds in the schemes disclosed herein may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts, *Protective Groups in Organic Synthesis,* 3d Edition, John Wiley & Sons, Inc., New York (1999) and the references cited therein (hereinafter "Greene & Wuts").

Thus, protecting group refers to a group of atoms that, when attached to a reactive functional group in a molecule, mask, reduce or prevent the reactivity of the functional group. Typically, a protecting group can be selectively removed as desired during the course of a synthesis. Examples of protecting groups can be found in Greene and Wuts, as mentioned above, and additionally, in Harrison et al., Compendium of Synthetic Organic Methods, Vols. 1-8, 1971 1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl ethanesulfonyl ("TES"), trityl and substituted trityl groups, allyloxycarbonyl, 9-fluorenylmethyloxycarbonyl ("FMOC"), nitro veratryloxycarbonyl ("NVOC") and the like. Representative hydroxyl protecting groups include, but are not limited to, those where the hydroxyl group is either acylated to form acetate and benzoate esters or alkylated to form benzyl and trityl ethers, as well as alkyl ethers, tetrahydropyranyl ethers, trialkylsilyl ethers (e.g., TMS or TIPPS groups) and allyl ethers.

Uracil Starting Materials and Intermediates

The uracil A-1 and A-7 starting materials can be purchased from commercial sources or prepared using standard techniques of organic chemistry. Commercially available uracils that can be used as starting materials in the schemes disclosed herein include, by way of example and not limitation, uracil (Aldrich #13, 078-8; CAS Registry 66-22-8); 5 bromouracil (Aldrich #85, 247-3; CAS Registry 51-20-7; 5 fluorouracil (Aldrich #85, 847-1; CAS Registry 51-21-8); 5 iodouracil (Aldrich #85, 785-8; CAS Registry 696-07-1); 5 nitrouracil (Aldrich #85, 276-7; CAS Registry 611-08-5); 5 (trifluoromethyl)-uracil (Aldrich #22, 327-1; CAS Registry 54-20-6). Additional 5-substituted uracils are available from General Intermediates of Canada, Inc., Edmonton, Calif. and/or Interchim, Cedex, France, or can be prepared using standard techniques. Myriad textbook references teaching suitable synthetic methods are provided infra.

Amino Starting Materials and Intermediates

Amines, such as A-3, A-5, A-11, A-13, A-15, and A-17, can be purchased from commercial sources or, alternatively, can be synthesized utilizing standard techniques. For example, suitable amines can be synthesized from nitro precursors using standard chemistry. See also Vogel, 1989, Practical Organic Chemistry, Addison Wesley Longman, Ltd. and John Wiley & Sons, Inc. By way of example and without limitation reduction of the nitro group to produce amine A-17 can be accomplished via catalytic hydrogenation using palladium on carbon or another suitable noble metal catalyst. Other nitro reduction techniques suitable for the synthesis of A-17 and other amines include the use of iron or tin (II) chloride in acidic media.

In particular, in Scheme 3, when m is two, p is zero, $R^a$ and $R^c$ are methyl and $R^b$ and $R^d$ are hydrogen A-11 is prepared as is known to those of skill in the art and according to the procedures provided by Langlois et al. *Eur. J. Med. Chem.* 1993, 28, 869-880.

With continued reference to structure A-11 in Scheme 3, when m is 1, this structure has a chiral center. Such amines are used in the synthesis of the present compounds in both racemic and optically active forms. Such optically active amines A-11 were prepared as illustrated in Scheme 5 and may be incorporated in to the present compounds according to the procedure illustrated in Scheme 3.

Scheme 5

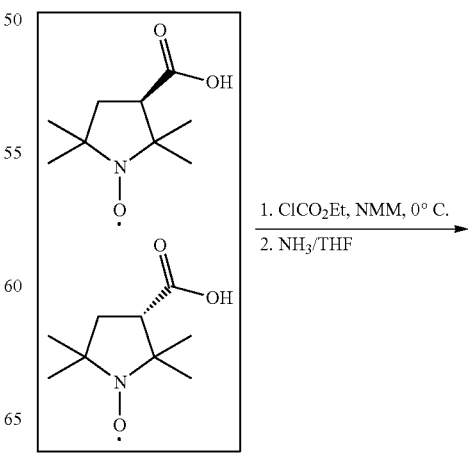

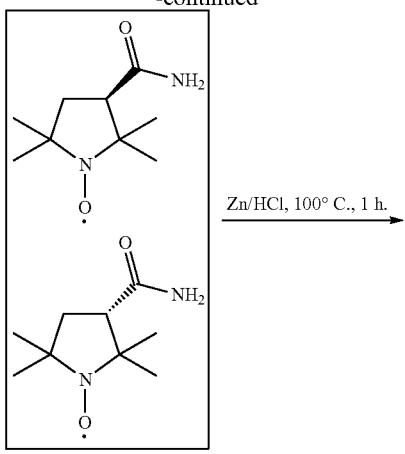
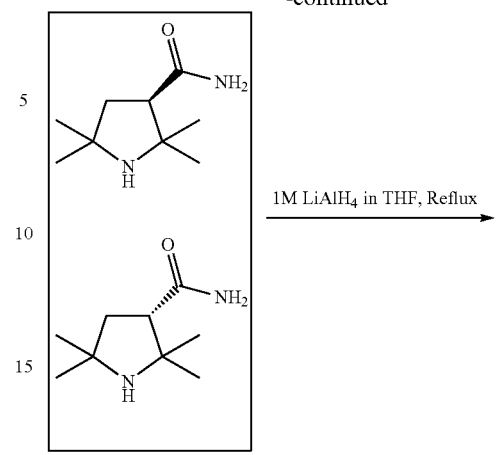
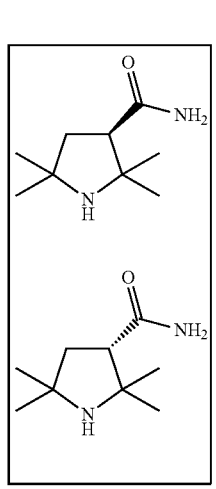
Synthesis of Compounds with Tetrazole Substituent
A specific embodiment of a synthetic scheme to produce a compound comprising a tetrazole substituent is illustrated in Schemes 6 and 7, below:
Scheme 6
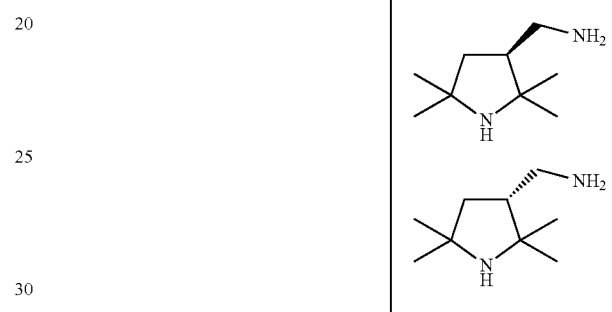
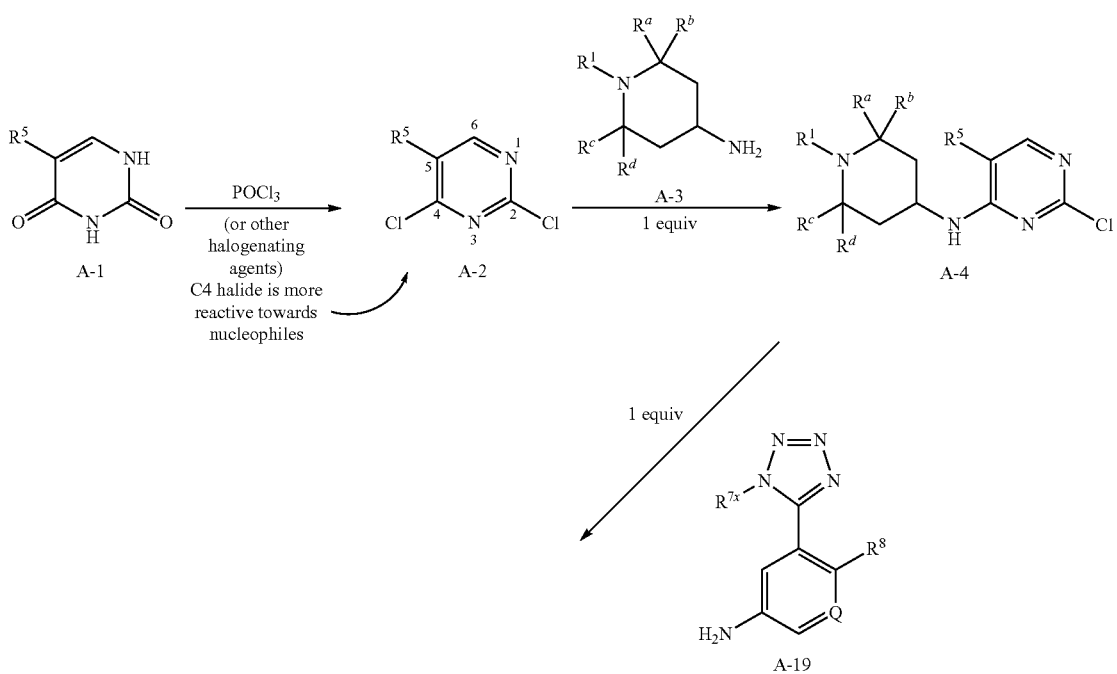

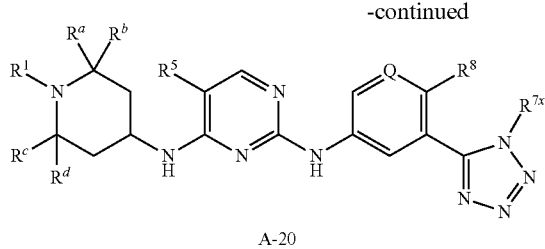

A-20

In Scheme 6, $R^1$, $R^a$, $R^b$, $R^c$, $R^d$, $R^5$, $R^8$, Q, and $R^{7x}$ are as previously defined. Compound A-20 can be obtained by reacting Compound A-2 with one equivalent of Compound A-3 (to yield Compound A-4) followed by one or more equivalents of Compound A-19.

In a certain embodiment, to couple compounds with an electrophilic leaving group, such as halides or pseudohalides, and compounds with an amino group, nucleophilic aromatic substitution can be used. For example, a halogen substituent on Compound A-2 and the amino group on Compound A-3 can react. Also for example, a halogen substituent on Compound A-4 and the amino group on Compound A-19 can react. Conditions for nucleophilic aromatic substitution include the compounds reacting in a polar aprotic solvent or polar protic solvent. Suitable solvents include alcohols (such as isopropanol, methanol, ethanol), formic acid, dimethylsulfoxide, dimethylformamide, dioxane, and tetrahydrofuran. The reaction can be run at room temperature or can be heated.

In a certain embodiment, to couple compounds with an electrophilic leaving group, such as halides or pseudohalides, and aryl compounds with an amino group, a coupling reaction, such as a Buchwald coupling reaction, can be used. The Buchwald coupling reaction involves palladium-catalyzed synthesis of aryl amines. Starting materials are aryl halides or pseudohalides (for example, triflates) and primary or secondary amines. Such reaction can be performed using a variety of methods well known in the art and specific examples can be had by reference to the Examples hereunder described.

Scheme 7

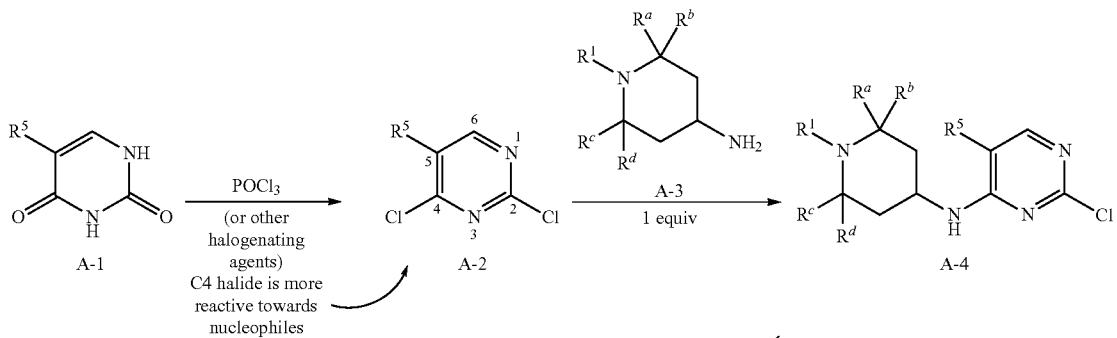

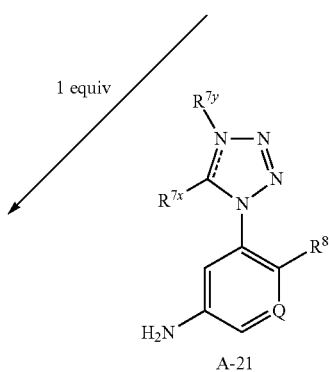

A-21

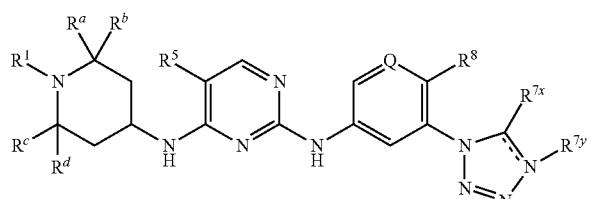

A-22

In Scheme 7, $R^1$, $R^a$, $R^b$, $R^c$, $R^d$, $R^5$, $R^8$, Q, $R^{7x}$, and $R^{7y}$ are as previously defined. Compound A-22 can be obtained by reacting Compound A-2 with one equivalent of Compound A-3 (to yield Compound A-4) followed by one or more equivalents of Compound A-21.

In a certain embodiment, to couple compounds with an electrophilic leaving group, such as a halide or a pseudohalide, and compounds with an amino group, nucleophilic aromatic substitution can be used. For example, a halogen substituent on Compound A-2 and the amino group on Compound A-3 can react. Also for example, a halogen substituent on Compound A-4 and the amino group on Compound A-21 can react. Conditions for nucleophilic aromatic substitution include the compounds reacting in a polar aprotic solvent or polar protic solvent. Suitable solvents include alcohols (such as isopropanol, methanol, ethanol), formic acid, dimethylsulfoxide, dimethylformamide, dioxane, and tetrahydrofuran. The reaction can be run at room temperature or can be heated.

In a certain embodiment, to couple compounds with an electrophilic leaving group, such as halides or pseudohalides, and aryl compounds with an amino group, a coupling reaction, such as a Buchwald coupling reaction, can be used. The Buchwald coupling reaction involves palladium-catalyzed synthesis of aryl amines. Starting materials are aryl halides or pseudohalides (for example, triflates) and primary or secondary amines. Such reaction can be performed using a variety of methods well known in the art and specific examples can be had by reference to the Examples hereunder described.

Tetrazole Intermediates

Compound A-19 with a C-linked tetrazole in Scheme 6 was prepared as illustrated in Schemes 8 and 9 and may be incorporated into the present compounds according to the procedure illustrated in Scheme 6.

J.-M. Fang, J. Org. Chem., 2007, 72, 3141-3144 which discloses reactions utilizing sodium azide.

Substitution of the ring with $R^8$ and $R^{7b}$ substituents can be performed with standard chemistry. In certain embodiment, substitution of the ring with $R^8$ and $R^{7b}$ substituents can be performed with nucleophilic aromatic substitution. For example, a halogen substituent at $R^8$ and $R^{7b}$ can be replaced with another substituent with nucleophilic aromatic substitution. In certain embodiment, substitution of the ring with $R^8$ and $R^{7b}$ substituents can be performed with a metal catalyzed coupling reaction. For example, a halogen substituent at $R^8$ and $R^{7b}$ can be replaced with another substituent with utilization of a metal catalyst. Suitable metal catalyzed reactions to place appropriate substituents at $R^8$ and $R^{7b}$ include Suzuki coupling, Stille coupling, Negishi coupling, and Buchwald coupling.

In certain embodiment, a substituent at $R^8$ and $R^{7b}$ is an ether group. In this case, a nucleophilic aromatic substitution with a corresponding alcohol can be used to place an ether substituent.

The nitro group of Compound A-24 was converted to an amino group to produce Compound A-19. The conversion of the nitro group to an amino group can be accomplished by various methods. A suitable method for reduction of nitro group is catalytic hydrogenation which uses hydrogen and a catalyst, such as, but not limited to, palladium on carbon, platinum oxide, Raney nickel, and samarium diiodide.

Compound A-23 can be purchased from commercial sources or prepared using standard techniques of organic chemistry. For example, Compound A-23 can be prepared from the corresponding amine with standard techniques of organic chemistry. Myriad textbook references teaching suitable synthetic methods are provided infra.

Compound A-19 in Scheme 6 was also prepared as illustrated in Scheme 8.

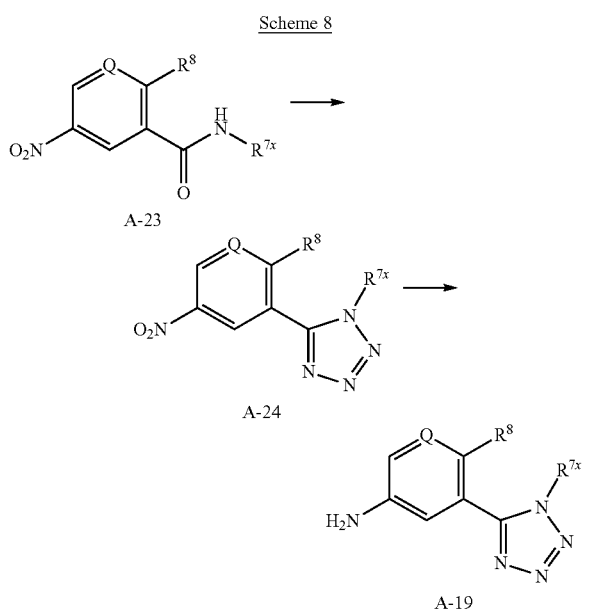

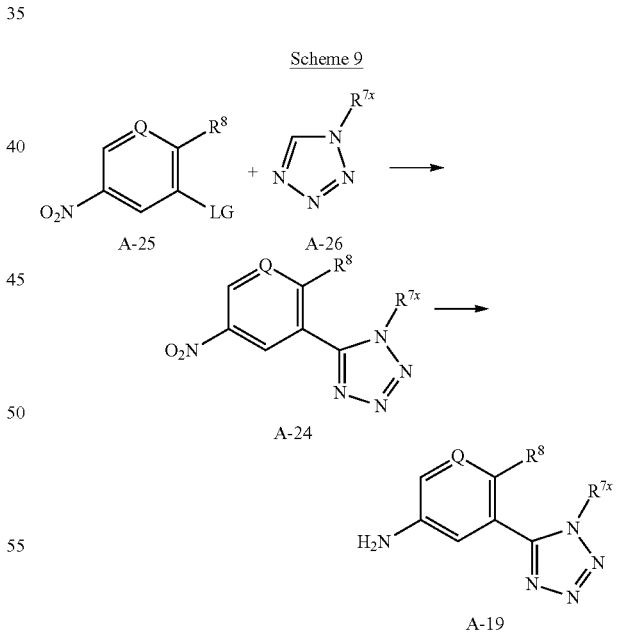

In Scheme 8, Q, $R^8$, and $R^{7x}$ are as previously defined.

To prepare Compound A-19, amide A-23 was converted to tetrazole A-24 by treatment with sodium azide. The reaction is general to any appropriate amide. In certain embodiments, the amide is a primary amide. Compound A-24 can also be prepared according to the procedures provided by Tetrahedron Letters, vol 38 (7), pg. 1257-1260 which discloses reactions utilizing triazidochlorosilane (TACS) and J.-J. Shie, In Scheme 9, Q, $R^8$, and $R^{7x}$ are as previously defined.

Compound A-24 can be prepared according to the procedures provided by Spulak et al, J. Org. Chem., 2010, 75(1), 241-244. To prepare Compound A-24, Compound A-25 with leaving group LG is treated with tetrazole A-26 and can undergo a coupling reaction that expels leaving group LG. The leaving group LG in Compound A-25 provides an electrophile for the reaction between Compound A-25 and Compound A-26. Examples of suitable leaving groups include, but not limited to, halogen, mesylate, tosylate, and triflate.

With continued reference to Scheme 9, the C5-H bond of tetrazole compound A-26 is activated to undergo a cross-coupling reaction with Compound A-25. Suitable cross-coupling reactions involve formation of C—C bond and include reactions such as, Suzuki coupling and Negishi coupling. Activation of C5-H bond of tetrazole compound A-26 can be activated with a suitable catalyst. Examples of suitable catalysts are based on metals such as, but not limited to, palladium, copper, and rhodium. In certain embodiments, the catalyst is palladium (II). Upon activation, Compound A-26 can react with Compound A-25. Optionally, triphenylphosphine can be used in the reaction.

Substitution of the ring with $R^8$ and $R^{7b}$ substituents can be performed with standard chemistry. In certain embodiment, substitution of the ring with $R^8$ and $R^{7b}$ substituents can be performed with nucleophilic aromatic substitution. For example, a halogen substituent at $R^8$ and $R^{7b}$ can be replaced with another substituent with nucleophilic aromatic substitution. In certain embodiment, substitution of the ring with $R^8$ and $R^{7b}$ substituents can be performed with a metal catalyzed coupling reaction. For example, a halogen substituent at $R^8$ and $R^{7b}$ can be replaced with another substituent with utilization of a metal catalyst. Suitable metal catalyzed reactions to place appropriate substituents at $R^8$ and $R^{7b}$ include Suzuki coupling, Stille coupling, and Buchwald coupling.

In certain embodiment, a substituent at $R^8$ and $R^{7b}$ is an ether group. In this case, a nucleophilic aromatic substitution with a corresponding alcohol can be used to place an ether substituent.

The nitro group of Compound A-24 was converted to an amino group to produce Compound A-19. The conversion of the nitro group to an amino group can be accomplished by various methods. A suitable method for reduction of nitro group is catalytic hydrogenation which uses hydrogen and a catalyst, such as, but not limited to, palladium on carbon, platinum oxide, Raney nickel, and samarium diiodide.

Compound A-25 can be purchased from commercial sources or prepared using standard techniques of organic chemistry. Myriad textbook references teaching suitable synthetic methods are provided infra.

Compound A-21 with an N-linked tetrazole in Scheme 7 was prepared as illustrated in Scheme 10 and may be incorporated into the present compounds according to the procedure illustrated in Scheme 7.

Scheme 10

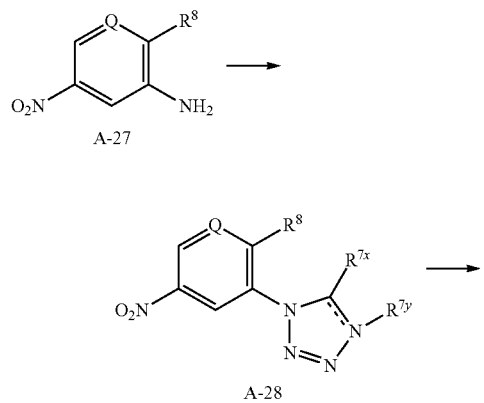

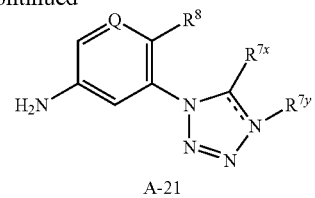

In Scheme 10, Q, $R^8$, $R^{7x}$, and $R^{7y}$ are as previously defined.

To prepare Compound A-21, Compound A-27 was coupled to tetrazole A-28 by treatment with sodium azide and trimethyl orthoformate or triethyl orthoformate. The reaction is general to any appropriate aminophenyl compound. Compound A-21 can also be prepared according to the procedures provided by Satoh et al., Tetrahedron Lett, 1995, 36, 1749; Gupta et al. Tetrahedron Lett, 2004, 45, 4113; Su et al. Eur. J. Org. Chem., 2006, 2723; and Potewar et al., Tetrahedron Lett, 2007, 48, 172.

Substitution of the ring with $R^8$ and $R^{7b}$ substituents can be performed with standard chemistry. In certain embodiment, substitution of the ring with $R^8$ and $R^{7b}$ substituents can be performed with nucleophilic aromatic substitution. For example, a halogen substituent at $R^8$ and $R^{7b}$ can be replaced with another substituent with nucleophilic aromatic substitution. In certain embodiment, substitution of the ring with $R^8$ and $R^{7b}$ substituents can be performed with a metal catalyzed coupling reaction. For example, a halogen substituent at $R^8$ and $R^{7b}$ can be replaced with another substituent with utilization of a metal catalyst. Suitable metal catalyzed reactions to place appropriate substituents at $R^8$ and $R^{7b}$ include Suzuki coupling, Stille coupling, and Buchwald coupling.

In certain embodiment, a substituent at $R^8$ and $R^{7b}$ is an ether group. In this case, a nucleophilic aromatic substitution with a corresponding alcohol can be used to place an ether substituent.

The nitro group of Compound A-28 was converted to an amino group to produce Compound A-21. The conversion of the nitro group to an amino group can be accomplished by various methods. A suitable method for reduction of nitro group is catalytic hydrogenation which uses hydrogen and a catalyst, such as, but not limited to, palladium on carbon, platinum oxide, Raney nickel, and samarium diiodide.

Compound A-27 can be purchased from commercial sources or prepared using standard techniques of organic chemistry. For example, Compound A-27 can be prepared from the corresponding amine with standard techniques of organic chemistry. In certain embodiment, Compound A-27 can be prepared from the corresponding dinitro compound in which one of the nitro groups is reduced to an amino group. Myriad textbook references teaching suitable synthetic methods are provided infra.

Although many of the synthetic schemes discussed above do not illustrate the use of protecting groups, skilled artisans will recognize that in some instances certain substituents may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in Greene & Wuts, supra.

Prodrugs as described herein can be prepared by routine modification of the above-described methods. Alternatively, such prodrugs can be prepared by reacting a suitably protected 2,4-pyrimidinediamine 6 with a suitable progroup.

Conditions for carrying out such reactions and for deprotecting the product to yield prodrugs as described herein are well-known.

Myriad references teaching methods useful for synthesizing pyrimidines generally, as well as starting materials described in Schemes (I)-(VII), are known in the art. For specific guidance, the reader is referred to Brown, D. J., "The Pyrimidines", in The Chemistry of Heterocyclic Compounds, Volume 16 (Weissberger, A., Ed.), 1962, Interscience Publishers, (A Division of John Wiley & Sons), New York ("Brown I"); Brown, D. J., "The Pyrimidines", in The Chemistry of Heterocyclic Compounds, Volume 16, Supplement I (Weissberger, A. and Taylor, E. C., Ed.), 1970, Wiley-Interscience, (A Division of John Wiley & Sons), New York (Brown II"); Brown, D. J., "The Pyrimidines", in The Chemistry of Heterocyclic Compounds, Volume 16, Supplement II (Weissberger, A. and Taylor, E. C., Ed.), 1985, An Interscience Publication (John Wiley & Sons), New York ("Brown III"); Brown, D. J., "The Pyrimidines" in The Chemistry of Heterocyclic Compounds, Volume 52 (Weissberger, A. and Taylor, E. C., Ed.), 1994, John Wiley & Sons, Inc., New York, pp. 1-1509 (Brown IV"); Kenner, G. W. and Todd, A., in Heterocyclic Compounds, Volume 6, (Elderfield, R. C., Ed.), 1957, John Wiley, New York, Chapter 7 (pyrimidines); Paquette, L. A., Principles of Modern Heterocyclic Chemistry, 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., Heterocyclic Chemistry, 3rd Edition, 1995, Chapman and Hall, London, UK, pp. 1-516; Vorbrüggen, H. and Ruh-Pohlenz, C., Handbook of Nucleoside Synthesis, John Wiley & Sons, New York, 2001, pp. 1-631 (protection of pyrimidines by acylation pp. 90-91; silylation of pyrimidines pp. 91-93); Joule, J. A., Mills, K. and Smith, G. F., Heterocyclic Chemistry, 4th Edition, 2000, Blackwell Science, Ltd, Oxford, UK, pp. 1-589; and Comprehensive Organic Synthesis, Volumes 1-9 (Trost, B. M. and Fleming, I., Ed.), 1991, Pergamon Press, Oxford, UK.

Pharmaceutical Compositions

The disclosed compounds are useful, at least, for the inhibition of PKC activity and the treatment of a disease or disorder that is mediated through the activity of a PKC activity. Accordingly, pharmaceutical compositions comprising at least one disclosed compound are also described herein.

A pharmaceutical composition comprising a subject compound may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A subject compound may be administered to the host using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations for pharmaceutical compositions are well known in the art. For example, Remington's Pharmaceutical Sciences, by E. W. Martin, Mack Publishing Co., Easton, Pa., 19th Edition, 1995, describes exemplary formulations (and components thereof) suitable for pharmaceutical delivery of disclosed compounds. Pharmaceutical compositions comprising at least one of the subject compounds can be formulated for use in human or veterinary medicine. Particular formulations of a disclosed pharmaceutical composition may depend, for example, on the mode of administration and/or on the location of the infection to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the affliction being treated can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in Remington's Pharmaceutical Sciences, 17th Edition, Mack Publishing Company, Easton, Pa., 1985. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are solidified at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions comprising a subject compound may be formulated in unit dosage form suitable for individual administration of precise dosages. The amount of active ingredient administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

Methods of Administration

The subject compounds can inhibit a protein kinase C activity. Accordingly, the subject compounds are useful for treating a disease or disorder that is mediated through the activity of a PKC activity in a subject. Accordingly, the subject compounds are useful for treating a disease or disorder that is associated with the activation of T-cells in a subject.

The route of administration will be selected according to a variety of factors including, but not necessarily limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a subject compound will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated. For example, this may be the amount of a subject compound necessary to prevent, inhibit, reduce or relieve a disease or disorder that is mediated through the activity of a PKC activity in a subject. Ideally, a therapeutically effective amount of a compound is an amount sufficient to prevent, inhibit, reduce or relieve a disease or disorder that is mediated through the activity of a PKC activity in a subject without causing a substantial cytotoxic effect on host cells.

Therapeutically effective doses (or growth inhibitory amounts) of a subject compound or pharmaceutical composition can be determined by one of skill in the art, with a goal of achieving local (e.g., tissue) concentrations that are at least as high as the $IC_{50}$ of an applicable compound disclosed herein.

An example of a dosage range is from about 0.1 to about 200 mg/kg body weight orally in single or divided doses. In particular examples, a dosage range is from about 1.0 to about 100 mg/kg body weight orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated. In one exemplary oral dosage regimen, a tablet containing from about 500 mg to about 1000 mg active ingredient is administered once (e.g., a loading dose) followed by administration of ½ dosage tablets (e.g., from about 250 to about 500 mg) each 6 to 24 hours for at least 3 days.

The specific dose level and frequency of dosage for any particular subject may be varied and will depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

The present disclosure also contemplates combinations of one or more disclosed compounds with one or more other agents or therapies useful in the treatment of a disease or disorder. In certain instances, the disease or disorder is mediated through the activity of a PKC activity in a subject. In certain instances, the disease or disorder is cell proliferative disorder. For example, one or more disclosed compounds may be administered in combination with effective doses of other medicinal and pharmaceutical agents, or in combination other non-medicinal therapies, such as hormone or radiation therapy. The term "administration in combination with" refers to both concurrent and sequential administration of the active agents.

Protein Kinase C

Protein Kinase C

PKC is a family of enzymes that function as serine/threonine kinases. The isoenzymes of PKC differ in their tissue distribution, enzymatic selectivity, requirement for $Ca^{2+}$, and regulation. PKCs play an important role in cell-cell signaling, gene expression and in the control of cell differentiation and growth.

The subject compound can be a selective inhibitor of PKC, e.g. an inhibitor selective for PKC over one or more other protein kinases, e.g. over one or more tyrosine kinases, for instance, over one or more non-receptor or receptor tyrosine kinases, e.g. over one or more of PKA, PKB, Abl Met, Src, Ins-R, Flt-3, JAK-2, KDR and/or Ret proteins. The selective PKC inhibitors may optionally be selective over one or more serine/threonine kinases, e.g. one or more serine/threonine kinases which do not belong to the CDK family. The subject compounds can exhibit a selectivity of at least 10 fold, or 20 fold, or 100 fold for the PKC over one or more other protein kinases, e.g. over one or more tyrosine kinases, e.g. over Flt-3, JAK-2, KDR and/or Ret proteins, or over one or more serine/threonine kinases which do not belong to the CDK family.

The selectivity of a selective inhibitor of PKC over other protein kinases may be calculated as the ratio of the $IC_{50}$ measured for PKC in an assay described herein over the $IC_{50}$ determined for another kinase. In a certain instance, there is provided a PKC inhibitor for which the ratio of the $IC_{50}$ value as determined in an Allogeneic Mixed Lymphocyte Reaction (MLR) assay to the $IC_{50}$ value as determined in a BM assay is higher than 5, 10, 20, or 30. MLR and BM assays can be done according to known methods, e.g. mouse or human MLR and BM assays, such as disclosed herein.

The disclosure provides an inhibitor of PKC, which can be an isozyme-selective PKC inhibitor, wherein the subject compound possesses selectivity for the isoforms θ and α of PKC over one or more of the other PKC isoforms. In a certain instance, the subject compound possesses selectivity for the isoform θ of PKC over one or more of the other PKC isoforms. In a certain instance, the subject compound possesses selectivity for the isoform α of PKC over one or more of the other PKC isoforms. In one embodiment, the disclosed compounds exhibit selectivity for PKC θ and PKC α over at least one PKC isoform.

A subject compound can show a selectivity of at least 10 fold, or 20 fold, or 100 fold for the isoforms θ or α of PKC over one or more of the other PKC isoforms. Selectivity for the isoforms θ or α of PKC over one or more of the other PKC isoforms can be measured by comparing the $IC_{50}$ of the subject compound for the isoforms θ or α of PKC to the $IC_{50}$ of the subject compound for the other PKC isoforms. In a certain instance, the selectivity can be determined by calculating the ratio of $IC_{50}$ of the subject compound for the other isoforms of PKC to the $IC_{50}$ of the subject compound for θ or α isoforms of PKC. In certain examples subject compounds exhibit a selectivity for PKC θ, α or both over another PKC isoform of at least about 2-fold, such as from about 3-fold to about 300-fold, from about 10-fold to about 100-fold or from about 5-fold to 50-fold. $IC_{50}$ values are obtained, for example, according to PKC assays described herein. The subject compounds can show an $IC_{50}$ value for the isoforms θ or α of PKC of 1 μM or less, such as less than about 300 nM, such as from about 1 nM to about 250 nM, less than 100 nM or even less than 10 nM in the assays disclosed herein.

The subject compounds can show a selectivity of the isoforms θ or t of PKC over other isoforms of PKC, as well as a selectivity over one or more of the other protein kinases, e.g. over one or more tyrosine kinases, or over one or more serine/threonine kinases which do not belong to the CDK-family, e.g. over one or more of PKA, PKB, Abl, Met, Src, Ins-it, Flt-3, JAK-2, KDR and Ret proteins, e.g. over one or more of Flt-3, JAK-2, KDR and Ret proteins.

Certain isozymes of PKC have been implicated in the mechanisms of various disease states, including, but not necessarily limited to, the following: cancer (PKC α, βI, βII, and δ); cardiac hypertrophy and heart failure (PKC βI and PKC βII) nociception (PKC γ and ε); ischemia including myocardial infarction (PKC ε and δ); immune response, particularly T-cell mediated (PKC θ and α); and fibroblast growth and memory (PKC ε and ζ). The role of PKC ε is also implicated in pain perception. PKC inhibitors can also be used for treating an ocular disease or disorder involving inflammatory and/or neovascular events.

The subject compounds can be used in the treatment of mammalian (especially human) disease states characterized by aberrant, elevated activity of a PKC isozyme in a tissue as compared to non-disease tissue of the same origin. PKC isozymes and disease states and/or biological functions amenable to therapy by inhibition of activity of the PKC isozyme include, but are not necessarily limited to: PKC α (hyperproliferative cellular diseases, such as cancer); PKC βI and PKC βII (cardiac hypertrophy and heart failure); PKC γ (pain management); PKC δ (ischemia, hypoxia (e.g., such as in myocardial infarction and in stroke); apoptosis induced by UV irradiation; and aberrant fibroblast growth (e.g., as may occur in wound healing)); PKC ε (pain management, myocardial dysfunction); PKC θ (immune system diseases, particularly those involving T-cell mediated responses); and PKC ζ (memory and fibroblast growth).

PKC Theta

PKC θ is expressed predominantly in lymphoid tissue and skeletal muscle. PKC θ is selectively expressed in T-cells and plays a role in mature T-cell activation. It has been shown that PKC θ is involved in T-cell receptor (TCR)-mediated T-cell activation but inessential during TCR-dependent thymocyte development. PKC θ, but not other PKC isoforms, translocates to the site of cell contact between antigen-specific T-cells and antigen presenting cells (APC), where it localizes with the TCR in the central core of the T-cell activation. PKC θ, but not the α, ε, or ζ isoenzymes, can selectively activate a FasL promoter-reporter gene and upregulate the mRNA or cell surface expression of endogenous FasL. On the other hand, PKC θ and ε can promote T-cell survival by protecting the cells from Fas-induced apoptosis, and this protective effect was mediated by promoting p90Rsk-dependent phosphorylation of BCL-2 family member BAD. Thus, PKC θ appears to play a dual regulatory role in T-cell apoptosis.

PKC θ inhibitors can find use in the treatment or prevention of disorders or diseases mediated by T lymphocytes, for example, autoimmune disease such as rheumatoid arthritis, psoriasis and lupus erythematosus, and inflammatory disease such as asthma and inflammatory bowel diseases.

PKC θ is a drug target for immunosuppression in transplantation and autoimmune diseases (Isakov et al. (2002) Annual Review of Immunology, 20, 761-794). PCT Publication WO2004/043386 identifies PKC θ as a target for treatment of transplant rejection and multiple sclerosis. PKC θ also plays a role in inflammatory bowel disease (The Journal of Pharmacology and Experimental Therapeutics (2005), 313 (3), 962-982), asthma (WO 2005062918), and lupus (Current Drug Targets: Inflammation & Allergy (2005), 4 (3), 295-298).

In addition, PKC θ is highly expressed in gastrointestinal stromal tumors (Blay, P. et al. (2004) Clinical Cancer Research, 10, 12, Pt. 1), it has been suggested that PKC θ is a molecular target for treatment of gastrointestinal cancer (Wiedmann, M. et al. (2005) Current Cancer Drug Targets 5(3), 171).

Experiments induced in PKC θ knock-out mice led to the conclusion that PKC θ inactivation prevented fat-induced defects in insulin signalling and glucose transport in skeletal muscle (Kim J. et al, 2004, The J. of Clinical Investigation 114 (6), 823). This data indicates PKC θ is a therapeutic target for the treatment of type 2 diabetes, and hence PKC θ inhibitors can be useful for treating such disease.

Therapeutic Applications

The subject compounds are useful for treating a disease or disorder that is mediated through, or exacerbated by, the activity of a PKC in a subject in need of treatment. Also, the compounds are useful for treating a disease or disorder that is associated with aberrant or otherwise undesirable T cell activation in a subject.

Accordingly, the present disclosure provides methods of treating an inflammatory disease in a subject by administering an effective amount of a subject compound, including a salt or solvate or stereoisomer thereof, so as to treat inflammation. Inflammatory diseases contemplated for therapy include acute and chronic inflammation mediated or exacerbated by PKC activity The present disclosure also provides methods of treating an autoimmune disease in a subject by administering to the subject an effective amount of a subject compound, including a salt or solvate or stereoisomer thereof, so as to treat the autoimmune disease.

The present disclosure also provides methods of treating an ocular disease or disorder involving inflammatory and/or neovascular events by administration of a subject compound, including a salt or solvate or stereoisomer thereof, in an effective amount.

Diseases or conditions of interest for treatment according to the present disclosure include, but are not limited to, atherosclerosis, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, cancer, infectious diseases such as: AIDS, septic shock or adult respiratory distress syndrome, ischemia/reperfusion injury, e.g.: myocardial infarction, stroke, gut ischemia, renal failure or hemorrhage shock, and traumatic shock, e.g. traumatic brain injury.

Further diseases or conditions of interest for treatment according to the present disclosure include, but are not limited to, T-cell mediated acute or chronic inflammatory diseases or disorders or autoimmune diseases, rheumatoid arthritis, osteoarthritis, systemic lupus erythematosus, Hashimoto's thyroidis, multiple sclerosis, myasthenia gravis, diabetes type I or II and the disorders associated therewith, transplant rejection, graft versus host disease, respiratory diseases, asthma, inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases (such as Sjoegren's syndrome, keratoconjunctivitis, uveitis) inflammatory bowel disease, Crohn's disease or ulcerative colitis, Guillain-Barre syndrome, and allergies.

The subject compounds can also be used for preventing or treating or delaying ocular diseases and disorders involving inflammation and/or neovascularization. Ocular diseases or disorders involving inflammatory and/or neovascular events include, but are not limited to, macular degeneration (AMD), diabetic ocular diseases or disorders, uveitis, optic neuritis, ocular edema, ocular angiogenesis, ischemic retinopathy, anterior ischemic optic neuropathy, optic neuropathy and neuritis, macular edema, cystoid macular edema (CME), retinal disease or disorder, such as retinal detachment, retinitis pigmentosa (RP), Stargart's disease, Best's vitelliform retinal degeneration, Leber's congenital amaurosis and other hereditary retinal degenerations, Sorsby's fundus dystrophy, pathologic myopia, retinopathy of prematurity (ROP), Leber's hereditary optic neuropathy, corneal transplantation or refractive corneal surgery, keratoconjunctivitis, or dry eye.

Generally, cell proliferative disorders treatable with the subject compound disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34; 22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9; 22)(qq34; q11)), chronic neutrophilic leukemia, chronic eosinophilic leukemialhypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome with t(9; 12) (q22; p12) (TEL-Syk fusion; see, e.g., Kuno et al., 2001, Blood 97:1050).

In some embodiments, the composition can be used to treat acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8; 21)(q22; q22), AML1 (CBF-alpha)/ETO, Acute promyelocytic leukemia (AML with t(15; 17)(q22; ql1-12) and variants, PML/RAR-alpha), AML with abnormal bone marrow eosinophils (inv(16) (p13q22) or t(16; 16)(p13; q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

In other aspects, cell proliferative disorders comprise virally mediated tumors. These can arise from infection of cells by an oncogenic virus that has the capability of transforming a normal cell into a tumor cell. Because rates of viral infection far exceed the number of actual incidence of cell transformation, viral mediated transformation generally act together with other cellular factors to generate a transformed tumor cell. Thus, a virally mediated tumor does not require the virus to be the sole causative agent of the cell proliferative disorder, but rather that the viral infection or persistent presence of virus is associated with the generation of the tumor. Generally, tumors where the causative agent is a virus typically has continual expression of a limited number of viral genes and that viral these oncogenes, expressed as part of the viral infection or through persistence of the virus, disrupts the normal cellular gene expression and signal transduction pathways. Without being bound by theory, viral oncogenes involved in cell transformation appear to disrupt four main cellular processes: cell surface receptors that interact with growth factors and extracellular matrix, transmembrane signaling networks, cytosolic elements such as soluble proteins and second messengers, and nuclear proteins including DNA binding proteins and factors which function directly and indirectly in gene regulation and replication.

In some embodiments, the virally mediated tumor treatable with the subject compound disclosed herein is associated with any virus that encodes an immunoreceptor tyrosine-based activation motif (ITAM) capable of modulating Syk activity. This motif, as noted above, refers to a conserved amino acid sequence motif that functions by interacting with and activating nonreceptor tyrosine kinases. ITAM motifs are found in, among others, the β and γ chains of FcεRI, the ε subunit of the T cell receptor, and immunoglobulin β(Igβ) and Igα of the B cell receptor. The canonical sequence motif is typically Yxx(L/I)x.sub.6-8Yxx(L/I), where x represents any amino acid. Generally, the tyrosine residues in the motif are involved in ITAM signaling and are substrates for phosphorylation by Src family of kinases. The phosphorylated form of ITAMs function as interaction sites for SH2 (src homology domain) containing signaling proteins, such as Syk/ZAP-70 kinases. In addition to its presence in a variety of cellular cell surface molecules, the ITAM sequences have been identified in virally encoded proteins. In view of the descriptions herein indicating function of Syk kinase as an oncogene, tumors associated with viruses carrying genes encoding proteins with ITAM sequences can be treated with Syk inhibitor compounds.

Accordingly, in some embodiments, the virally mediated tumor treatable with the subject compounds is associated with Kaposi's sarcoma (KS) associated herpes virus, a lymphotropic virus implicated in Kaposi's sarcoma, a rare malignancy found at higher incidence among HIV infected population. The KS associated herpes virus encodes a transmembrane protein termed KI having an immunoreceptor tyrosine-based activation motif (ITAM)-like sequence. The KI gene product is thought to act in a constitutive manner through its cysteine-rich ectodomain to activate Syk and its related kinase Zap-70 (Lagunoff, M. et al., 1999, Proc. Natl. Acad. Sci. USA 96(10):5704-5709). In further support of the methods herein, transgenic mice bearing the KI gene appears to increase the incidence of certain sarcomas and lymphomas in an infected animal, indicating a role for KI activity in oncogenesis (Prakash et al., 2002, J. Natl. Cancer Inst. 94:926-35).

In some embodiments, the virally mediated tumor is associated with Epstein Barr Virus (EBV). Epstein Barr Virus is a member of the Herpesviridae family that, following primary infection, replicates in the epithelial cells of the oropharynx and infect recirculating B lymphocytes. Infection can lead to acute infectious mononucleosis, also known as glandular fever. Infectious mononucleosis is a benign lymphoproliferative disease characterized by transient immunosuppression and an expansion of atypical lymphocytes, the majority of which are $CD8^+$ T cells. In these T cells, EBV establishes a latent but persistent infection during which a select set of viral genes are expressed. The entire genome can persist in the proliferating lymphocytes as episomal DNA. EBV infection is associated with Burkitt's lymphoma, Hodgkin's lymphoma, and adult T cell leukemia.

The LMP2A protein encoded by the EBV genome is a transmembrane protein thought to play a role in maintaining the latency of the EBV virus following infection. It consists of an extended amino terminal tail, 12 membrane spanning domains, and a cytoplasmic domain. The amino terminal region contains the ITAM motif, which allows interaction of LMP2A with Syk kinase (Fruehling et al., 1997, Virology, 235:241-251). LMP2A appears to regulate Syk kinase in lymphoid cells to promote B-cell survival and maintain latency. Because Syk plays a role in the signal transduction pathways that regulate other signaling pathways, such as PI-3K, BLNK, and phospholipase γ2 and is involved in enhancing lymphoid cell survival, improper Syk activation through LMP2A protein or other virally mediated effectors may play a role in inducing aberrant lymphoproliferation (Caldwell et al., 2000, J Virol 74(19):9115; Caldwell et al., 1998, Immunity 9:405)).

In some embodiments, the virally mediated tumor to be treated with the subject composition is associated with Human T-cell Lymphotropic Virus (HTLV-1 virus), a retrovirus in the same class of virus as the AIDS virus, HIV-1. The virus is tropic for $CD4^+$ T-cells although $CD8^+$ T-cells can also serve as a viral reservoir. HTLV-1 infection is associated with, among others, adult T-cell Leukemia/lymphoma (ATLL) and a number of other lymphocyte disorders. During HTLV-1 infection, Syk is expressed in infected cells while expression of the Syk related kinase, ZAP-70, is absent (Weil et al., 1999, J. Virol. 73(5):3709-17). Dysregulation of a number of kinases, including Syk, is implicated in HTLV-1 mediated induction of adult T-cell leukemia.

In some embodiments, the virally mediated tumor is associated with mammary tumor virus (MTV). ITAM sequences are found within the Env gene of murine mammary tumor virus (MMTV), a B type retrovirus identified as an etiological agent for breast cancer in mice. Mouse mammary epithelial cells transfected with MMTV Env gene display characteristics of a transformed phenotype, such as colony formation in soft agar and invasiveness in basement membrane preparations (Katz et al., 2005, J Exp Med. 201(3):431-9). Murine mammary tumor virus-like sequences are also present in human cancers, such as breast cancer and T cell lymphomas (Wang et al., 2000, Clinical Cancer Res. 6:1273-1278), and correlated with tumorigenesis as these sequences are not observed in the majority of normal breast tissue.

It is to be understood that use of subject composition for treating virally mediated tumors is not limited to tumors associated with the viruses specified above. As noted, any tumors associated with an oncogenic virus in which Syk is activated as part of its oncogenic mechanism, whether or not it involves ITAM sequences, can be targeted using the subject compounds.

Characterization of Functional Properties

The following are exemplary assays useful in characterizing activities of a compound of interest.

A. In Vitro

1. Protein Kinase C assay

The inhibition of PKC activity was measured by monitoring the production of phosphorylated peptide by fluorescence polarization at different concentrations of the inhibitor. Reactions were carried out in 96-well plate format with a total volume of 20 μL containing 20 mM HEPES, pH 7.4, 5 mM $MgCl_2$, 0.2 mM $CaCl_2$, 1 mM DTT, 0.02% Brij-35, 0.1 mg/mL phosphatidylserine, 0.02 mg/mL dioleoyl-sn-glycerol and 5 μM each of ATP and the peptide substrate. Compounds were first diluted serially in DMSO and then transferred to a solution containing the above concentrations of HEPES, $MgCl_2$, $CaCl_2$, DTT, and Brij-35 to yield 5× compound solutions in 2% DMSO, which was then added to the reaction solution. Reactions were initiated by the addition of PKC at a typical concentration as described in the table below, and then allowed to incubate at room temperature for 20 minutes. At the end of this time, a combination of quench (EDTA) and detection (peptide tracer and antibody) reagents was added using the protocol of Invitrogen P2748 (Carlsbad, Calif.), a Protein Kinase C Fluorescence polarization Assay Kit. After a 30 minute period of incubation, the amount of phosphorylated peptide generated was measured by fluorescence polarization (Ex=485 nm, Em=535 nm) using a Tecan Polarian instrument (Switzerland).

TABLE 4

| | Peptide substrate | SEQ ID | Enzyme source | enzyme concentration |
|---|---|---|---|---|
| PKC theta | RFARKGSLRQKNV | Seq ID No. 1 | Upstate Biotechnologies, Temecula, CA, cat. #14-444 | 40 ng/mL |
| PKC epsilon | RFARKGSLRQKNV | Seq ID No. 1 | Upstate Biotechnologies, Temecula, CA, cat. #14-518 | 50 ng/mL |

2. IL-2 ELISA, Human Primary T Cell, Anti-CD3+CD28+ Assays

Human Primary T Cell Isolation and Culture:

Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 minutes at 4° C. at 1750 rpm. The cells at the serum:ficoll interface were recovered and washed twice with 5 volumes of PBS. These freshly isolated human peripheral blood mononuclear cells were cultured in Yssel's medium containing 40 U/mL IL2 in a flask pre-coated with 1 µg/mL αCD3 and 5 µg/mL αCD28 (Anti-Human CD3, BD Pharmingen Catalog #555336, Anti-Human CD28, Beckman Coulter Catalog #IM1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/mL IL-2. The primary T-cells were then washed twice with PBS to remove the IL-2.

Primary T Cell Stimulation and IL2 ELISA:

Human primary T cells (100,000 cells per well) were pre-incubated with or without test compound in Yssel's medium for 1 hr at 37° C. Cells were then stimulated by transferring them to round-bottom 96-well plates pre-coated with 1 µg/ml µCD3 and 5 µg/ml µCD28. For counter assay, cells were instead stimulated by adding 8x stock solutions of PMA and ionomycin in Yssels (for final concentrations of 0.5 ng/ml PMA and 0.1 µM ionomycin, both from Calbiochem). Cells were incubated at 37° C. for 24 hours before 100 µL supernatants were harvested for quantification of IL-2 by ELISA using Human IL-2 Duoset ELISA Kit from R and D Systems, Cat. #DY202E.

3. Protein Kinase C assay

The subject compounds can be tested for activity on different PKC isoforms according to the following method. Assay is performed in a white with clear bottom 384-well microtiterplate with non-binding surface. The reaction mixture (25 µl) contains 1.5 µM of a tridecapeptide acceptor substrate that mimics the pseudo substrate sequence of PKC α with the Ala→Ser replacement, 10 µM $^{33}$P-ATP, 10 mM Mg(NO$_3$)$_2$, 0.2 mM CaCl$_2$, PKG at a protein concentration varying from 25 to 400 ng/ml (depending on the isotype used), lipid vesicles (containing 30 mol % phosphatidylserine, 5 mol % DAG and 65 mol % phosphatidylcholine) at a final lipid concentration of 0.5 mM, in 20 mM Tris-HCl buffer pH 7.4+0.1% BSA. Incubation is performed for 60 minutes at room temperature. Reaction is stopped by adding 50 µl of stop mix (100 mM EDTA, 200 µM ATP, 0.1% Triton X-100, 0.375 mg/well streptavidin-coated SPA beads in phosphate buffered saline w/o Ca, Mg. After 10 minutes incubation at room temperature, the suspension is spun down for 10 minutes at 300 g. Incorporated radioactivity is measured in a Trilux counter for 1 minute. IC$_{50}$ measurement is performed on a routine basis by incubating a serial dilution of inhibitor at concentrations ranging between 1-1000 µM. IC$_{50}$ values are calculated from the graph by curve fitting with XL Fit® software.

4. Protein Kinase C α Assay

Human recombinant PKC α is obtained from Oxford Biomedical Research and is used under the assay conditions as described under Section A.1 above.

5. Protein Kinase C β1 Assay

Human recombinant PKC β1 is obtained from Oxford Biomedical Research and is used under the assay conditions as described under Section A.1 above.

6. Protein Kinase C δ Assay

Human recombinant PKC δ is obtained from Oxford Biomedical Research and is used under the assay conditions as described under Section A.1 above.

7. Protein Kinase C ε Assay

Human recombinant PKC ε is obtained from Oxford Biomedical Research and is used under the assay conditions as described under Section A.1 above.

8. Protein Kinase C η Assay

Human recombinant PKC η is obtained from PanVera and is used under the assay conditions as described under Section A.1 above.

9. Protein Kinase C θ Assay

Human recombinant PKC θ is used under the assay conditions as described above.

10. CD28 Costimulation Assay

The assay is performed with Jurkat cells transfected with a human interleukin-2 promoter/reporter gene construct as described by Baumann G et al. in Transplant. Proc. 1992; 24:43-8, the β-galactosidase reporter gene being replaced by the luciferase gene (de Wet J., et al., Mol. Cell. Biol. 1987, 7(2), 725-737). Cells are stimulated by solid phase-coupled antibodies or phorbol myristate acetate (PMA) and the Ca$^{++}$ ionophore ionomycin as follows. For antibody-mediated stimulation Microlite TM1 microtiter plates (Dynatech) are coated with 3 µg/ml goat anti-mouse IgG Fc antibodies (Jackson) in 55 µl phosphate-buffered saline (PBS) per well for three hours at room temperature. Plates are blocked after removing the antibodies by incubation with 2% bovine serum albumin (BSA) in PBS (300 µl per well) for 2 hours at room temperature. After washing three times with 300 µl PBS per well, 10 ng/ml anti-T cell receptor antibodies (WT31, Becton & Dickinson) and 300 ng/ml anti-CD28 antibodies (15E8) in 50 µl 2% BSA/PBS are added as stimulating antibodies and incubated overnight at 4° C. Finally the plates are washed three times with 300 µl PBS per well. Seven three-fold serial dilutions of test compounds in duplicates in assay medium (RPMI 1640/10% fetal calf serum (FCS) containing 50 µM 2-mercaptoethanol, 100 units/ml penicillin and 100 µg/ml streptomycin) are prepared in separate plates, mixed with transfected Jurkat cells (clone K22 290_H23) and incubated for 30 minutes at 37° C. in 5% CO$_2$ 100 µl of this mixture containing 1×10$^5$ cells are then transferred to the antibody-coated assay plates. In parallel 100 µl are incubated with 40 ng/ml PMA and 2 µM ionomycin. After incubation for 5.5 hours at 37° C. in 5% $CO_2$, the level of luciferase is determined by bioluminescence measurement. The plates are centrifuged for 10 minutes at 500 g and the supernatant is removed by flicking. Lysis buffer containing 25 mM Tris-phosphate, pH 7.8, 2 mM DTT, 2 mM 1,2-diaminocyclohexane-N,N,N',N-tetraacetic acid, 10% (v/v) glycerol and 1% (v/v) Triton X-100 is added (20 µl per well). The plates are incubated at room temperature for 10 minutes under constant shaking. Luciferase activity is assessed with a bioluminescence reader (Labsystem, Helsinki, Finland) after automatic addition of 50 µl per well luciferase reaction buffer containing 20 mM Tricine, 1.07 mM $(MgCO_3)_4Mg(OH)_2 \times 5H_2O$, 2.67 mM $MgSO_4$, 0.1 mM EDTA, 33.3 mM DTT, 270 µM coenzyme A, 470 µM luciferin (Chemie Brunschwig AG), 530 µM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition ($IC_{50}$) is determined from the dose-response curves.

11. Bone Marrow Proliferation (BM) Assay

Bone marrow cells from CBA mice (2.5×104 cells per well in flat bottom tissue culture microtiter plates) are incubated in 100 µl RPMI medium containing 10% FCS, 100 U/ml penicillin, 100 µg/ml streptomycin (Gibco BRL, Basel, Switzerland), 50 tJM 2-mercaptoethanol (Fluke, Buchs, Switzerland), WEHI-3 conditioned medium (7.5% v/v) and L929 conditioned medium (3% v/v) as a source of growth factors and serially diluted compounds. Seven three-fold dilution steps in duplicates per test compound are performed. After four days of incubation 1 µCi $^3$H-thymidine is added. Cells are harvested after an additional five-hour incubation period, and incorporated $^3$H-thymidine is determined according to standard procedures. Conditioned media are prepared as follows. WEHI-3 cells 1 (ATCC TIB68) and L929 cells (ATCC CCL 1) are grown in RPMI medium until confluence for 4 days and one week, respectively. Cells are harvested, resuspended in the same culture flasks in medium C containing 1% FCS (Schreier and Tees 1981) for WEHI-3 cells and RPMI medium for L929 cells and incubated for 2 days (WEHI-3) or one week (L929). The supernatant is collected, filtered through 0.2 µm and stored in aliquots at –80° C. Cultures without test compounds and without WEHI-3 and L929 supernatants are used as low control values. Low control values are subtracted from all values. High controls without any sample are taken as 100% proliferation. Percent inhibition by the samples is calculated and the concentrations required for 50% inhibition ($IC_{50}$ values) are determined.

12. Allogeneic Mixed Lymphocyte Reaction (MLR)

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice (1.6×10$^5$ cells from each strain per well in flat bottom tissue culture microtiter plates, 3.2×10$^5$ in total) are incubated in RPMI medium containing 10% FCS, 100 U/ml penicillin, 100 µg/ml streptomycin (Gibco BRL, Basel, Switzerland), 50 µM 2-mercaptoethanol (Fluka, Buchs, Switzerland) and serially diluted compounds. Seven three-fold dilution steps in duplicates per test compound are performed. After four days of incubation 1 µCi $^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined.

B. In vivo

Heart Transplantation Model

The strain combination used: Male Lewis ($RT^1$ haplotype) and BN($RT^1$ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 1010 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when-heart beat stops. Graft survival is monitored in animals treated with compounds.

Graft v. Host Model

Spleen cells (2×10$^7$) from Wistar/F rats are injected subcutaneously into the right hind footpad of (Wistar/F×Fischer 344)$F_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the experimental groups to the weight difference between the corresponding lymph nodes from a group of animals left untreated with a test compound. In certain instances the test compound is a selective PKC inhibitor. For example, disclosed compounds that are particularly useful for treating graft versus host disease and related disorders are selective PKC α and θ inhibitors.

Research Applications

Since subject compounds can inhibit a PKC activity, such compounds are also useful as research tools. The present disclosure also provides a method for using subject compounds as a research tool for studying a biological system or sample, or for discovering new chemical compounds that can inhibit a PKC activity.

The disclosure provides for a method of studying a biological system or sample known to comprise PKC, the method comprising: (a) contacting the biological sample with a compound of formulae I-XIII or a salt or solvate or stereoisomer thereof; and (b) determining the inhibiting effects caused by the compound on the biological sample.

Any suitable biological sample having PKC can be employed in such studies which can be conducted either in vitro or in vivo. Representative biological samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest.

When used as a research tool, a biological sample comprising PKC is typically contacted with a PKC activity-inhibiting amount of a subject compound. After the biological sample is exposed to the compound, the effects of inhibition of a PKC activity are determined using conventional procedures and equipment, such as the assays disclosed herein. Exposure encompasses contacting the biological sample with the compound or administering the compound to a subject. The determining step can involve measuring a response (a quantitative analysis) or can involve making an observation (a qualitative analysis). Measuring a response involves, for example, determining the effects of the compound on the biological sample using conventional procedures and equipment, such as radioligand binding assays and measuring ligand-mediated changes in functional assays. The assay results can be used to determine the activity level as well as the amount of compound necessary to achieve the desired result, that is, a PKC activity-inhibiting amount.

Additionally, subject compounds can be used as research tools for evaluating other chemical compounds, and thus are also useful in screening assays to discover, for example, new compounds having a PKC inhibiting activity. In this manner, a subject compound can be used as a standard in an assay to allow comparison of the results obtained with a test compound and with the subject compounds to identify those test compounds that have about equal or superior activity, if any. For example, $IC_{50}$ data for a test compound or a group of test compounds is compared to the $IC_{50}$ data for a subject compound to identify those test compounds that have the desired properties, for example, test compounds having an $IC_{50}$ about equal or superior to a subject compound, if any.

This aspect includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a subject compound to provide a second assay value; wherein step (a) is conducted either before, after or concurrently with step (b); and (c) comparing the first assay value from step (a) with the second assay value from step (b). The assays that can be used for generation of comparison data are disclosed herein, such as the PKC assays.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

Example 1

5-Fluoro-N2-[4-(4-methylpiperazino)-3-trifluoromethyl]phenyl-N4-(1,2,2,6,6-pentamethylpiperidin-4-yl)-2,4-pyrimidinediamine 5-Fluoro-5-nitrobenzotrifluoride (2 g) and 1-methylpiperazine (2 mL) were dissolved in methanol (5 mL). The yellow solution was stirred at rt overnight. The reaction mixture was diluted with water (100 mL) and extracted with ethyl acetate (2×100 mL). The organic solutions were evaporated to give 2-(4-methylpiperazino)-5-nitrobenzotrifluoride.

2-(4-Methylpiperazino)-5-nitrobenzotrifluoride was dissolved in methanol (100 mL) and to the solution was added 10% Pd—C. The reaction mixture was reacted under hydrogen atmosphere (~40 psi) for 1 h. The catalyst was filtered off over cellite and washed with methanol. The filtrate was evaporated to give [4-(4-methylpiperazino)-3-trifluoromethyl]aniline (2.25 g, 91% in two steps). $^1$H NMR (DMSO-d6): δ 2.19 (s, 3H), 2.38 (br, 4H), 2.70 (t, J=4.5 Hz, 4H), 5.31 (br, 2H), 6.73 (dd, J=2.4, 8.7 Hz, 1H), 6.78 (d, J=2.7 Hz, 1H), 7.20 (d, J=8.1 Hz, 1H).

4-Amino-1,2,2,6,6-pentamethylpiperidine (1 g) and 2,6-dichloro-5-fluoropyrimidine (1.5 g) were dissolved in methanol (10 mL). The reaction solution was stirred at rt overnight. The reaction solution was evaporated and crystallized from ethyl acetate and hexanes to give 2-chloro-5-fluoro-N4-(1,2,2,6,6-pentamethylpiperidin-4-yl)-4-pyrimidineamine HCl salt (1.65 g, 93%). $^1$H NMR (DMSO-d6): δ 1.38 (s, 6H), 1.48 (s, 6H), 2.02 (m, 4H), 2.68 (d, J=4.8 Hz, 3H), 4.33 (br, 1H), 8.10 (d, J=3.3 Hz, 1H), 8.32 (d, J=6.9 Hz, 1H), 9.66 (br, 1H).

2-Chloro-5-fluoro-N4-(1,2,2,6,6-pentamethylpiperidin-4-yl)-4-pyrimidineamine (300 mg) and [4-(4-methylpiperazino)-3-trifluoromethyl]aniline (300 mg) were suspended in isopropanol (1 mL) and TFA (5 drops). The solution was heated at 100° C. overnight, then cooled to room temperature. The solution was evaporated and purified by flash column chromatography (2.0 M NH3/MeOH in dichloromethane=2, 4, 6, 10%) to give 5-fluoro-N2-[4-(4-methylpiperazino)-3-trifluoromethyl]phenyl-N4-(1,2,2,6,6-pentamethylpiperidin-4-yl)-2,4-pyrimidinediamine (440 mg, 84%). $^1$H NMR (DMSO-d6): δ 1.04 (s, 6H), 1.07 (s, 6H), 1.44 (t, J=11.7 Hz, 2H), 1.68 (d, J=9.9 Hz, 2H), 2.18 (s, 3H), 2.20 (s, 3H), 2.41 (br, 4H), 2.76 (t, J=4.2 Hz, 4H), 4.29 (br, 1H), 7.16 (d, J=8.4 Hz, 1H), 7.32 (d, J=8.4 Hz, 1H), 7.75 (d, J=2.1 Hz, 1H), 7.84 (d, J=3.6 Hz, 1H), 8.07 (d, J=8.7 Hz, 1H), 9.13 (s, 1H); $^{19}$F NMR (282 MHz, DMSO-d6): δ −165.87, −59.89; LCMS: purity: 100%; MS (m/e): 524.43 (MH+).

Example 2

5-fluoro-N2-(3-(1-methyl-1H-tetrazol-5-yl)-5-(trifluoromethyl)phenyl)-N4-(2,2,6,6-tetramethylpiperidin-4-yl)pyrimidine-2,4-diamine

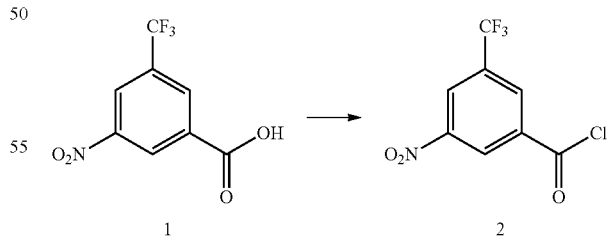

A solution of 3-nitro-5-(trifluoromethyl)benzoic acid 1 (5.0 g, 21.3 mmol, 1 equiv) in $SOCl_2$ (15 mL, 213 mmol, 10 equiv) was heated to reflux for 2 hours. After the reaction mixture had cooled to ambient temperature, it was concentrated to dryness. The residue was co-evaporated with toluene 2× and dried in vacuo to afford Compound 2 (5.39 g, 100%) as a brown oil.

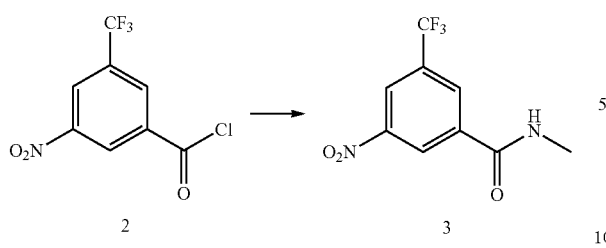

A solution of Compound 2 (5.39 g, 21.3 mmol, 1 equiv) in dichloromethane (40 mL) under argon gas was cooled to −10° C. (brine and ice), and diisopropylethylamine (20 mL, 106.3 mmol, 5 equiv) was added dropwise. A solution of methylamine (2M THF, 32 mL, 64 mmol, 3 equiv) was added slowly dropwise. Completion of the reaction was confirmed by LCMS. The reaction mixture was diluted with ethyl acetate and water. The layers were separated, and the organic layer was washed with water 2×, dried over $Na_2SO_4$, filtered, and concentrated to provide Compound 3 (4.51 g, 85%) as a solid which was used in the next step without further purification.

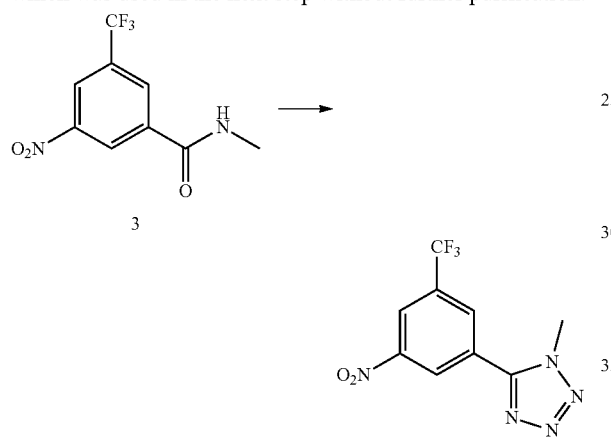

A solution of Compound 3 (2.0 g, 8.06 mmol, 1 equiv) in acetonitrile (40 mL) under argon gas was added $NaN_3$ (2.10 g, 32.2 mmol, 4 equiv) in one portion. The suspension was cooled to −10° C. (brine and ice), and $Tf_2O$ (2.71 mL, 4.55 g, 16.1 mmol, 2 equiv) was slowly added dropwise while keeping the temperature between −7° C. and −2° C. The reaction mixture was allowed to warm up to ambient temperature over 1 hour. Both TLC and LCMS confirmed completion of the reaction. The reaction mixture was cooled back to −10° C. and quenched by the slow dropwise addition of ice-cold saturated sodium bicarbonate and diluted with ice-cold ethyl acetate. The layers were separated, and the organic layer was washed with water 1×, dried over $Na_2SO_4$, filtered, and concentrated. The crude product was purified by flash chromatography and eluted with hexane:EtOAc=100:0 to 80:20 using 10% EtOAc increments to give Compound 4 (1.88 g, 85%) as a solid.

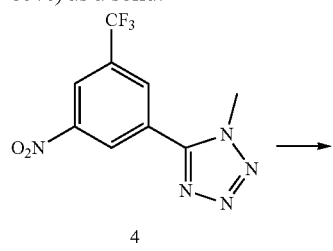

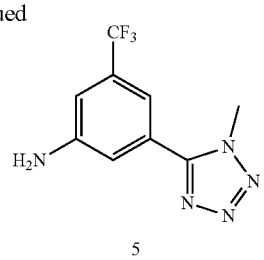

A suspension of Compound 4 (1.88 g, 6.88 mmol, 1 equiv) in ethanol (13 mL) was charged with 10% Pd/C (50% water, 1.46 g, 0.688 mmol, 0.10 equiv) and air was evacuated with vacuum. The vacuum was replaced with a balloon filled with hydrogen gas, and the reaction was allowed to stir for 8 hours. The catalyst was filtered off using a pad of celite and rinsed with ethanol. The filtrate was concentrated to give Compound 5 (1.40 g, 84%) as a solid which was used in the next step without further purification.

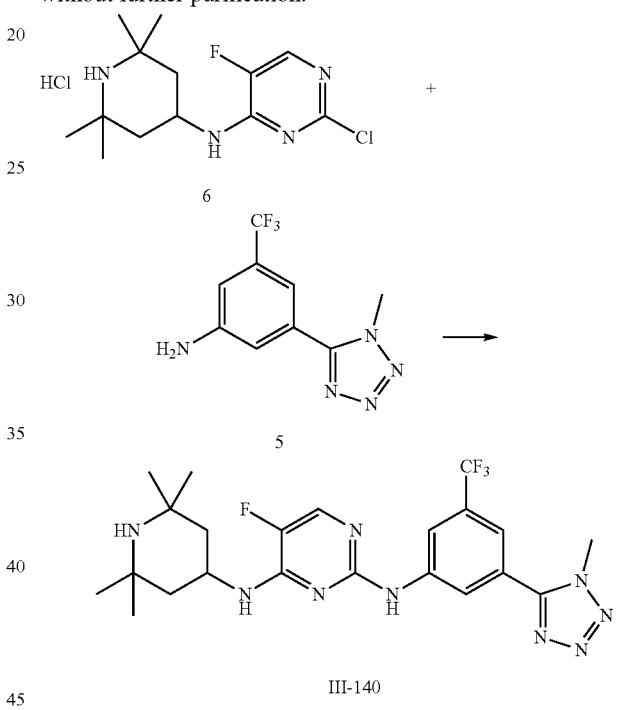

A slurry of Compound 6 (100 mg, 0.309 mmol, 1 equiv) and Compound 5 (120 mg, 0.495 mmol, 1.6 equiv) in isopropanol (3 mL) was charged with TFA (100 uL, 1.24 mmol, 4 equiv). The acidic slurry was heated to 100° C. for 23 hours affording a melt. The crude solid was dissolved in isopropanol (3 mL), neutralized with 2M $NH_3$/MeOH, and concentrated. The crude product was purified by flash chromatography and eluted with DCM:2M $NH_3$/MeOH=100:0 to 95:5 using 1% 2M $NH_3$/MeOH increments to provide Compound III-140 (135 mg, 88%) as a solid.

Example 3

N2-(3-cyclopropyl-5-(1H-tetrazol-1-yl)phenyl)-5-fluoro-N4-(2,2,6,6-tetramethylpiperidin-4-yl)pyrimidine-2,4-diamine (Compound III-116)

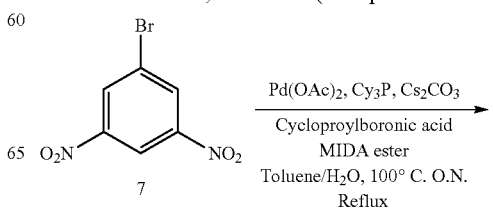

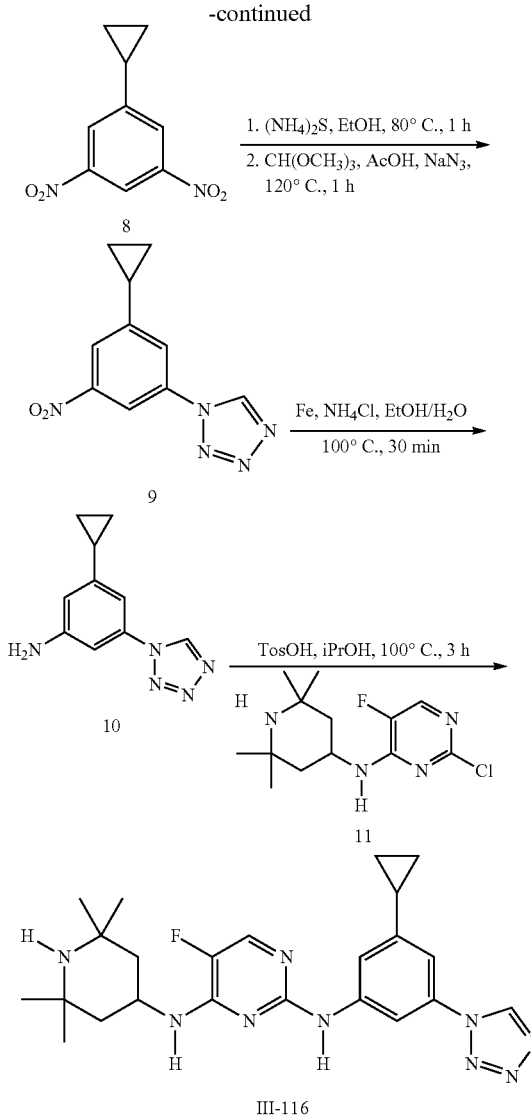

Step 1: Preparation of 1-Cyclopropyl 3,5-dinitrobenzene (Compound 8)

In a 250 mL round bottom flask to a solution of 3-bromo 1,5-dinitrobenzene (2.1 g, 8.50 mmol) in toluene (90 mL) tricyclohexylphosphine (0.72 g, 2.55 mmol), $Cs_2CO_3$ (16.58 g, 51 mmol), cyclopropylboronic acid MIDA ester (2.35 g, 11.90 mmol) and 10 ml de-ionized water were added and the solution was degassed with nitrogen for 30 minutes. To the above solution Pd $(OAc)_2$ (0.29 g, 1.28 mmol) was added under nitrogen and the reaction mixture was refluxed for 12 hours. LC MS analysis of the crude reaction indicated the completion of the reaction. The crude reaction mixture was filtered on celite pad and the volatiles were removed under reduced pressure. The dark brown oil was worked-up with 2×100 mL ethyl acetate and water (100 mL), dried on $MgSO_4$ and ethyl acetate was evaporated under reduced pressure. The crude reaction mixture was separated by column chromatography to give Compound 8 in 64% yield.

$^1$H NMR ($CDCl_3$, 300 MHz): δ 8.81 (t, J=1.92 Hz & 1.93 Hz, 1H), 8.22 (d, J=1.90 Hz, 2H), 2.14 (m, 1H), 1.23-1.26 (m, 2H), 0.90-0.92 (m, 2H); LCMS (m/z): 248 (MH$^+$).

Step 2: Preparation of 1-(3-Cyclopropyl-5-nitrophenyl)-1H-tetrazole (Compound 9)

In a 100 mL round bottom flask to a solution of 3-cyclopropyl 1,5-dinitrobenzene (1.50 g, 7.21 mmol) in 30 mL ethanol, 8.32 mL of aqueous $(NH_4)_2S$ (20% in $H_2O$) was added and the reaction mixture was heated at 100° C. for 1 hour. LC MS indicated the complete consumption of the starting material and appearance of the intermediate. The reaction mixture was concentrated on a rotary evaporator to give light yellow solid in 90% yield which was taken to the next step without further purification. LCMS (m/z): 209 (MH$^+$).

In a 100 mL round bottom flask to a solution of 3-cyclopropyl 5-dinitroaniline (0.25 g, 1.4 mmol) in acetic acid (10 mL), trimethyl orthoformate (0.45 g, 4.21 mmol) was added at once and the reaction mixture was stirred for 5 minutes at room temperature. To the above reaction mixture, $NaN_3$ (0.127 g, 1.96 mmol) was added and the reaction mixture was heated to 120° C. for 1 hour. By this time LCMS analysis indicated the complete consumption of the starting aniline and appearance of Compound 9. The reaction mixture was cooled to 0° C. in ice bath and 15 mL of 6N aqueous HCl was added. To the above solution sodium nitrite (0.050 g, 0.7 mmol) in 5 ml of $H_2O$ was introduce drop wise. The solution was stirred at 0° C. in ice bath for 15 min. and the precipitate was filtered to obtain Compound 9 as a tan solid at 73% yield.

$^1$H NMR ($CDCl_3$, 300 MHz): δ 9.13 (s, 1H), 8.32 (t, J=1.65 Hz & 1.92 Hz, 1H), 8.04 (d, J=1.37 Hz, 1H), 7.84 (d, J=1.65 Hz, 1H), 2.14 (m, 1H), 1.21-1.26 (m, 2H), 0.89-0.94 (m, 2H); LCMS (m/z): 232 (MH$^+$).

Step 3: Preparation of 3-Cyclopropyl-5-(1H-tetrazol-1-yl)benzenamine (Compound 10)

In a 100 mL round bottom flask to a solution of tetrazole compound (0.50 g, 2.16 mmol) in 25 mL ethanol and 5 mL water, Fe (0.36 g, 6.48 mmol) and $NH_4Cl$ (0.35 g, 6.48 mmol) were added. The reaction mixture was refluxed for 30 minutes. The reaction mixture was then cooled to room temperature and filtered on celite pad and concentrated under reduced pressure. The crude solid was dissolved in 10 mL DCM/MeOH (3:1) and filtered to remove the inorganic impurities. The filtrate was concentrated on rotary evaporator and dried under vacuum to obtain Compound 10.

$^1$H NMR (DMSO $d_6$, 300 MHz): δ 9.97 (s, 1H), 6.80 (s, 1H), 6.64 (s, 1H), 6.43 (s, 1H), 5.53 (s, 2H), 1.82 (m, 1H), 0.91 (m, 2H), 0.66 (m, 2H); LCMS (m/z): 202 (MH$^+$).

Step 4: Preparation of N$^2$-(3-cyclopropyl-5-(1H-tetrazol-1-yl)phenyl)-5-fluoro-N$^4$(2,2,6,6-tetramethylpiperidin-4-yl)pyrimidine-2,4-diamine (Compound III-116)

In a 100 mL round bottom flask to a solution of 2-chloro-5-fluoro-N-(2,2,6,6,-tetramethylpiperidin-4-yl)pyrimidin-4-amine (Compound 11; 0.16 g, 0.56 mmol) in 10 mL isopropanol, 3-cyclopropyl-5-(1H-tetrazol-1-yl)benzenamine (0.125 g, 0.622 mmol) and TosOH (0.085 g, 0.448 mmol) were added. The reaction mixture was heated at 100° C. for 3 hours. LCMS analysis indicated the complete consumption of the mono-SNAr product and appearance of Compound III-116. The reaction mixture was then cooled to room temperature and volatiles were removed under reduced pressure. The crude reaction mixture was purified by column chromatography using DCM/2 M $NH_3$ in MeOH to obtain Compound III-116 as a tan solid that was further purified by trituration using DCM/hexanes.

¹H NMR (DMSO d$_6$, 300 MHz): δ 10.01 (s, 1H), 9.16 (s, 1H), 8.14 (d, J=1.65 Hz, 1H), 7.89 (d, J=3.85 Hz, 1H), 7.42 (s, 1H), 7.17 (d, J=7.98 Hz, 1H), 6.97 (s, 1H), 4.33 (br m, 1H), 1.93 (m, 1H), 1.61-1.65 (m, 2H), 1.09-1.14 (m, 2H), 0.98-1.07 (m, 2H), 0.94-0.96 (m, 12H), 0.72-0.77 (m, 2H); LCMS (m/z): 452 (MH$^+$).

Example 4

N2-(4-cyclopropyl-3-(1H-tetrazol-1-yl)phenyl)-5-fluoro-N4-(2,2,6,6-tetramethylpiperidin-4-yl)pyrimidine-2,4-diamine (Compound III-118)

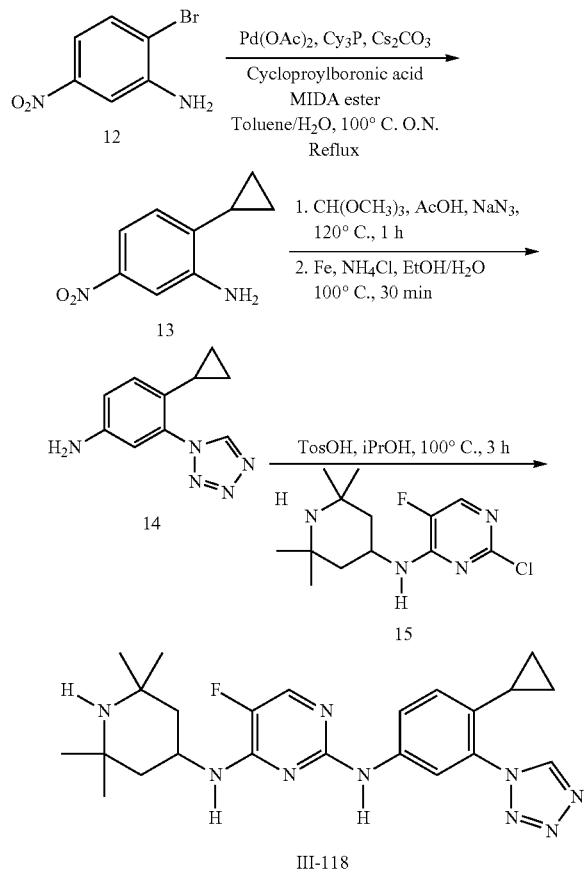

Step 1: Preparation of 2-Cyclopropyl 5-nitrobenzenamine (Compound 13)

In a 250 mL round bottom flask to a solution of 2-bromo 5-nitroaniline (2.30 g, 10.60 mmol) in toluene (90 mL) tricyclohexylphosphine (0.89 g, 3.18 mmol), Cs$_2$CO$_3$ (17.22 g, 52.99 mmol), cyclopropylboronic acid MIDA ester (2.92 g, 14.84 mmol) and 10 ml de-ionized water were added and the solution was degassed with nitrogen for 30 minutes. To the above solution Pd(OAc)$_2$ (0.36 g, 1.59 mmol) was added under nitrogen and the reaction mixture was refluxed for 12 hours. LC MS analysis of the crude reaction indicated the completion of the reaction. The crude reaction mixture was filtered on celite pad and the volatiles were removed under reduced pressure. The dark brown oil was worked-up with 2×100 mL ethyl acetate and water (100 mL), dried on MgSO$_4$ and ethyl acetate was evaporated under reduced pressure. The crude reaction mixture was separated by column chromatography to give Compound 13 in 70% yield.

¹H NMR (DMSO d$_6$, 300 MHz): δ 7.43 (d, J=2.48 Hz, 1H), 7.26 (dd, J=1.90 Hz & 8.25 Hz, 1H), 6.95 (d, J=8.25 Hz, 1H), 5.70 (s, 2H), 1.75 (m, 1H), 0.92-0.95 (m, 2H), 0.56-0.59 (m, 2H); LCMS (m/z): 179 (MH$^+$).

Step 2: Preparation of 4-Cyclopropyl-3-(1H-tetrazol-1-yl)benzeneamine (Compound 14)

In a 100 mL round bottom flask to a solution of 2-cyclopropyl 5-nitroaniline (0.112 g, 0.67 mmol) in acetic acid (10 mL), trimethyl orthoformate (0.22 mL, 2.02 mmol) was added at once and the reaction mixture was stirred for 5 minutes at room temperature. To the above reaction mixture, NaN$_3$ (0.061 g, 0.94 mmol) was added and the reaction mixture was heated to 120° C. for 1 hour. By this time, LCMS analysis indicated the complete consumption of the starting aniline and appearance of intermediate. The reaction mixture was cooled to 0° C. in ice bath and 10 mL of 6N aqueous HCl was added. To the above solution sodium nitrite (0.040 g, 0.58 mmol) in 5 ml of H$_2$O was introduce dropwise. The solution was stirred at 0° C. in ice bath for 15 minutes and the precipitate was filtered to obtain an intermediate as a tan solid 70% yield. The crude solid was taken further to the next step without purification.

In a 100 mL round bottom flask to a solution of tetrazole compound (1.00 g, 4.33 mmol) in 25 mL ethanol and 5 mL water, Fe (0.73 g, 12.99 mmol) and NH$_4$Cl (0.70 g, 12.99 mmol) were added. The reaction mixture was refluxed for 30 minutes. Then the reaction mixture was cooled to room temperature and filtered on celite pad and concentrated under reduced pressure. The crude solid was dissolved in 10 mL DCM/MeOH (3:1) and filtered to remove the inorganic impurities. The filtrate was concentrated on rotary evaporator and dried under vacuum to obtain Compound 14.

¹H NMR (DMSO d$_6$, 300 MHz): δ 9.80 (s, 1H), 6.94 (d, J=8.53 Hz, 1H), 6.70 (dd, J=1.92 Hz & 8.52 Hz, 1H), 6.60 (d, J=2.20 Hz, 1H), 5.45 (s, 2H), 1.44 (m, 1H), 0.55-0.58 (m, 2H), 0.33-0.35 (m, 2H); LCMS (m/z): 202 (MH$^+$).

Step 3: Preparation of N²-(4-cyclopropyl-3-(1H-tetrazol-1-yl)phenyl)-5-fluoro-N⁴-(2,2,6,6-tetramethylpiperidin-4-yl)pyrimidine-2,4-diamine (Compound III-118)

In a 100 mL round bottom flask to a solution of 2-chloro-5-fluoro-N-(2,2,6,6,-tetramethylpiperidin-4-yl)pyrimidin-4-amine (Compound 15; 0.18 g, 0.63 mmol) in 10 mL iPrOH, 4-cyclopropyl-3-(1H-tetrazol-1-yl)benzeneamine (0.18 g, 0.88 mmol) and TosOH (0.095 g, 0.50 mmol) were added. The reaction mixture was heated at 100° C. for 3 hours. LCMS analysis indicated the complete consumption of the mono-SNAr product and appearance of Compound III-118. The reaction mixture was then cooled to room temperature and volatiles were removed under reduced pressure. The crude reaction mixture was purified by column chromatography using DCM/2 M NH$_3$ in MeOH to get tan solid that was further purified by tituration using DCM/hexanes.

¹H NMR (DMSO d$_6$, 300 MHz): δ 9.87 (s, 1H), 9.29 (s, 1H), 7.89 (d, J=2.2 Hz, 1H), 7.86 (d, J=3.6 Hz, 1H), 7.79 (d, J=1.93 Hz, 1H), 7.22 (d, J=8.25 Hz, 1H), 7.09 (d, J=8.52 Hz, 1H), 4.34 (br m, 1H), 1.65 (d, J=3.3 Hz, 1H), 1.61 (d, J=3.3

Hz, 1H), 1.48 (m, 1H), 1.09-1.17 (m, 2H), 1.02 (s, 6H), 0.99 (s, 6H), 0.63-0.67 (m, 2H), 0.42-0.45 (m, 2H); LCMS (m/z): 452 (MH+).

Example 5

5-fluoro-N2-(3-(1-methyl-1H-tetrazol-5-yl)-5-(oxetan-3-yloxy)phenyl)-N4-(2,2,6,6-tetramethylpiperidin-4-yl)pyrimidine-2,4-diamine (Compound III-145)

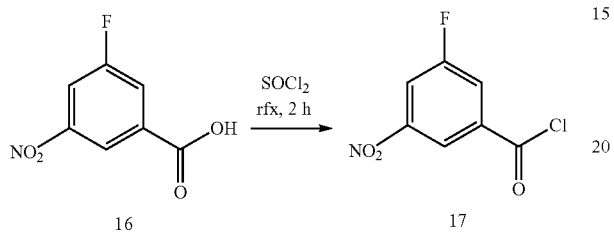

A solution of 3-fluoro-5-nitrobenzoic acid 16 (10.0 g, 54 mmol, 1 equiv) in SOCl₂ (40 mL, 540 mmol, 10 equiv) was heated to reflux for 2 hours. After the reaction mixture had cooled to ambient temperature, it was concentrated to dryness. The residue was co-evaporated with toluene 2× and dried in vacuo to afford acid chloride 17 (11.0 g, 100%) as a brown oil.

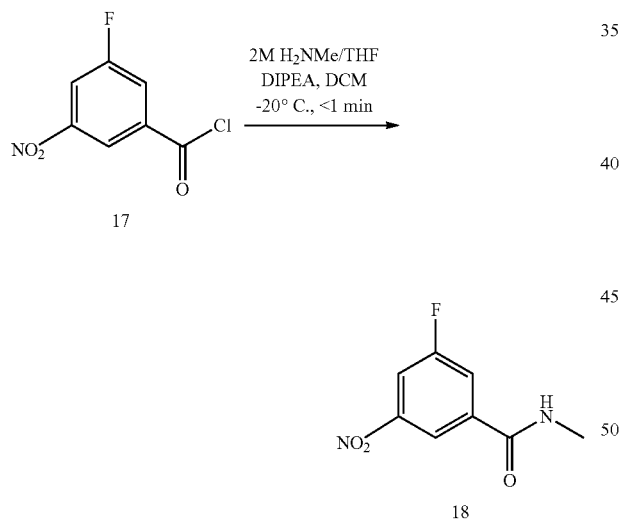

A solution of acid chloride 17 (11.0 g, 54.04 mmol, 1 equiv) in dichloromethane (100 mL) under argon gas was cooled to −20° C., and diisopropylethylamine (47 mL, 270 mmol, equiv) was added dropwise. A solution of methylamine (2M THF, 81 mL, 162 mmol, 3 equiv) was added slowly dropwise. Completion of the reaction was immediately confirmed by LCMS. The reaction mixture was diluted with ethyl acetate and water. The layers were separated, and the organic layer was washed with water 2×, dried over Na₂SO₄, filtered, and concentrated to provide amide 18 (10.2 g, 95%) as a solid which was used in the next step without further purification.

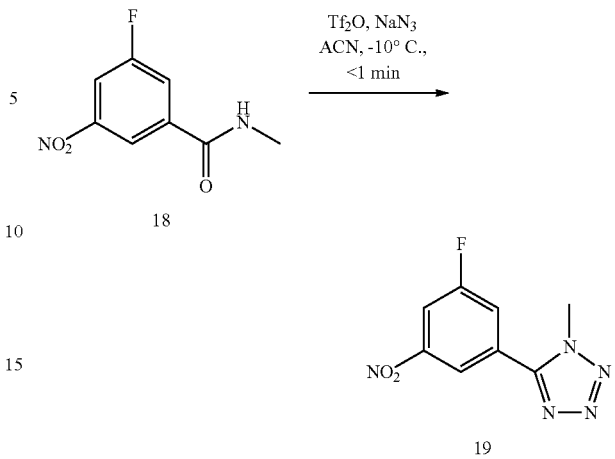

A solution of amide 18 (10.20 g, 51.48 mmol, 1 equiv) in acetonitrile (250 mL) under argon gas was added NaN₃ (13.40 g, 206 mmol, 4 equiv) in one portion. The suspension was cooled to −10° C. (brine and ice), and Tf₂O (17.32 mL, 29.05 g, 103 mmol, 2 equiv) was slowly added dropwise while keeping the temperature between −7° C. and −2° C. Both TLC and LCMS confirmed completion of the reaction. The reaction mixture was cooled back to −10° C. and quenched by the slow dropwise addition of ice-cold saturated sodium bicarbonate and diluted with ice-cold ethyl acetate. The layers were separated, and the organic layer was washed with water 1×, dried over Na₂SO₄, filtered, and concentrated. The crude product was purified by flash chromatography and eluted with hexane:EtOAc=100:0 to 50:50 using 10% EtOAc increments to give tetrazole 19 (5.13 g, 45%) as a solid.

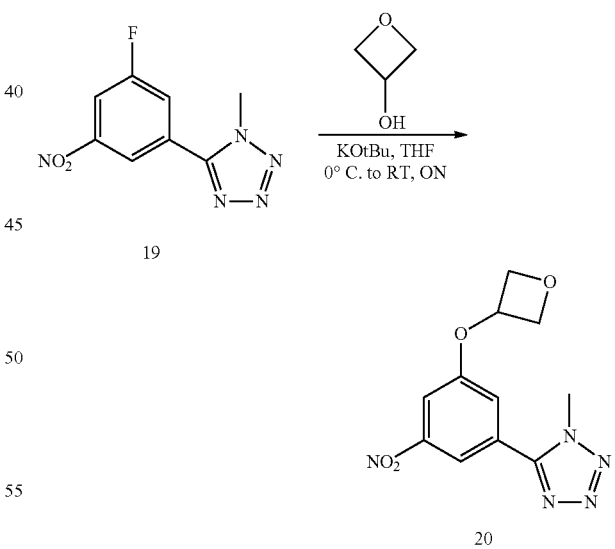

3-Hydroxy oxetane (0.665 g, 8.96 mmol, 2 equiv) in THF (10 mL) under nitrogen gas, was cooled to 0° C. Potassium tert-butoxide (1.11 g, 9.86 mmol, 2.2 equiv) was added in one portion, and the reaction mixture was stirred for 20 minutes at 0° C. Then, fluoro tetrazole 19 (1.0 g, 4.48 mmol, 1 equiv) was added in one portion, and the reaction mixture was stirred for 10 minutes at 0° C. and allowed to warm up to ambient temperature overnight. The reaction mixture was concentrated, and the residue was taken in dichloromethane and water. The layers were separated, and the organic layer was washed with water 2×, dried over Na₂SO₄, filtered, and concentrated. The crude product was purified by flash chromatography and eluted with DCM:ACE=100:0 to 97:3 using 1% ACE increments to give nitro 20 (561 mg, 45%) as a solid.

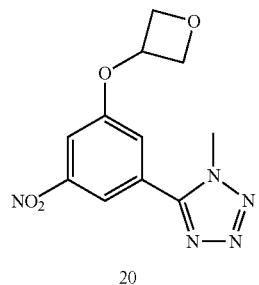

20

H₂ (1 amt), 10% Pd/C
EtOH, 2 h

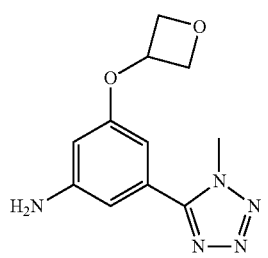

21

A suspension of nitro 20 (561 mg, 2.02 mmol, 1 equiv) in ethanol (4 mL) was charged with 10% Pd/C (50% water, 430 mg, 0.202 mmol, 0.10 equiv) and air was evacuated with vacuum. The vacuum was replaced with a balloon filled with hydrogen gas, and the reaction was allowed to stir for 2 hours. The catalyst was filtered off using a pad of celite and rinsed with ethanol. The filtrate was concentrated, and the crude product was purified by flash chromatography and eluted with DCM:ACE=100:0 to 70:30 using 10% ACE increments to give aniline 21 (375 mg, 75%) as a solid.

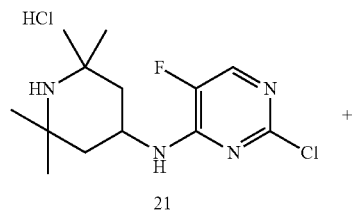

21

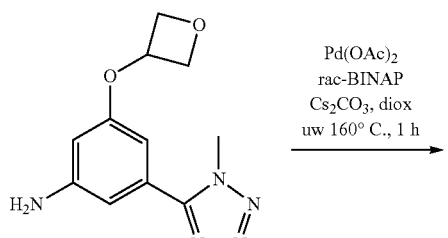

22

Pd(OAc)₂
rac-BINAP
Cs₂CO₃, diox
uw 160° C., 1 h

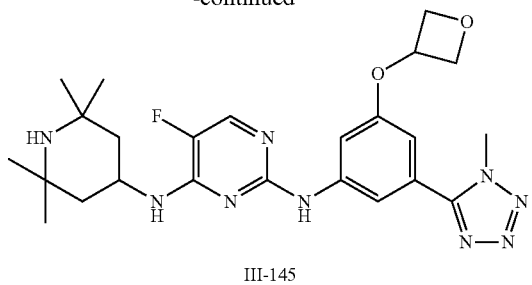

III-145

To a microwave vial, was added pyrimidine hydrochloride 22 (100 mg, 0.309 mmol, 1 equiv), aniline 21 (150 mg, 0.619 mmol, 2 equiv), rac-BINAP (40 mg, 0.0619 mmol, 0.2 equiv), Cs₂CO₃ (510 mg, 1.55 mmol, 5 equiv), Pd(OAc)₂ (7 mg, 0.0309 mmol, 0.1 equiv), and dioxane (3 mL). The microwave vial was capped and sonicated under vacuum for 5 minutes. The reaction mixture was heated in the microwave at 160° C. for 1 hour. The cooled reaction mixture was filtered using a pad of celite and rinsed with methanol and concentrated. The crude product was purified by flash chromatography and eluted with DCM:2M NH₃/MeOH 100:0 to 96:4 using 1% 2M NH₃/MeOH increments to provide Compound III-145 (143 mg, 93%) as a solid.

Example 6

5-fluoro-N2-(3-(1-methyl-1H-tetrazol-5-yl)-5-(oxetan-3-yloxy)phenyl)-N4-(1,2,2,6,6-pentamethylpiperidin-4-yl)pyrimidine-2,4-diamine (Compound III-146)

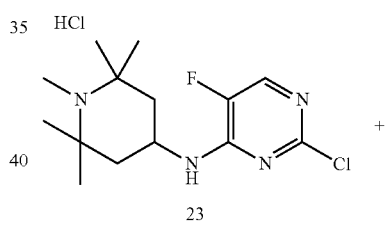

23

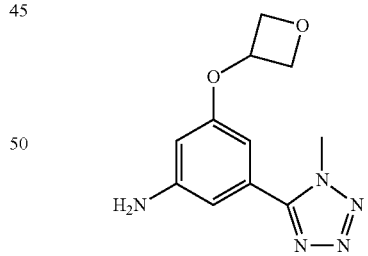

22

Pd(OAc)₂
rac-BINAP
Cs₂CO₃, diox
uw 160° C., 1 h

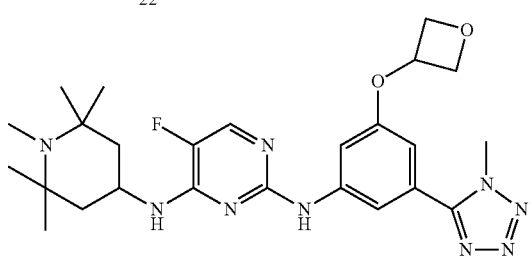

III-146

To a microwave vial, was added pyrimidine hydrochloride 23 (105 mg, 0.309 mmol, 1 equiv), aniline 22 (150 mg, 0.619 mmol, 2 equiv), rac-BINAP (40 mg, 0.0619 mmol, 0.2 equiv), Cs$_2$CO$_3$ (510 mg, 1.55 mmol, 5 equiv), Pd(OAc)$_2$ (7 mg, 0.0309 mmol, 0.1 equiv), and dioxane (3 mL). The microwave vial was capped and sonicated under vacuum for 5 minutes. The reaction mixture was heated in the microwave at 160° C. for 1 hour. The cooled reaction mixture was filtered using a pad of celite and rinsed with methanol and concentrated. The crude product was purified by flash chromatography and eluted with DCM:2M NH$_3$/MeOH=100:0 to 96:4 using 1% 2M NH$_3$/MeOH increments to provide Compound III-146 (147 mg, 93%) as a solid.

Example 7

N2-(4-cyclopropyl-3-(1-methyl-1H-tetrazol-5-yl) phenyl)-5-fluoro-N4-(2,2,6,6-tetramethylpiperidin-4-yl)pyrimidine-2,4-diamine (Compound III-148) and N2-(3-cyclopropyl-5-(1-methyl-1H-tetrazol-5-yl) phenyl)-5-fluoro-N4-(2,2,6,6-tetramethylpiperidin-4-yl)pyrimidine-2,4-diamine (Compound III-147)

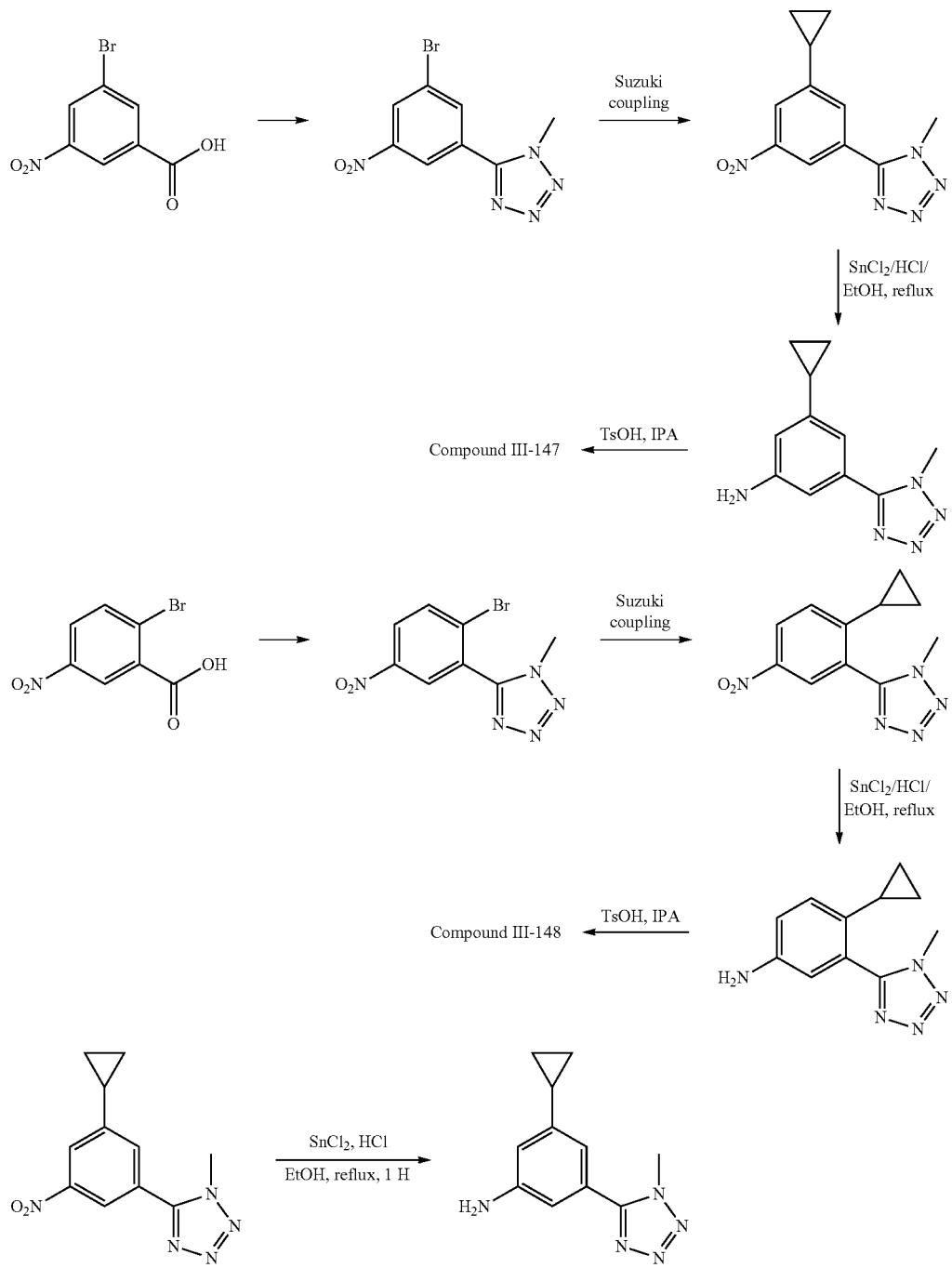

Preparation of 3-Cyclopropyl-5-(1-methyl-1H-tetrazol-5-yl)benzenamine 5-(3-Cyclopropyl-5-nitrophenyl)-1-methyl-1H-tetrazole (1.4 g, 5.7 mmol) was treated with tin (II) chloride (4.3 g, 22.8 mmol) and hydrochloric acid (0.5 mL) in ethanol (15 mL) at reflux for 1 hour. The solvent was removed under vacuum. The residue was partitioned between ethyl acetate and water. The organic layer was washed with 1M aqueous potassium carbonate solution, dried over anhydrous sodium sulfate and concentrated under vacuum. The resulting residue was purified by column chromatography, on silica gel, eluting with hexanes:ethyl acetate (70:30), to yield 3-cyclopropyl-5-(1-methyl-1H-tetrazol-5-yl)benzenamine (520 mg, 43% yield) as an off-white solid.

$^1$H NMR (DMSO d$_6$, 300 MHz): δ 6.75 (s, 1H), 6.61 (s, 1H), 6.48 (s, 1H), 5.38 (s, 2H), 4.13 (s, 3H), 1.84-1.79 (m, 1H), 0.92 (d, 2H), 0.61 (d, 2H); LCMS (m/z): 216 (MH$^+$).

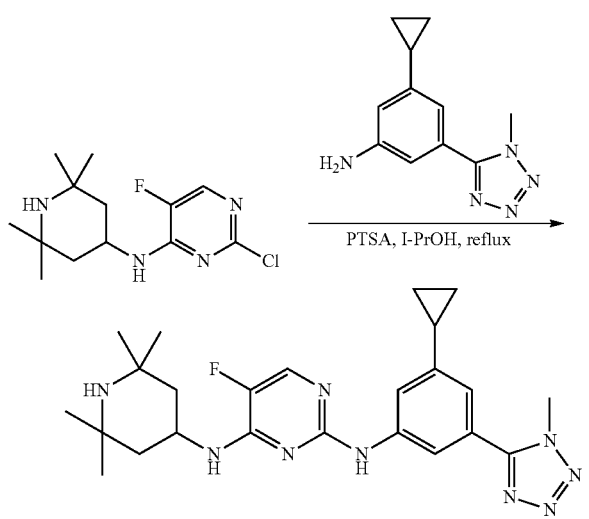

III-147

Preparation of N2-(3-Cyclopropyl-5-(1-methyl-1H-tetrazol-5-yl)phenyl)-5-fluoro-N4-(2,2,6,6-tetramethylpiperidin-4-yl)pyrimidine-2,4-diamine (Compound III-147)

2-Chloro-5-fluoro-N-(2,2,6,6-tetramethylpiperidin-4-yl)pyrimidin-4-amine (90 mg, 0.31 mmol) was treated with 3-cyclopropyl-5-(1-methyl-1H-tetrazol-5-yl)benzenamine (80 mg, 0.37 mmol) and p-toluenesulfonic acid monohydrate (48 mg, 0.25 mmol) in isopropanol (5 mL) and heated at reflux, in a loosely capped vial, overnight. The solvent evaporated, over the course of the reaction. 2-Chloro-5-fluoro-N-(2,2,6,6-tetramethylpiperidin-4-yl)pyrimidin-4-amine remained in the reaction mixture. An additional equivalent of 3-cyclopropyl-5-(1-methyl-1H-tetrazol-5-yl)benzenamine was added, along with more isopropanol. The reaction was allowed to heat at reflux for an additional 8 hours. This process was repeated until the 2-chloro-5-fluoro-N-(2,2,6,6-tetramethylpiperidin-4-yl)pyrimidin-4-amine was consumed, 4 days later. The resulting residue was purified by column chromatography, on silica gel, eluting with methanol:methylene chloride (1:99) followed by 2M ammonia in methanol:methylene chloride (2:98), to yield N2-(3-cyclopropyl-5-(1-methyl-1H-tetrazol-5-yl)phenyl)-5-fluoro-N4-(2,2,6,6-tetramethylpiperidin-4-yl)pyrimidine-2,4-diamine (60 mg, 42% yield) as an off-white solid.

$^1$H NMR (DMSO d$_6$, 300 MHz): δ 9.18 (s, 1H), 8.05 (s, 1H), 7.94 (d, 1H), 7.45 (s, 1H), 7.00 (s, 1H), 4.40-4.30 (m, 1H), 4.11 (s, 3H), 1.99-1.82 (m, 3H), 1.37-1.10 (m, 11H), 1.00 (d, 3H), 0.86 (t, 3H), 0.72 (d, 2H); LCMS (m/z): 466 (MH$^+$).

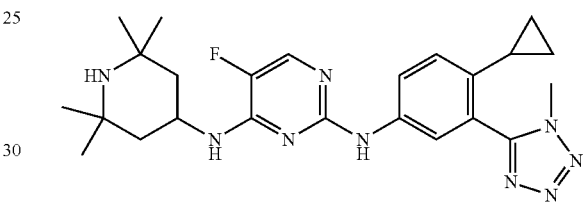

Preparation of N2-(4-cyclopropyl-3-(1-methyl-1H-tetrazol-5-yl)phenyl)-5-fluoro-N4-(2,2,6,6-tetramethylpiperidin-4-yl)pyrimidine-2,4-diamine (Compound III-148)

$^1$H NMR (DMSO d$_6$, 300 MHz): δ 9.15 (s, 1H), 7.92 (d, 1H), 7.86 (d, 1H), 7.60 (s, 1H), 7.22 (d, 1H), 6.94 (d, 1H), 4.42-4.30 (m, 1H), 3.95 (s, 3H), 1.67 (d, 2H), 1.49-1.40 (m, 1H), 1.19 (t, 3H), 1.08 (s, 6H), 1.00 (s, 6H), 0.75 (d, 2H), 0.50 (d, 2H); LCMS (m/z): 466 (MH$^+$).

Example 8

Certain compounds are synthesized as illustrated in the scheme below. In the scheme below, R is hydrogen or methyl.

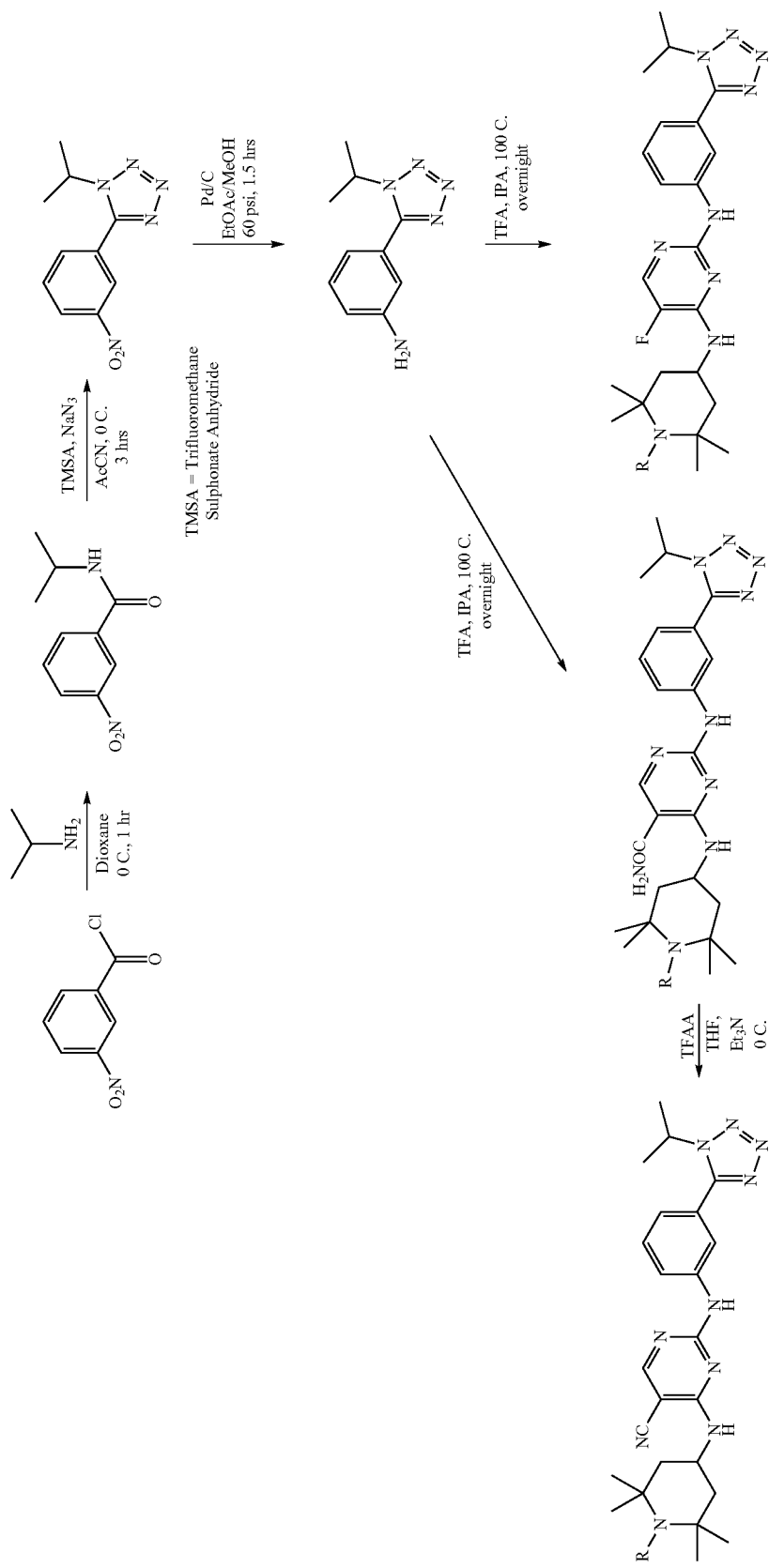

Example 9

3-methyl(1-methyl-tetrazol-5-yl)benzeneamine

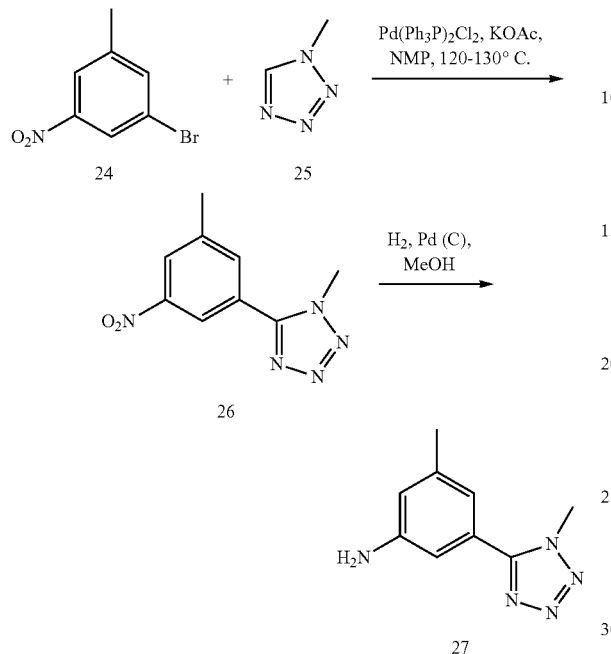

Step 1: Preparation of 1-methyl-5-(3-methyl-5-nitrophenyl)-1H-tetrazole

A mixture of 3-bromo-5-nitrotoluene (Compound 24; 0.33 g, 1.5 mmol), 1-methyltetrazole (Compound 25; 84 mg, 1.0 mmol), bis(triphenylphosphine)palladium(II) chloride (36 mg, 0.05 mmol) and KOAc (194 mg, 2.0 mmol) in N-methyl-2-pyrrolidinone (2 mL) in an open sealed tube was sparged with nitrogen for 5 minutes. The mixture was sealed and then heated to 120° C. in an oil bath and stirred overnight. After allowing to cool to room temperature, the mixture was poured into water (50 mL) and ethyl acetate (50 mL). The aqueous and organic layers were partitioned and the aqueous layer was extracted with ethyl acetate (1×20 mL). The combined organic extracts were washed with brine (1×30 mL), dried (MgSO$_4$), filtered and the solvent removed under vacuum to leave a crude oil. The oil was dry-loaded on to silica gel and then purified by column chromatography on silica gel using EtOAc/hexanes (1:9 to 6:4) as eluent to give Compound 26 (48 mg, 21%) as a solid. $^1$H NMR (DMSO d$_6$, 300 MHz): δ 8.44 (s, 1H), 8.32 (s, 1H), 8.10 (s, 1H), 4.19 (s, 1H), 2.54 (s, 1H).

A larger scale reaction performed at an oil bath temperature of 130° C. with 3.0 mmol of 3-bromo-5-nitrotoluene and using the other reagents in the appropriate stoichiometry as illustrated above gave Compound 26 (232 mg, 35%) as a solid. Compound 26 from both of these reactions were combined and used in the next step (Example 8, Step 2).

Step 2: Preparation of 3-methyl(1-methyl-tetrazol-5-yl)benzeneamine

A mixture of 1-methyl-5-(3-methyl-5-nitrophenyl)-1H-tetrazole (Compound 26; 280 mg, 1.3 mmol) suspended in methanol (10 mL) was hydrogenated over palladium on charcoal (40 mg) under a balloon of hydrogen. The mixture was stirred for about 2 hours. The reaction mixture was filtered through a pad of celite and the filter cake washed with methylene chloride (2×15 mL). The filtrate was concentrated under vacuum to leave a crude solid. The solid was dry-loaded onto silica gel and purified by column chromatography on silica gel using EtOAc/hexanes (0:1 to 1:0) as eluent to give Compound 27 (180 mg, 74%) as a solid.

Example 10

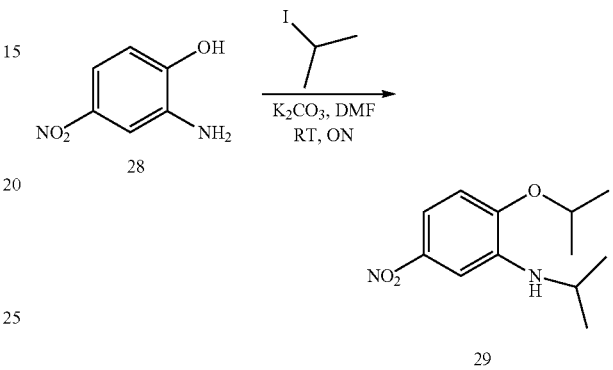

To a solution of 2-amino-4-nitrophenol 28 (15 g, 97.32 mmol, 1 equiv) in dimethylformamide (300 mL) under nitrogen gas, was added potassium carbonate (40.35 g, 292 mmol, 3 equiv) and isopropyl iodide (9.73 mL, 16.54 g, 97.32 mmol, 1 equiv), then the reaction mixture was stirred at ambient temperature overnight. LCMS analysis of the reaction mixture indicated a mixture of starting material:phenol alkylation:aniline phenol dialkylation (20:13:67). The reaction mixture was diluted with ethyl acetate and water. The layers were separated, and the organic layer was washed with water 1×, dried over Na$_2$SO$_4$, filtered, and concentrated. The crude reaction mixture was purified by flash chromatography and eluted with dichloromethane to provide 2-isopropoxy-N-isopropyl-5-nitrobenzenamine 29 (2.42 g, 10%) as an oil.

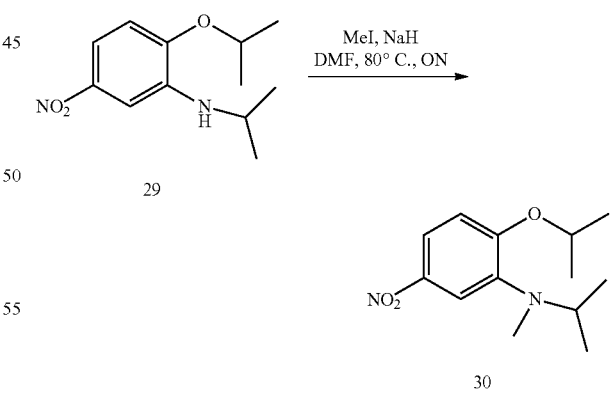

2-Isopropoxy-N-isopropyl-5-nitrobenzenamine 29 (218 mg, 0.915 mmol, 1 equiv) in DMF (4 mL) under nitrogen gas, was cooled to 0° C. Sodium hydride (60% oil, 168 mg, 3.84 mmol, 4.2 equiv) was added in one portion, and the reaction mixture was stirred for 10 minutes at 0° C. Methyl iodide (525 uL, 7.68 mmol, 8.4 equiv) was added at 0° C., then the reaction mixture was stirred at ambient temperature for 2 hours, and heated at 80° C. overnight. The reaction mixture was concentrated to dryness and directly loaded into a silica gel flash column and eluted with dichloromethane to provide 2-isopropoxy-N-isopropyl-N-methyl-5-nitrobenzenamine 30 (205 mg, 89%) as a solid.

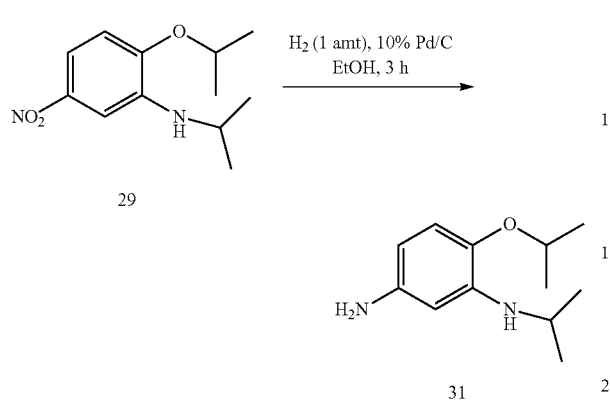

A suspension of 2-isopropoxy-N-isopropyl-5-nitrobenzenamine 29 (385 mg, 1.62 mmol, 1 equiv) in ethanol (3 mL) was charged with 10% Pd/C (50% water, 253 mg, 0.162 mmol, 0.10 equiv) and air was evacuated with vacuum. The vacuum was replaced with a balloon filled with hydrogen gas, and the reaction was allowed to stir for 2 hours. The catalyst was filtered off using a pad of celite and rinsed with ethanol. The filtrate was concentrated, and the crude product was purified by flash chromatography and eluted with hexane:EtOAc=100:0 to 50:50 using 5% EtOAc increments to give 6-isopropoxy-N1-isopropylbenzene-1,3-diamine 31 (263 mg, 78%) as a solid.

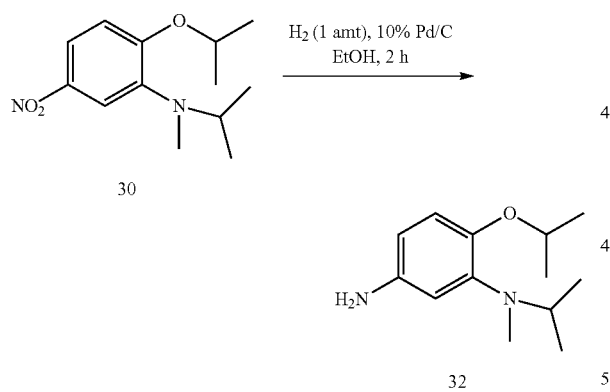

A suspension of 2-isopropoxy-N-isopropyl-N-methyl-5-nitrobenzenamine 3 (300 mg, 1.19 mmol, 1 equiv) in ethanol (3 mL) was charged with 10% Pd/C (50% water, 253 mg, 0.119 mmol, 0.10 equiv) and air was evacuated with vacuum. The vacuum was replaced with a balloon filled with hydrogen gas, and the reaction was allowed to stir for 2 hours. The catalyst was filtered off using a pad of celite and rinsed with ethanol. The filtrate was concentrated to give 6-isopropoxy-N-1-isopropyl-N-1-methylbenzene-1,3-diamine 5 (264 mg, 100%) as a solid which was used in the next step without further purification.

Example 11

Certain intermediates are synthesized as illustrated in the scheme below. In the scheme below, Ref 1 refers to WO 2005/040120 and Ref 2 refers to WO 2008/121687, which are incorporated by reference in their entireties.

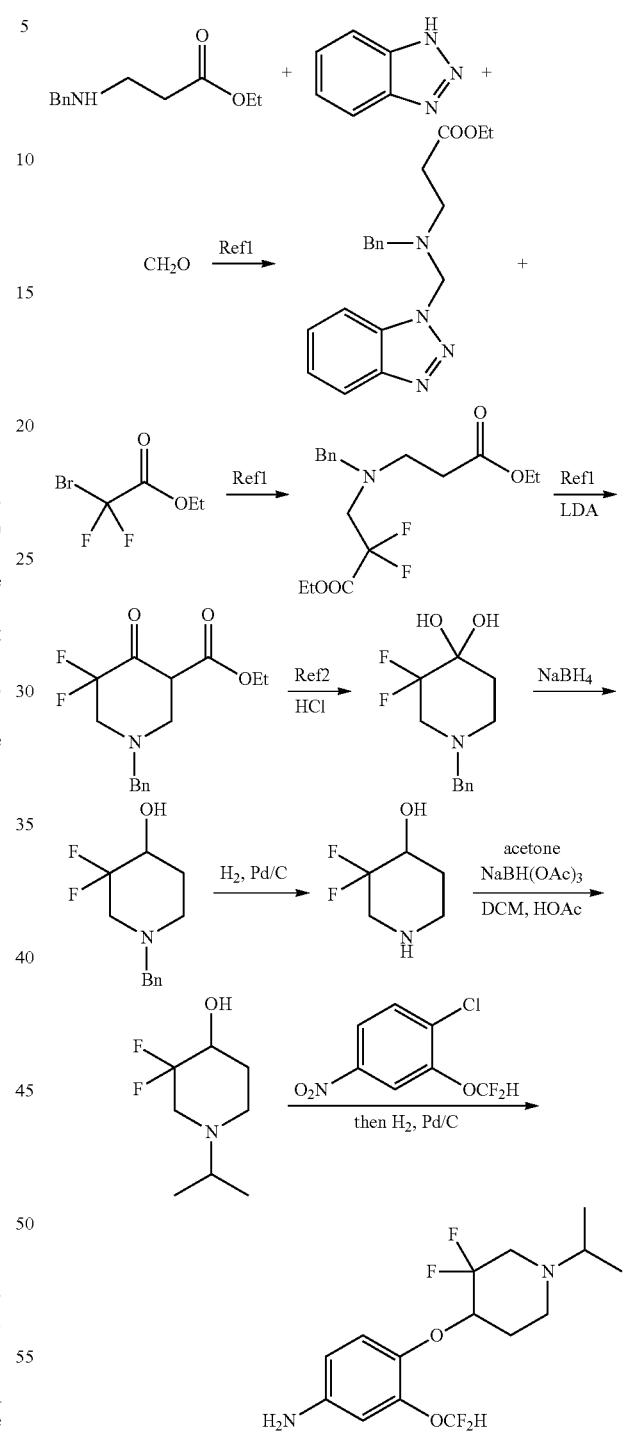

Example 12

Certain intermediates are synthesized as illustrated in the scheme below. In the scheme below. The starting material 2,3-difluoro-5-nitrobenzoic acid can be obtained from Butt Park Screening Library (United Kingdom).

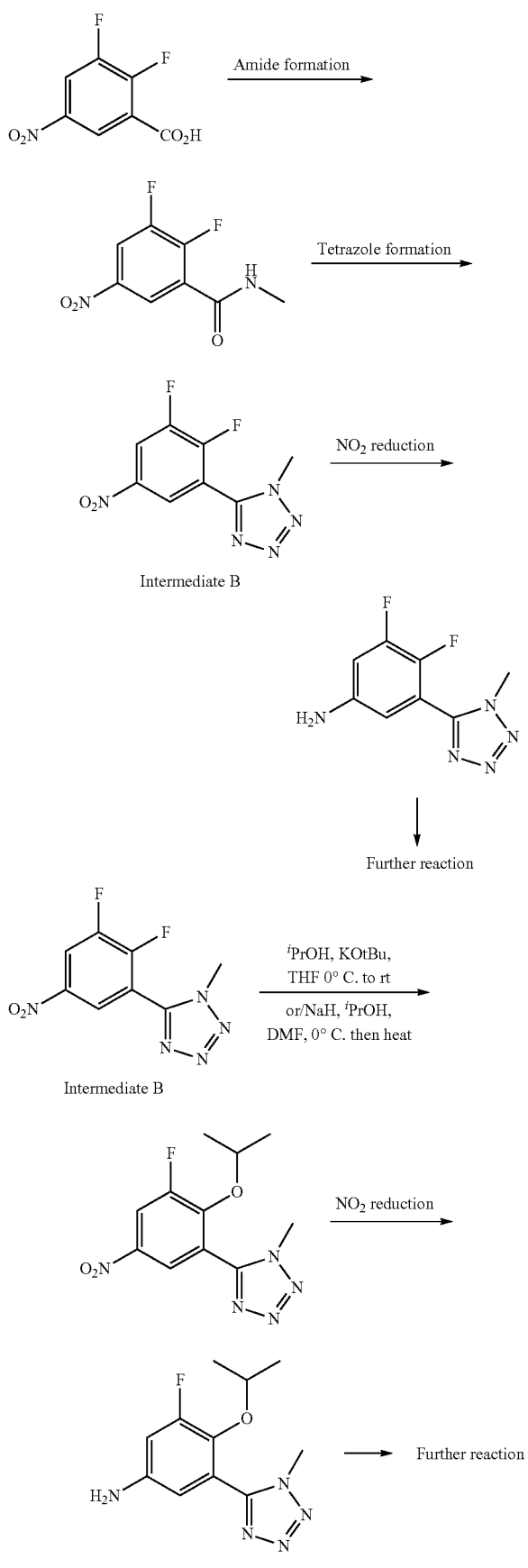

Example 13

The following compounds were made in a similar fashion to the foregoing Examples or by methods described herein or known to skilled artisans.

I-1: 5-fluoro-N2-(3-(3-methyl-1H-pyrazol-1-yl)phenyl)-N4-(1,2,2,6,6-pentamethylpiperidin-4-yl)pyrimidine-2,4-diamine MS (ES) 438 (M+H). $^1$H NMR (DMSO-$d_6$, 300 MHz) 9.21 (s, 1H), 8.19 (s, 1H), 8.16 (d, 1H), 7.89 (s, 2H), 7.44 (d, 1H), 7.19 (s, 2H), 6.26 (d, 1H), 4.39 (m, 1H), 2.39 (s, 3H), 2.23 (s, 3H), 1.91-1.82 (d, 2H), 1.72-1.62 (t, 2H), 1.21 (s, 6H), 1.15 (s, 6H) ppm.

I-2: 5-fluoro-N2-(3-(3-(trifluoromethyl)-1H-pyrazol-1-yl)phenyl)-N4-(1,2,2,6,6-pentamethylpiperidin-4-yl)pyrimidine-2,4-diamine MS (ES) 492 (M+H). $^1$H NMR (DMSO-$d_6$, 300 MHz) 9.25 (s, 1H), 8.59 (s, 1H), 8.16 (s, 1H), 7.96 (s, 2H), 7.38 (d, 1H), 7.29 (s, 2H), 6.96 (d, 1H), 4.39 (m, 1H), 2.29 (s, 3H), 1.85-1.75 (d, 2H), 1.62-1.49 (t, 2H), 1.19 (s, 6H), 1.05 (s, 6H) ppm.

I-3: 5-fluoro-N2-(3-(3-(trifluoromethyl)-1H-pyrazol-1-yl)phenyl)-N4-(2,2,6,6-tetramethylpiperidin-4-yl)pyrimidine-2,4-diamine MS (ES) 478 (M+H). $^1$H NMR (DMSO-$d_6$, 300 MHz) 9.15 (s, 1H), 8.32 (s, 2H), 7.79 (s, 2H), 7.68 (d, 1H), 7.49 (d, 1H), 7.25 (d, 2H), 6.25 (s, 1H), 4.42 (m, 1H), 1.92-1.85 (d, 2H), 1.58-1.49 (t, 2H), 1.31 (d, 12H) ppm.

I-4: N2-(4-(difluoromethoxy)-3-(2,5-dimethyl-1H-pyrrol-1-yl)phenyl)-5-fluoro-N4-(1,2,2,6,6-pentamethylpiperidin-4-yl)pyrimidine-2,4-diamine MS (ES) 517 (M+H). $^1$H NMR (DMSO-$d_6$, 300 MHz) 9.21 (s, 1H), 7.96 (d, 1H), 7.88 (d, 1H), 7.53 (s, 1H), 7.35 (bs, 1H), 7.19 (d, 1H), 6.82 (t, 1H), 5.75 (s, 2H), 4.42 (m, 1H), 2.39 (s, 3H), 1.92 (s, 6H), 1.85-1.75 (d, 2H), 1.65-1.55 (t, 2H), 1.15 (d, 12H) ppm.

I-5: N2-(4-(difluoromethoxy)-3-(2,5-dimethyl-1H-pyrrol-1-yl)phenyl)-5-fluoro-N4-(2,2,6,6-tetramethylpiperidin-4-yl)pyrimidine-2,4-diamine MS (ES) 503 (M+H). $^1$H NMR (DMSO-$d_6$, 300 MHz) 9.37 (s, 1H), 8.65 (d, 1H), 7.93 (d, 1H), 7.85 (dd, 2H), 7.59 (s, 1H), 7.23 (d, 1H), 6.82 (t, 1H), 5.75 (s, 2H), 4.49 (m, 1H), 2.05-1.92 (d, 2H), 1.89 (s, 6H), 1.65-1.51 (t, 2H), 1.35 (s, 12H) ppm.

I-6: N2-(3-(2-(1H-1,2,3-triazol-1-yl)ethoxy)-5-fluorophenyl)-5-fluoro-N4-(1,2,2,6,6-pentamethylpiperidin-4-yl)pyrimidine-2,4-diamine MS (ES) 487 (M+H). $^1$H NMR (DMSO-$d_6$, 300 MHz) 8.55 (d, 1H), 8.05 (d, 1H), 7.79 (s, 1H), 7.46 (d, 1H), 7.28 (d, 1H), 7.22 (s, 1H), 6.89 (s, 1H), 6.44 (d, 1H), 4.77 (t, 2H), 4.42 (t, 3H), 2.29 (s, 3H), 2.09-2.01 (d, 2H), 1.89-1.75 (t, 2H), 1.42 (d, 12H) ppm.

I-7: 5-fluoro-N2-(3-(3-methyl-1H-pyrazol-1-yl)phenyl)-N4-(2,2,6,6-tetramethylpiperidin-4-yl)pyrimidine-2,4-diamine MS (ES) 424 (M+H). $^1$H NMR (DMSO-$d_6$, 300 MHz) 9.19 (s, 1H), 8.35 (s, 1H), 8.19 (d, 1H), 7.91 (s, 2H), 7.68 (d, 1H), 7.49 (d, 1H), 7.21 (bs, 2H), 6.28 (s, 1H), 4.41 (m, 1H), 2.21 (s, 3H), 1.91-1.84 (d, 2H), 1.59-1.47 (t, 2H), 1.32 (d, 12H) ppm.

I-8: N2-(3-(2-(1H-1,2,3-triazol-1-yl)ethoxy)-5-fluorophenyl)-5-fluoro-N4-(2,2,6,6-tetramethylpiperidin-4-yl)pyrimidine-2,4-diamine MS (ES) 473 (M+H). $^1$H NMR (DMSO-d$_6$, 300 MHz) 8.65 (d, 1H), 8.29 (s, 1H), 8.16 (d, 1H), 7.78 (s, 1H), 7.48 (d, 1H), 7.23 (d, 1H), 7.15 (d, 1H), 6.82 (s, 1H), 6.47 (d, 1H), 4.72 (t, 2H), 4.45 (t, 3H), 1.99-1.81 (d, 2H), 1.65-1.55 (t, 2H), 1.42 (d, 12H) ppm.

I-9: 5-fluoro-N2-(4-fluoro-3-(5-methyl-1H-tetrazol-1-yl)phenyl)-N4-(1,2,2,6,6-pentamethylpiperidin-4-yl)pyrimidine-2,4-diamine MS (ES) 458 (M+H). $^1$H NMR (DMSO-d$_6$, 300 MHz) 8.63 (d, 1H), 7.98 (d, 1H), 7.85 (m, 2H), 7.78 (d, 1H), 7.46 (t, 1H), 4.39 (m, 1H), 2.45 (s, 6H), 2.09-2.05 (d, 2H), 1.85-1.73 (t, 2H), 1.35 (d, 12H) ppm.

I-10: 5-fluoro-N2-(4-fluoro-3-(5-methyl-1H-tetrazol-1-yl)phenyl)-N4-(2,2,6,6-tetramethylpiperidin-4-yl)pyrimidine-2,4-diamine MS (ES) 444 (M+H). $^1$H NMR (DMSO-d$_6$, 300 MHz) 8.71 (d, 1H), 8.06 (d, 1H), 7.95 (dd, 2H), 7.89 (m, 2H), 7.46 (t, 1H), 4.39 (m, 1H), 2.41 (s, 3H), 1.99-1.82 (d, 2H), 1.65-1.53 (t, 2H), 1.35 (d, 12H) ppm.

I-11: N4-(1-(cyclopropylmethyl)-2,2,6,6-tetramethylpiperidin-4-yl)-5-fluoro-N-2-(4-fluoro-3-(5-methyl-1H-tetrazol-1-yl)phenyl)pyrimidine-2,4-diamine MS (ES) 498 (M+H). $^1$H NMR (DMSO-d$_6$, 300 MHz) 8.23 (s, 1H), 8.12 (d, 1H), 8.06 (d, 1H), 7.95 (dd, 1H), 7.85 (m, 1H), 7.46 (t, 1H), 4.35 (m, 1H), 3.11 (d, 2H), 2.41 (s, 3H), 1.95 (d, 4H), 1.39 (s, 6H), 1.22 (s, 6H), 1.15 (m, 1H), 0.65 (d, 2H), 0.41 (d, 2H) ppm.

I-12: N2-(3-(1H-1,2,4-triazol-1-yl)phenyl)-5-fluoro-N4-(1,2,2,6,6-pentamethylpiperidin-4-yl)pyrimidine-2,4-diamine MS (ES) 425 (M+H). $^1$H NMR (DMSO-d$_6$, 300 MHz) 9.26 (s, 1H), 9.14 (s, 1H), 8.16 (d, 2H), 8.42 (s, 1H), 7.88 (d, 1H), 7.82 (d, 1H), 7.31 (m, 2H), 4.35 (m, 1H), 2.25 (s, 3H), 1.81-1.72 (d, 2H), 1.55-1.43 (t, 2H), 1.15 (s, 6H), 1.01 (s, 6H) ppm.

I-13: N2-(4-ethoxy-3-(2,5-dimethyl-1H-pyrrol-1-yl)phenyl)-5-fluoro-N4-(1,2,2,6,6-pentamethylpiperidin-4-yl)pyrimidine-2,4-diamine MS (ES) 495 (M+H). $^1$H NMR (DMSO-d$_6$, 300 MHz) 8.51 (s, 1H), 8.11 (d, 1H), 7.57 (s, 1H), 7.45 (d, 1H), 7.39 (s, 1H), 7.09 (d, 1H), 5.71 (s, 2H), 4.42 (m, 1H), 3.89 (q, 2H), 2.29 (s, 3H), 2.11-2.05 (d, 2H), 1.89 (s, 6H), 1.85-1.72 (t, 2H), 1.39 (d, 12H), 1.14 (t, 3H) ppm.

I-14: N2-(4-ethoxy-3-(2,5-dimethyl-1H-pyrrol-1-yl)phenyl)-5-fluoro-N4-(2,2,6,6-tetramethylpiperidin-4-yl)pyrimidine-2,4-diamine MS (ES) 481 (M+H). $^1$H NMR (DMSO-d$_6$, 300 MHz) 8.81 (s, 1H), 8.55 (d, 1H), 8.11 (d, 1H), 7.81 (d, 1H), 7.45 (d, 1H), 7.21 (s, 1H), 7.15 (d, 1H), 5.71 (s, 2H), 4.42 (m, 1H), 3.82 (q, 2H), 1.89 (m, 8H), 1.65-1.52 (t, 2H), 1.39 (d, 12H), 1.14 (t, 3H) ppm.

I-15: N2-(4-isopropyloxy-3-(2,5-dimethyl-1H-pyrrol-1-yl)phenyl)-5-fluoro-N4-(1,2,2,6,6-pentamethylpiperidin-4-yl)pyrimidine-2,4-diamine MS (ES) 509 (M+H). $^1$H NMR (DMSO-d$_6$, 300 MHz) 8.55 (s, 1H), 8.05 (s, 1H), 7.99 (s, 1H), 7.49 (d, 1H), 7.29 (s, 1H), 7.05 (d, 1H), 5.71 (s, 2H), 4.42 (m, 1H), 4.15 (m, 1H), 2.29 (s, 3H), 2.09-2.01 (d, 2H), 1.89 (s, 6H), 1.85-1.79 (t, 2H), 1.35 (d, 12H), 1.05 (d, 6H) ppm.

I-16: N2-(4-isopropyloxy-3-(2,5-dimethyl-1H-pyrrol-1-yl)phenyl)-5-fluoro-N4-(2,2,6,6-tetramethylpiperidin-4-yl)pyrimidine-2,4-diamine MS (ES) 495 (M+H). $^1$H NMR (DMSO-d$_6$, 300 MHz) 8.59 (d, 1H), 8.19 (s, 1H), 8.09 (d, 1H), 7.79 (d, 1H), 7.49 (d, 1H), 7.32 (s, 1H), 7.09 (d, 1H), 5.71 (s, 2H), 4.42 (m, 1H), 4.15 (m, 1H), 1.89 (m, 8H), 1.65-1.55 (t, 2H), 1.35 (d, 12H), 1.05 (d, 6H) ppm.

I-17: 4-(2,2,6,6-tetramethylpiperidin-4-ylamino)-2-(3-(2-(1H-1,2,3-triazol-1-yl)ethoxy)-5-fluorophenylamino)pyrimidine-5-carbonitrile MS (ES) 480 (M+H). $^1$H NMR (DMSO-d$_6$, 300 MHz) 9.95 (bs, 1H), 8.69 (d, 1H), 8.39 (s, 1H), 7.89 (d, 2H), 7.78 (s, 1H), 7.34 (d, 1H), 6.89 (s, 1H), 6.49 (d, 1H), 4.79 (t, 2H), 4.61 (m, 1H), 4.42 (t, 2H), 1.95-1.87 (d, 2H), 1.75-1.61 (t, 2H), 1.39 (d, 12H) ppm.

I-18: 4-(2,2,6,6-tetramethylpiperidin-4-ylamino)-2-(4-fluoro-3-(5-methyl-1H-tetrazol-1-yl)phenylamino)pyrimidine-5-carbonitrile MS (ES) 480 (M+H). $^1$H NMR (DMSO-d$_6$, 300 MHz) 10.14 (bs, 1H), 8.64 (d, 1H), 8.39 (s, 1H), 7.89 (m, 3H), 7.55 (t, 1H), 4.49 (m, 1H), 2.49 (s, 3H), 1.91-1.87 (d, 2H), 1.69-1.59 (t, 2H), 1.31 (d, 12H) ppm.

I-19: N2-(3-(1H-1,2,4-triazol-1-yl)phenyl)-5-fluoro-N4-(2,2,6,6-tetramethylpiperidin-4-yl)pyrimidine-2,4-diamine MS (ES) 425 (M+H). $^1$H NMR (DMSO-d$_6$, 300 MHz) 9.79 (s, 1H), 9.21 (s, 1H), 8.69 (d, 1H), 8.19 (s, 1H), 8.05 (d, 2H), 7.81 (d, 1H), 7.62 (s, 1H), 7.39 (m, 2H), 4.42 (m, 1H), 1.98-1.92 (d, 2H), 1.62-1.52 (t, 2H), 1.32 (s, 6H), 1.25 (s, 6H) ppm.

I-20: 5-fluoro-N2-(3-(5-methyl-1H-tetrazol-1-yl)-4-(trifluoromethoxy)phenyl)-N4-(1,2,2,6,6-pentamethylpiperidin-4-yl)pyrimidine-2,4-diamine MS (ES) 524 (M+H). $^1$H NMR (DMSO-d$_6$, 300 MHz) 8.53 (d, 1H), 8.12 (d, 1H), 7.98 (s, 1H), 7.78 (d, 1H), 7.46 (d, 1H), 7.09 (d, 1H), 4.39 (m, 1H), 2.45 (s, 3H), 2.29 (s, 3H), 2.09-2.01 (d, 2H), 1.85-1.73 (t, 2H), 1.35 (d, 12H) ppm.

I-21: 5-fluoro-N2-(3-(5-methyl-1H-tetrazol-1-yl)-4-(trifluoromethoxy)phenyl)-N4-(2,2,6,6-tetramethylpiperidin-4-yl)pyrimidine-2,4-diamine MS (ES) 524 (M+H). $^1$H NMR (DMSO-d$_6$, 300 MHz) 8.53 (d, 1H), 8.02 (s, 1H), 7.98 (d, 1H), 7.78 (d, 1H), 7.62 (bm, 1H), 7.46 (d, 1H), 7.09 (d, 1H), 4.39 (m, 1H), 2.45 (s, 3H), 1.99-1.91 (d, 2H), 1.62-1.52 (t, 2H), 1.35 (d, 12H) ppm.

I-22: N2-(3-(1H-pyrazol-1-yl)phenyl)-5-fluoro-N4-(1,2,2,6,6-pentamethylpiperidin-4-yl)pyrimidine-2,4-diamine MS (ES) 424 (M+H). $^1$H NMR (DMSO-d$_6$, 300 MHz) 8.32 (d, 1H), 8.18 (d, 1H), 7.98 (s, 1H), 7.88 (d, 1H), 7.78 (d, 1H), 7.66 (s, 1H), 7.26 (m, 3H), 6.48 (t, 1H), 4.35 (m, 1H), 2.29 (s, 3H), 1.83-1.72 (d, 2H), 1.59-1.49 (t, 2H), 1.09 (d, 12H) ppm.

I-23: N2-(3-(1H-pyrazol-1-yl)phenyl)-5-fluoro-N4-(2,2,6,6-tetramethylpiperidin-4-yl)pyrimidine-2,4-diamine MS (ES) 410 (M+H). $^1$H NMR (DMSO-$d_6$, 300 MHz) 9.21 (s, 1H), 8.34 (d, 1H), 8.26 (d, 1H), 8.04 (s, 1H), 7.91 (d, 1H), 7.68 (m, 2H), 7.48 (d, 1H), 7.26 (d, 2H), 6.49 (t, 1H), 4.45 (m, 1H), 1.93-1.84 (d, 2H), 1.53-1.49 (t, 2H), 1.39 (s, 12H) ppm.

I-24: N2-(4-(2-(1H-1,2,3-triazol-1-yl)ethoxy)-3-(difluoromethoxy)phenyl)-5-fluoro-N4-(2,2,6,6-tetramethylpiperidin-4-yl)pyrimidine-2,4-diamine MS (ES) 521 (M+H). $^1$H NMR (DMSO-$d_6$, 300 MHz) 9.94 (s, 1H), 8.97 (s, 1H), 8.64 (d, 1H), 8.14 (d, 1H), 7.79-7.81 (m, 2H), 7.35 (s, 1H), 7.26 (dd, 1H), 7.12 (s, 1H), 6.77 (t, 1H), 4.82 (t, 2H), 4.51 (t, 2H), 4.33-4.43 (m, 1H), 1.90 (d, 2H), 1.62 (t, 2H), 1.36 (s, 6H), 1.30 (s, 6H) ppm.

I-25: N2-(4-(2-(1H-1,2,4-triazol-1-yl)ethoxy)-3-(difluoromethoxy)phenyl)-5-fluoro-N4-(2,2,6,6-tetramethylpiperidin-4-yl)pyrimidine-2,4-diamine MS (ES) 521 (M+H). $^1$H NMR (DMSO-$d_6$, 300 MHz) 9.99 (s, 1H), 9.01 (s, 1H), 8.68 (d, 1H), 8.59 (s, 1H), 8.15 (d, 1H), 8.05 (s, 1H), 7.83 (d, 1H), 7.30 (s, 1H), 7.26 (dd, 1H), 6.88 (t, 1H), 4.61 (d, 2H), 4.37 (d, 2H), 1.88 (d, 2H), 1.61 (d, 2H), 1.36 (s, 6H), 1.28 (s, 6H) ppm.

I-26: N2-(4-(2-(1H-1,2,3-triazol-1-yl)ethoxy)-3-(difluoromethoxy)phenyl)-5-fluoro-N4-(1,2,2,6,6-pentamethylpiperidin-4-yl)pyrimidine-2,4-diamine MS (ES) 535 (M+H). $^1$H NMR (DMSO-$d_6$, 300 MHz) 8.99 (s, 1H), 7.82 (d, 1H), 7.80 (s, 2H), 7.48-7.51 (m, 2H), 7.31 (d, 1H), 6.96 (d, 1H), 6.70 (t, 1H), 4.79 (t, 2H), 4.45 (t, 2H), 4.39-4.45 (m, 1H), 2.39 (s, 3H), 1.83 (dd, 2H), 1.60 (t, 2H), 1.19 (s, 12H) ppm.

I-27: N2-(4-(2-(1H-1,2,4-triazol-1-yl)ethoxy)-3-(difluoromethoxy)phenyl)-5-fluoro-N4-(1,2,2,6,6-pentamethylpiperidin-4-yl)pyrimidine-2,4-diamine MS (ES) 535 (M+H). $^1$H NMR (DMSO-$d_6$, 300 MHz) 8.99 (s, 1H), 8.50 (s, 1H), 7.98 (s, 1H), 7.84 (d, 1H), 7.48-7.52 (m, 2H), 7.34 (d, 1H), 6.93 (d, 1H), 6.80 (t, 1H), 4.57 (t, 2H), 4.30-4.44 (m, 1H), 4.31 (t, 2H), 2.41 (s, 3H), 1.82 (d, 2H), 1.64 (t, 2H), 1.22 (s, 6H), 1.20 (s, 6H) ppm.

I-28: N2-(3-(2-(1H-1,2,4-triazol-1-yl)ethoxy)-5-(trifluoromethyl)phenyl)-5-fluoro-N4-(2,2,6,6-tetramethylpiperidin-4-yl)pyrimidine-2,4-diamine MS (ES) 523 (M+H). $^1$H NMR (DMSO-$d_6$, 300 MHz) 9.51 (s, 1H), 8.58-8.63 (m, 2H), 8.06 (d, 1H), 8.03 (d, 1H), 7.78 (d, 1H), 7.55 (s, 1H), 7.52 (s, 1H), 6.83 (s, 1H), 4.56 (t, 2H), 4.40-4.49 (m, 1H), 4.40 (t, 2H), 1.93 (d, 2H), 1.59 (t, 2H), 1.36 (s, 12H) ppm.

I-29: N2-(3-(2-(1H-1,2,4-triazol-1-yl)ethoxy)-5-(trifluoromethyl)phenyl)-5-fluoro-N4-(1,2,2,6,6-pentamethylpiperidin-4-yl)pyrimidine-2,4-diamine MS (ES) 537 (M+H). $^1$H NMR (DMSO-$d_6$, 300 MHz) 9.42 (s, 1H), 8.54-8.56 (m, 1H), 8.11 (s, 1H), 7.99 (s, 1H), 7.70-7.72 (m, 1H), 7.63 (s, 1H), 7.54 (s, 1H), 6.76 (s, 1H), 4.57 (t, 2H), 4.41 (t, 2H), 4.40-4.48 (m, 1H), 2.75 (s, 3H), 2.07 (d, 2H), 1.80 (t, 2H), 1.40 (s, 6H), 1.38 (s, 6H) ppm.

I-30: 1-(2-(4-(4-(2,2,6,6-tetramethylpiperidin-4-ylamino)-5-fluoropyrimidin-2-ylamino)-2-(difluoromethoxy)phenoxy)ethyl)pyrrolidin-2-one MS (ES) 537 (M+H). $^1$H NMR (DMSO-$d_6$, 300 MHz) 9.94 (s, 1H), 8.96 (s, 1H), 8.66 (d, 1H), 8.14 (d, 1H), 7.82 (d, 1H), 7.37 (s, 1H), 7.28 (s, 1H), 7.03 (t, 1H), 4.32-4.45 (m, 1H), 4.10 (t, 2H), 3.55 (t, 2H), 3.45 (t, 2H), 2.21 (t, 2H), 1.89-1.97 (m, 4H), 1.62 (t, 2H), 1.36 (s, 6H), 1.31 (s, 6H) ppm.

I-31: 1-(2-(4-(4-(1,2,2,6,6-pentamethylpiperidin-4-ylamino)-5-fluoropyrimidin-2-ylamino)-2-(difluoromethoxy)phenoxy)ethyl)pyrrolidin-2-one MS (ES) 551 (M+H). $^1$H NMR (DMSO-$d_6$, 300 MHz) 9.88 (s, 1H), 8.90 (s, 1H), 8.59 (d, 1H), 8.13 (s, 1H), 7.36 (s, 1H), 7.33 (d, 1H), 7.05 (t, 1H), 4.32-4.43 (m, 1H), 4.10 (t, 2H), 3.55 (t, 2H), 3.46 (t, 2H), 2.73 (s, 3H), 2.21 (t, 2H), 1.79-2.03 (m, 6H), 1.39 (s, 6H), 1.27 (s, 6H) ppm.

I-32: N2-(3-(2-(1H-1,2,3-triazol-1-yl)ethoxy)-5-(trifluoromethyl)phenyl)-5-fluoro-N4-(2,2,6,6-tetramethylpiperidin-4-yl)pyrimidine-2,4-diamine MS (ES) 523 (M+H). $^1$H NMR (DMSO-$d_6$, 300 MHz) 9.41 (s, 1H), 8.61 (d, 1H), 8.01 (d, 1H), 7.79-7.81 (m, 3H), 7.60 (s, 1H), 7.50 (s, 1H), 6.76 (s, 1H), 4.78 (t, 2H), 4.53 (t, 2H), 4.40-4.50 (m, 1H), 1.95 (d, 2H), 1.59 (t, 2H), 1.41 (s, 6H), 1.37 (s, 6H) ppm.

I-33: N2-(3-(2-(1H-1,2,3-triazol-1-yl)ethoxy)-5-(trifluoromethyl)phenyl)-5-fluoro-N4-(1,2,2,6,6-pentamethylpiperidin-4-yl)pyrimidine-2,4-diamine MS (ES) 537 (M+H). $^1$H NMR (DMSO-$d_6$, 300 MHz) 9.37 (s, 1H), 8.53 (s, 1H), 8.00 (d, 1H), 7.79-7.80 (m, 3H), 7.64 (s, 1H), 7.47 (s, 1H), 6.75 (s, 1H), 4.79 (t, 2H), 4.53 (t, 2H), 4.39-4.50 (m, 1H), 2.75 (s, 3H), 2.06 (d, 2H), 1.80 (t, 2H), 1.40 (s, 6H), 1.38 (s, 6H) ppm.

I-34: 4-(2,2,6,6-tetramethylpiperidin-4-ylamino)-2-(4-(2-(1H-1,2,3-triazol-1-yl)ethoxy)-3-(difluoromethoxy)phenylamino)pyrimidine-5-carbonitrile MS (ES) 528 (M+H). $^1$H NMR (DMSO-$d_6$, 300 MHz) 9.80 (s, 1H), 8.31 (s, 2H), 7.80 (s, 2H), 7.47-7.56 (m, 4H), 7.00 (d, 1H), 6.73 (t, 1H), 4.80 (t, 2H), 4.49-4.59 (m, 1H), 4.47 (t, 2H), 1.72 (d, 2H), 1.45 (t, 2H), 1.27 (s, 6H), 1.19 (s, 6H) ppm.

I-35: N2-(3-(3-(1H-pyrrol-1-yl)propoxy)-5-fluorophenyl)-5-fluoro-N4-(2,2,6,6-tetramethylpiperidin-4-yl)pyrimidine-2,4-diamine MS (ES) 485 (M+H). $^1$H NMR (DMSO-$d_6$, 300 MHz) 9.43 (s, 1H), 8.63 (d, 1H), 8.00 (d, 1H), 7.80 (d, 1H), 7.25 (d, 1H), 6.97 (s, 1H), 6.72 (s, 2H), 6.36 (d, 1H), 5.97 (d, 2H), 4.47-4.58 (m, 1H), 4.01 (t, 2H), 3.82 (t, 2H), 2.06-2.14 (m, 2H), 1.97 (d, 2H), 1.61 (t, 2H), 1.45 (s, 6H), 1.38 (s, 6H) ppm.

I-36: N2-(3-(3-(1H-pyrrol-1-yl)propoxy)-5-fluorophenyl)-5-fluoro-N4-(1,2,2,6,6-pentamethylpiperidin-4-yl)pyrimidine-2,4-diamine MS (ES) 499 (M+H). $^1$H NMR (DMSO-$d_6$, 300 MHz) 9.29 (s, 1H), 8.54 (d, 1H), 7.95 (d, 1H), 7.73 (d, 1H), 7.28 (d, 1H), 6.94 (s, 1H), 6.71 (s, 2H), 6.31 (d, 1H), 5.96 (d, 2H), 4.45-4.55

(m, 1H), 4.00 (t, 2H), 3.81 (t, 2H), 2.73 (s, 3H), 2.05-2.14 (m, 4H), 1.82 (t, 2H), 1.40 (s, 12H) ppm.

I-37: 1-(2-(3-(4-(2,2,6,6-tetramethylpiperidin-4-ylamino)-5-fluoropyrimidin-2-ylamino)-5-fluorophenoxy)ethyl)pyrrolidin-2-one MS (ES) 489 (M+H). $^1$H NMR (DMSO-d$_6$, 300 MHz) 9.66 (s, 1H), 8.65 (d, 1H), 8.07 (d, 1H), 7.81 (d, 1H), 7.25 (d, 1H), 6.90 (s, 1H), 6.51 (s, 1H), 4.44-4.58 (m, 1H), 4.03 (t, 2H), 3.51 (t, 2H), 3.42 (t, 2H), 2.22 (t, 2H), 1.89-1.98 (m, 4H), 1.62 (t, 2H), 1.42 (s, 6H), 1.38 (s, 6H) ppm.

I-38: 1-(2-(3-(4-(1,2,2,6,6-pentamethylpiperidin-4-ylamino)-5-fluoropyrimidin-2-ylamino)-5-fluorophenoxy)ethyl)pyrrolidin-2-one MS (ES) 503 (M+H). $^1$H NMR (DMSO-d$_6$, 300 MHz) 9.60 (s, 1H), 8.56 (s, 1H), 8.05 (d, 1H), 7.23 (d, 1H), 6.90 (s, 1H), 6.47 (d, 1H), 4.42-4.53 (m, 1H), 4.01 (t, 2H), 3.51 (t, 2H), 3.41 (t, 2H), 2.74 (s, 3H), 2.20 (t, 2H), 2.06 (d, 2H), 1.79-1.95 (m, 4H), 1.39 (s, 12H) ppm.

I-39: N2-(3-(2-(1H-1,2,4-triazol-1-yl)ethoxy)-5-fluorophenyl)-5-fluoro-N4-(2,2,6,6-pentamethylpiperidin-4-yl)pyrimidine-2,4-diamine MS (ES) 473 (M+H). $^1$H NMR (DMSO-d$_6$, 300 MHz) 9.58 (s, 1H), 8.60 (d, 1H), 8.03 (d, 1H), 7.77-7.79 (m, 2H), 7.24 (d, 1H), 6.84 (s, 1H), 6.45 (d, 1H), 4.76 (t, 2H), 4.45-4.54 (m, 1H), 4.43 (t, 2H), 1.94 (d, 2H), 1.60 (t, 2H), 1.39 (s, 6H), 1.36 (s, 6H) ppm.

I-40: N2-(3-(2-(1H-1,2,4-triazol-1-yl)ethoxy)-5-fluorophenyl)-5-fluoro-N4-(1,2,2,6,6-pentamethylpiperidin-4-yl)pyrimidine-2,4-diamine MS (ES) 487 (M+H). $^1$H NMR (DMSO-d$_6$, 300 MHz) 9.37 (s, 1H), 8.54 (s, 1H), 7.99 (d, 1H), 7.84-7.86 (m, 1H), 7.78 (s, 1H), 7.26 (d, 1H), 6.90 (s, 1H), 6.38 (d, 1H), 4.76 (t, 2H), 4.45-4.53 (m, 1H), 4.43 (t, 2H), 2.74 (s, 3H), 2.05 (d, 2H), 1.81 (t, 2H), 1.39 (s, 12H) ppm.

I-41: N2-(4-(3-(1H-pyrrol-1-yl)propoxy)-3-(difluoromethoxy)phenyl)-5-fluoro-N4-(1,2,2,6,6-pentamethylpiperidin-4-yl)pyrimidine-2,4-diamine MS (ES) 547 (M+H). $^1$H NMR (DMSO-d$_6$, 300 MHz) 8.97 (s, 1H), 7.85 (d, 1H), 7.51-7.53 (m, 2H), 7.24-7.28 (m, 1H), 6.99 (s, 1H), 6.89 (t, 1H), 6.71 (s, 2H), 5.97 (s, 2H), 4.33-4.44 (m, 1H), 4.04 (t, 2H), 3.84 (t, 2H), 2.35 (s, 3H), 2.06-2.14 (m, 2H), 1.80 (d, 2H), 1.57 (t, 2H) 1.18 (s, 12H) ppm.

I-42: N2-(4-(3-(1H-pyrrol-1-yl)propoxy)-3-(difluoromethoxy)phenyl)-5-fluoro-N4-(2,2,6,6-tetramethylpiperidin-4-yl)pyrimidine-2,4-diamine MS (ES) 533 (M+H). $^1$H NMR (DMSO-d$_6$, 300 MHz) 8.99 (s, 1H), 7.83 (s, 1H), 7.52-7.55 (m, 2H), 7.23-7.25 (m, 1H), 6.96 (s, 1H), 6.88 (t, 1H), 6.71 (s, 2H), 5.97 (s, 2H), 4.33-4.44 (m, 1H), 4.04 (t, 2H), 3.84 (t, 2H), 2.07-2.16 (m, 2H), 1.83 (d, 2H), 1.56 (t, 2H) 1.20 (s, 12H) ppm.

I-43: N2-(3-(difluoromethoxy)-4-(pyridin-4-yloxy)phenyl)-5-fluoro-N4-(1,2,2,6,6-pentamethylpiperidin-4-yl)pyrimidine-2,4-diamine MS (ES) 517 (M+H). $^1$H NMR (DMSO-d$_6$, 300 MHz) 9.45 (s, 1H), 7.90 (d, 1H), 7.83 (dd, 1H), 7.67 (s, 1H), 7.63 (d, 2H), 7.45 (d, 1H), 7.36 (d, 1H), 7.08 (t, 1H), 6.17 (d, 2H), 4.35-4.47 (m, 1H), 2.45 (s, 3H), 1.88 (d, 2H), 1.66 (t, 2H) 1.24 (s, 12H) ppm.

I-44: N2-(3-(difluoromethoxy)-4-(pyridin-3-yloxy)phenyl)-5-fluoro-N4-(1,2,2,6,6-pentamethylpiperidin-4-yl)pyrimidine-2,4-diamine MS (ES) 517 (M+H). $^1$H NMR (DMSO-d$_6$, 300 MHz) 9.61 (s, 1H), 8.55 (s, 1H), 8.33-8.36 (m, 2H), 8.00-8.15 (m, 2H), 7.63 (s, 1H), 7.60 (d, 1H), 7.36 (d, 1H), 7.16 (d, 1H), 7.09 (t, 1H), 4.40-4.51 (m, 1H), 2.72 (s, 3H), 2.06 (d, 2H), 1.82 (t, 2H) 1.40 (s, 6H), 1.36 (s, 6H), ppm.

I-45: N2-(3-(difluoromethoxy)-4-(pyridin-3-yloxy)phenyl)-5-fluoro-N4-(2,2,6,6-tetramethylpiperidin-4-yl)pyrimidine-2,4-diamine MS (ES) 503 (M+H). $^1$H NMR (DMSO-d$_6$, 300 MHz) 9.58 (s, 1H), 8.62 (d, 1H), 8.31-8.34 (m, 2H), 8.01 (d, 1H), 7.80 (d, 1H), 7.64 (s, 1H), 7.59 (d, 1H), 7.41 (s, 1H), 7.35 (s, 1H), 7.08 (t, 1H), 4.39-4.52 (m, 1H), 1.96 (d, 2H), 1.59 (t, 2H) 1.36 (s, 12H), ppm.

I-46: N2-(4-(2-(pyrrolidin-1-yl)ethoxy)-3-(difluoromethoxy)phenyl)-5-fluoro-N4-(1,2,2,6,6-pentamethylpiperidin-4-yl)pyrimidine-2,4-diamine MS (ES) 537 (M+H). $^1$H NMR (DMSO-d$_6$, 300 MHz) 8.99 (s, 1H), 8.23 (s, 1H), 7.85-7.86 (m, 1H), 7.50-7.52 (m, 1H), 7.34 (d, 1H), 7.07 (t, 1H), 6.99 (d, 1H), 4.34-4.48 (m, 1H), 4.13 (t, 2H), 2.97 (t, 2H), 2.73 (s, 4H), 2.41 (s, 3H), 1.64-1.82 (m, 8H), 1.22 (s, 12H) ppm.

I-47: N2-(4-(3-morpholinopropoxy)-3-(difluoromethoxy)phenyl)-5-fluoro-N4-(2,2,6,6-tetramethylpiperidin-4-yl)pyrimidine-2,4-diamine MS (ES) 553 (M+H). $^1$H NMR (DMSO-d$_6$, 300 MHz) 9.02 (s, 1H), 8.62 (d, 1H), 7.90 (d, 1H), 7.78 (d, 1H), 7.61 (s, 1H), 7.02 (t, 1H), 6.53 (s, 1H), 4.44-4.54 (m, 1H), 4.01 (t, 2H), 3.68-3.72 (m, 4H), 2.49-2.52 (m, 6H), 1.95-1.99 (m, 4H), 1.58 (t, 2H), 1.46 (s, 6H), 1.38 (s, 6H) ppm.

I-48: N2-(4-(3-morpholinopropoxy)-3-(difluoromethoxy)phenyl)-5-fluoro-N4-(1,2,2,6,6-pentamethylpiperidin-4-yl)pyrimidine-2,4-diamine MS (ES) 567 (M+H). $^1$H NMR (DMSO-d$_6$, 300 MHz) 8.96 (s, 1H), 7.85 (d, 1H), 7.52 (s, 1H), 7.47 (dd, 1H), 7.41 (d, 1H), 6.96 (d, 1H), 6.94 (t, 1H), 4.35-4.45 (m, 1H), 3.97 (t, 2H), 3.56 (s, 4H), 2.42-2.51 (m, 6H), 2.63 (s, 3H), 1.71-1.87 (m, 6H), 1.30 (s, 6H), 1.27 (s, 6H) ppm.

I-49: N2-(3-(3-(1H-pyrrol-1-yl)propoxy)-5-(trifluoromethyl)phenyl)-5-fluoro-N4-(1,2,2,6,6-pentamethylpiperidin-4-yl)pyrimidine-2,4-diamine MS (ES) 549 (M+H). $^1$H NMR (DMSO-d$_6$, 300 MHz) 9.27 (s, 1H), 7.96 (d, 1H), 7.71 (s, 1H), 7.44-7.53 (m, 3H), 7.10 (d, 1H), 6.74 (s, 1H), 6.72 (d, 1H), 5.97 (s, 1H), 4.39-4.50 (m, 1H), 4.03 (t, 2H), 3.89 (t, 2H), 2.60 (s, 3H), 2.08-2.16 (m, 2H), 1.98 (d, 2H), 1.72 (t, 2H), 1.32 (s, 12H) ppm.

I-50: 1-(2-(4-(4-(2,2,6,6-tetramethylpiperidin-4-ylamino)-5-fluoropyrimidin-2-ylamino)-2-(difluoromethoxy)phenoxy)ethyl)imidazolidin-2-one MS (ES) 538 (M+H). $^1$H NMR (DMSO-d$_6$, 300 MHz) 9.00 (s, 1H), 7.87 (d, 1H), 7.55 (s, 2H), 7.44 (t, 1H), 7.02 (d, 1H), 6.99 (t, 1H), 6.37 (s, 1H), 4.40-4.51 (m, 1H), 4.04 (t, 2H), 3.39-3.47 (m, 4H), 3.22 (t, 2H), 1.88 (d, 2H), 1.52 (t, 2H), 1.41 (s, 6H), 1.32 (s, 6H) ppm.

I-51: 1-(2-(4-(4-(1,2,2,6,6-pentamethylpiperidin-4-ylamino)-5-fluoropyrimidin-2-ylamino)-2-(difluoromethoxy)phenoxy)ethyl)imidazolidin-2-one MS (ES) 552 (M+H). $^1$H NMR (DMSO-d$_6$, 300 MHz) 8.96 (s, 1H), 7.85 (d, 1H), 7.53 (s, 2H), 7.28 (d, 1H), 6.98 (t, 1H), 6.96 (d, 1H), 6.36 (s, 1H) 4.34-4.45 (m, 1H), 4.03 (t, 2H), 3.40-3.45 (m, 4H), 3.23 (t, 2H), 2.39 (s, 3H), 1.82 (d, 2H), 1.62 (t, 2H), 1.20 (s, 12H) ppm.

I-52: 4-(1,2,2,6,6-pentamethylpiperidin-4-ylamino)-2-(3-(difluoromethoxy)-4-(pyridin-3-yloxy)phenylamino)pyrimidine-5-carbonitrile MS (ES) 524 (M+H). $^1$H NMR (DMSO-d$_6$, 300 MHz) 9.95 (s, 1H), 8.35 (s, 1H), 8.26-8.31 (m, 2H), 7.73 (d, 1H), 7.55-7.58 (m, 2H), 7.34-7.36 (m, 2H), 7.26 (s, 1H), 7.10 (t, 1H), 4.42-4.48 (m, 1H), 2.22 (s, 3H), 1.55-1.70 (m, 4H), 1.11 (s, 6H), 1.04 (s, 6H) ppm.

I-53: 4-(1,2,2,6,6-pentamethylpiperidin-4-ylamino)-2-(3-(difluoromethoxy)-4-(pyridin-4-yloxy)phenylamino)pyrimidine-5-carbonitrile MS (ES) 524 (M+H). $^1$H NMR (DMSO-d$_6$, 300 MHz) 8.83 (s, 1H), 8.45 (s, 1H), 8.18 (d, 1H), 8.00 (d, 1H), 7.88 (d, 1H), 7.68 (s, 1H), 7.13 (t, 1H), 6.82 (d, 1H), 4.52-4.63 (m, 1H), 2.75 (s, 3H), 1.89-2.02 (m, 4H), 1.41 (s, 12H) ppm.

I-54: 4-(1,2,2,6,6-pentamethylpiperidin-4-ylamino)-2-(4-(2-(1H-1,2,4-triazol-1-yl)ethoxy)-3-(difluoromethoxy)phenylamino)pyrimidine-5-carbonitrile MS (ES) 542 (M+H). $^1$H NMR (DMSO-d$_6$, 300 MHz) 9.76 (s, 1H), 8.48 (s, 1H), 8.31 (s, 1H), 7.97 (s, 1H), 7.40-7.44 (m, 3H), 6.99 (d, 1H), 6.83 (t, 1H), 4.58 (t, 2H), 4.40-4.48 (m, 1H), 4.33 (t, 2H), 2.85 (s, 3H), 1.65-1.85 (m, 4H), 1.23 (s, 12H) ppm.

I-55: 4-(1,2,2,6,6-pentamethylpiperidin-4-ylamino)-2-(4-(2-(1H-1,2,3-triazol-1-yl)ethoxy)-3-(difluoromethoxy)phenylamino)pyrimidine-5-carbonitrile MS (ES) 542 (M+H). $^1$H NMR (DMSO-d$_6$, 300 MHz) 9.73 (s, 1H), 8.28 (s, 1H), 7.78-7.80 (m, 2H), 7.56 (d, 1H), 7.37-7.42 (m, 2H), 6.99 (d, 1H), 6.72 (t, 1H), 4.81 (t, 2H), 4.47 (t, 2H), 4.37-4.45 (m, 1H), 2.19 (s, 3H), 1.50-1.1.64 (m, 4H), 1.08 (s, 6H), 1.03 (s, 6H) ppm.

I-56: 1-(2-(4-(4-(1,2,2,6,6-pentamethylpiperidin-4-ylamino)-5-fluoropyrimidin-2-ylamino)-2-(trifluoromethyl)phenoxy)ethyl)pyrrolidin-2-one MS (ES) 553 (M+H). $^1$H NMR (DMSO-d$_6$, 300 MHz) 9.06 (s, 1H), 8.64 (d, 1H), 8.19 (d, 1H), 7.72 (d, 1H), 7.63 (s, 1H), 7.25 (d, 1H), 4.26-4.34 (m, 1H), 4.19 (t, 2H), 3.56 (t, 2H), 3.44 (t, 2H), 2.71 (s, 3H), 2.21 (t, 2H), 1.79-1.99 (m, 6H), 1.38 (s, 6H), 1.19 (s, 6H) ppm.

I-57: 1-(2-(4-(4-(2,2,6,6-tetramethylpiperidin-4-ylamino)-5-fluoropyrimidin-2-ylamino)-2-(trifluoromethyl)phenoxy)ethyl)pyrrolidin-2-one MS (ES) 539 (M+H). $^1$H NMR (DMSO-d$_6$, 300 MHz) 8.89 (s, 1H), 8.67 (d, 1H), 8.15 (d, 1H), 7.82 (d, 1H), 7.70 (d, 1H), 7.66 (s, 1H), 7.25 (d, 1H), 4.29-4.37 (m, 1H), 4.18 (t, 2H), 3.56 (t, 2H), 3.43 (t, 2H), 2.22 (t, 2H), 1.86-1.94 (m, 4H), 1.60 (s, 2H), 1.35 (s, 6H), 1.24 (s, 6H) ppm.

I-58: 4-(2,2,6,6-tetramethylpiperidin-4-ylamino)-2-(3-(difluoromethoxy)-4-(pyridin-4-yloxy)phenylamino)pyrimidine-5-carbonitrile MS (ES) 510 (M+H). $^1$H NMR (DMSO-d$_6$, 300 MHz) 8.81 (s, 1H), 8.46 (s, 1H), 8.19 (s, 1H), 8.01 (d, 1H), 7.88 (d, 1H), 7.65 (s, 1H), 7.11 (t, 1H), 6.82 (d, 1H), 4.52-4.63 (m, 1H), 1.88-2.03 (m, 4H), 1.39 (s, 12H) ppm.

I-59: 5-fluoro-N2-(3-(trifluoromethyl)-4-(pyridin-3-yloxy)phenyl)-N4-(2,2,6,6-tetramethylpiperidin-4-yl)pyrimidine-2,4-diamine MS (ES) 505 (M+H). $^1$H NMR (DMSO-d$_6$, 300 MHz) 9.51 (s, 1H), 8.59 (d, 1H), 8.32-8.36 (m, 2H), 7.99-8.01 (m, 2H), 7.92 (s, 1H), 7.77-7.81 (m, 2H), 7.37-7.39 (m, 1H), 7.12 (s, 1H), 4.35-4.46 (m, 1H), 1.96 (d, 2H), 1.55 (t, 2H), 1.35 (s, 12H) ppm.

I-60: N2-(4-(2-(pyrrolidin-1-yl)ethoxy)-3-(difluoromethoxy)phenyl)-5-fluoro-N4-(2,2,6,6-tetramethylpiperidin-4-yl)pyrimidine-2,4-diamine MS (ES) 523 (M+H). $^1$H NMR (DMSO-d$_6$, 300 MHz) 9.73 (s, 1H), 9.10 (s, 1H), 8.70 (s, 1H), 8.18 (d, 1H), 7.86 (d, 1H), 7.41 (s, 1H), 7.32 (d, 1H), 7.16 (t, 1H), 4.37-4.43 (m, 1H), 4.30 (t, 2H), 3.61 (t, 2H), 3.08-3.18 (m, 2H), 1.84-1.2.06 (m, 6H), 1.59 (t, 2H), 1.35 (s, 6H), 1.31 (s, 6H) ppm.

I-61: 5-fluoro-N2-(3-(trifluoromethyl)-4-(pyridin-3-yloxy)phenyl)-N4-(1,2,2,6,6-pentamethylpiperidin-4-yl)pyrimidine-2,4-diamine MS (ES) 519 (M+H). $^1$H NMR (DMSO-d$_6$, 300 MHz) 9.54 (s, 1H), 8.50-8.53 (m, 1H), 8.35-8.38 (m, 3H), 8.02 (d, 1H), 7.98 (s, 1H), 7.94 (s, 1H), 7.38-7.41 (d, 1H), 7.12 (s, 1H), 4.34-4.46 (m, 1H), 2.71 (s, 3H), 2.06 (d, 2H), 1.79 (t, 2H), 1.38 (s, 6H), 1.32 (s, 6H) ppm.

I-62: 5-fluoro-N2-(3-(trifluoromethyl)-4-(pyridin-4-yloxy)phenyl)-N4-(1,2,2,6,6-pentamethylpiperidin-4-yl)pyrimidine-2,4-diamine MS (ES) 519 (M+H). $^1$H NMR (DMSO-d$_6$, 300 MHz) 9.65 (s, 1H), 8.55 (s, 1H), 8.26 (d, 1H), 8.05 (s, 1H), 8.01 (d, 1H), 7.70-7.76 (m, 2H), 7.51 (d, 1H), 6.28 (d, 2H), 4.38-4.51 (m, 1H), 2.74 (s, 3H), 2.11 (d, 2H), 1.81 (t, 2H), 1.40 (s, 12H) ppm.

I-63: N2-(3-(difluoromethoxy)-4-(pyridin-3-yl)phenyl)-5-fluoro-N4-(2,2,6,6-tetramethylpiperidin-4-yl)pyrimidine-2,4-diamine MS (ES) 487 (M+H). $^1$H NMR (DMSO-d$_6$, 300 MHz) 9.66 (s, 1H), 8.83 (d, 1H), 8.75 (s, 1H), 8.66 (d, 1H), 8.15 (d, 1H), 8.03-8.05 (m, 2H), 7.77 (d, 1H), 7.68-7.72 (m, 1H), 7.63 (s, 1H), 7.44 (d, 1H), 7.11 (t, 1H), 4.39-4.47 (m, 1H), 2.01 (d, 2H), 1.79 (t, 2H), 1.38 (s, 12H) ppm.

I-64: N2-(3-(difluoromethoxy)-4-(pyridin-3-yl)phenyl)-5-fluoro-N4-(1,2,2,6,6-pentamethylpiperidin-4-yl)pyrimidine-2,4-diamine MS (ES) 501 (M+H). $^1$H NMR (DMSO-d$_6$, 300 MHz) 9.81 (s, 1H), 8.87-8.89 (m, 1H), 8.77 (s, 1H), 8.67 (d, 1H), 8.14 (d, 1H), 8.05 (d, 1H), 7.76 (d, 1H), 7.69-7.72 (m, 1H), 7.60 (s, 1H), 7.43 (d, 1H), 7.06 (t, 1H), 4.43-4.50 (m, 1H), 2.75 (s, 3H), 2.08 (d, 2H), 1.86 (t, 2H), 1.41 (s, 12H) ppm.

I-65: N2-(4-(2-morpholinoethyoxy)-3-(trifluoromethyl)phenyl)-5-fluoro-N4-(2,2,6,6-tetramethylpiperidin-4-yl)pyrimidine-2,4-diamine MS (ES) 541 (M+H). $^1$H NMR (DMSO-$d_6$, 300 MHz) 8.99 (s, 1H), 8.34 (s, 1H), 7.93 (d, 1H), 7.85 (d, 1H), 7.76 (s, 1H), 7.30 (d, 1H), 7.07 (d, 1H), 4.31-4.43 (m, 1H), 4.12 (t, 2H), 3.53 (t, 4H), 2.66 (t, 2H), 2.45-2.49 (m, 4H), 1.77 (d, 2H), 1.34 (t, 2H), 1.27 (s, 6H), 1.18 (s, 6H) ppm.

I-66: N2-(4-(3-morpholinopropoxy)-3-(difluoromethoxy)phenyl)-5-fluoro-N4-(1-(2,2,2-trifluoroethyl)-2,2,6,6-tetramethylpiperidin-4-yl)pyrimidine-2,4-diamine MS (ES) 635 (M+H). $^1$H NMR (DMSO-$d_6$, 300 MHz) 8.94 (s, 1H), 7.83 (d, 1H), 7.50-7.54 (m, 2H), 7.18 (d, 1H), 6.95 (d, 1H), 6.94 (t, 1H), 4.37-4.48 (m, 1H), 3.98 (t, 2H), 3.55-3.63 (m, 4H), 3.26-3.30 (m, 2H), 2.28-2.45 (m, 6H), 1.80-1.90 (m, 2H), 1.71 (d, 2H), 1.50 (t, 2H), 1.13 (s, 6H), 1.06 (s, 6H) ppm.

I-67: 5-aminocarbonyl-N2-[4-fluoro-3-(1H-tetrazol-1-yl)]phenyl-N4-(2,2,6,6-tetramethylpiperidin-4-yl)-2,4-pyrimidinediamine MS (ES): 455.13 (M+H). $^1$H NMR (DMSO-$d_6$, 300 MHz) 9.96 (br, 2H), 9.32 (s, 1H), 8.57 (br, 2H), 8.20 (s, 1H), 7.90 (m, 2H), 7.69 (m, 1H), 7.52 (m, 1H), 7.27 (br, 1H), 4.37 (br, 1H), 2.06 (d, J=14.1 Hz, 2H), 1.38 (m, 2H), 1.32 (s, 6H), 1.21 (s, 6H) ppm.

I-68: 5-aminocarbonyl-N2-[4-ethoxy-3-(5-ethyl-1H-tetrazol-1-yl)]phenyl-N4-(2,2,6,6-tetramethylpiperidin-4-yl)-2,4-pyrimidinediamine MS (ES): 509.37 (M+H). $^1$H NMR (DMSO-$d_6$, 300 MHz) 9.75 (br, 1H), 9.35 (br, 1H), 8.59 (d, 1H), 8.53 (s, 1H), 7.82 (m, 3H), 7.71 (d, 1H), 7.24 (d, J=9.3 Hz, 2H), 4.34 (br, 1H), 4.04 (q, J=7.2 Hz, 2H), 2.69 (q, J=7.5 Hz, 2H), 2.02 (d, 2H), 1.39 (m, 2H), 1.34 (s, 6H), 1.25 (s, 6H), 1.22 (t, J=7.8 Hz, 3H), 1.14 (t, J=6.9 Hz, 3H) ppm.

I-69: 5-fluoro-N4-(1,2,2,6,6-pentamethylpiperidin-4-yl)-N2-{3-[5-(2,2,2-trifluoroethyl)thio]-1H-tetrazol-1-yl}phenyl-2,4-pyrimidinediamine MS (ES): 540.23 (M+H). $^1$H NMR (DMSO-$d_6$, 300 MHz) 9.54 (br, 1H), 8.58 (br, 1H), 7.98 (d, J=3.9 Hz, 1H), 7.92 (m, 2H), 7.69 (d, 1H), 7.48 (t, J=8.4 Hz, 1H), 7.13 (d, J=7.5 Hz, 1H), 4.41 (q, J=10.2 Hz, 3H), 2.71 (s, 3H), 2.08 (d, J=11.7 Hz, 2H), 1.79 (t, J=12.3 Hz, 2H), 1.39 (s, 6H), 1.31 (s, 6H) ppm. $^{19}$F NMR (DMSO-$d_6$, 282 MHz) −81.32 (d, J=10.7 Hz), −179.85 ppm.

I-70: 5-fluoro-N4-(2,2,6,6-tetramethylpiperidin-4-yl)-N2-{3-[5-(2,2,2-trifluoroethyl)thio]-1H-tetrazol-1-yl}phenyl-2,4-pyrimidinediamine MS (ES): 526.20 (M+H). $^1$H NMR (DMSO-$d_6$, 300 MHz) 9.58 (br, 1H), 8.57 (br, 1H), 7.98 (d, J=3.3 Hz, 1H), 7.95 (s, 1H), 7.90 (d, J=8.7 Hz, 1H), 7.74 (d, 1H), 7.68 (d, 1H), 7.48 (t, J=8.1 Hz, 1H), 7.12 (d, J=6.9 Hz, 1H), 4.40 (q, J=9.9 Hz, 3H), 1.96 (d, J=12.6 Hz, 2H), 1.56 (t, J=12.3 Hz, 2H), 1.34 (s, 6H), 1.30 (s, 6H) ppm. $^{19}$F NMR (DMSO-$d_6$, 282 MHz) −81.31 (d, J=9.0 Hz) ppm.

I-71: 5-aminocarbonyl-N4-(1,2,2,6,6-pentamethylpiperidin-4-yl)-N2-{3-[5-(2,2,2-trifluoroethyl)thio]-1H-tetrazol-1-yl}phenyl-2,4-pyrimidinediamine MS (ES): 565.20 (M+H). $^1$H NMR (DMSO-$d_6$, 300 MHz) 9.96 (br, 1H), 9.30 (br, 1H), 8.59 (br, 2H), 8.03 (d, 1H), 7.92 (br, 2H), 7.52 (t, 1H), 7.30 (br, 1H), 7.22 (d, J=7.2 Hz, 1H), 4.41 (q, J=9.6 Hz, 3H), 2.72 (d, J=4.8 Hz, 3H), 2.20 (d, J=11.7 Hz, 2H), 1.63 (t, J=13.5 Hz, 2H), 1.38 (s, 6H), 1.28 (s, 6H) ppm. $^{19}$F NMR (DMSO-$d_6$, 282 MHz) −81.30 (d, J=9.3 Hz) ppm.

I-72: 5-aminocarbonyl-N4-(2,2,6,6-tetramethylpiperidin-4-yl)-N2-{3-[5-(2,2,2-trifluoroethyl)thio]-1H-tetrazol-1-yl}phenyl-2,4-pyrimidinediamine MS (ES): 551.56 (M+H). $^1$H NMR (DMSO-$d_6$, 300 MHz) 9.98 (br, 1H), 9.34 (br, 1H), 8.58 (br, 2H), 8.00 (m, 3H), 7.68 (br, 1H), 7.53 (t, 1H), 7.30 (br, 1H), 7.22 (d, J=8.7 Hz, 1H), 4.40 (q, J=10.2 Hz, 3H), 2.09 (d, J=11.4 Hz, 2H), 1.41 (m, 2H), 1.34 (s, 6H), 1.28 (s, 6H) ppm. $^{19}$F NMR (DMSO-$d_6$, 282 MHz) −81.31 ppm.

I-73: 5-cyano-N2-[4-fluoro-3-(1H-tetrazol-1-yl)]phenyl-N4-(1,2,2,6,6-pentamethylpiperidin-4-yl)-2,4-pyrimidinediamine MS (ES): 451.39 (M+H). $^1$H NMR (DMSO-$d_6$, 300 MHz) 9.95 (s, 1H), 8.50 (br, 1H), 8.41 (s, 1H), 8.02 (br, 1H), 7.88 (d, J=8.1 Hz, 2H), 7.53 (t, 1H), 4.46 (br, 1H), 2.67 (s, 3H), 1.96 (d, 2H), 1.83 (t, J=12.3 Hz, 2H), 1.36 (s, 6H), 1.17 (br, 6H) ppm.

I-74: 5-fluoro-N2-[4-methoxy-3-(5-propyl-1H-tetrazol-1-yl)]phenyl-N4-(2,2,6,6-tetramethylpiperidin-4-yl)-2,4-pyrimidinediamine MS (ES): 483.96 (M+H). $^1$H NMR (DMSO-$d_6$, 300 MHz) 9.25 (br, 1H), 8.54 (br, 1H), 7.93 (d, J=3.3 Hz, 1H), 7.77 (m, 3H), 7.65 (br, 1H), 7.22 (d, J=9.9 Hz, 1H), 4.35 (br, 1H), 3.72 (s, 3H), 2.63 (t, J=7.5 Hz, 2H), 1.92 (d, J=12.9 Hz, 2H), 1.65 (q, J=7.2 Hz, 2H), 1.53 (t, J=12.3 Hz, 2H), 1.34 (s, 6H), 1.27 (s, 6H), 0.87 (t, J=7.5 Hz, 3H) ppm.

I-75: 5-aminocarbonyl-N2-[4-methoxy-3-(5-propyl-1H-tetrazol-1-yl)]phenyl-N4-(1,2,2,6,6-pentamethylpiperidin-4-yl)-2,4-pyrimidinediamine MS (ES): 523.49 (M+H). $^1$H NMR (DMSO-$d_6$, 300 MHz) 9.55 (br, 1H), 9.23 (br, 1H), 8.53 (br, 2H), 7.92 (d, J=9.0 Hz, 1H), 7.80 (br, 1H), 7.70 (br, 1H), 7.22 (d, J=9.3 Hz, 2H), 4.36 (br, 1H), 3.74 (s, 3H), 2.71 (s, 3H), 2.64 (t, J=7.2 Hz, 2H), 2.17 (d, J=11.4 Hz, 2H), 1.64 (m, 4H), 1.38 (s, 6H), 1.28 (s, 6H), 0.87 (t, J=7.2 Hz, 3H) ppm.

I-76: 5-aminocarbonyl-N2-[4-methoxy-3-(5-propyl-1H-tetrazol-1-yl)]phenyl-N4-(2,2,6,6-tetramethylpiperidin-4-yl)-2,4-pyrimidinediamine MS (ES): 509.56 (M+H). $^1$H NMR (DMSO-$d_6$, 300 MHz) 9.60 (br, 1H), 9.28 (br, 1H), 8.60 (br, 1H), 8.53 (s, 1H), 7.88 (d, J=7.8 Hz, 1H), 7.79 (s, 2H), 7.70 (br, 1H), 7.24 (d, J=9.3 Hz, 2H), 4.39 (br, 1H), 3.74 (s, 3H), 2.64 (t, J=7.5 Hz, 2H), 2.05 (d, J=12.6 Hz, 2H), 1.65 (q, J=7.2 Hz, 2H), 1.39 (m, 2H), 1.34 (s, 6H), 1.28 (s, 6H), 0.88 (t, J=7.5 Hz, 3H) ppm.

I-77: 5-cyano-N2-[4-fluoro-3-(1H-tetrazol-1-yl)]phenyl-N4-(2,2,6,6-tetramethylpiperidin-4-yl)-2,4-pyrimidinediamine MS (ES): 437.50 (M+H). $^1$H NMR (DMSO-$d_6$, 300 MHz) 10.09 (br, 1H), 9.95 (s, 1H), 8.37 (s, 1H), 8.23 (s, 1H), 8.08

(m, 1H), 7.88 (m, 1H), 7.60 (d, J=7.8 Hz, 1H), 7.50 (t, J=9.3 Hz, 1H), 4.41 (br, 1H), 1.69 (d, J=13.2 Hz, 2H), 1.38 (t, J=11.7 Hz, 2H), 1.12 (s, 6H), 1.03 (s, 6H) ppm.

I-78: 5-cyano-N4-(1,2,2,6,6-pentamethylpiperidin-4-yl)-N2-{3-[5-(2,2,2-trifluoroethyl)thio]-1H-tetrazol-1-yl}phenyl-2,4-pyrimidinediamine

MS (ES): 547.01 (M+H).

I-79: 5-cyano-N4-(2,2,6,6-tetramethylpiperidin-4-yl)-N2-{3-[5-(2,2,2-trifluoroethyl)thio]-1H-tetrazol-1-yl}phenyl-2,4-pyrimidinediamine

MS (ES): 532.99 (M+H).

I-80: 5-cyano-N2-[4-methoxy-3-(5-propyl-1H-tetrazol-1-yl)]phenyl-N4-(1,2,2,6,6-pentamethylpiperidin-4-yl)-2,4-pyrimidinediamine

*MS (ES): 505.28 (M+H). $^1$H NMR (DMSO-d$_6$, 300 MHz) 9.87 (br, 1H), 8.30 (s, 1H), 7.91 (m, 1H), 7.64 (br, 1H), 7.46 (d, 1H), 7.21 (d, 1H), 4.36 (br, 1H), 3.73 (s, 3H), 2.62 (t, J=7.2 Hz, 2H), 2.19 (s, 3H), 1.68-1.54 (m, 6H), 1.07 (s, 6H), 0.90 (s, 6H), 0.87 (t, J=7.5 Hz, 3H) ppm.

I-81: 5-cyano-N2-[4-methoxy-3-(5-propyl-1H-tetrazol-1-yl)]phenyl-N4-(2,2,6,6-tetramethylpiperidin-4-yl)-2,4-pyrimidinediamine MS (ES): 491.07 (M+H). $^1$H NMR (DMSO-d$_6$, 300 MHz) 9.97 (br, 1H), 8.52 (br, 1H), 8.35 (s, 1H), 7.83-7.73 (m, 4H), 7.26 (d, J=9.0 Hz, 1H), 3.74 (s, 3H), 2.63 (t, J=7.2 Hz, 2H), 1.84 (d, 2H), 1.68-1.61 (m, 4H), 1.33 (s, 6H), 1.19 (s, 6H), 0.87 (t, J=7.2 Hz, 3H) ppm.

I-82: N2-[4-difluoromethoxy-3-(5-ethyl-1H-tetrazol-1-yl)]phenyl-5-fluoro-N4-(2,2,6,6-tetramethylpiperidin-4-yl)-2,4-pyrimidinediamine MS (ES): 506.48 (M+H). $^1$H NMR (DMSO-d$_6$, 300 MHz) 9.54 (s, 1H), 8.58 (d, J=9.9 Hz, 1H), 7.96 (d, J=3.6 Hz, 1H), 7.94 (s, 1H), 7.89 (d, J=9.0 Hz, 1H), 7.76 (d, J=12.3 Hz, 1H), 7.68 (d, J=8.1 Hz, 1H), 7.41 (d, J=9.3 Hz, 1H), 7.07 (t, J=72.6 Hz, 1H), 4.39 (br, 1H), 2.72 (q, J=7.2 Hz, 2H), 1.94 (d, J=12.3 Hz, 2H), 1.54 (t, J=12.3 Hz, 2H), 1.34 (s, 6H), 1.28 (s, 6H), 1.23 (t, J=7.5 Hz, 3H) ppm. $^{19}$F NMR (DMSO-d$_6$, 282 MHz) −98.47 (d, J=73 Hz), −179.88 ppm.

I-83: 5-aminocarbonyl-N2-[4-difluoromethoxy-3-(5-ethyl-1H-tetrazol-1-yl)]phenyl-N4-(2,2,6,6-tetramethylpiperidin-4-yl)-2,4-pyrimidinediamine MS (ES): 531.74 (M+H). $^1$H NMR (DMSO-d$_6$, 300 MHz) 9.91 (br, 1H), 9.31 (br, 1H), 8.56 (br, 2H), 7.98 (d, 1H), 7.93 (br, 1H), 7.66 (br, 1H), 7.44 (d, J=8.1 Hz, 1H), 7.30 (br, 1H), 7.10 (t, J=72.0 Hz, 1H), 4.35 (br, 1H), 2.73 (q, J=7.5 Hz, 2H), 2.06 (d, J=11.1 Hz, 2H), 1.39 (m, 2H), 1.34 (s, 6H), 1.27 (s, 6H), 1.24 (t, J=7.2 Hz, 3H) ppm. $^{19}$F NMR (DMSO-d$_6$, 282 MHz) −98.75 ppm.

I-84: 5-cyano-N2-[4-difluoromethoxy-3-(5-ethyl-1H-tetrazol-1-yl)]phenyl-N4-(2,2,6,6-tetramethylpiperidin-4-yl)-2,4-pyrimidinediamine MS (ES): 513.47 (M+H). $^1$H NMR (DMSO-d$_6$, 300 MHz) 10.14 (br, 1H), 8.58 (d, 1H), 8.40 (s, 1H), 7.94 (d, J=9.0 Hz, 1H), 7.83 (m, 3H), 7.46 (d, J=9.3 Hz, 1H), 7.13 (t, J=72.3 Hz, 1H), 4.46 (br, 1H), 2.72 (q, J=7.5 Hz, 2H), 1.88 (d, J=12.3 Hz, 2H), 1.62 (t, J=12.3 Hz, 2H), 1.33 (s, 6H), 1.25 (s, 6H), 1.23 (t, J=7.2 Hz, 3H) ppm. $^{19}$F NMR (DMSO-d$_6$, 282 MHz) −99.03 ppm.

I-85: 5-Cyano-N4-(2,2,6,6-tetramethylpiperidin-4-yl)-N2-[3-(tetrazol-5-yl)]phenyl-2,4-pyrimidinediamine MS (ES) 419.10 (M+H). $^1$H NMR (DMSO-d$_6$, 300 MHz) 9.87 (s, 1H), 8.35 (s, 1H), 8.24 (s, 1H), 7.69-7.67 (d, J=7.8 Hz, 1H), 7.47 (s, 1H), 7.27 (s, 1H), 4.47 (s, 1H), 1.92-1.88 (d, J=12.3 Hz, 2H), 1.77 (m, 2H), 1.29-1.22 (m, 12H) ppm.

I-86: 5-Fluoro-N2-{3-[1-N-isopropyl-(tetrazol-5-yl)]}phenyl-N4-(1,2,2,6,6-pentamethylpiperidin-4-yl)-2,4-pyrimidinediamine MS (ES) 468.11 (M+H). $^1$H NMR (DMSO-d$_6$, 300 MHz) 9.34 (s, 1H), 8.13-8.1 (d, J=8.1 Hz, 1H), 7.89 (s, 2H), 7.42-7.36 (t, J=8.1 Hz, 1H), 7.29-7.26 (d, J=8.4 Hz, 1H), 7.18-7.16 (d, J=7.5 Hz, 1H), 4.86-7.82 (m, 1H), 4.36 (bs, 1H), 2.19 (s, 3H), 1.72-1.69 (d, J=9.9 Hz, 2H), 1.55-1.44 (m, 10H), 1.09 (s, 6H), 1.01 (s, 6H) ppm.

I-87: 5-Fluoro-N2-{3-[1-N-isopropyl-(tetrazol-5-yl)]}phenyl-N4-(2,2,6,6-tetramethylpiperidin-4-yl)-2,4-pyrimidinediamine MS (ES) 454.13 (M+H). $^1$H NMR (DMSO-d$_6$, 300 MHz) 9.35 (s, 1H), 8.08-8.05 (d, J=8.4 Hz, 1H), 7.9 (s, 2H), 7.43-7.35 (m, 2H), 7.18-7.16 (d, J=7.5 Hz, 1H), 4.86-7.81 (m, 1H), 4.42 (bs, 1H), 1.81-1.77 (d, J=12 Hz, 2H), 1.54 (s, 3H), 1.52 (s, 3H), 1.39-1.31 (t, J=12 Hz, 2H), 1.22 (s, 6H), 1.16 (s, 6H) ppm.

I-88: 5-Cyano-N2-{3-[1-N-isopropyl-(tetrazol-5-yl)]}phenyl-N4-(1,2,2,6,6-pentamethylpiperidin-4-yl)-2,4-pyrimidinediamine MS (ES) 475.12 (M+H). $^1$H NMR (DMSO-d$_6$, 300 MHz) 10.05 (s, 1H), 8.18 (bs, 1H), 7.8 (s, 2H), 7.53-7.51 (d, J=7.8 Hz, 2H), 7.47-7.42 (t, J=8.1 Hz, 1H), 7.33-7.3 (d, J=6.6 Hz, 1H), 4.88-7.79 (m, 1H), 4.43 (bs, 1H), 2.17 (s, 3H), 1.66-1.63 (m, 4H), 1.54 (s, 3H), 1.52 (s, 3H), 1.07 (s, 6H), 0.96 (s, 6H) ppm.

I-89: N2-{3-[1-N-Cyclopropyl-(tetrazol-5-yl)]}phenyl-5-fluoro-N4-(1,2,2,6,6-pentamethylpiperidin-4-yl)-2,4-pyrimidinediamine MS (ES) 466.16 (M+H). $^1$H NMR (DMSO-d$_6$, 300 MHz) 9.32 (s, 1H), 8.15 (s, 1H), 8.11-8.08 (d, J=7.8 Hz, 1H), 7.88-7.87 (d, J=3.3 Hz, 1H), 7.48-7.45 (d, J=7.5 Hz, 1H), 7.4-7.35 (t, J=7.8 Hz, 1H), 7.26-7.23 (d, J=7.8 Hz, 1H), 4.35 (bs, 1H), 3.96 (bs, 1H), 2.19 (s, 3H), 1.72-1.68 (d, J=12.6 Hz, 2H), 1.24 (m, 2H), 1.14 (m, 2H), 1.08 (s, 6H), 0.98 (s, 6H) ppm.

I-90: N2-{3-[1-N-Cyclopropyl-(tetrazol-5-yl)]}phenyl-5-fluoro-N4-(2,2,6,6-tetramethylpiperidin-4-yl)-2,4-pyrimidinediamine MS (ES) 451.00 (M+H). $^1$H NMR (DMSO-d$_6$, 300 MHz) 9.33 (s, 1H), 8.18 (s, 1H), 8.05-8.03 (d, J=8.1 Hz, 1H), 7.91-7.89 (d, J=3.6 Hz, 1H), 7.49-7.47 (d, J=7.8 Hz, 1H), 7.42-7.33 (m, 2H), 4.44 (bs, 1H), 3.97 (bs, 1H), 1.81-1.78 (d, J=9.9 Hz, 2H), 1.38-1.30 (t, J=12.6 Hz, 2H), 1.24 (m, 4H), 1.19 (s, 6H), 1.16 (s, 6H) ppm.

I-91: N2-{3-[1-N-(2-Fluoroethyl)-(tetrazol-5-yl)]}phenyl-5-fluoro-N4-(1,2,2,6,6-pentamethylpiperidin-4-yl)-2,4-pyrimidinediamine MS (ES) 472.16 (M+H), $^1$H NMR (DMSO-$d_6$, 300 MHz) 9.29 (s, 1H), 8.09-8.06 (d, J=8.7 Hz, 1H), 7.93 (s, 1H), 7.88-7.87 (d, J=3.6 Hz, 1H), 7.41-7.36 (d, J=8.1 Hz, 1H), 7.27-7.2 (m, 2H), 4.94 (bs, 1H), 4.86 (bs, 1H), 4.77 (bs, 2H), 4.35 (bs, 1H), 2.2 (s, 3H), 1.72-1.68 (d, J=11.4 Hz, 2H), 1.52-1.43 (t, J=12 Hz, 2H), 1.08 (s, 6H), 0.99 (s, 6H) ppm.

I-92: N2-{3-[1-N-(2-Fluoroethyl)-(tetrazol-5-yl)]}phenyl-5-fluoro-N4-(2,2,6,6-tetramethylpiperidin-4-yl)-2,4-pyrimidinediamine MS (ES) 458.13 (M+H), $^1$H NMR (DMSO-$d_6$, 300 MHz) 9.32 (s, 1H), 8.05-8.02 (d, J=8.4 Hz, 1H), 7.96 (s, 1H), 7.9-7.89 (d, J=3.9 Hz, 1H), 7.42-7.35 (m, 2H), 7.24-7.21 (d, J=7.5 Hz, 1H), 4.94 (bs, 1H), 4.84 (bs, 1H), 4.77 (bs, 2H), 4.4 (bs, 1H), 1.8-1.77 (d, J=9.9 Hz, 2H), 1.39-1.31 (t, J=12.9 Hz, 2H), 1.2 (s, 6H), 1.17 (s, 6H) ppm.

I-93: N2-[3-(2,5-Dimethyl-pyrrol-1-yl)-4-methoxy]phenyl-5-fluoro-N4-(2,2,6,6-tetramethylpiperidin-4-yl)-2,4-pyrimidinediamine MS (ES) 467.13 (M+H), $^1$H NMR (DMSO-$d_6$, 300 MHz) 8.89 (s, 1H), 7.86-7.82 (m, 2H), 7.34 (s, 1H), 7.22-7.19 (d, J=7.5 Hz, 1H), 6.99-6.96 (d, J=9 Hz, 1H), 5.69 (bs, 2H), 4.4 (bs, 1H), 3.61 (s, 3H), 1.86 (s, 3H), 1.78-1.77 (d, J=13.2 Hz, 2H), 1.32-1.24 (t, J=11.7 Hz, 2H), 1.22 (s, 6H), 1.12 (s, 6H) ppm.

I-94: 5-Cyano-N2-{3-[1-N-cyclopropyl-(tetrazol-5-yl)]}phenyl-N4-(1,2,2,6,6-pentamethylpiperidin-4-yl)-2,4-pyrimidinediamine MS (ES) 473.14 (M+H). $^1$H NMR (DMSO-$d_6$, 300 MHz) 10.04 (bs, 1H), 8.13 (bs, 2H), 7.63-7.61 (d, J=7.5 Hz, 1H), 7.53-7.5 (d, J=7.5 Hz, 1H), 7.47-7.42 (t, J=7.8 Hz, 1H), 4.42 (bs, 1H), 4.35 (bs, 1H), 3.98 (bs, 1H), 2.18 (s, 3H), 1.67-1.52 (m, 4H), 1.25 (m, 2H), 1.13 (m, 2H), 1.07 (s, 6H), 0.94 (s, 6H) ppm.

I-95: 5-Cyano-N2-{3-[1-N-cyclopropyl-(tetrazol-5-yl)]}phenyl-N4-(2,2,6,6-tetramethylpiperidin-4-yl)-2,4-pyrimidinediamine MS (ES) 459.14 (M+H), $^1$H NMR (DMSO-$d_6$, 300 MHz) 10.05 (bs, 1H), 8.11 (bs, 2H), 7.64-7.57 (m, 3H), 7.48-7.43 (t, J=8.1 Hz, 1H), 4.54 (bs, 1H), 3.99 (bs, 1H), 1.72-1.68 (d, J=12 Hz, 2H), 1.42-1.34 (t, J=12 Hz, 2H), 1.25 (m, 2H), 1.12 (bs, 14H) ppm.

I-96: 5-Cyano-N2-{3-[1-N-(2-fluoroethyl)-(tetrazol-5-yl)]}phenyl-N4-(1,2,2,6,6-pentamethylpiperidin-4-yl)-2,4-pyrimidinediamine MS (ES) 479.13 (M+H), $^1$H NMR (DMSO-$d_6$, 300 MHz) 10.03 (bs, 1H), 8.12 (s, 1H), 7.88 (bs, 1H), 7.55-7.52 (d, J=8.4 Hz, 1H), 7.47-7.42 (t, J=7.2 Hz, 1H), 7.38-7.35 (d, J=7.2 Hz, 1H), 4.95 (bs, 1H), 4.85 (bs, 1H), 4.77 (bs, 2H), 4.42 (bs, 1H), 2.21 (s, 3H), 1.68-1.53 (m, 4H), 1.08 (s, 6H), 0.59 (s, 6H) ppm.

I-97: 5-Cyano-N2-{3-[1-N-(2-fluoroethyl)-(tetrazol-5-yl)]}phenyl-N4-(2,2,6,6-tetramethylpiperidin-4-yl)-2,4-pyrimidinediamine MS (ES) 465.12 (M+H), $^1$H NMR (DMSO-$d_6$, 300 MHz) 10.04 (bs, 1H), 8.05 (bs, 1H), 7.91 (bs, 1H), 7.63-7.61 (d, J=7.8 Hz, 1H), 7.49-7.44 (m, 2H), 7.38-7.36 (d, J=8.1 Hz, 1H), 4.95 (bs, 1H), 4.85 (bs, 1H), 4.77 (bs, 2H), 4.5 (bs, 1H), 1.75-1.7 (d, J=12.3 Hz, 2H), 1.46-1.38 (t, J=12.3 Hz, 2H), 1.15 (s, 12H) ppm.

I-98: 5-Fluoro-N2-{3-[1-N-(2-morpholinoethyl)-(tetrazol-5-yl)]}phenyl-N4-(1,2,2,6,6-pentamethylpiperidin-4-yl)-2,4-pyrimidinediamine MS (ES) 539.17 (M+H). $^1$H NMR (DMSO-$d_6$, 300 MHz) 9.28 (s, 1H), 8.11-8.08 (d, J=8.4 Hz, 1H), 7.88 (s, 2H), 7.39-7.34 (t, J=7.8 Hz, 1H), 7.26 (m, 2H), 4.58 (bs, 2H), 4.36 (bs, 1H), 2.68 (bs, 2H), 2.19 (s, 6H), 1.72-1.68 (d, J=10.8 Hz, 2H), 1.51-1.43 (t, J=12.6 Hz, 2H), 1.08 (s, 6H), 1.0 (s, 6H) ppm.

I-99: 5-Fluoro-N2-{3-[1-N-(2-morpholinoethyl)-(tetrazol-5-yl)]}phenyl-N4-(2,2,6,6-tetramethylpiperidin-4-yl)-2,4-pyrimidinediamine MS (ES) 525.24 (M+H). $^1$H NMR (DMSO-$d_6$, 300 MHz) 9.31 (s, 1H), 8.05-8.03 (d, J=8.4 Hz, 1H), 7.91 (s, 2H), 7.41-7.36 (m, 2H), 7.27 (m, 1H), 4.58 (bs, 2H), 4.45 (bs, 1H), 2.69 (bs, 3H), 2.18 (s, 6H), 1.83-1.79 (d, J=12.6 Hz, 2H), 1.44-1.39 (t, J=12.6 Hz, 2H), 1.25 (s, 6H), 1.2 (s, 6H) ppm.

I-100: N2-[3-(2,5-Dimethyl-pyrrol-1-yl)-4-fluoro]phenyl-5-fluoro-N4-(1,2,2,6,6-pentamethylpiperidin-4-yl)-2,4-pyrimidinediamine MS (ES) 469.21 (M+H). $^1$H NMR (DMSO-$d_6$, 300 MHz) 9.17 (s, 1H), 7.86 (bs, 2H), 7.53 (bs, 1H), 7.26-7.16 (m, 2H), 5.77 (s, 2H), 4.32 (bs, 1H), 2.24 (bs, 3H), 1.9 (s, 6H), 1.75-1.71 (d, J=11.1 Hz, 2H), 1.51 (m, 2H), 1.11 (s, 6H), 1.04 (s, 6H) ppm.

I-101: N2-[3-(2,5-Dimethyl-pyrrol-1-yl)-4-fluoro]phenyl-5-fluoro-N4-(2,2,6,6-tetramethylpiperidin-4-yl)-2,4-pyrimidinediamine MS (ES) 455.17 (M+H). $^1$H NMR (DMSO-$d_6$, 300 MHz) 9.18 (s, 1H), 7.88 (bs, 2H), 7.58-7.57 (d, J=4.5 Hz, 1H), 7.39-7.37 (d, J=7.5 Hz, 1H), 7.24-7.18 (t, J=9.6 Hz, 1H), 5.77 (s, 2H), 4.4 (bs, 1H), 1.93 (s, 6H), 1.83-1.79 (d, J=12.6 Hz, 2H), 1.42-1.33 (d, J=12.3 Hz, 2H), 1.24 (s, 6H), 1.19 (s, 6H) ppm.

I-102: N2-[4-Cyano-3-(2,5-dimethyl-pyrrol-1-yl)]phenyl-5-fluoro-N4-(1,2,2,6,6-pentamethylpiperidin-4-yl)-2,4-pyrimidinediamine MS (ES) 476.18 (M+H). $^1$H NMR (DMSO-$d_6$, 300 MHz) 9.75 (s, 1H), 8.1-8.08 (d, J=8.7 Hz, 1H), 7.93 (s, 1H), 7.73-7.7 (d, J=8.1 Hz, 1H), 7.65 (s, 1H), 7.41-7.38 (d, J=7.5 Hz, 1H), 5.81 (s, 2H), 4.29 (bs, 1H), 2.17 (s, 3H), 1.94 (s, 6H), 1.7-1.66 (d, J=12 Hz, 2H), 1.51-1.43 (d, J=12 Hz, 2H), 1.07 (s, 6H), 1.01 (s, 6H) ppm.

I-103: N2-[3-(2,5-Dimethyl-pyrrol-1-yl)-4-(isopropylaminocarboxyloxy)]phenyl-5-fluoro-N4-(1,2,2,6,6-pentamethylpiperidin-4-yl)-2,4-pyrimidinediamine MS (ES) 552.28 (M+H). $^1$H NMR (DMSO-$d_6$, 300 MHz) 9.11 (s, 1H), 7.97-7.95 (d, J=6.9 Hz, 1H), 7.85 (s, 1H), 7.39 (s, 1H), 7.25-7.19 (m, 2H), 6.99-6.97 (d, J=8.1 Hz, 1H), 5.67 (s, 2H), 4.32 (bs, 1H), 2.17 (s, 3H), 1.89 (s, 6H), 1.7-1.66 (d, J=12 Hz, 2H), 1.51-1.42 (d, J=12.6 Hz, 2H), 1.07 (s, 6H), 1.02 (s, 6H), 0.95-0.93 (m, 6H) ppm.

I-104: N2-(4-(1-isopropylpiperidin-4-yloxy)-3-(difluoromethoxy)phenyl)-5-fluoro-N4-(2,2,6,6-tetramethylpiperidin-4-yl)pyrimidine-2,4-diamine MS (ES) 551 (M+H). $^1$H NMR (DMSO-d$_6$, 300 MHz) 9.29 (s, 1H), 8.88 (d, 1H), 7.95 (d, 1H), 7.86 (d, 1H), 7.60 (s, 1H), 7.44 (t, 1H), 7.10 (d, 1H), 7.05 (t, 1H), 4.65-4.70 (m, 1H), 4.37-4.52 (m, 1H), 3.42-3.52 (m, 2H), 3.25-3.29 (m, 1H), 3.02-3.17 (m, 2H), 1.94-2.06 (m, 6H), 1.60 (t, 2H), 1.44 (s, 6H), 1.39 (s, 6H), 1.26 (d, 6H) ppm.

I-105: N2-(4-(1-isopropylpiperidin-4-yloxy)-3-(difluoromethoxy)phenyl)-5-fluoro-N4-(1,2,2,6,6-pentamethylpiperidin-4-yl)pyrimidine-2,4-diamine MS (ES) 565 (M+H). $^1$H NMR (DMSO-d$_6$, 300 MHz) 9.59 (br s, 1H), 9.03 (s, 1H), 7.88 (s, 1H), 7.58 (s, 1H), 7.46-7.50 (m, 2H), 7.07 (d, 1H), 7.00 (t, 1H), 4.38-4.54 (m, 2H), 3.33-3.43 (m, 5H), 2.67 (s, 3H), 1.90-2.12 (m, 6H), 1.78 (t, 2H), 1.37 (s, 12H), 1.22 (d, 6H) ppm.

I-106: N2-(3-(difluoromethoxy)-5-(trifluoromethyl)phenyl)-5-fluoro-N4-(2,2,6,6-tetramethylpiperidin-4-yl)pyrimidine-2,4-diamine MS (ES) 478 (M+H). $^1$H NMR (DMSO-d$_6$, 300 MHz) 9.59 (s, 1H), 8.12 (s, 1H), 8.06 (s, 1H) 8.00 (d, 1H), 7.68-7.70 (m, 2H), 7.35 (t, 1H), 6.99 (s, 1H), 4.46-4.56 (m, 1H), 1.98 (d, 2H), 1.60 (t, 2H), 1.46 (s, 6H), 1.38 (s, 6H) ppm.

I-107: N2-(3-(difluoromethoxy)-5-(trifluoromethyl)phenyl)-5-fluoro-N4-(1,2,2,6,6-pentamethylpiperidin-4-yl)pyrimidine-2,4-diamine MS (ES) 492 (M+H). $^1$H NMR (DMSO-d$_6$, 300 MHz) 9.55 (s, 1H), 8.12 (s, 1H), 8.03 (s, 1H) 8.01 (d, 1H), 7.74 (s, 1H), 7.70 (d, 1H), 7.33 (t, 1H), 6.99 (s, 1H), 4.42-4.53 (m, 1H), 2.73 (s, 3H), 2.08 (d, 2H), 1.81 (t, 2H), 1.40 (s, 12H) ppm.

I-108: N2-(3-(difluoromethoxy)-4-ethoxyphenyl)-5-fluoro-N4-(2,2,6,6-tetramethylpiperidin-4-yl)pyrimidine-2,4-diamine MS (ES) 454 (M+H). $^1$H NMR (DMSO-d$_6$, 300 MHz) 8.95 (s, 1H), 8.31 (s, 1H), 7.85 (d, 1H), 7.46 (s, 1H), 7.43 (d, 1H), 7.18 (d, 1H), 6.88-6.90 (m, 2H), 6.37 (t, 1H), 4.40-4.52 (m, 1H), 3.96 (q, 2H), 1.83 (d, 2H), 1.44 (t, 2H), 1.35 (s, 6H), 1.29 (t, 3H), 1.25 (s, 6H) ppm.

I-109: N2-(3-(difluoromethoxy)-4-ethoxyphenyl)-5-fluoro-N4-(1,2,2,6,6-pentamethylpiperidin-4-yl)pyrimidine-2,4-diamine MS (ES) 468 (M+H). $^1$H NMR (DMSO-d$_6$, 300 MHz) 9.89 (s, 1H), 8.94 (s, 1H), 8.59 (d, 1H), 8.12 (d, 1H), 7.32 (s, 1H), 7.30 (d, 1H), 7.08 (t, 1H), 4.31-4.40 (m, 1H), 4.04 (q, 2H), 2.72 (s, 3H), 2.00 (d, 2H), 1.83 (t, 2H), 1.38 (s, 6H), 1.32 (t, 3H), 1.26 (s, 6H) ppm.

I-110: N2-(3-acetylamino-5-methoxyphenyl)-5-fluoro-N4-(1,2,2,6,6-pentamethylpiperidin-4-yl)-2,4-pyrimidinediamine $^1$H NMR (DMSO-d$_6$, 300 MHz) 9.75 (s, 1H), 8.87 (s, 1H), 7.82-7.81 (d, J=3.3 Hz, 1H), 7.3 (s, 1H), 7.15-7.13 (d, J=7.8 Hz, 1H), 7.05 (s, 1H), 6.8 (s, 1H), 4.35 (bs, 1H), 3.63 (s, 3H), 2.24 (s, 3H), 1.98 (s, 3H), 1.73-1.70 (d, J=9.3 Hz, 2H), 1.5-1.42 (t, J=12 Hz, 2H), 1.10 (s, 6H), 1.07 (s, 6H) ppm. MS (ES) 445.10 (M+H)

I-111: N2-(3,5-Dimethoxyphenyl)-5-fluoro-N4-(1-N-oxide-2,2,6,6-pentamethylpiperidin-4-yl)-2,4-pyrimidinediamine MS (ES) 419.10 (M+H). $^1$H NMR (DMSO-d$_6$, 300 MHz) 9.1 (bs, 1H), 7.94-7.92 (d, J=3.6 Hz, 1H), 7.9 (bs, 1H), 6.9 (bs, 1H), 6.1 (bs, 1H), 4.58 (bs, 1H), 3.68 (s, 6H), 2.06 (bs, 2H), 1.92 (bs, 2H), 1.41 (s, 6H), 1.36 (s, 6H) ppm.

I-112: 5-(4-(1,2,2,6,6-pentamethylpiperidin-4-ylamino)-5-fluoropyrimidin-2-ylamino)-3-(5-methyl-1H-tetrazol-1-yl)pyridin-2-ol MS (ES) 457.50 (M+H). $^1$H NMR (DMSO-d$_6$, 300 MHz) 9.36 (s, 1H), 8.75 (s, 1H), 8.20 (d, 1H), 8.00 (s, br, 1H), 7.85 (s, 1H), 4.20 (s, 1H), 2.65 (s, 3H), 2.41 (s, 3H), 2.10 (d, 2H), 1.80 (t, 2H), 1.05 (s, 6H), 1.00 (s, 6H) ppm.

I-113: 5-fluoro-N2-(6-isopropoxy-5-(5-methyl-1H-tetrazol-1-yl)pyridin-3-yl)-N4-(1,2,2,6,6-pentamethylpiperidin-4-yl)pyrimidine-2,4-diamine MS (ES) 499.60 (M+H). $^1$H NMR (DMSO-d$_6$, 300 MHz) 9.40 (s, 1H), 8.78 (s, 1H), 7.90 (s, 1H), 7.40 (d, 1H), 7.10 (d, 1H), 5.24 (m, 1H), 4.40 (s, 1H), 2.70 (s, 3H), 2.40 (s, 3H), 2.05 (d, 2H), 1.75 (t, 2H), 1.35 (s, 6H), 1.30 (s, 6H), 1.20 (d, 6H) ppm.

I-114: 5-fluoro-N2-(6-isopropoxy-5-(5-methyl-1H-tetrazol-1-yl)pyridin-3-yl)-N4-(2,2,6,6-tetramethylpiperidin-4-yl)pyrimidine-2,4-diamine MS (ES) 485.57 (M+H). $^1$H NMR (DMSO-d$_6$, 300 MHz) 9.45 (s, 1H), 8.75 (s, 1H), 8.00 (s, 1H), 7.43 (d, 1H), 7.15 (d, 1H), 5.20 (m, 1H), 4.38 (s, br, 1H), 2.43 (s, 3H), 1.95 (d, 2H), 1.58 (t, 2H), 1.38 (s, 6H), 1.30 (s, 6H), 1.20 (d, 6H) ppm.

I-115: 5-fluoro-N2-(6-isopropoxy-5-(2,5-dimethyl-1H-pyrrol-1-yl)pyridin-3-yl)-N4-(1,2,2,6,6-pentamethylpiperidin-4-yl)pyrimidine-2,4-diamine MS (ES) 510.60 (M+H). $^1$H NMR (DMSO-d$_6$, 300 MHz) 9.30 (s, 1H), 8.65 (s, 1H), 7.85 (s, 1H), 7.40 (d, 1H), 7.05 (d, 1H), 5.70 (s, 2H), 5.18 (m, 1H), 4.38 (s, 1H), 2.75 (s, 3H), 2.25 (s, 6H), 2.05 (d, 2H), 1.85 (t, 2H), 1.45 (s, 6H), 1.35 (s, 6H), 1.15 (d, 6H) ppm.

I-116: 5-fluoro-N2-(6-isopropoxy-5-(2,5-dimethyl-1H-pyrrol-1-yl)pyridin-3-yl)-N4-(2,2,6,6-tetramethylpiperidin-4-yl)pyrimidine-2,4-diamine MS (ES) 496.64 (M+H). $^1$H NMR (DMSO-d$_6$, 300 MHz) 9.50 (s, 1H), 8.70 (s, 1H), 7.90 (s, 1H), 7.45 (d, 1H), 7.15 (d, 1H), 5.75 (s, 2H), 5.19 (m, 1H), 4.40 (s, 1H), 2.30 (s, 6H), 1.95 (d, 2H), 1.58 (t, 2H), 1.58 (s, 12H), 1.20 (d, 6H) ppm.

I-117: N2-(5-(difluoromethoxy)-6-ethoxypyridin-3-yl)-5-fluoro-N4-(1,2,2,6,6-pentamethylpiperidin-4-yl)pyrimidine-2,4-diamine MS (ES) 469.52 (M+H). $^1$H NMR (DMSO-d$_6$, 300 MHz) 9.44 (s, 1H), 8.55 (s, 1H), 8.00 (d, 1H), 7.82 (d, 1H), 7.75 (d, 1H), 7.10 (m, 1H), 4.00 (q, 2H), 3.95 (m, 1H), 2.85 (s, 3H), 2.15 (d, 2H), 2.00 (t, 2H), 1.42 (t, 3H), 1.35 (s, 6H), 1.25 (s, 6H) ppm.

I-118: N2-(5-(difluoromethoxy)-6-ethoxypyridin-3-yl)-5-fluoro-N4-(2,2,6,6-tetramethylpiperidin-4-yl)pyrimidine-2,4-diamine MS (ES) 455.59 (M+H). $^1$H NMR (DMSO-d$_6$, 300 MHz) 9.50 (s, 1H), 8.62 (s, 1H), 7.95 (d, 1H), 7.79 (d, 1H), 7.80 (d, 1H), 7.15 (m, 1H), 3.95 (q, 2H), 3.85 (m, 1H), 2.10 (d, 2H), 1.95 (t, 2H), 1.48 (t, 3H), 1.45 (s, 6H), 1.35 (s, 6H) ppm.

I-119: N2-(4-(2-morpholinoethyoxy)-3-(trifluoromethyl)phenyl)-5-fluoro-N4-(1,2,2,6,6-pentamethylpiperidin-4-yl)pyrimidine-2,4-diamine MS (ES) 555 (M+H). $^1$H NMR (DMSO-d$_6$, 300 MHz) 8.97 (s, 1H), 7.95 (d, 1H), 7.82 (d, 1H), 7.75 (s, 1H), 7.18 (d, 1H), 7.06 (d, 1H), 4.25-4.36 (m, 1H), 4.12 (t, 2H), 3.54 (t, 4H), 2.67 (t, 2H), 2.46-2.49 (m, 4H), 2.27 (s, 3H), 1.71 (d, 2H), 1.47 (t, 2H), 1.10 (s, 6H), 1.06 (s, 6H) ppm.

I-120: N2-(4-(2-morpholinoethyoxy)-3-(difluoromethoxy)phenyl)-5-fluoro-N4-(2,2,6,6-tetramethylpiperidin-4-yl)pyrimidine-2,4-diamine MS (ES) 539 (M+H). $^1$H NMR (DMSO-d$_6$, 300 MHz) 9.89 (br s, 1H), 9.73 (br s, 1H), 8.66 (d, 1H), 8.08 (d, 1H), 7.83 (d, 1H), 7.37 (d, 1H), 7.17 (d, 1H), 7.07 (t, 1H), 4.35-4.50 (m, 1H), 4.36 (br s, 2H), 4.00 (d, 2H), 3.51-3.73 (m, 6H), 3.18-3.30 (m, 2H), 1.94 (d, 2H), 1.62 (t, 2H), 1.37 (s, 12H) ppm.

I-121: N2-(4-(2-morpholinoethyoxy)-3-(difluoromethoxy)phenyl)-5-fluoro-N4-(1,2,2,6,6-pentamethylpiperidin-4-yl)pyrimidine-2,4-diamine MS (ES) 553 (M+H). $^1$H NMR (DMSO-d$_6$, 300 MHz) 9.91 (br s, 1H), 9.70 (br s, 1H), 8.58 (br s, 1H), 8.07 (d, 1H), 7.38 (d, 1H), 7.16 (d, 1H), 7.06 (t, 1H), 4.28-4.45 (m, 3H), 3.98 (br d, 2H), 3.50-3.72 (m, 6H), 3.15-3.31 (m, 2H), 2.70 (s, 3H), 2.02 (d, 2H), 1.82 (t, 2H), 1.38 (s, 6H), 1.30 (s, 6H) ppm.

I-122: N2-(4-(2-methyl-1-morpholinopropan-2-yloxy)-3-(difluoromethoxy)phenyl)-5-fluoro-N4-(2,2,6,6-tetramethylpiperidin-4-yl)pyrimidine-2,4-diamine MS (ES) 567 (M+H). $^1$H NMR (DMSO-d$_6$, 300 MHz) 9.12 (s, 1H), 8.24 (s, 2H), 7.88 (d, 1H), 7.44-7.52 (m, 3H), 6.98 (d, 1H), 6.97 (t, 1H), 4.40-4.53 (m, 1H), 3.51-3.56 (m, 4H), 2.46-2.53 (m, 6H), 1.88 (d, 2H), 1.55 (t, 2H), 1.41 (s, 3H), 1.38 (s, 3H), 1.33 (s, 6H), 1.17 (s, 6H) ppm.

I-123: N2-(4-(2-methyl-1-morpholinopropan-2-yloxy)-3-(difluoromethoxy)phenyl)-5-fluoro-N4-(1,2,2,6,6-pentamethylpiperidin-4-yl)pyrimidine-2,4-diamine MS (ES) 581 (M+H). $^1$H NMR (DMSO-d$_6$, 300 MHz) 9.08 (s, 1H), 7.84 (d, 1H), 7.61 (d, 1H), 7.42 (s, 1H), 7.20-7.24 (m, 1H), 7.00 (t, 1H), 6.94 (d, 1H), 4.33-4.44 (m, 1H), 3.56-3.58 (m, 4H), 2.47-2.56 (m, 6H), 2.19 (s, 3H), 1.70 (d, 2H), 1.47 (t, 2H), 1.19 (s, 6H), 1.08 (s, 12H) ppm.

I-124: N2-(4-(2-methyl-1-(pyrrolidin-1-yl)propan-2-yloxy)-3-(difluoromethoxy)phenyl)-5-fluoro-N4-(2,2,6,6-tetramethylpiperidin-4-yl)pyrimidine-2,4-diamine MS (ES) 551 (M+H). $^1$H NMR (DMSO-d$_6$, 300 MHz) 9.14 (s, 1H), 7.89 (br s, 1H), 7.46-7.51 (m, 3H), 7.44 (d, 1H), 7.01 (d, 1H), 7.00 (t, 1H), 4.39-4.49 (m, 1H), 3.45 (dd, 2H), 2.57-2.67 (m, 4H), 1.84-1.92 (m, 2H), 1.68 (br s, 4H), 1.57 (t, 2H), 1.43 (s, 3H), 1.36 (s, 3H), 1.19 (s, 12H) ppm.

I-125: 5-aminocarbonyl-N2-[4-fluoro-3-(1H-tetrazol-1-yl)]phenyl-N4-(2,2,6,6-tetramethylpiperidin-4-yl)-2,4-pyrimidinediamine MS (ES) 565 (M+H). $^1$H NMR (DMSO-d$_6$, 300 MHz) 9.57 (br s, 1H), 9.27 (br s, 1H), 8.57-8.60 (br s, 1H), 8.04 (d, 1H), 7.52 (s, 1H), 7.14 (d, 1H), 7.11 (t, 1H), 4.38-4.50 (m, 1H), 3.69-3.77 (m, 2H), 3.49-3.53 (m, 3H), 3.20-3.26 (m, 2H), 2.72 (s, 3H), 1.78-2.07 (m, 8H), 1.39 (s, 6H), 1.35 (s, 6H), 1.29 (s, 6H) ppm.

I-126: 5-fluoro-N2-(6-isopropoxy-5-(1-methyl-1H-tetrazol-5-yl)pyridin-3-yl)-N4-(1,2,2,6,6-pentamethylpiperidin-4-yl)pyrimidine-2,4-diamine MS (ES) 499 (M+H); $^1$H NMR (CD$_3$OD, 300 MHz) 8.20 (s, 1H), 8.04 (d, 1H), 7.98 (d, 1H), 5.44 (m, 1H), 4.68 (m, 1H), 4.09 (s, 3H), 2.82-1.35 (m, 22H) ppm.

I-127: 5-fluoro-N2-(6-isopropoxy-5-(1-methyl-1H-tetrazol-5-yl)pyridin-3-yl)-N4-(2,2,6,6-tetramethylpiperidin-4-yl)pyrimidine-2,4-diamine MS (ES) 485 (M+H); $^1$H NMR (CD$_3$OD, 300 MHz) 8.10 (s, 1H), 7.99 (d, 1H), 7.58 (d, 1H), 5.54 (m, 1H), 4.78 (m, 1H), 4.01 (s, 3H), 2.82-1.35 (m, 19H) ppm.

I-128: 2-(6-isopropoxy-5-(1-methyl-1H-tetrazol-5-yl)pyridin-3-ylamino)-4-(1,2,2,6,6-pentamethylpiperidin-4-ylamino)pyrimidine-5-carboxamide MS (ES) 524 (M+H); $^1$H NMR (CD$_3$OD, 300 MHz) 8.12 (s, 1H), 7.98 (d, 1H), 7.78 (d, 1H), 5.54 (m, 1H), 4.48 (m, 1H), 4.01 (s, 3H), 2.88-1.30 (m, 25H) ppm.

I-129: 2-(6-isopropoxy-5-(1-methyl-1H-tetrazol-5-yl)pyridin-3-ylamino)-4-(1,2,2,6,6-pentamethylpiperidin-4-ylamino)pyrimidine-5-carbonitrile MS (ES) 506 (M+H); $^1$H NMR (CD$_3$OD, 300 MHz) 8.64 (s, 1H), 8.47 (d, 1H), 8.25 (d, 1H), 5.42 (m, 1H), 4.62 (m, 1H), 4.04 (s, 3H), 2.79-1.33 (m, 25H) ppm.

I-130: 2-(6-isopropoxy-5-(1-methyl-1H-tetrazol-5-yl)pyridin-3-ylamino)-4-(2,2,6,6-tetramethylpiperidin-4-ylamino)pyrimidine-5-carbonitrile MS (ES) 492 (M+H); $^1$H NMR (CD$_3$OD, 300 MHz) 8.60 (s, 1H), 8.45 (d, 1H), 8.21 (d, 1H), 5.40 (m, 1H), 4.61 (m, 1H), 4.01 (s, 3H), 2.80-1.33 (m, 22H) ppm;

I-131: 5-fluoro-N2-(6-isopropoxy-5-(1-isopropyl-1H-tetrazol-5-yl)pyridin-3-yl)-N4-(1,2,2,6,6-pentamethylpiperidin-4-yl)pyrimidine-2,4-diamine MS (ES) 527 (M+H); $^1$H NMR (CD$_3$OD, 300 MHz) 8.60 (s, 1H), 8.21 (d, 1H), 7.91 (d, 1H), 5.39 (m, 1H), 4.61 (m, 1H), 2.88-1.20 (m, 32H) ppm.

I-132: 5-fluoro-N2-(6-isopropoxy-5-(1-isopropyl-1H-tetrazol-5-yl)pyridin-3-yl)-N4-(2,2,6,6-tetramethylpiperidin-4-yl)pyrimidine-2,4-diamine MS (ES) 513 (M+H); $^1$H NMR (CD$_3$OD, 300 MHz) 8.58 (s, 1H), 8.20 (d, 1H), 7.90 (d, 1H), 5.35 (m, 1H), 4.55 (m, 1H), 2.86-1.21 (m, 29H) ppm.

I-133: 2-(6-isopropoxy-5-(1-isopropyl-1H-tetrazol-5-yl)pyridin-3-ylamino)-4-(1,2,2,6,6-pentamethylpiperidin-4-ylamino)pyrimidine-5-carboxamide MS (ES) 552 (M+H); $^1$H NMR (CD$_3$OD, 300 MHz) 8.58 (s, 1H), 8.21 (d, 1H), 7.90 (d, 1H), 5.39 (m, 1H), 4.61 (m, 1H), 2.90-1.20 (m, 32H) ppm.

I-134: 2-(6-isopropoxy-5-(1-isopropyl-1H-tetrazol-5-yl)pyridin-3-ylamino)-4-(2,2,6,6-tetramethylpiperidin-4-ylamino)pyrimidine-5-carboxamide MS (ES) 538 (M+H); $^1$H NMR (CD$_3$OD, 300 MHz) 8.61 (s, 1H), 8.31 (d, 1H), 7.98 (d, 1H), 5.44 (m, 1H), 4.67 (m, 1H), 2.88-1.18 (m, 29H) ppm.

I-135: 2-(6-isopropoxy-5-(1-isopropyl-1H-tetrazol-5-yl)pyridin-3-ylamino)-4-(1,2,2,6,6-pentamethylpiperidin-4-ylamino)pyrimidine-5-carbonitrile MS (ES) 534 (M+H); $^1$H NMR (CD$_3$OD, 300 MHz) 8.69 (s, 1H), 8.25 (d, 1H), 7.94 (d, 1H), 5.41 (m, 1H), 4.66 (m, 1H), 2.84-1.27 (m, 32H) ppm.

I-136: 2-(6-isopropoxy-5-(1-isopropyl-1H-tetrazol-5-yl)pyridin-3-ylamino)-4-(2,2,6,6-tetramethylpiperidin-4-ylamino)pyrimidine-5-carbonitrile MS (ES) 520 (M+H); $^1$H NMR (CD$_3$OD, 300 MHz) 8.65 (s, 1H), 8.23 (d, 1H), 7.90 (d, 1H), 5.40 (m, 1H), 4.65 (m, 1H), 2.88-1.27 (m, 29H) ppm.

I-137: N2-(5-(1-cyclopropyl-1H-tetrazol-5-yl)-6-isopropoxypyridin-3-yl)-5-fluoro-N4-(1,2,2,6,6-pentamethylpiperidin-4-yl)pyrimidine-2,4-diamine MS (ES) 525 (M+H); $^1$H NMR (CD$_3$OD, 300 MHz) 8.58 (s, 1H), 8.19 (d, 1H), 7.86 (d, 1H), 5.35 (m, 1H), 4.55 (m, 1H), 2.88-0.80 (m, 30H) ppm.

I-138: N2-(5-(1-cyclopropyl-1H-tetrazol-5-yl)-6-isopropoxypyridin-3-yl)-5-fluoro-N4-(2,2,6,6-tetramethylpiperidin-4-yl)pyrimidine-2,4-diamine MS (ES) 511 (M+H); $^1$H NMR (CD$_3$OD, 300 MHz) 8.59 (s, 1H), 8.20 (d, 1H), 7.87 (d, 1H), 5.37 (m, 1H), 4.57 (m, 1H), 2.90-0.80 (m, 27H) ppm.

I-139: 2-(5-(1-cyclopropyl-1H-tetrazol-5-yl)-6-isopropoxypyridin-3-ylamino)-4-(1,2,2,6,6-pentamethylpiperidin-4-ylamino)pyrimidine-5-carbonitrile MS (ES) 532 (M+H); $^1$H NMR (CD$_3$OD, 300 MHz) 8.28 (s, 1H), 7.88 (d, 1H), 7.56 (d, 1H), 5.15 (m, 1H), 4.25 (m, 1H), 2.98-0.80 (m, 30H) ppm.

I-140: 2-(5-(1-cyclopropyl-1H-tetrazol-5-yl)-6-isopropoxypyridin-3-ylamino)-4-(2,2,6,6-tetramethylpiperidin-4-ylamino)pyrimidine-5-carbonitrile MS (ES) 518 (M+H); $^1$H NMR (CD$_3$OD, 300 MHz) 8.26 (s, 1H), 7.86 (d, 1H), 7.55 (d, 1H), 5.13 (m, 1H), 4.23 (m, 1H), 2.95-0.80 (m, 27H) ppm.

I-141: 1-(2-(3-(difluoromethoxy)-5-(5-fluoro-4-(2,2,6,6-tetramethylpiperidin-4-ylamino)pyrimidin-2-ylamino)pyridin-2-yloxy)ethyl)pyrrolidin-2-one MS (ES) 538 (M+H); $^1$H NMR (CD$_3$OD, 300 MHz) 7.84 (s, 1H), 7.70 (d, 1H), 7.23 (d, 1H), 6.85 (t, 1H), 4.49 (t, 1H), 4.42 (t, 1H), 3.68 (t, 1H), 3.64 (t, 1H), 2.02-1.58 (m, 11H), 1.48 (m, 12H) ppm.

I-142: N2-(5-(difluoromethoxy)-6-(2-(pyrrolidin-1-yl)ethoxy)pyridin-3-yl)-5-fluoro-N4-(1,2,2,6,6-pentamethylpiperidin-4-yl)pyrimidine-2,4-diamine MS (ES) 538 (M+H); $^1$H NMR (CD$_3$OD, 300 MHz) 7.99 (s, 1H), 7.58 (d, 1H), 7.06 (d, 1H), 6.88 (t, 1H), 4.75 (m, 2H), 3.62 (m, 2H), 3.55-1.48 (m, 24H) ppm.

I-143: N2-(5-(difluoromethoxy)-6-(2-(pyrrolidin-1-yl)ethoxy)pyridin-3-yl)-5-fluoro-N4-(2,2,6,6-tetramethylpiperidin-4-yl)pyrimidine-2,4-diamine MS (ES) 524 (M+H); $^1$H NMR (CD$_3$OD, 300 MHz) 8.01 (s, 1H), 7.56 (d, 1H), 7.05 (d, 1H), 6.87 (t, 1H), 4.70 (m, 2H), 3.66 (m, 2H), 3.45-1.48 (m, 21H) ppm.

I-144: N2-(4-(1-(2,2,2-trifluoroethyl)piperidin-4-yloxy)-3-(difluoromethoxy)phenyl)-5-fluoro-N4-(2,2,6,6-tetramethylpiperidin-4-yl)pyrimidine-2,4-diamine MS (ES) 591 (M+H); $^1$H NMR (DMSO-d$_6$, 300 MHz) 9.03 (s, 1H), 8.74 (d, 1H), 7.86-7.89 (m, 1H), 7.49-7.51 (m, 1H), 7.49 (d, 1H), 7.46 (d, 1H), 7.03 (d, 1H), 6.96 (t, 1H), 4.30-4.48 (m, 1H), 4.24-4.29 (m, 1H), 3.13 (q, 2H), 2.82-2.86 (m, 2H), 2.47-2.49 (m, 2H), 1.85-1.98 (m, 4H), 1.54-1.63 (m, 4H), 1.45 (s, 6H), 1.38 (s, 6H) ppm.

I-145: N2-(4-(1-(2,2,2-trifluoroethyl)piperidin-4-yloxy)-3-(difluoromethoxy)phenyl)-5-fluoro-N4-(1,2,2,6,6-pentamethylpiperidin-4-yl)pyrimidine-2,4-diamine $^1$H NMR (DMSO-d$_6$, 300 MHz) 9.00 (s, 1H), 8.86 (s, 1H), 7.88-7.89 (m, 1H), 7.52-7.55 (m, 1H), 7.40 (d, 1H), 7.03 (d, 1H), 6.94 (t, 1H), 4.26-4.44 (m, 1H), 4.23-4.26 (m, 1H), 3.11 (q, 2H), 2.81-2.84 (m, 2H), 2.71 (s, 3H), 2.49-2.52 (m, 2H), 2.02-2.08 (m, 2H), 1.86-1.89 (m, 4H), 1.62-1.67 (m, 2H), 1.41 (s, 6H), 1.40 (s, 6H) ppm; MS (ES) 605 (M+H).

I-146: N2-(4-((R)-1-isopropylpyrrolidin-3-yloxy)-3-(difluoromethoxy)phenyl)-5-fluoro-N4-(2,2,6,6-tetramethylpiperidin-4-yl)pyrimidine-2,4-diamine $^1$H NMR (DMSO-d$_6$, 300 MHz) 8.94 (s, 1H), 7.81-7.82 (m, 1H), 7.52 (d, 1H), 7.47 (s, 1H), 7.14 (d, 1H), 7.01 (t, 1H), 6.88 (d, 1H), 4.77-4.83 (m, 1H), 4.40-4.47 (m, 1H), 2.65-2.82 (m, 4H), 2.47-2.50 (m, 3H), 2.09-2.14 (m, 1H), 1.67-1.90 (m, 3H), 1.21 (s, 6H), 1.04 (s, 6H), 1.01 (d, 6H) ppm; MS (ES) 537 (M+H).

I-147: N2-(4-((R)-1-isopropylpyrrolidin-3-yloxy)-3-(difluoromethoxy)phenyl)-5-fluoro-N4-(1,2,2,6,6-pentamethylpiperidin-4-yl)pyrimidine-2,4-diamine $^1$H NMR (DMSO-d$_6$, 300 MHz) 8.95 (s, 1H), 7.81-7.82 (m, 1H), 7.51 (d, 1H), 7.47 (s, 1H), 7.17 (d, 1H), 7.01 (t, 1H), 6.88 (d, 1H), 4.75-4.82 (m, 1H), 4.31-4.38 (m, 1H), 2.55-2.69 (m, 3H), 2.45-2.48 (m, 2H), 2.13 (s, 3H), 2.10-2.13 (m, 1H), 1.78-1.82 (m, 1H), 1.68 (d, 2H), 1.42 (t, 2H), 1.08 (s, 12H), 0.99 (d, 6H) ppm; MS (ES) 551 (M+H).

I-148: N2-(4-((S)-1-isopropylpyrrolidin-3-yloxy)-3-(difluoromethoxy)phenyl)-5-fluoro-N4-(2,2,6,6-tetramethylpiperidin-4-yl)pyrimidine-2,4-diamine $^1$H NMR (DMSO-d$_6$, 300 MHz) 8.95 (s, 1H), 7.81-7.83 (m, 1H), 7.52 (d, 1H), 7.47 (s, 1H), 7.14 (d, 1H), 7.01 (t, 1H), 6.88 (d, 1H), 4.77-4.83 (m, 1H), 4.39-4.46 (m, 1H), 2.65-2.82

(m, 4H), 2.47-2.50 (m, 3H), 2.09-2.14 (m, 1H), 1.67-1.90 (m, 3H), 1.22 (s, 6H), 1.03 (s, 6H), 1.02 (d, 6H) ppm; MS (ES) 537 (M+H).

I-149: N2-(4-((S)-1-isopropylpyrrolidin-3-yloxy)-3-(difluoromethoxy)phenyl)-5-fluoro-N4-(1,2,2,6,6-pentamethylpiperidin-4-yl)pyrimidine-2,4-diamine $^1$H NMR (DMSO-d$_6$, 300 MHz) 8.95 (s, 1H), 7.81-7.83 (m, 1H), 7.51 (d, 1H), 7.47 (s, 1H), 7.17 (d, 1H), 7.01 (t, 1H), 6.88 (d, 1H), 4.76-4.82 (m, 1H), 4.30-4.40 (m, 1H), 2.55-2.69 (m, 3H), 2.45-2.48 (m, 2H), 2.13 (s, 3H), 2.10-2.13 (m, 1H), 1.78-1.82 (m, 1H), 1.68 (d, 2H), 1.42 (t, 2H), 1.08 (s, 12H), 0.99 (d, 6H) ppm; MS (ES) 551 (M+H).

II-1: (6-(4-(1,2,2,6,6-pentamethylpiperidin-4-ylamino)-5-fluoropyrimidin-2-ylamino)-2,3-dihydrobenzo[b][1,4]dioxin-2-yl)(piperidin-1-yl)methanone MS (ES) 527 (M+H). $^1$H NMR (DMSO-d$_6$, 300 MHz) 8.76 (s, 1H), 8.17 (s, 1H), 7.78 (d, 1H), 7.18 (s, 1H), 7.08 (d, 1H), 6.61 (d, 1H), 4.19 (m, 1H), 4.35 (m, 2H), 4.09 (m, 1H), 3.45 (m, 4H), 2.22 (s, 3H), 1.78-1.42 (m, 10H), 1.19 (s, 12H) ppm.

II-2: (6-(4-(1,2,2,6,6-pentamethylpiperidin-4-ylamino)-5-fluoropyrimidin-2-ylamino)-2,3-dihydrobenzo[b][1,4]dioxin-2-yl)(morpholino)methanone MS (ES) 529 (M+H). $^1$H NMR (DMSO-d$_6$, 300 MHz) 8.81 (s, 1H), 8.12 (s, 1H), 7.78 (d, 1H), 7.22 (d, 1H), 7.18 (dd, 1H), 6.61 (d, 1H), 5.25 (m, 1H), 4.81 (m, 1H), 4.31 (d, 1H), 4.05 (m, 1H), 3.61-3.41 (m, 8H), 2.41 (s, 3H), 1.81-1.71 (d, 2H), 1.59-1.51 (t, 2H), 1.21-1.09 (d, 12H) ppm.

II-3: (6-(4-(2,2,6,6-tetramethylpiperidin-4-ylamino)-5-fluoropyrimidin-2-ylamino)-2,3-dihydrobenzo[b][1,4]dioxin-2-yl)(piperidin-1-yl)methanone MS (ES) 513 (M+H). $^1$H NMR (DMSO-d$_6$, 300 MHz) 8.86 (s, 1H), 8.19 (s, 1H), 7.81 (d, 1H), 7.39 (d, 1H), 7.29 (s, 1H), 7.08 (d, 1H), 6.65 (d, 1H), 5.15 (d, 1H), 4.48 (m, 1H), 4.31 (d, 1H), 4.05 (dd, 1H), 3.51-3.41 (m, 4H), 1.65-1.41 (bm, 10H), 1.35 (d, 6H), 1.25 (d, 6H) ppm.

II-4: (6-(4-(2,2,6,6-tetramethylpiperidin-4-ylamino)-5-fluoropyrimidin-2-ylamino)-2,3-dihydrobenzo[b][1,4]dioxin-2-yl)(morpholino)methanone MS (ES) 515 (M+H). $^1$H NMR (DMSO-d$_6$, 300 MHz) 8.83 (s, 1H), 8.29 (s, 1H), 8.08 (d, 1H), 7.82 (d, 1H), 7.24 (d, 1H), 7.14 (dd, 1H), 6.66 (d, 1H), 5.15 (d, 1H), 4.49 (m, 1H), 4.31 (d, 1H), 4.05 (dd, 1H), 3.61-3.41 (bm, 8H), 1.81-1.71 (d, 2H), 1.39-1.09 (m, 14H), ppm.

II-5: 5-fluoro-N2-(2,3-dihydro-2-((piperidin-1-yl)methyl)benzo[b][1,4]dioxin-6-yl)-N4-(1,2,2,6,6-pentamethylpiperidin-4-yl)pyrimidine-2,4-diamine MS (ES) 513 (M+H). $^1$H NMR (DMSO-d$_6$, 300 MHz) 8.11 (s, 1H), 7.85 (d, 1H), 7.55 (d, 1H), 7.28 (s, 1H), 7.09 (dd, 1H), 6.69 (d, 1H), 4.69 (bm, 1H), 4.45 (bm, 1H), 4.25 (d, 1H), 3.97 (m, 1H), 2.95 (bm, 6H), 2.45 (s, 3H), 2.05-1.96 (t, 2H), 1.75-1.62 (d, 2H), 1.49-1.35 (d, 18H) ppm.

II-6: 5-fluoro-N2-(2,3-dihydro-2-(morpholinomethyl)benzo[b][1,4]dioxin-6-yl)-N4-(1,2,2,6,6-pentamethylpiperidin-4-yl)pyrimidine-2,4-diamine MS (ES) 515 (M+H). $^1$H NMR (DMSO-d$_6$, 300 MHz) 9.05 (s, 1H), 7.85 (d, 1H), 7.75 (d, 1H), 7.29 (s, 1H), 7.08 (d, 1H), 6.71 (d, 1H), 4.79 (m, 1H), 4.47 (m, 1H), 4.27 (d, 1H), 4.01 (m, 1H), 3.82 (bm, 4H), 3.35 (bm, 4H), 2.69 (s, 3H), 2.44 (t, 2H), 2.15-2.01 (t, 2H), 1.95-1.90 (d, 2H), 1.59-1.35 (d, 12H) ppm.

II-7: 5-fluoro-N2-(2,3-dihydro-2-((piperidin-1-yl)methyl)benzo[b][1,4]dioxin-6-yl)-N4-(2,2,6,6-tetramethylpiperidin-4-yl)pyrimidine-2,4-diamine MS (ES) 499 (M+H). $^1$H NMR (DMSO-d$_6$, 300 MHz) 8.89 (s, 1H), 8.11 (s, 1H), 7.85 (d, 1H), 7.49 (d, 1H), 7.31 (s, 1H), 7.09 (dd, 1H), 6.69 (d, 1H), 4.59 (m, 2H), 4.25 (d, 1H), 3.91 (m, 1H), 2.85 (bm, 6H), 1.95-84 (d, 2H), 1.65 (m, 8H), 1.46-1.39 (d, 12H) ppm.

II-8: 5-fluoro-N2-(2,3-dihydro-2-(morpholinomethyl)benzo[b][1,4]dioxin-6-yl)-N4-(2,2,6,6-tetramethylpiperidin-4-yl)pyrimidine-2,4-diamine MS (ES) 501 (M+H). $^1$H NMR (DMSO-d$_6$, 300 MHz) 8.92 (s, 1H), 8.06 (d, 1H), 7.85 (d, 1H), 7.55 (d, 1H), 7.32 (s, 1H), 7.05 (bs, 1H), 6.69 (d, 1H), 4.51 (m, 1H), 4.27 (d, 1H), 3.92 (m, 1H), 3.69 (bm, 4H), 3.36 (bm, 4H), 2.42 (t, 2H), 1.95-1.86 (d, 2H), 1.68-1.59 (t, 2H), 1.49-1.35 (d, 12H) ppm.

II-9: N2-[2,2-Dimethyl-4-(2-fluoroethyl)-1,4-benzoxazin-3-one-7-yl]-5-fluoro-N4-(2,2,6,6-tetramethylpiperidin-4-yl)-2,4-pyrimidinediamine MS (ES) 489.55 (M+H). $^1$H NMR (DMSO-d$_6$, 300 MHz) 9.08 (s, 1H), 7.83 (d, J=3.9 Hz, 1H), 7.78 (s, 1H), 7.2-7.17 (d, J=7.8 Hz, 1H), 7.12-7.11 (d, J=6.6 Hz, 1H), 7.02-6.99 (d, J=9 Hz, 1H), 4.66 (s, 1H), 4.5 (m, 2H), 4.2 (s, 1H), 4.12 (s, 1H), 1.68-1.65 (d, J=11.4 Hz, 2H), 1.35 (s, 6H), 1.29-1.16 (m, 8H), 1.04 (s, 6H) ppm.

II-10: N2-(3,4-Ethylenedioxy)phenyl-5-fluoro-N4-(2,2,6,6-tetramethylpiperidin-4-yl)-2,4-pyrimidinediamine MS (ES) 402.08 (M+H). $^1$H NMR (DMSO-d$_6$, 300 MHz) 8.79 (s, 1H), 7.81-7.79 (d, J=3.6 Hz, 2H), 7.24 (bs, 2H), 7.11-7.08 (d, J=8.4 Hz, 1H), 6.63-6.6 (d, J=9 Hz, 1H), 4.5 (bs, 1H), 4.14 (s, 4H), 1.77-1.73 (d, J=11.7 Hz, 2H), 1.36-1.29 (m, 8H), 1.15 (s, 6H) ppm.

III-3: N2-(3-(Difluoromethoxy)-4-(1-isopropylpiperidin-4-yloxy)phenyl)-5-fluoro-N4-(2,2,6,6-tetramethyl-1-(2,2,2-trifluoroethyl)piperidin-4-yl)pyrimidine-2,4-diamine $^1$H NMR (DMSO d$_6$, 300 MHz): δ 9.00 (s, 1H), 7.85 (d, 1H), 7.53 (d, 2H), 7.19 (d, 1H), 7.00 (t, 2H), 4.49-4.33 (m, 2H), 3.36-3.29 (m, 2H), 3.17 (d, 1H), 2.05-1.90 (m, 4H), 1.72-1.68 (m, 4H), 1.51-1.43 (m, 4H), 1.11 (s, 12H), 1.06 (s, 6H); LCMS (m/z): 633 (MH$^+$).

III-4: 1-(4-(2-(3-(Difluoromethoxy)-4-(1-isopropylpiperidin-4-yloxy)phenylamino)-5-fluoropyrimidin-4-ylamino)-2,2,6,6-tetramethylpiperidin-1-yl)ethanone $^1$H NMR (DMSO d$_6$, 300 MHz): δ 8.89 (s, 1H), 8.81 (s, 1H), 7.78 (d, 1H), 7.59-7.49 (m, 1H), 7.22-7.16 (m, 1H), 7.07-6.91 (m, 2H), 4.67 (s, 1H), 4.49-4.40 (m, 1H), 4.23-4.15 (m, 1H), 2.71-2.62 (m, 2H), 2.31-2.19 (m, 4H), 2.15-1.95 (m, 3H), 1.90-1.80 (m, 3H), 1.68-1.59 (m, 9H), 1.20 (s, 6H), 0.96 (d, 6H); LCMS (m/z): 593 (MH$^+$).

III-5: N$^2$-(3-(1H-tetrazol-1yl)phenyl)-N$^4$-(1-cyclopropyl-2,6-dimethylpiperidin-4yl)-5-fluoropyrimidine-2,4-diamine $^1$H NMR (DMSO d$_6$, 300 MHz): δ 10.03 (s, 1H), 9.45 (s, 1H), 8.10 (s, 1H), 7.89 (d, J=3.90 Hz, 1H), 7.77 (d, J=8.53 Hz, 1H), 7.43 (t, J=8.10 Hz, 1H), 7.24-7.32 (m, 2H), 4.27-4.32 (m, 1H), 3.20-3.26 (m, 2H), 1.61-1.80 (m, 4H), 1.14-1.19 (m, 1H), 1.06 (d, J=6.05 Hz, 3H), 0.91 (d, J=6.87 Hz, 3H), 0.56-0.59 (m, 1H), 0.36-0.38 (m, 2H), 0.20-0.23 (m, 1H); LCMS (m/z): 424 (MH+).

III-6: $N^4$-(1-cyclopropyl-2,6-dimethylpiperidin-4-yl)-5-fluoro-$N^2$-(4-methyl-3-(1H-tetrazol-1-yl)phenyl)pyrimidine-2,4-diamine 1H NMR (DMSO d6, 300 MHz): δ 9.85 (s, 1H), 8.11 (s, 1H), 8.01 (s, 1H), 7.86 (d, J=3.60 Hz, 1H), 7.69 (d, J=10.73 Hz, 1H), 7.32 (d, J=8.30 Hz, 1H), 7.24 (d, J=8.30 Hz, 1H), 4.05-4.18 (m, 1H), 3.19-3.21 (m, 2H), 1.98 (s, 3H), 1.54-1.76 (m, 4H), 1.02-1.12 (m, 1H), 1.03 (d, J=6.33 Hz, 3H), 0.88 (d, J=6.89 Hz, 3H), 0.58-0.60 (m, 1H), 0.34-0.38 (m, 2H), 0.21-0.22 (m, 1H); LCMS (m/z): 438 (MH+).

III-7: $N^4$-(1-cyclopropyl-2,6-dimethylpiperidin-4-yl)-5-fluoro-$N^2$-(3-methoxy-5-(1H-tetrazol-1-yl)phenyl)pyrimidine-2,4-diamine 1H NMR (DMSO d6, 300 MHz): δ 10.03 (s, 1H), 8.12 (s, 1H), 7.95 (s, 1H), 7.89 (d, J=3.90 Hz, 1H), 7.45 (s, 1H), 7.26 (d, J=8.0 Hz, 1H), 6.97 (1H) 4.20-4.28 (m, 1H), 3.80 (s, 3H), 3.20-3.22 (m, 2H), 2.75 (m, 1H), 1.60-1.83 (m, 4H), 1.11-1.15 (m, 1H), 1.06 (d, J=6.05 Hz, 3H), 0.92 (d, J=6.60 Hz, 3H), 0.55-0.58 (m, 1H), 0.35-0.37 (br m, 2H), 0.20-0.23 (m, 1H); LCMS (m/z): 454 (MH+).

III-8: $N^4$-(1-cyclopropyl-2,6-dimethylpiperidin-4-yl)-5-fluoro-$N^2$-(3-(5-methyl-1H-tetrazol-1-yl)phenyl)pyrimidine-2,4-diamine 1H NMR (DMSO d6, 300 MHz): δ 9.48 (s, 1H), 8.11 (s, 1H), 7.87-7.88 (m, 1H), 7.81 (d, J=8.0 Hz, 1H), 7.43 (t, J=8.10 Hz, 1H), 7.28 (d, J=7.7 Hz, 1H), 7.11 (d, J=7.50 Hz, 1H), 4.10-4.18 (m, 1H), 3.21-3.22 (m, 1H), 2.50-2.57 (m, 1H), 2.54 (s, 3H), 1.61-1.79 (m, 4H), 1.11-1.15 (m, 1H), 1.05 (d, J=6.05 Hz, 3H), 0.91 (d, J=6.60 Hz, 3H), 0.57-0.60 (m, 1H), 0.37-0.39 (m, 2H), 0.20-0.24 (m, 1H); LCMS (m/z): 438 (MH+).

III-9: $N^4$-(1-cyclopropyl-2,6-dimethylpiperidin-4-yl)-5-fluoro-$N^2$-(3-(5-(2,2,2-trifluoroethylthio)-1H-tetrazol-1-yl)phenyl)pyrimidine-2,4-diamine 1H NMR (DMSO d6, 300 MHz): δ 9.57 (s, 1H), 8.10 (s, 1H), 7.88 (s, 1H), 7.80 (d, J=8.50 Hz, 1H), 7.48 (t, J=8.20 Hz, 1H), 7.30 (d, J=7.6 Hz, 1H), 7.09 (d, J=7.50 Hz, 1H), 4.42 (q, J=9.60 Hz, 2H), 4.10-4.19 (m, 1H), 3.20 (m, 1H), 2.58 (m, 1H), 1.61-1.78 (m, 4H), 1.13-1.16 (m, 1H), 1.05 (d, J=6.10 Hz, 3H), 0.88 (d, J=6.50 Hz, 3H), 0.56-0.59 (m, 1H), 0.37-0.39 (m, 2H), 0.20-0.23 (m, 1H); LCMS (m/z): 538 (MH+).

III-10: $N^4$-(1-cyclopropyl-2,6-dimethylpiperidin-4-yl)-5-fluoro-$N^2$-(3-(5-(methylthio)-1H-tetrazol-1-yl)phenyl)pyrimidine-2,4-diamine 1H NMR (DMSO d6, 300 MHz): δ 9.56 (s, 1H), 8.23 (s, 1H), 7.88 (s, 1H), 7.69 (d, J=8.45 Hz, 1H), 7.45 (t, J=8.10 Hz, 1H), 7.30 (d, J=7.50 Hz, 1H), 7.06 (d, J=7.40 Hz, 1H), 4.10-4.19 (m, 1H), 3.18-3.25 (m, 1H), 2.75 (s, 3H), 1.58-1.74 (m, 4H), 1.09-1.13 (m, 1H), 1.04 (d, J=6.15 Hz, 3H), 0.83 (d, J=6.45 Hz, 3H), 0.55-0.60 (m, 1H), 0.37-0.39 (m, 2H), 0.20-0.25 (m, 1H); LCMS (m/z): 470 (MH+).

III-11: $N^4$-(1-cyclopropyl-2,6-dimethylpiperidin-4-yl)-5-fluoro-$N^2$-(4-fluoro-3-(1H-tetrazol-1-yl)phenyl)pyrimidine-2,4-diamine 1H NMR (DMSO d6, 300 MHz): δ 9.96 (s, 1H), 9.48 (s, 1H), 8.34 (d, J=6.33 Hz, 1H), 7.87 (s, 1H), 7.74 (s, 1H), 7.45 (t, J=9.60 Hz, 1H), 7.27 (d, J=7.43 Hz, 1H), 4.05-4.18 (m, 1H), 3.18-3.20 (m, 1H), 2.53 (m, 1H), 1.58-1.77 (m, 1H), 1.09-1.13 (m, 1H), 1.03 (d, J=5.90 Hz, 3H), 0.87 (d, J=6.90 Hz, 3H), 0.54-0.60 (m, 1H), 0.35-0.37 (m, 2H), 0.19-0.23 (m, 1H); LCMS (m/z): 442 (MH+).

III-12: 1-(4-(2-fluoro-4-(5-fluoro-4-(1,2,2,6,6-pentamethylpiperidin-4-ylamino)pyrimidin-2ylamino)phenoxy)piperidin-1-yl)ethanone 1H NMR (DMSO d6, 300 MHz): δ 9.05 (s, 1H), 7.83 (d, J=3.85 Hz, 1H), 7.77 (d, J=2.50 Hz, 0.5H), 7.73 (d, J=2.35 Hz, 0.5H), 7.23 (t, J=9.80 Hz, 2H), 7.02 (t, J=9.45 Hz, 1H), 4.35-4.37 (m, 2H), 3.74-3.77 (m, 1H), 3.61-3.68 (m, 1H), 2.18 (s, 3H), 1.99 (s, 3H), 1.57-1.80 (m, 3H), 1.42-1.50 (m, 4H), 1.24 (s, 3H), 1.07 (s, 6H), 1.06 (s, 6H); LCMS (m/z): 517 (MH+).

III-13: 1-(4-(2-fluoro-4-(5-fluoro-4-(2,2,6,6-tetramethylpiperidin-4-ylamino)pyrimidin-2-ylamino)phenoxy)piperidin-1-yl)ethanone 1H NMR (DMSO d6, 300 MHz): δ 9.05 (s, 1H), 7.83 (d, J=3.85 Hz, 1H), 7.76 (s, 0.5H), 7.72 (s, 0.5H), 7.17-7.25 (m, 2H), 7.01 (t, J=9.35 Hz, 1H), 4.36-4.43 (m, 1H), 3.75-3.76 (m, 1H), 3.61-3.69 (m, 1H), 3.12-3.20 (m, 2H), 2.00 (s, 3H), 1.75-1.84 (m, 3H), 1.60-1.72 (m, 4H), 1.46-1.57 (m, 1H), 1.19 (s, 6H), 1.03 (s, 6H); LCMS (m/z): 503 (MH+).

III-14: 5-fluoro-N2-(3-fluoro-4-(1-(methylsulfonyl)piperidin-4-yloxy)phenyl)-N4-(1,2,2,6,6-pentamethylpiperidin-4-yl)pyrimidine-2,4-diamine 1H NMR (DMSO d6, 300 MHz): δ 9.07 (s, 1H), 7.81 (d, J=3.85 Hz, 1H), 7.76 (d, J=2.30 Hz, 0.5H), 7.74 (d, J=2.35 Hz, 0.5H), 7.19-7.23 (m, 2H), 7.01 (t, J=9.25 Hz, 1H), 4.31-4.34 (m, 2H), 4.19 (m, 1H), 3.15 (s, 3H), 3.04-3.11 (m, 2H), 2.88 (s, 3H), 2.18 (s, 1H), 1.90-1.98 (m, 2H), 1.66-1.73 (m, 4H), 1.47 (t, J=12.5 Hz, 2H), 1.07 (s, 6H), 1.06 (s, 6H); LCMS (m/z): 553 (MH+).

III-15: 5-fluoro-N2-(3-fluoro-4-(1-(methylsulfonyl)piperidin-4-yloxy)phenyl)-N4-(2,2,6,6-tetramethylpiperidin-4-yl)pyrimidine-2,4-diamine 1H NMR (DMSO d6, 300 MHz): δ 9.07 (s, 1H), 7.83 (d, J=3.85 Hz, 1H), 7.78 (d, J=2.5 Hz, 0.5H), 7.73 (d, J=2.5 Hz, 0.5H), 7.22-7.24 (m, 2H), 7.01 (t, J=9.35 Hz, 1H), 4.35-4.46 (m, 1H), 4.30-4.32 (m, 1H), 3.15 (s, 1H), 3.03-3.15 (m, 3H), 2.88 (s, 3H), 1.90-1.97 (m, 3H), 1.68-1.72 (m, 5H), 1.22 (s, 6H), 1.06 (s, 6H); LCMS (m/z): 539 (MH+).

III-16: N-ethyl-4-(2-fluoro-4-(5-fluoro-4-(1,2,2,6,6-pentamethylpiperidin-4-ylamino)pyrimidin-2-ylamino)phenoxy)piperidine-1-carboxamide 1H NMR (DMSO d6, 300 MHz): δ 9.06 (s, 1H), 7.71-7.75 (d, J=3.85 Hz, 0.5H), 7.71-7.72 (d, J=2.30 Hz, 0.5H), 7.19-7.24 (m, 2H), 7.01 (t, J=9.25 Hz, 1H), 6.46-6.49 (m, 1H), 4.29-4.35 (m, 2H), 3.60-3.64 (m, 2H), 3.15 (s, 3H), 2.97-3.07 (m, 4H), 2.18 (s, 3H), 1.79 (m, 4H), 1.65-1.70 (m, 1H), 1.07 (s, 6H), 1.06 (s, 6H), 0.99 (t, J=7.0 Hz, 3H); LCMS (m/z): 546 (MH+).

III-17: N-ethyl-4-(2-fluoro-4-(5-fluoro-4-(2,2,6,6-tetramethylpiperidin-4-ylamino)pyrimidin-2-ylamino)phenoxy)piperidine-1-carboxamide 1H NMR (DMSO d6, 300 MHz): δ 9.05 (s, 1H), 7.82 (d, J=3.85 Hz, 1H), 7.76 (d, J=2.5 Hz, 0.5H), 7.71 (d, J=2.5 Hz, 0.5H), 7.19-7.24 (m, 2H), 6.99 (t, J=9.40 Hz, 1H), 6.46-6.49 (m, 1H), 4.34-4.38 (m, 1H), 4.27-4.29 (m, 1H), 3.60-3.64 (m, 2H), 2.97-3.06 (m, 5H), 1.65-1.78 (m, 4H), 1.40-1.49 (m, 3H), 1.20 (s, 6H), 1.04 (s, 6H), 0.98 (t, J=7.2 Hz, 3H); LCMS (m/z): 532 (MH$^+$).

III-18: 5-fluoro-N2-(3-fluoro-4-(1-isopropylpiperidin-4-yloxy)phenyl)-N4-(1,2,2,6,6-pentamethylpiperidin-4-yl)pyrimidine-2,4-diamine $^1$H NMR (300 MHz, DMSO) δ 9.03 (s, 1H), 7.81 (d, J=3.9, 1H), 7.70 (dd, J=14.2, 2.3, 1H), 7.20 (t, J=6.9, 2H), 6.95 (t, J=9.3, 1H), 4.44-4.29 (m, 1H), 4.14-4.09 (m, 1H), 2.72-2.62 (m, 3H), 2.33-2.18 (m, 2H), 2.17 (s, 3H), 1.90-1.80 (m, 2H), 1.73-1.62 (m, 2H), 1.61-1.40 (m, 4H), 1.06 (s, 6H), 1.05 (s, 6H), 0.95 (s, 3H), 0.93 (s, 3H); LCMS (m/z): 517 (MH$^+$).

III-19: 5-fluoro-N2-(3-fluoro-4-(1-isopropylpiperidin-4-yloxy)phenyl)-N4-(2,2,6,6-tetramethylpiperidin-4-yl)pyrimidine-2,4-diamine $^1$H NMR (300 MHz, DMSO) δ 9.02 (s, 1H), 7.81 (d, J=3.8, 1H), 7.69 (d, J=14.5, 1H), 7.34-7.05 (m, 2H), 6.95 (t, J=9.3, 1H), 4.50-4.40 (m, 1H), 4.34-4.04 (m, 1H), 2.70-2.62 (m, 3H), 2.22 (app. t, J=8.8, 3H), 1.90-1.80 (s, 1H), 1.69-1.47 (m, 4H), 1.23-1.13 (m, 2H), 1.19 (s, 6H), 1.02 (s, 6H), 0.96 (s, 3H), 0.93 (s, 3H); LCMS (m/z): 503 (MH$^+$).

III-20: N2-(3-(difluoromethoxy)-4-(1-(methylsulfonyl)piperidin-4-yloxy)phenyl)-5-fluoro-N4-(1,2,2,6,6-pentamethylpiperidin-4-yl)pyrimidine-2,4-diamine $^1$H NMR (300 MHz, DMSO) δ 8.97 (s, 1H), 7.81 (d, J=3.8, 1H), 7.53 (m, 2H), 7.26-7.09 (m, 1H), 7.06-6.86 (m, 1H), 6.98 (t, J=75, 1H), 4.44-4.28 (m, 2H), 3.30-3.23 (m, 2H), 3.26-3.06 (m, 2H), 2.38 (s, 3H), 1.98-1.86 (m, 2H), 1.80-1.62 (m, 4H), 1.44 (t, J=12.3, 2H), 1.07 (s, 6H), 1.06 (s, 6H); LCMS (m/z): 601 (MH$^+$).

III-21: N2-(3-(difluoromethoxy)-4-(1-(methylsulfonyl)piperidin-4-yloxy)phenyl)-5-fluoro-N4-(2,2,6,6-tetramethylpiperidin-4-yl)pyrimidine-2,4-diamine $^1$H NMR (300 MHz, DMSO) δ 8.96 (s, 1H), 7.81 (d, J=3.8, 1H), 7.65-7.39 (m, 2H), 7.16 (d, J=6.0, 1H), 7.00 (t, J=75, 1H), 6.97 (d, J=6.0, 1H), 4.50-4.33 (m, 2H), 3.33-3.27 (m, 2H), 3.15-3.03 (m, 2H), 2.86 (s, 3H), 1.96-1.84 (m, 2H), 1.80-1.61 (m, 4H), 1.19 (s, 6H), 1.02 (s, 6H); LCMS (m/z): 587 (MH$^+$).

III-22: N2-(3-(difluoromethoxy)-4-(tetrahydro-2H-pyran-4-yloxy)phenyl)-5-fluoro-N4-(1,2,2,6,6-pentamethylpiperidin-4-yl)pyrimidine-2,4-diamine $^1$H NMR (300 MHz, DMSO) δ 8.94 (s, 1H), 7.81 (d, J=3.8, 1H), 7.52 (d, J=8.9, 2H), 7.15 (d, J=8.0, 1H), 7.00 (t, J=75, 1H), 6.95 (d, J=5.0, 1H), 4.43-4.27 (m, 2H), 3.85-3.78 (m, 2H), 3.48-3.37 (m, 2H), 2.17 (s, 3H), 1.96-1.84 (m, 2H), 1.71-1.38 (m, 6H), 1.06 (s, 3H), 1.05 (s, 6H); LCMS (m/z): 524 (MH$^+$).

III-23: N2-(3-(difluoromethoxy)-4-(tetrahydro-2H-pyran-4-yloxy)phenyl)-5-fluoro-N4-(2,2,6,6-tetramethylpiperidin-4-yl)pyrimidine-2,4-diamine $^1$H NMR (300 MHz, DMSO) δ 8.94 (s, 1H), 7.81 (d, J=3.8, 1H), 7.60-7.45 (m, 2H), 7.14 (d, J=8.1, 1H), 6.97 (t, J=75, 1H), 6.94 (m, 1H), 4.48-4.33 (m, 2H), 3.84-3.77 (m, 2H), 3.47-3.38 (m, 2H), 1.93-1.85 (m, 2H), 1.67-1.53 (m, 4H), 1.18 (s, 6H), 1.12-1.15 (m, 2H), 1.02 (s, 6H); LCMS (m/z): 510 (MH$^+$).

III-24: 5-fluoro-N2-(3-fluoro-4-(tetrahydro-2H-pyran-4-yloxy)phenyl)-N4-(1,2,2,6,6-pentamethylpiperidin-4-yl)pyrimidine-2,4-diamine $^1$H NMR (300 MHz, DMSO) δ 9.05 (s, 1H), 7.82 (d, J=3.8, 1H), 7.74 (d, J=14.1, 1H), 7.21 (t, J=7.5, 2H), 6.99 (t, J=9.2, 1H), 4.43-4.28 (m, 2H), 3.85-3.78 (m, 2H), 3.44-3.35 (m, 2H), 2.17 (s, 3H), 1.90-1.87 (m, 2H), 1.68-1.42 (m, 6H), 1.06 (s, 6H), 1.05 (s, 6H); LCMS (m/z): 476 (MH$^+$).

III-25: N2-(3,5-difluoro-4-(tetrahydro-2H-pyran-4-yloxy)phenyl)-5-fluoro-N4-(1,2,2,6,6-pentamethylpiperidin-4-yl)pyrimidine-2,4-diamine $^1$H NMR (300 MHz, DMSO) δ 9.30 (s, 1H), 7.86 (d, J=3.8, OH), 7.45 (d, J=11.1, 2H), 7.30 (d, J=8.8, 1H), 4.40-4.29 (m, 1H), 4.16-4.07 (m, 1H), 3.86-3.79 (m, 2H), 3.39-3.32 (m, 2H), 2.17 (s, 3H), 1.91-1.80 (m, 2H), 1.68-1.42 (m, 6H), 1.06 (s, 6H), 1.05 (s, 6H); LCMS (m/z): 494 (MH$^+$).

III-26: N2-(3,5-difluoro-4-(tetrahydro-2H-pyran-4-yloxy)phenyl)-5-fluoro-N4-(2,2,6,6-tetramethylpiperidin-4-yl)pyrimidine-2,4-diamine $^1$H NMR (300 MHz, DMSO) δ 9.29 (s, 1H), 7.86 (d, J=3.8, 1H), 7.45 (d, J=11.3, 2H), 7.29 (d, J=7.9, 1H), 4.49-4.36 (m, 1H), 4.13-4.07 (m, 1H), 3.86-3.77 (m, 2H), 3.39-3.33 (m, 2H), 1.88-1.83 (m, 2H), 1.69-1.51 (m, 4H), 1.19 (s, 6H), 1.15-1.19 (m, 2H), 1.02 (s, 6H); LCMS (m/z): 480 (MH$^+$).

III-28: N2-(3-(difluoromethoxy)-4-(piperidin-4-yloxy)phenyl)-5-fluoro-N4-(2,2,6,6-tetramethylpiperidin-4-yl)pyrimidine-2,4-diamine $^1$H NMR (300 MHz, DMSO) δ 8.93 (s, 1H), 7.80 (s, 1H), 7.46 (m, 2H), 7.16 (m, 1H), 6.92 (m, 1H), 6.91 (t, J=75, 1H), 4.43-4.34 (m, 1H), 4.24-4.14 (m, 1H), 2.92-2.89 (m, 3H), 1.90-1.75 (m, 3H), 1.69-1.64 (m, 3H), 1.43-1.35 (m, 3H), 1.19 (s, 6H), 1.12-1.19 (m, 2H), 1.03 (s, 6H); LCMS (m/z): 509 (MH$^+$).

III-29: N2-[4-(1,1-Dioxo-hexahydro-1Λ6-thiopyran-4-yloxy)-3-fluoro-phenyl]-5-fluoro-N4-(1,2,2,6,6-pentamethyl-piperidin-4-yl)-pyrimidine-2,4-diamine $^1$H NMR (DMSO d$_6$, 300 MHz): δ 9.10 (s, 1H), 7.83-7.73 (m, 2H), 7.29-7.10 (m, 2H), 7.06 (t, J=9.3, 1H), 4.50-4.33 (m, 2H), 3.22-3.05 (m, 4H), 2.20-2.16 (m, 7H), 1.73-1.67 (m, 2H), 1.51-1.49 (m, 2H), 1.15-1.03 (m, 12H); LCMS (m/z): 524 (MH$^+$).

III-30: N2-[4-(1,1-Dioxo-hexahydro-1Λ6-thiopyran-4-yloxy)-3-fluoro-phenyl]-5-fluoro-N4-(2,2,6,6-tetramethyl-piperidin-4-yl)-pyrimidine-2,4-diamine $^1$H NMR (DMSO d$_6$, 300 MHz): δ 9.09 (s, 1H), 7.83-7.76 (m, 2H), 7.26-7.08 (m, 2H), 7.06 (t, J=9.3, 1H), 4.57-4.30 (m, 1H), 3.22-3.05 (m, 4H), 2.20-2.16 (m, 4H), 1.73-1.67 (m, 2H), 1.20-1.03 (m, 16H); LCMS (m/z): 510 (MH$^+$).

III-31: N2-[3-Difluoromethoxy-4-(1,1-dioxo-hexahydro-1Λ6-thiopyran-4-yloxy)-phenyl]-5-fluoro-N4-(1,2,2,6,6-pentamethyl-piperidin-4-yl)-pyrimidine-2,4-diamine $^1$H NMR (DMSO d$_6$, 300 MHz): δ 8.99 (s, 1H), 7.81 (d, J=3.8, 1H), 7.57-7.54 (m, 2H), 7.24-7.11 (m, 1H), 7.04-6.92

(m, 2H), 4.54-4.50 (m, 1H), 4.27-4.11 (m, 1H), 3.26-3.03 (m, 4H), 2.17 (bs, 7H), 1.67 (d, J=8.9, 2H), 1.48-1.40 (m, 2H), 1.05-0.982 (m, 12H); LCMS (m/z): 572 (MH$^+$).

III-32: N2-[3-Difluoromethoxy-4-(1,1-Dioxohexahydro-1Λ6-thiopyran-4-yloxy)-phenyl]-5-fluoro-N4-(2,2,6,6-tetramethyl-piperidin-4-yl)-pyrimidine-2,4-diamine $^1$H NMR (DMSO d$_6$, 300 MHz): δ 8.99 (s, 1H), 7.81 (d, J=3.8, 1H), 7.55 (d, J=8.3, 2H), 7.17 (d, J=3.8, 1H), 7.05-6.92 (m, 2H), 4.54-4.35 (m, 2H), 3.26-3.03 (m, 4H), 2.17 (d, J=5.0, 4H), 1.67 (d, J=8.9, 2H), 1.20-1.02 (m, 16H); LCMS (m/z): 558 (MH$^+$).

III-33: 2-(4-(2-Fluoro-4-(5-fluoro-4-(1,2,2,6,6-pentamethylpiperidin-4-ylamino)pyrimidin-2-ylamino)phenoxy)piperidin-1-yl)acetamide $^1$H NMR (DMSO d$_6$, 300 MHz): δ 9.03 (s, 1H), 7.82 (d, J=3.8 Hz, 1H), 7.74-7.67 (m, 1H), 7.35-6.79 (m, 5H), 4.40-4.29 (m, 1H), 4.20-4.11 (m, 1H), 2.85 (bs, 2H), 2.70-2.62 (m, 2H), 2.27-2.18 (m, 4H), 1.85-1.41 (m, 8H), 1.12-0.997 (m, 12H); LCMS (m/z): 532 (MH$^+$).

III-34: 2-(4-(2-Fluoro-4-(5-fluoro-4-(2,2,6,6-tetramethylpiperidin-4-ylamino)pyrimidin-2-ylamino)phenoxy)piperidin-1-yl)acetamide $^1$H NMR (DMSO d$_6$, 300 MHz): δ 9.02 (s, 1H), 7.82 (d, J=4.0 Hz, 1H), 7.75-7.68 (m, 1H), 7.25-6.93 (m, 6H), 4.40-4.29 (m, 1H), 4.20-4.11 (m, 1H), 2.82 (bs, 2H), 2.70-2.62 (m, 2H), 2.27-2.18 (m, 2H), 1.85-1.61 (m, 6H), 1.20-1.03 (m, 14H); LCMS (m/z): 518 (MH$^+$).

III-35: 2-(4-(2-(Difluoromethoxy)-4-(5-fluoro-4-(1,2,2,6,6-pentamethylpiperidin-4-ylamino)pyrimidin-2-ylamino)phenoxy)piperidin-1-yl)acetamide $^1$H NMR (DMSO d$_6$, 300 MHz): δ 8.93 (s, 1H), 7.82 (d, J=4.0 Hz, 1H), 7.55-7.48 (m, 2H), 7.17-7.09 (m, 3H), 6.97-6.90 (m, 1H), 4.45-4.19 (m, 2H), 2.82 (bs, 2H), 2.70-2.62 (m, 2H), 2.33-2.18 (m, 2H), 2.16 (s, 3H), 1.95-1.71 (m, 2H), 1.65-1.41 (m, 6H), 1.05-0.953 (m, 14H); LCMS (m/z): 580 (MH$^+$).

III-36: 2-(4-(2-(Difluoromethoxy)-4-(5-fluoro-4-(2,2,6,6-tetramethylpiperidin-4-ylamino)pyrimidin-2-ylamino)phenoxy)piperidin-1-yl)acetamide $^1$H NMR (DMSO d$_6$, 300 MHz): δ 8.94 (s, 1H), 7.82 (d, J=4.0 Hz, 1H), 7.57-7.48 (m, 2H), 7.17-7.09 (m, 3H), 6.97-6.93 (m, 1H), 4.45-4.19 (m, 2H), 2.82 (bs, 2H), 2.70-2.62 (m, 2H), 2.33-2.18 (m, 2H), 1.90-1.64 (m, 6H), 1.18-1.03 (m, 14H); LCMS (m/z): 566 (MH$^+$).

III-37: 2-(4-(2-(Difluoromethoxy)-4-(5-fluoro-4-(1,2,2,6,6-pentamethylpiperidin-4-ylamino)pyrimidin-2-ylamino)phenoxy)piperidin-1-yl)ethanol $^1$H NMR (DMSO d$_6$, 300 MHz): δ 8.95 (s, 1H), 7.82 (d, J=4.0 Hz, 1H), 7.57-7.48 (m, 2H), 7.17-7.12 (m, 1H), 6.97-6.93 (m, 1H), 4.40-4.13 (m, 3H), 3.49-340 (m, 2H), 2.77-2.62 (m, 2H), 2.37-2.30 (m, 2H), 2.22-2.15 (m, 5H), 1.90-1.34 (m, 8H), 1.08-1.01 (m, 12H); LCMS (m/z): 567 (MH$^+$).

III-38: 2-(4-(2-(Difluoromethoxy)-4-(5-fluoro-4-(2,2,6,6-tetramethylpiperidin-4-ylamino)pyrimidin-2-ylamino)phenoxy)piperidin-1-yl)ethanol $^1$H NMR (DMSO d$_6$, 300 MHz): δ 8.95 (s, 1H), 7.82 (d, J=4.0 Hz, 1H), 7.56-7.46 (m, 1H), 7.17-7.12 (m, 1H), 6.97-6.93 (m, 1H), 4.40-4.13 (m, 3H), 3.46-3.26 (m, 4H), 2.77-2.62 (m, 2H), 2.37-2.30 (m, 2H), 2.22-2.15 (m, 2H), 1.90-1.44 (m, 4H), 1.28-1.01 (m, 14H); LCMS (m/z): 553 (MH$^+$).

III-39: N$^2$-(3-(Difluoromethoxy)-4-(1-isopropylazetidin-3-yloxy)phenyl)-5-fluoro-N$^4$—(2,2,6,6-tetramethylpiperidin-4-yl)pyrimidine-2,4-diamine LCMS (m/z): 523 (MH$^+$).

III-61: 5-Fluoro-N2-(4-isopropoxy-3-(isopropylamino)phenyl)-N4-(2,2,6,6-tetramethylpiperidin-4-yl)pyrimidine-2,4-diamine $^1$H NMR (DMSO d$_6$, 300 MHz): δ 8.53 (s, 1H), 7.77 (d, 1H, J=3.9 Hz), 7.23-7.19 (m, 1H), 7.07-7.04 (m, 1H), 6.56-6.53 (m, 2H), 4.46-4.43 (m, 1H), 4.30-4.22 (m, 1H), 4.07-4.04 (m, 1H), 3.47-3.40 (m, 1H), 1.70-1.66 (m, 2H), 1.21-1.03 (m, 28H); LCMS (m/z): 459 (MH$^+$).

III-62: 5-Fluoro-N2-(4-isopropoxy-3-(isopropylamino)phenyl)-N4-(1,2,2,6,6-pentamethylpiperidin-4-yl)pyrimidine-2,4-diamine $^1$H NMR (DMSO d$_6$, 300 MHz): δ 8.55 (s, 1H), 7.79 (d, 1H, J=3 Hz), 7.20-7.00 (m, 2H), 6.56-6.53 (m, 2H), 4.40-4.24 (m, 2H), 4.07-4.04 (m, 1H), 3.50-3.40 (m, 1H), 2.17-1.07 (m, 31H); LCMS (m/z): 473 (MH$^+$).

III-63: 5-Fluoro-N2-(4-methyl-3-(1-methyl-1H-tetrazol-5-yl)phenyl)-N4-(2,2,6,6-tetramethylpiperidin-4-yl)pyrimidine-2,4-diamine $^1$H NMR (DMSO d$_6$, 300 MHz): δ 9.13 (s, 1H), 8.11 (dd, 1H, J=2.1 Hz, J=8.7 Hz), 7.85 (d, 1H, J=3.9 Hz), 7.60 (d, 1H, J=1.5 Hz), 7.23-7.18 (m, 2H), 4.58-4.34 (m, 2H), 3.92 (s, 3H), 2.05 (s, 3H), 1.70-1.02 (m, 16H); LCMS (m/z): 440 (MH$^+$).

III-64: 5-Fluoro-N2-(4-methyl-3-(1-methyl-1H-tetrazol-5-yl)phenyl)-N4-(1,2,2,6,6-pentamethylpiperidin-4-yl)pyrimidine-2,4-diamine $^1$H NMR (DMSO d$_6$, 300 MHz): δ 9.13 (s, 1H), 8.00 (d, 1H, J=7.8 Hz), 7.85 (d, 1H, J=3.9 Hz), 7.60 (d, 1H, J=1.5 Hz), 7.23 (d, 2H, J=8.4 Hz), 4.46-4.14 (m, 1H), 3.92 (s, 3H), 2.20-2.10 (m, 2H), 2.05 (s, 3H), 1.70-0.955 (m, 17H); LCMS (m/z): 454 (MH$^+$).

III-65: 5-Fluoro-N2-(4-isopropoxy-3-(isopropyl(methyl)amino)phenyl)-N4-(2,2,6,6-tetramethylpiperidin-4-yl)pyrimidine-2,4-diamine $^1$H NMR (DMSO d$_6$, 300 MHz): δ 8.63 (s, 1H), 8.36 (s, 1H), 7.80-7.78 (m, 1H), 7.55-7.52 (m, 1H), 7.18-7.16 (m, 1H), 6.82 (bs, 1H), 6.16 (d, 1H, J=8.7 Hz), 4.46-4.35 (m, 2H), 3.84-3.76 (m, 1H), 1.80-1.72 (m, 2H), 1.33-0.980 (m, 29H); LCMS (m/z): 473 (MH$^+$).

III-66: 5-Fluoro-N2-(4-isopropoxy-3-(isopropyl(methyl)amino)phenyl)-N4-(1,2,2,6,6-pentamethylpiperidin-4-yl)pyrimidine-2,4-diamine $^1$H NMR (DMSO d$_6$, 300 MHz): δ 8.63 (s, 1H), 7.78 (d, 1H, J=3.9 Hz), 7.59-7.52 (m, 1H), 7.11 (bs, 1H), 6.83 (s, 1H), 6.61 (d, 1H, J=8.7 Hz), 4.43-4.35 (m, 2H), 3.84-3.74 (m, 1H), 2.30-1.92 (m, 2H), 1.73-1.40 (m, 2H), 1.20-0.980 (m, 30H); LCMS (m/z): 487 (MH$^+$).

III-68: 5-Fluoro-N4-(1,2,2,6,6-pentamethylpiperidin-4-yl)-N2-[3-(tetrazol-5-yl)]phenyl-2,4-pyrimidinediamine $^1$H NMR (DMSO d$_6$, 300 MHz): δ 8.97 (s, 1H), 7.97 (d, J=8.7 Hz, 1H), 7.91 (s, 1H), 7.82 (d, J=3.6 Hz, 1H), 7.45 (d, J=7.5 Hz, 1H), 7.10 (m, 2H), 4.40 (s, 1H), 2.18 (s, 3H), 1.70 (d, J=12 Hz, 2H), 1.46 (t, J=11.7 Hz, 2H), 1.07 (s, 12H); LCMS (m/z): 426.11 (MH$^+$).

III-69: 5-Fluoro-N4-(2,2,6,6-tetramethylpiperidin-4-yl)-N2-[3-(tetrazol-5-yl)]phenyl-2,4-pyrimidinediamine $^1$H NMR (DMSO d$_6$, 300 MHz): δ 8.97 (s, 1H), 7.99 (d, J=7.5 Hz, 1H), 7.91 (s, 1H), 7.82 (d, J=3.9 Hz, 1H), 7.45 (d, J=6.6 Hz 1H), 7.10 (m, 2H), 4.48 (s, 3H), 1.72 (d, J=12 Hz, 2H), 1.21 (m, 8H), 1.03 (s, 6H); LCMS (m/z): 412.07 (MH$^+$).

III-78: N2-{3,5-Difluoro-4-[(N-methylsulfonamide-piperidin-4-yl)oxy]}phenyl-5-fluoro-N4-(1,2,2,6,6-pentamethylpiperidin-4-yl)-2,4-pyrimidinediamine $^1$H NMR (DMSO d$_6$, 300 MHz): δ 9.39 (s, 1H), 8.78 (s, 1H), 7.94 (d, J=3.6 Hz, 1H), 7.68 (d, J=8.7 Hz, 1H), 7.44 (d, J=11.1 Hz, 2H), 4.46 (s, 1H), 4.10 (s, 1H), 3.47-3.14 (m, 2H), 3.05 (m, 2H), 2.87 (s, 3H), 2.73 (d, J=4.2 Hz, 3H), 2.07 (m, 2H), 1.90 (m, 4H), 1.83 (m, 2H), 1.42 (m, 12H); LCMS (m/z): 571.07 (MH$^+$).

III-79: N2-{3,5-Difluoro-4-[(N-methylsulfonamide-azepan-4-yl)oxy]}phenyl-5-fluoro-N4-(1,2,2,6,6-pentamethylpiperidin-4-yl)-2,4-pyrimidinediamine $^1$H NMR (DMSO d$_6$, 300 MHz): δ 9.37 (s, 1H), 9.01 (s, 1H), 7.94 (d, J=3.6 Hz, 1H), 7.69 (d, J=7.8 Hz, 1H), 7.42 (d, J=11.1 Hz, 2H), 4.46 bs, 1H), 4.14 (s, 1H), 3.39-3.12 (m, 4H), 2.87 (d, J=4.3 Hz, 3H), 2.47 (d, J=11.7 Hz, 3H), 2.07-1.84 (m, 8H), 1.59-1.53 (s, 12H); LCMS (m/z): 585.07 (MH$^+$).

III-80: N2-{3,5-Difluoro-4-[(N-methylsulfonamide-azepan-4-yl)oxy]}phenyl-5-fluoro-N4-(2,2,6,6-tetramethylpiperidin-4-yl)-2,4-pyrimidinediamine $^1$H NMR (DMSO d$_6$, 300 MHz): δ 9.34 (s, 1H), 8.06 (s, 1H), 7.90 (s, 1H), 7.43 (m, 2H), 4.44 (s, 2H), 4.13 (s, 1H), 3.38 (m, 2H), 3.25 (m, 2H), 2.87 (s, 3H), 1.94-1.83 (m, 10H), 1.36 (m, 12H); LCMS (m/z): 571.06 (MH$^+$).

III-81: N2-{4-[(N-Acetyl-azepan-4-yl)oxy]-3,5-difluoro-}phenyl-5-fluoro-N4-(1,2,2,6,6-pentamethylpiperidin-4-yl)-2,4-pyrimidinediamine $^1$H NMR (DMSO d$_6$, 300 MHz): δ 9.36 (s, 1H), 9.06 (bs, 1H), 7.92 (bs, 1H), 7.68 (bs, 1H), 7.42 (d, J=11.4 Hz, 2H), 4.46 (s, 1H), 4.07 (bs, 1H), 3.47-3.36 (m, 4H), 2.72 (s, 3H), 2.02-1.76 (m, 13H), 1.41 (bs, 12H); LCMS (m/z): 549.21 (MH$^+$).

III-82: N2-{4-[(N-Acetyl-azepan-4-yl)oxy]-3,5-difluoro}phenyl-5-fluoro-N4-(2,2,6,6-tetramethylpiperidin-4-yl)-2,4-pyrimidinediamine $^1$H NMR (DMSO d$_6$, 300 MHz): δ 9.30 (s, 1H), 7.89 (s, 1H), 7.43 (d, J=11.4 Hz, 2H), 7.25 (s, 1H), 4.45 (s, 1H), 4.04 (s, 1H), 3.46-3.38 (m, 4H), 1.92-1.51 (m, 13H), 1.19 (bs, 6H), 1.04 (bs, 6H); LCMS (m/z): 535.09 (MH$^+$).

III-83: N2-{3,5-Difluoro-4-[(N-ethylurea-azepan-4-yl)oxy]}phenyl-5-fluoro-N4-(1,2,2,6,6-pentamethylpiperidin-4-yl)-2,4-pyrimidinediamine $^1$H NMR (DMSO d$_6$, 300 MHz): δ 9.29 (s, 1H), 7.86 (s, 1H), 7.45-7.41 (m, 2H), 6.19 (s, 2H), 4.34 (m, 1H), 4.04 (s, 1H), 3.66-3.22 (m, 2H), 3.02 (m, 2H), 2.73 (s, 2H), 2.17 (s, 3H), 1.85-1.65 (m, 8H), 1.44 (m, 8H), 1.05 (6, s, H), 0.98 (t, J=6.9 Hz, 3H); LCMS (m/z): 578.17 (MH$^+$).

III-84: N2-{3,5-Difluoro-4-[(N-methylsulfonamide-piperidin-4-yl)oxy]}phenyl-5-fluoro-N4-(2,2,6,6-tetramethylpiperidin-4-yl)-2,4-pyrimidinediamine $^1$H NMR (DMSO d$_6$, 300 MHz): δ 9.33 (s, 1H), 8.26 (s, 1H), 7.89 (d, J=3.8 Hz, 1H), 7.44 (m, 3H), 4.45 (bs, 1H), 4.10 (bs, 1H), 3.35 (m, 2H), 3.08 (m, 2H), 2.87 (s, 3H), 1.92 (m, 2H), 1.68 (m, 4H), 1.37 (m, 2H), 1.3 (s, 6H), 1.18 (s, 6H); LCMS (m/z): 557.10 (MH$^+$).

III-85: N2-{3,5-Difluoro-4-[(N-ethylurea-azepan-4-yl)oxy]}phenyl-5-fluoro-N4-(2,2,6,6-tetramethylpiperidin-4-yl)-2,4-pyrimidinediamine $^1$H NMR (DMSO d$_6$, 300 MHz): δ 9.30 (s, 1H), 8.26 (s, 1H), 7.89 (d, J=3.8 Hz, 2H), 7.43 (d, J=10.8 Hz, 2H), 6.18 (t, J=5.1 Hz, 1H), 4.45 (s, 1H), 4.04 (s, 1H), 3.41-3.18 (m, 6H), 3.02 (m, 2H), 1.92-1.71 (m, 6H), 1.53-1.37 (m, 2H), 1.31 (s, 6H), 1.19 (s, 6H), 0.98 (t, J=6.9 Hz, 3H); LCMS (m/z): 564.19 (MH$^+$).

III-86: N2-{3-Difluoromethoxy-4-[(N-ethylurea-piperidin-4-yl)oxy]}phenyl-5-fluoro-N4-(2,2,6,6-tetramethylpiperidin-4-yl)-2,4-pyrimidinediamine $^1$H NMR (DMSO d$_6$, 300 MHz): δ 8.96 (s, 1H), 8.27 (s, 1H), 7.83 (d, J=3.8 Hz, 1H), 7.49 (m, 2H), 7.27 (d, J=7.8 Hz, 1H), 6.99 (d, J=9 Hz, 1H), 6.93 (t, J=75 Hz, 1H), 6.47 (m, 1H), 4.37 (m, 2H), 3.55 (bs, 2H), 3.25-2.96 (m, 4H), 1.77 (m, 4H), 1.54-1.47 (m, 2H), 1.33 (m, 2H), 1.28 (s, 6H), 1.16 (s, 6H), 0.99 (t, J=7.2 Hz, 3H); LCMS (m/z): 580.12 (MH$^+$).

III-87: N2-{3-Difluoromethoxy-4-[(N-ethylurea-azepan-4-yl)oxy]}phenyl-5-fluoro-N4-(1,2,2,6,6-pentamethylpiperidin-4-yl)-2,4-pyrimidinediamine $^1$H NMR (DMSO d$_6$, 300 MHz): δ 8.93 (s, 1H), 7.81 (d, J=3.8 Hz, 1H), 7.55 (d, J=8.9 Hz, 1H), 7.46 (s, 1H), 7.18-6.65 (m, 3H), 6.18 (t, J=5.4 Hz, 1H), 4.32 (s, 2H), 3.42-3.32 (m, 4H), 3.03 (m, 2H), 2.22 (s, 3H), 1.92 (s, 2H), 1.8-1.68 (m, 6H), 1.47 (m, 4H), 1.12 (s, 2H), 1.09 (s, 12H), 0.99 (t, J=7.2 Hz, 3H); LCMS (m/z): 608.2 (MH$^+$).

III-88: N2-{3-Difluoromethoxy-4-[(N-ethylurea-azepan-4-yl)oxy]}phenyl-5-fluoro-N4-(2,2,6,6-tetramethylpiperidin-4-yl)-2,4-pyrimidinediamine $^1$H NMR (DMSO d$_6$, 300 MHz): δ 8.96 (s, 1H), 7.85 (s, 1H), 7.50 (s, 1H), 7.27 (d, J=7.8 Hz, 1H), 7.16-6.66 (m, 2H), 6.19 (m, 1H), 4.32 (s, 2H), 4.32 (s, 1H), 3.34 (s, 4H), 3.07-2.99 (m, 2H), 1.91 (s, 2H), 1.78 (m, 4H), 1.57 (s, 2H), 1.39-1.32 (m, 8H), 1.18 (s, 6H), 0.99 (t, J=7.2 Hz, 3H); LCMS (m/z): 594.20 (MH$^+$).

III-89: N2-{3-Difluoromethoxy-4-[(N-methylsulfonamide-azepan-4-yl)oxy]}phenyl-5-fluoro-N4-(1,2,2,6,6-pentamethylpiperidin-4-yl)-2,4-pyrimidinediamine $^1$H NMR (DMSO d$_6$, 300 MHz): δ 8.95 (s, 1H), 7.81 (d, J=3.9 Hz, 1H), 7.55 (d, J=98.4 Hz, 1H), 7.47 (s, 1H), 7.17-6.68 (m, 3H), 4.42 (m, 2H), 3.29 (m, 4H), 2.88 (s, 3H), 2.20 (s, 3H), 2.02-1.86 (m, 6H), 1.69 (m, 2H), 1.46 (m, 2H), 1.08 (s, 12H); LCMS (m/z): 615.16 (MH$^+$).

III-90: N2-{3-Difluoromethoxy-4-[(N-methylsulfonamide-azepan-4-yl)oxy]}phenyl-5-fluoro-N4-(2,2,6,6-tetramethylpiperidin-4-yl)-2,4-pyrimidinediamine ¹H NMR (DMSO d₆, 300 MHz): δ 8.99 (s, 1H), 8.28 (s, 1H), 7.84 (d, J=3.7 Hz, 1H), 7.49 (m, 2H), 7.34 (d, J=7.5 Hz, 1H), 6.96 (t, J=62.7 Hz, 1H), 6.94 (s, 2H), 4.43 (s, 2H), 3.28 (m, 4H), 3.22 (s, 3H), 2.1 (m, 1H), 1.86 (m, 6H), 1.63 (m, 1H), 1.41 (m, 2H), 1.33 (s, 6H), 1.21 (s, 6H); LCMS (m/z): 601.11 (MH⁺).

III-91: N2-{4-[(N-Acetyl-piperidin-4-yl)oxy-]3,5-difluoro}phenyl-5-fluoro-N4-(1,2,2,6,6-pentamethylpiperidin-4-yl)-2,4-pyrimidinediamine ¹H NMR (DMSO d₆, 300 MHz): δ 9.32 (s, 1H), 7.88 (d, J=3.9 Hz, 1H), 7.46 (m, 2H), 7.34 (d, J=8.1 Hz, 1H), 4.38 (bs, 1H), 4.16 (bs, 1H), 3.78 (m, 1H), 3.63 (m, 1H), 3.16 (m, 2H), 2.24 (s, 3H), 1.99 (s, 3H), 1.85 (m, 6H), 1.51 (m, 2H), 1.11 (s, 12H); LCMS (m/z): 535.15 (MH⁺).

III-92: N2-{4-[(N-Acetyl-piperidin-4-yl)oxy-]3,5-difluoro}phenyl-5-fluoro-N4-(2,2,6,6-tetramethylpiperidin-4-yl)-2,4-pyrimidinediamine ¹H NMR (DMSO d₆, 300 MHz): δ 9.34 (s, 1H), 8.25 (s, 1H), 7.90 (d, J=3.9 Hz, 1H), 7.45 (d, J=6.6 Hz, 2H), 4.48 (bs, 1H), 4.16 (bs, 2H), 3.79 (m, 1H), 3.65 (m, 1H), 3.28-3.13 (m, 4H), 1.99 (s, 3H), 1.79 (m, 2H), 1.31 (s, 6H), 1.20 (s, 6H); LCMS (m/z): 521.13 (MH⁺).

III-95: N2-(3-chloro-4-(1-isopropylpiperidin-4-yloxy)phenyl)-5-fluoro-N4-(1,2,2,6,6-pentamethylpiperidin-4-yl)pyrimidine-2,4-diamine ¹H NMR (DMSO d₆, 300 MHz): δ 8.94 (br. s, 1H), 7.82 (d, 1H, J=3.6 Hz), 7.73 (br. s, 1H), 7.49 (d, 1H, J=9.3 Hz), 7.15 (d, 1H, J=8.4 Hz), 6.96 (d, 1H, J=9.0 Hz), 4.38-4.28 (m, 1H), 4.28-4.17 (m, 1H), 2.69-2.64 (m, 3H), 2.25 (t, 2H, J=9.3 Hz), 2.16 (s, 3H), 1.86-1.81 (m, 2H), 1.66-1.58 (m, 4H), 1.43 (t, 2H, J=11.7 Hz), 1.05 (s, 6H), 1.03 (s, 6H), 0.94 (d, 6H, J=6.6 Hz); LCMS (m/z): 533 (M⁺).

III-96: N2-(3-chloro-4-(1-(2-fluoroethyl)piperidin-4-yloxy)phenyl)-5-fluoro-N4-(2,2,6,6-tetramethylpiperidin-4-yl)pyrimidine-2,4-diamine ¹H NMR (DMSO d₆, 300 MHz): δ 8.95 (br. s, 1H), 7.81 (d, 1H, J=3.9 Hz), 7.72 (br. s, 1H), 7.53 (d, 1H, J=9.0 Hz), 7.14 (d, 1H, J=8.4 Hz), 6.96 (d, 1H, J=9.0 Hz), 4.58 (dt, 1H, J=47.7, 4.8 Hz), 4.42 (dt, 1H, J=47.7, 4.8 Hz), 4.50-4.38 (m, 1H), 4.30-4.20 (m, 1H), 2.75-2.65 (m, 2H), 2.64 (t, 2H, J=4.8 Hz), 2.54 (t, 2H, J=4.8 Hz), 2.27 (t, 2H, J=9.0 Hz), 1.90-1.80 (m, 2H), 1.70-1.56 (m, 2H), 1.17-1.10 (m, 2H), 1.17 (s, 6H), 1.00 (s, 6H); LCMS (m/z): 523 (M⁺).

III-97: N2-(3-chloro-4-(1-(2-fluoroethyl)piperidin-4-yloxy)phenyl)-5-fluoro-N4-(1,2,2,6,6-pentamethylpiperidin-4-yl)pyrimidine-2,4-diamine ¹H NMR (DMSO d₆, 300 MHz): δ 8.95 (br. s, 1H), 7.82 (d, 1H, J=3.6 Hz), 7.74 (br. s, 1H), 7.51 (d, 1H, J=9.0 Hz), 7.16 (d, 1H, J=8.4 Hz), 6.97 (d, 1H, J=9.0 Hz), 4.58 (dt, 1H, J=47.1, 4.8 Hz), 4.42 (dt, 1H, J=47.1, 4.8 Hz), 4.40-4.30 (m, 1H), 4.20-4.10 (m, 1H), 2.70-2.60 (m, 2H), 2.35-2.25 (m, 4H), 2.16 (s, 3H), 1.90-1.80 (m, 2H), 1.70-1.60 (m, 4H), 1.43 (t, 2H, J=11.7 Hz), 1.05 (s, 6H), 1.04 (s, 6H); LCMS (m/z): 537 (M⁺).

III-98: N2-(3-chloro-4-(1-isopropylpiperidin-4-yloxy)phenyl)-5-fluoro-N4-(2,2,6,6-tetramethylpiperidin-4-yl)pyrimidine-2,4-diamine ¹H NMR (DMSO d₆, 300 MHz): δ 8.97 (br. s, 1H), 7.85 (d, 1H, J=3.6 Hz), 7.72 (br. s, 1H), 7.48 (d, 1H, J=9.3 Hz), 7.22 (d, 1H, J=8.4 Hz), 6.97 (d, 1H, J=9.0 Hz), 4.50-4.38 (m, 1H), 4.28-4.15 (m, 1H), 2.69-2.65 (m, 1H), 2.67 (t, 1H, J=6.3 Hz), 2.25 (t, 2H, J=9.3 Hz), 1.95-1.88 (m, 3H), 1.90-1.80 (m, 2H), 1.65-1.50 (m, 1H), 1.22 (s, 6H), 1.08 (s, 6H), 0.94 (d, 6H, J=6.3 Hz); LCMS (m/z): 519 (M⁺).

III-99: (S)—N2-(3-(difluoromethoxy)-4-(tetrahydrofuran-3-yloxy)phenyl)-5-fluoro-N4-(1,2,2,6,6-pentamethylpiperidin-4-yl)pyrimidine-2,4-diamine ¹H NMR (DMSO d₆, 300 MHz): δ 8.97 (br. s, 1H), 7.82 (d, 1H, J=3.6 Hz), 7.56 (d, 1H, J=9.3 Hz), 7.50 (br. s, 1H), 7.16 (d, 1H, J=8.4 Hz), 6.91 (d, 1H, J=150.0 Hz), 6.90 (d, 1H, J=9.0 Hz), 4.96-4.90 (m, 1H), 4.40-4.25 (m, 1H), 3.84-3.73 (m, 4H), 2.17 (s, 3H), 2.17-2.08 (m, 1H), 1.96-1.90 (m, 1H), 1.65 (d-like, 2H, J=11.7 Hz), 1.43 (t, 2H, J=12.0 Hz), 1.05 (s, 12H); LCMS (m/z): 510 (MH⁺).

III-100: (S)—N2-(3-(difluoromethoxy)-4-(tetrahydrofuran-3-yloxy)phenyl)-5-fluoro-N4-(2,2,6,6-tetramethylpiperidin-4-yl)pyrimidine-2,4-diamine ¹H NMR (DMSO d₆, 300 MHz): δ 9.44 (br. s, 1H), 7.99 (d, 1H, J=4.2 Hz), 7.51 (br. s, 1H), 7.38 (d, 1H, J=9.3 Hz), 7.02 (d, 1H, J=9.3 Hz), 6.96 (d, 1H, J=150.0 Hz), 6.95 (s, 1H), 5.02-4.95 (m, 1H), 4.52-4.38 (m, 1H), 3.86-3.70 (m, 4H), 2.17-2.11 (m, 1H), 1.96-1.90 (m, 1H), 1.93 (d-like, 2H, J=14.4 Hz), 1.57 (t, 2H, J=12.6 Hz), 1.39 (s, 6H), 1.35 (s, 6H); LCMS (m/z): 496 (MH⁺).

III-101: 5-fluoro-N2-(4-(1-isopropylpiperidin-4-yloxy)-3-(trifluoromethyl)phenyl)-N4-(1,2,2,6,6-pentamethylpiperidin-4-yl)pyrimidine-2,4-diamine ¹H NMR (DMSO d₆, 300 MHz): δ 8.94 (br. s, 1H), 7.90 (d, 1H, J=10.5 Hz), 7.81 (d, 1H, J=3.6 Hz), 7.74 (br. s, 1H), 7.13 (d, 1H, J=8.4 Hz), 7.06 (d, 1H, J=9.3 Hz), 4.48-4.40 (m, 1H), 4.35-4.25 (m, 1H), 2.71-2.60 (m, 3H), 2.29 (t, 2H, J=7.5 Hz), 2.15 (s, 3H), 1.90-1.80 (m, 2H), 1.66-1.55 (m, 4H), 1.41 (t, 2H, J=11.7 Hz), 1.04 (s, 6H), 0.99 (s, 6H), 0.93 (d, 6H, J=6.6 Hz); LCMS (m/z): 567 (MH⁺).

III-102: 5-fluoro-N2-(4-(1-isopropylpiperidin-4-yloxy)-3-(trifluoromethyl)phenyl)-N4-(2,2,6,6-tetramethylpiperidin-4-yl)pyrimidine-2,4-diamine ¹H NMR (DMSO d₆, 300 MHz): δ 9.19 (br. s, 1H), 8.70 (d, 1H, J=10.5 Hz), 7.94 (d, 1H, J=3.6 Hz), 7.84 (br. s, 1H), 7.69 (d, 1H, J=8.4 Hz), 7.17 (d, 1H, J=9.9 Hz), 4.95-4.90 (m, 1H), 4.70-4.60 (m, 1H), 4.45-4.35 (m, 1H), 3.36-3.31 (m, 2H), 3.08-2.97 (m, 2H), 2.25-2.20 (m, 2H), 2.10-2.00 (m, 2H), 1.96-1.92 (m, 2H), 1.54 (t, 2H, J=12.6 Hz), 1.37 (s, 6H), 1.35 (s, 6H), 1.22 (d, 6H, J=6.3 Hz); LCMS (m/z): 553 (MH⁺).

III-103: (cis) N2-(3-(difluoromethoxy)-4-(3-fluoro-1-isopropylpiperidin-4-yloxy)phenyl)-5-fluoro-N4-(1,2,2,6,6-pentamethylpiperidin-4-yl)pyrimidine-2,4-diamine.TFA ¹H NMR (DMSO d₆, 300 MHz): δ 8.98 (br. s, 1H), 7.82 (d, 1H, J=3.6 Hz), 7.53 (d, 1H, J=7.8 Hz), 7.52 (br. s, 1H), 7.16 (d, 1H, J=7.8 Hz), 7.01 (d, 1H, J=9.0 Hz), 6.92 (d, 1H, J=150.6 Hz), 4.60 (d, 1H, J=48.3 Hz), 4.48-4.38 (m, 1H), 4.35-4.30 (m, 1H), 2.90-2.80 (m, 1H), 2.75-2.68 (m, 1H), 2.65-2.55 (m, 1H), 2.35-2.25 (m, 2H), 2.16 (s, 3H), 1.90-1.80 (m, 1H), 1.75-1.65 (m, 1H), 1.67-1.64 (m, 2H), 1.43 (t, 2H, J=12.3 Hz), 1.05 (s, 12H), 0.95 (d, 3H, J=6.6 Hz), 0.94 (d, 6H, J=6.6 Hz); LCMS (m/z): 583 (MH$^+$).

III-104: (cis) N2-(3-(difluoromethoxy)-4-(3-fluoro-1-isopropylpiperidin-4-yloxy)phenyl)-5-fluoro-N4-(2,2,6,6-tetramethylpiperidin-4-yl)pyrimidine-2,4-diamine $^1$H NMR (DMSO d$_6$, 300 MHz): δ 8.98 (br. s, 1H), 7.82 (d, 1H, J=3.6 Hz), 7.54 (d, 1H, J=9.0 Hz), 7.52 (br. s, 1H), 7.16 (d, 1H, J=6.0 Hz), 7.01 (d, 1H, J=8.7 Hz), 6.92 (d, 1H, J=150.9 Hz), 4.77 (d, 1H, J=48.3 Hz), 4.50-4.35 (m, 2H), 2.90-2.80 (m, 1H), 2.75-2.70 (m, 1H), 2.65-2.55 (m, 1H), 2.35-2.25 (m, 2H), 1.90-1.80 (m, 1H), 1.75-1.65 (m, 1H), 1.68-1.65 (m, 2H), 1.18 (s, 6H), 1.12 (t, 2H, J=9.6 Hz), 1.01 (s, 6H), 0.94 (d, 3H, J=6.3 Hz), 0.92 (d, 6H, J=6.3 Hz); LCMS (m/z): 569 (MH$^+$).

III-105: (trans) N2-(3-(difluoromethoxy)-4-(3-fluoro-1-isopropylpiperidin-4-yloxy)phenyl)-5-fluoro-N4-(1,2,2,6,6-pentamethylpiperidin-4-yl)pyrimidine-2,4-diamine $^1$H NMR (DMSO d$_6$, 300 MHz): δ 8.98 (br. s, 1H), 7.82 (d, 1H, J=3.9 Hz), 7.53 (d, 1H, J=9.0 Hz), 7.51 (br. s, 1H), 7.16 (d, 1H, J=9.0 Hz), 7.02 (d, 1H, J=8.7 Hz), 6.93 (d, 1H, J=149.7 Hz), 4.60 (dm, 1H, J=48.3 Hz), 4.40-4.25 (m, 1H), 4.25-4.10 (m, 1H), 3.10-2.95 (m, 1H), 2.80-2.65 (m, 1H), 2.65-2.60 (m, 1H), 2.32-2.24 (m, 2H), 2.16 (s, 3H), 2.05-1.95 (m, 1H), 1.67-1.64 (m, 2H), 1.55-1.50 (m, 1H), 1.43 (t, 2H, J=12.3 Hz), 1.05 (s, 6H), 1.04 (s, 6H), 0.95 (d, 3H, J=6.3 Hz), 0.94 (d, 6H, J=6.6 Hz); LCMS (m/z): 583 (MH$^+$).

III-106: (trans) N2-(3-(difluoromethoxy)-4-(3-fluoro-1-isopropylpiperidin-4-yloxy)phenyl)-5-fluoro-N4-(2,2,6,6-tetramethylpiperidin-4-yl)pyrimidine-2,4-diamine $^1$H NMR (DMSO d$_6$, 300 MHz): δ 8.98 (br. s, 1H), 7.82 (d, 1H, J=3.9 Hz), 7.55 (d, 1H, J=9.0 Hz), 7.49 (br. s, 1H), 7.15 (d, 1H, J=8.1 Hz), 7.02 (d, 1H, J=9.0 Hz), 6.93 (d, 1H, J=150.0 Hz), 4.50 (d, 1H, J=50.4 Hz), 4.50-4.35 (m, 1H), 4.20-4.10 (m, 1H), 3.10-2.96 (m, 1H), 2.78-2.71 (m, 1H), 2.67-2.63 (m, 1H), 2.32-2.16 (m, 2H), 2.05-1.96 (m, 1H), 1.68-1.64 (m, 1H), 1.55-1.45 (m, 1H), 1.18 (s, 6H), 1.12 (t, 2H, J=12.6 Hz), 1.01 (s, 6H), 0.95 (d, 3H, J=6.3 Hz), 0.94 (d, 6H, J=6.3 Hz); LCMS (m/z): 569 (MH$^+$).

III-107: N2-(4-(3,3-difluoro-1-isopropylpiperidin-4-yloxy)-3-(difluoromethoxy)phenyl)-5-fluoro-N4-(1,2,2,6,6-pentamethylpiperidin-4-yl)pyrimidine-2,4-diamine $^1$H NMR (DMSO d$_6$, 300 MHz): δ 8.99 (br. s, 1H), 7.82 (d, 1H, J=3.6 Hz), 7.56 (d, 1H, J=9.0 Hz), 7.52 (br. s, 1H), 7.16 (d, 1H, J=7.2 Hz), 7.05 (d, 1H, J=9.3 Hz), 6.92 (d, 1H, J=149.7 Hz), 4.50-4.40 (m, 1H), 4.40-4.30 (m, 1H), 3.00-2.85 (m, 1H), 2.82-2.77 (m, 1H), 2.71-2.63 (m, 2H), 2.45-2.35 (m, 1H), 2.17 (s, 3H), 1.95-1.89 (m, 1H), 1.80-1.70 (m, 1H), 1.68-1.64 (m, 2H), 1.43 (t, 2H, J=12.9 Hz), 1.05 (s, 12H), 0.95 (d, 6H, J=6.6 Hz); LCMS (m/z): 601 (MH$^+$).

III-108: N2-(4-(3,3-difluoro-1-isopropylpiperidin-4-yloxy)-3-(difluoromethoxy)phenyl)-5-fluoro-N4-(2,2,6,6-tetramethylpiperidin-4-yl)pyrimidine-2,4-diamine $^1$H NMR (DMSO d$_6$, 300 MHz): δ 8.99 (br. s, 1H), 7.82 (d, 1H, J=3.9 Hz), 7.57 (d, 1H, J=9.0 Hz), 7.51 (br. s, 1H), 7.15 (d, 1H, J=9.6 Hz), 7.05 (d, 1H, J=9.6 Hz), 6.92 (d, 1H, J=148.5 Hz), 4.50-4.35 (m, 2H), 3.00-2.88 (m, 1H), 2.83-2.75 (m, 1H), 2.70-2.60 (m, 2H), 2.45-2.35 (m, 1H), 1.95-1.85 (m, 1H), 1.80-1.70 (m, 1H), 1.68-1.64 (m, 2H), 1.18 (s, 6H), 1.43 (t, 2H, J=12.3 Hz), 1.01 (s, 6H), 0.95 (d, 6H, J=6.3 Hz); LCMS (m/z): 587 (MH$^+$)

III-109: 5-fluoro-N2-(3-fluoro-4-(tetrahydro-2H-pyran-4-yloxy)phenyl)-N4-(2,2,6,6-tetramethylpiperidin-4-yl)pyrimidine-2,4-diamine $^1$H NMR (300 MHz, DMSO) δ 9.04 (s, 1H), 7.81 (d, J=3.9, 0H), 7.74 (dd, J=14.2, 2.3, 1H), 7.30-7.11 (m, 2H), 6.99 (t, J=9.3, 1H), 4.49-4.37 (m, 1H), 4.36-4.26 (m, 1H), 3.85-3.78 (m, 2H), 3.43-3.36 (m, 2H), 1.90-1.87 (m, 2H), 1.65-1.49 (m, 4H), 1.19 (s, 6H), 1.19-1.12 9m, 2H), 1.02 (s, 6H); LCMS (m/z): 462 (MH$^+$).

III-110: N2-(3-(difluoromethoxy)-4-(1-isopropylpiperidin-4-yloxy)phenyl)-5-fluoro-N4-(1-trideuteromethyl-2,2,6,6-tetramethylpiperidin-4-yl)pyrimidine-2,4-diamine $^1$H NMR (DMSO d$_6$, 300 MHz): δ 7.76 (d, J=2.8 Hz, 1H), 7.63 (s, 1H), 7.23-7.31 (m, 2H), 6.90 (d, J=8.80 Hz, 1H), 6.51 (t, J=75 Hz, 1H), 5.62 (d, J=7.43 Hz, 1H), 4.50-4.53 (m, 2H), 3.39-3.44 (m, 1H), 3.13-3.24 (m, 4H), 2.23-2.36 (m, 4H), 1.98-2.09 (m, 4H), 1.44 (s, 6H), 1.41 (s, 6H), 1.31 (d, J=6.60 Hz, 6H); LCMS (m/z): 568 (MH$^+$).

III-111: N2-(3-(chloro)-4-(1-isopropylpiperidin-4-yloxy)phenyl)-5-fluoro-N4-(1-trideuteromethyl-2,2,6,6-tetramethylpiperidin-4-yl)pyrimidine-2,4-diamine $^1$H NMR (DMSO d$_6$, 300 MHz): δ 7.73 (d, J=3.3 Hz, 1H), 7.61 (d, J=2.50 Hz, 1H), 7.33 (dd, J=2.75 Hz & 6.06 Hz, 1H), 6.88 (d, J=2.75 Hz, 1H), 6.85 (s, 1H), 4.73 (d, J=8.26 Hz, 1H), 4.30-4.39 (m, 1H), 4.20-4.28 (m, 1H), 2.72-2.83 (m, 3H), 2.33-2.41 (m, 2H), 1.85-2.03 (m, 6H), 1.34 (t, J=12.0 Hz, 2H), 1.15 (s, 6H), 1.11 (s, 6H), 1.05 (d, J=6.60 Hz, 6H); LCMS (m/z): 537 (MH$^+$).

III-112: N2-(3-(difluoromethoxy)-4-(3-fluoro-1-isopropylpiperidin-4-yloxy)phenyl)-5-fluoro-N4-(1-trideuteromethyl-2,2,6,6-tetramethylpiperidin-4-yl)pyrimidine-2,4-diamine $^1$H NMR (DMSO d$_6$, 300 MHz): δ 7.76 (d, J=3.3 Hz, 1H), 7.71 (d, J=2.20 Hz, 1H), 7.23 (s, 1H), 7.09 (dd, J=2.33 Hz & 6.60 Hz, 1H), 6.96 (s, 1H), 6.69 (t, J=73.50 Hz, 1H), 5.50 (d, J=8.00 Hz, 1H), 4.88-4.89 (m, 0.5H), 4.71-4.73 (m, 0.5H), 4.54-4.57 (m, 1H), 4.35-4.39 (m, 1H), 2.96-3.00 (m, 1H), 2.82-2.87 (m, 1H), 2.70-279 (m, 2H), 2.41-2.46 (m, 1H), 2.12-2.25 (m, 2H), 1.97-2.03 (m, 3H), 1.80-1.88 (m, 1H), 1.43 (s, 6H), 1.41 (s, 6H), 1.06 (d, J=6.60 Hz, 6H); LCMS (m/z): 586 (MH$^+$).

III-113: 5-fluoro-N2-(4-methyl-3-(1H-tetrazol-1-yl)phenyl)-N4-(1-trideuteromethyl-2,2,6,6-tetramethylpiperidin-4-yl)pyrimidine-2,4-diamine $^1$H NMR (DMSO d$_6$, 300 MHz): δ 9.84 (s, 1H), 9.29 (s, 1H), 7.89 (s, 1H), 7.86 (s, 1H), 7.77 (s, 1H), 7.31 (s, 1H), 7.28 (s, 1H), 4.20-4.28 (m, 1H), 1.99 (s, 3H), 1.62-1.78 (m, 2H), 1.40-1.51 (m, 2H), 1.22 (s, 6H), 1.13 (s, 6H); LCMS (m/z): 443 (MH$^+$).

III-114: 5-fluoro-N2-(3-(1H-tetrazol-1-yl)phenyl)-N4-(1-trideuteromethyl-2,2,6,6-tetramethylpiperidin-4-yl)pyrimidine-2,4-diamine $^1$H NMR (DMSO d$_6$, 300 MHz): δ 10.03 (s, 1H), 9.40 (s, 1H), 8.13 (s, 1H), 7.89-7.95 (m, 2H), 7.40 (t, J=8.10 Hz, 1H), 7.26-7.33 (m, 2H), 4.28-4.30 (m, 1H), 1.67 (d, J=9.63 Hz, 2H), 1.43 (t, J=12.10 Hz, 2H), 1.04 (s, 6H), 0.90 (s, 6H); LCMS (m/z): 429 (MH$^+$).

III-115: 5-fluoro-N2-(3-(5-methyl-1H-tetrazol-1-yl)phenyl)-N4-(1-trideuteromethyl-2,2,6,6-tetramethylpiperidin-4-yl)pyrimidine-2,4-diamine $^1$H NMR (DMSO d$_6$, 300 MHz): δ 9.44 (s, 1H), 8.64 (s, 1H), 7.97 (d, J=3.60 Hz, 2H), 7.93 (s, 1H), 7.90 (s, 1H), 7.64 (d, J=7.15 Hz, 1H), 7.44 (t, J=7.98 Hz, 1H), 7.15 (d, J=7.15 Hz, 1H), 4.39-4.48 (m, 1H), 2.54 (s, 3H), 2.06 (d, J=12.65 Hz, 2H), 1.78 (t, J=12.45 Hz, 2H), 1.37 (s, 6H), 1.29 (s, 6H); LCMS (m/z): 443 (MH$^+$).

III-116: N$^2$-(3-cyclopropyl-5-(1H-tetrazol-1-yl)phenyl)-5-fluoro-N$^4$(2,2,6,6-tetramethylpiperidin-4-yl)pyrimidine-2,4-diamine $^1$H NMR (DMSO d$_6$, 300 MHz): δ 10.01 (s, 1H), 9.16 (s, 1H), 8.14 (d, J=1.65 Hz, 1H), 7.89 (d, J=3.85 Hz, 1H), 7.42 (s, 1H), 7.17 (d, J=7.98 Hz, 1H), 6.97 (s, 1H), 4.33 (br m, 1H), 1.93 (m, 1H), 1.61-1.65 (m, 2H), 1.09-1.14 (m, 2H), 0.98-1.07 (m, 2H), 0.94-0.96 (m, 12H), 0.72-0.77 (m, 2H); LCMS (m/z): 452 (MH$^+$).

III-117: N$^2$-(3-cyclopropyl-5-(1H-tetrazol-1-yl)phenyl)-5-fluoro-N$^4$(1,2,2,6,6-pentamethylpiperidin-4-yl)pyrimidine-2,4-diamine $^1$H NMR (DMSO d$_6$, 300 MHz): δ 10.01 (s, 1H), 9.17 (s, 1H), 8.13 (d, J=1.92 Hz, 1H), 7.89 (d, J=3.57 Hz, 1H), 7.41 (s, 1H), 7.18 (d, J=8.53 Hz, 1H), 6.97 (s, 1H), 4.23 (br m, 1H), 2.09 (s, 3H), 1.89-1.95 (m, 1H), 1.61-1.65 (m, 2H), 1.34-1.42 (m, 2H), 1.00 (s, 6H), 0.95-0.97 (m, 2H), 0.80 (s, 6H), 0.73-0.75 (m, 2H); LCMS (m/z): 466 (MH$^+$).

III-118: N$^2$-(4-cyclopropyl-3-(1H-tetrazol-1-yl)phenyl)-5-fluoro-N$^4$(2,2,6,6-tetramethylpiperidin-4-yl)pyrimidine-2,4-diamine $^1$H NMR (DMSO d$_6$, 300 MHz): δ 9.87 (s, 1H), 9.29 (s, 1H), 7.89 (d, J=2.2 Hz, 1H), 7.86 (d, J=3.6 Hz, 1H), 7.79 (d, J=1.93 Hz, 1H), 7.22 (d, J=8.25 Hz, 1H), 7.09 (d, J=8.52 Hz, 1H), 4.34 (br m, 1H), 1.65 (d, J=3.3 Hz, 1H), 1.61 (d, J=3.3 Hz, 1H), 1.48 (m, 1H), 1.09-1.17 (m, 2H), 1.02 (s, 6H), 0.99 (s, 6H), 0.63-0.67 (m, 2H), 0.42-0.45 (m, 2H); LCMS (m/z): 452 (MH$^+$)

III-119: N$^2$-(4-cyclopropyl-3-(1H-tetrazol-1-yl)phenyl)-5-fluoro-N$^4$(1,2,2,6,6-pentamethylpiperidin-4-yl)pyrimidine-2,4-diamine $^1$H NMR (DMSO d$_6$, 300 MHz): δ 9.87 (s, 1H), 9.30 (s, 1H), 7.86 (d, J=4.13 Hz, 1H), 7.84 (s, 1H), 7.80 (s, 1H), 7.23 (d, J=8.53 Hz, 1H), 7.09 (d, J=8.52 Hz, 1H), 4.24 (br m, 1H), 2.13 (s, 3H), 1.61-1.64 (m, 2H), 1.37-1.47 (m, 3H), 1.03 (s, 6H), 0.87 (s, 6H), 0.65 (m, 2H), 0.43 (m, 2H); LCMS (m/z): 466 (MH$^+$).

III-120: 5-Fluoro-N2-(4-fluoro-3-(1-methyl-1H-tetrazol-5-yl)phenyl)-N4-(2,2,6,6-tetramethylpiperidin-4-yl)pyrimidine-2,4-diamine $^1$H NMR (DMSO d$_6$, 300 MHz): δ 9.29 (s, 1H), 7.93-8.03 (m, 2H), 7.87 (d, 1H, J=3.9 Hz), 7.30 (t, 1H, J=9.9 Hz), 7.22 (d, 1H, J=8.1 Hz), 4.58-4.30 (m, 1H), 4.02 (s, 3H), 1.70-1.58 (m, 2H), 1.17-0.992 (m, 15H); LCMS (m/z): 444 (MH$^+$).

III-121: 5-Fluoro-N2-(4-fluoro-3-(1-methyl-1H-tetrazol-5-yl)phenyl)-N4-(1,2,2,6,6-pentamethylpiperidin-4-yl)pyrimidine-2,4-diamine $^1$H NMR (DMSO d$_6$, 300 MHz): δ 9.29 (s, 1H), 8.13-7.63 (m, 3H), 7.40-7.15 (m, 2H), 4.48-4.20 (m, 1H), 4.02 (s, 3H), 2.70-2.55 (m, 1H), 2.12-1.18 (m, 6H), 1.13-0.872 (m, 12H); LCMS (m/z): 458 (MH$^+$).

III-122: 5-Fluoro-N2-(4-isopropoxy-3-(1-methyl-1H-tetrazol-5-yl)phenyl)-N4-(2,2,6,6-tetramethylpiperidin-4-yl)pyrimidine-2,4-diamine $^1$H NMR (DMSO d$_6$, 300 MHz): δ 9.07 (s, 1H), 7.90-7.78 (m, 2H), 7.78-7.75 (m, 1H), 7.18 (bs, 1H), 7.10 (d, 1H, J=9 Hz), 4.52 (h, 1H, J=6 Hz), 4.39-4.29 (m, 1H), 3.92 (s, 3H), 1.71-1.62 (m, 2H), 1.30-1.01 (m, 21H); LCMS (m/z): 484 (MH$^+$).

III-123: 5-Fluoro-N2-(4-isopropoxy-3-(1-methyl-1H-tetrazol-5-yl)phenyl)-N4-(1,2,2,6,6-pentamethylpiperidin-4-yl)pyrimidine-2,4-diamine $^1$H NMR (DMSO d$_6$, 300 MHz): δ 9.08 (s, 1H), 7.84 (bs, 2H), 7.10 (d, 1H, J=2.7 Hz), 7.15-7.02 (m, 1H), 4.52 (h, 1H, J=6 Hz), 4.39-4.29 (m, 1H), 3.91 (s, 3H), 2.70-2.61 (m, 1H), 2.12-0.850 (m, 24H); LCMS (m/z): 498 (MH$^+$).

III-124: 5-Fluoro-N2-(3-(1-methyl-1H-tetrazol-5-yl)-4-(tetrahydro-2H-pyran-4-yloxy)phenyl)-N4-(2,2,6,6-tetramethylpiperidin-4-yl)pyrimidine-2,4-diamine $^1$H NMR (DMSO d$_6$, 300 MHz): δ 9.08 (s, 1H), 7.86-7.79 (m, 3H), 7.18-7.10 (m, 2H), 4.52-4.44 (m, 1H), 4.39-4.29 (m, 1H), 3.91 (s, 3H), 3.55-3.48 (m, 2H), 3.36-3.28 (m, 3H), 1.85-1.77 (m, 2H), 1.65-1.59 (m, 2H), 1.45-1.33 (m, 2H), 1.17-1.05 (m, 2H), 0.984 (bs, 12H); LCMS (m/z): 526 (MH$^+$).

III-125: 5-Fluoro-N2-(3-(1-methyl-1H-tetrazol-5-yl)-4-(tetrahydro-2H-pyran-4-yloxy)phenyl)-N4-(1,2,2,6,6-pentamethylpiperidin-4-yl)pyrimidine-2,4-diamine $^1$H NMR (DMSO d$_6$, 300 MHz): δ 9.04 (s, 1H), 7.80-7.72 (m, 3H), 7.18-7.10 (m, 2H), 4.50-4.44 (m, 1H), 4.39-4.29 (m, 1H), 3.88 (s, 3H), 3.51-3.40 (m, 2H), 3.35-3.24 (m, 2H), 2.60-2.54 (m, 1H), 1.85-1.77 (m, 2H), 2.05-1.55 (m, 7H), 1.35-1.13 (m, 6H), 0.977-0.780 (m, 9H); LCMS (m/z): 540 (MH$^+$).

III-126: 5-Fluoro-N2-(3-(1-methyl-1H-tetrazol-5-yl)-4-(oxetan-3-yloxy)phenyl)-N4-(2,2,6,6-tetramethylpiperidin-4-yl)pyrimidine-2,4-diamine $^1$H NMR (DMSO d$_6$, 300 MHz): δ 9.11 (s, 1H), 7.86-7.79 (m, 3H), 7.18-7.10 (m, 1H), 6.70-6.65 (m, 1H), 5.28 (p, 1H, J=5.4 Hz), 4.84 (t, 2H, J=6.9 Hz), 4.64 (t, 2H, J=6.9 Hz), 4.39-4.29 (m, 1H), 3.97 (s, 3H), 1.69-1.59 (m, 2H), 1.17-0.984 (m, 15H); LCMS (m/z): 498 (MH$^+$).

III-127: 5-Fluoro-N2-(3-(1-methyl-1H-tetrazol-5-yl)-4-(oxetan-3-yloxy)phenyl)-N4-(1,2,2,6,6-pentamethylpiperidin-4-yl)pyrimidine-2,4-diamine $^1$H NMR (DMSO d$_6$, 300 MHz): δ 9.11 (s, 1H), 7.86-7.79 (m, 3H), 7.18-7.10 (m, 1H), 6.70 (d, 1H, J=9.6 Hz), 5.28 (p, 1H, J=5.4 Hz), 4.84 (t, 2H, J=6.9 Hz), 4.46 (t, 2H, J=6.9 Hz), 4.30-4.19 (m, 1H), 3.98 (s, 3H), 2.12 (bs, 3H), 1.69-1.59 (m, 2H), 1.45-1.33 (m, 2H), 1.07-0.839 (m, 12H); LCMS (m/z): 512 (MH$^+$).

III-128: 5-fluoro-N2-(4-fluoro-3-(1-(2-Methoxyethyl)-1H-tetrazol-5-yl)phenyl)-N4-(1,2,2,6,6-pentamethylpiperidin-4-yl)pyrimidine-2,4-diamine $^1$H NMR (DMSO d$_6$, 300 MHz): δ 9.28 (s, 1H), 8.09-8.02 (m, 2H), 7.88-7.81 (m, 2H), 7.32-7.21 (m, 2H), 4.50 (t, 2H), 4.31-4.20 (m, 1H), 3.68 (t, 2H), 3.05 (s, 3H), 2.14 (s, 3H), 1.66 (d, 2H), 1.42 (t, 2H), 1.06 (s, 6H); 0.95 (s, 6H); LCMS (m/z): 502 (MH$^+$).

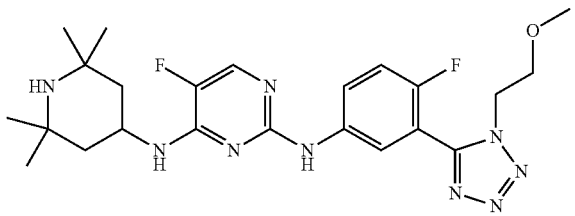

III-129: 5-fluoro-N2-(4-fluoro-3-(1-(2-Methoxyethyl)-1H-tetrazol-5-yl)phenyl)-N4-(2,2,6,6-tetramethylpiperidin-4-yl)pyrimidine-2,4-diamine $^1$H NMR (DMSO d$_6$, 300 MHz): δ 9.27 (s, 1H), 8.08-8.02 (m, 1H), 7.84-7.80 (m, 2H), 7.29-7.20 (m, 2H), 4.50 (t, 2H), 4.42-4.30 (m, 1H), 3.68 (t, 2H), 3.31 (s, 1H), 3.09 (s, 2H), 1.68 (d, 2H), 1.10 (s, 6H), 1.00 (s, 6H); LCMS (m/z): 488 (MH$^+$).

III-130: N2-(4-Chloro-3-(1-methyl-1H-tetrazol-5-yl)phenyl)-5-fluoro-N4-(2,2,6,6-tetramethylpiperidin-4-yl)pyrimidine-2,4-diamine $^1$H NMR (DMSO d$_6$, 300 MHz): δ 9.45s, 1H), 8.08 (dd, 1H, J=2.1 Hz, J=8.7 Hz), 7.89-7.83 (m, 2H), 7.47 (d, 1H, J=9 Hz), 7.27 (d, 1H, J=7.8 Hz), 4.48-4.30 (m, 1H), 3.94 (s, 3H), 1.67-1.60 (m, 2H), 1.20-0.984 (m, 15H); LCMS (m/z): 460 (MH$^+$).

III-131: N2-(4-Chloro-3-(1-methyl-1H-tetrazol-5-yl)phenyl)-5-fluoro-N4-(1,2,2,6,6-pentamethylpiperidin-4-yl)pyrimidine-2,4-diamine $^1$H NMR (DMSO d$_6$, 300 MHz): δ 9.45s, 1H), 8.08 (dd, 1H, J=2.1 Hz, J=8.7 Hz), 7.89-7.83 (m, 2H), 7.47 (d, 1H, J=9 Hz), 7.27 (d, 1H, J=7.8 Hz), 4.31-4.20 (m, 1H), 3.95 (s, 3H), 2.14 (bs, 3H), 1.69-1.60 (m, 2H), 1.50-1.35 (m, 2H), 1.06-0.914 (m, 12H); LCMS (m/z): 474 (MH$^+$).

III-132: 5-Fluoro-N2-(3-methyl-5-(1-methyl-1H-tetrazol-5-yl)phenyl)-N4-(2,2,6,6-tetramethylpiperidin-4-yl)pyrimidine-2,4-diamine $^1$H NMR (DMSO d$_6$, 300 MHz): δ 9.13 (s, 1H), 7.97 (bs, 1H), 7.86 (d, 1H, J=3.9 Hz), 7.67 (bs, 1H), 7.20-7.08 (m, 2H), 4.41-4.31 (m, 1H), 4.11 (s, 3H), 2.35 (s, 3H), 1.69-1.60 (m, 2H), 1.18-0.915 (m, 15H); LCMS (m/z): 440 (MH$^+$).

III-133: 5-Fluoro-N2-(3-methyl-5-(1-methyl-1H-tetrazol-5-yl)phenyl)-N4-(1,2,2,6,6-pentamethylpiperidin-4-yl)pyrimidine-2,4-diamine $^1$H NMR (DMSO d$_6$, 300 MHz): δ 9.14 (s, 1H), 7.97 (bs, 1H), 7.87 (d, 1H, J=3.9 Hz), 7.67 (bs, 1H), 7.22-7.10 (m, 2H), 4.39-4.21 (m, 1H), 4.12 (s, 3H), 2.34 (s, 3H), 2.12 (bs, 3H), 1.69-1.60 (m, 2H), 1.49-1.30 (m, 2H), 1.08-0.855 (m, 15H); LCMS (m/z): 454 (MH$^+$).

III-134: N2-(3-chloro-5-(1-methyl-1H-tetrazol-5-yl)phenyl)-5-fluoro-N4-(2,2,6,6-tetramethylpiperidin-4-yl)pyrimidine-2,4-diamine $^1$H NMR (DMSO d$_6$, 300 MHz): δ 9.46 (s, 1H), 8.15 (bs, 1H), 7.99 (bs, 1H), 7.91 (d, 1H, J=3.9 Hz), 7.35 (bs, 1H), 7.27 (d, 1H, J=8.1 Hz), 4.41-4.31 (m, 1H), 4.14 (s, 3H), 3.18-3.11 (m, 1H), 1.69-1.60 (m, 2H), 1.18-0.935 (m, 14H); LCMS (m/z): 460 (MH$^+$).

III-135: N2-(3-chloro-5-(1-methyl-1H-tetrazol-5-yl)phenyl)-5-fluoro-N4-(1,2,2,6,6-pentamethylpiperidin-4-yl)pyrimidine-2,4-diamine $^1$H NMR (DMSO d$_6$, 300 MHz): δ 9.47 (s, 1H), 8.15 (bs, 1H), 7.97 (bs, 1H), 7.91 (d, 1H, J=3.9 Hz), 7.36-7.25 (m, 2H), 4.37-4.18 (m, 1H), 4.14 (s, 3H), 2.14 (bs, 3H), 1.69-1.60 (m, 2H), 1.49-1.32 (m, 2H), 1.08-0.945 (m, 12H); LCMS (m/z): 474 (MH$^+$).

III-136: N2-(3,4-difluoro-5-(1-methyl-1H-tetrazol-5-yl)phenyl)-5-fluoro-N4-(2,2,6,6-tetramethylpiperidin-4-yl)pyrimidine-2,4-diamine $^1$H NMR (DMSO d$_6$, 300 MHz): δ 9.50 (s, 1H), 8.31-8.22 (m, 1H), 7.90 (d, 1H), 7.62-7.58 (m, 1H), 7.33 (d, 1H), 4.45-4.33 (m, 1H), 4.06 (s, 2H), 3.31 (s, 6H), 1.69 (d, 2H), 1.10 (s, 6H), 1.00 (s, 3H); LCMS (m/z): 462 (MH$^+$).

III-137: N2-(3,4-difluoro-5-(1-methyl-1H-tetrazol-5-yl)phenyl)-5-fluoro-N4-(1,2,2,6,6-pentamethylpiperidin-4-yl)pyrimidine-2,4-diamine $^1$H NMR (DMSO d$_6$, 300 MHz): δ 9.50 (s, 1H), 8.30-8.21 (m, 1H), 7.91 (s, 1H), 7.60 (s, 1H), 7.35 (d, 1H), 4.36-4.22 (m, 1H), 4.11 (s, 3H), 2.20 (s, 3H), 1.64 (d, 2H), 1.45 (t, 2H), 1.10 (s, 6H), 1.00 (s, 6H); LCMS (m/z): 476 (MH$^+$).

III-138: 5-Fluoro-N2-(3-fluoro-5-(1-methyl-1H-tetrazol-5-yl)phenyl)-N4-(2,2,6,6-tetramethylpiperidin-4-yl)pyrimidine-2,4-diamine $^1$H NMR (DMSO d$_6$, 300 MHz): δ 9.55 (s, 1H), 8.12 (d, 1H, J=4 Hz), 7.91 (d, 1H, J=3.6 Hz), 7.75 (bs, 1H), 7.31 (d, 1H, J=6.6 Hz), 7.19-7.13 (m, 1H), 4.45-4.31 (m, 1H), 4.15 (s, 3H), 1.69-1.60 (m, 2H), 1.28-0.998 (m, 15H); LCMS (m/z): 444 (MH$^+$).

III-139: 5-Fluoro-N2-(3-fluoro-5-(1-methyl-1H-tetrazol-5-yl)phenyl)-N4-(1,2,2,6,6-pentamethylpiperidin-4-yl)pyrimidine-2,4-diamine $^1$H NMR (DMSO d$_6$, 300 MHz): δ 9.55 (s, 1H), 8.12 (d, 1H, J=4 Hz), 7.91 (d, 1H, J=3.6 Hz), 7.75 (bs, 1H), 7.31 (d, 1H, J=6.6 Hz), 7.16 (d, 1H, J=8.7 Hz), 4.43-4.28 (m, 1H), 4.15 (s, 3H), 2.16 (bs, 1H), 1.71-1.60 (m, 2H), 1.53-1.42 (m, 2H), 1.08-0.973 (m, 12H); LCMS (m/z): 458 (MH$^+$).

III-140: 5-Fluoro-N2-(3-(1-methyl-1H-tetrazol-5-yl)-5-(trifluoromethyl)phenyl)-N4-(2,2,6,6-tetramethylpiperidin-4-yl)pyrimidine-2,4-diamine $^1$H NMR (DMSO d$_6$, 300 MHz): δ 9.55 (s, 1H), 8.47 (bs, 1H), 8.26 (bs, 1H), 7.94 (d, 1H, J=3.3 Hz), 7.62 (bs, 1H), 7.31 (d, 1H, J=8.1 Hz), 4.41-4.29 (m, 1H), 4.16 (s, 3H), 1.69-1.60 (m, 2H), 1.18-0.988 (m, 15H); LCMS (m/z): 494 (MH$^+$).

III-141: 5-Fluoro-N2-(3-(1-methyl-1H-tetrazol-5-yl)-5-(trifluoromethyl)phenyl)-N4-(1,2,2,6,6-pentamethylpiperidin-4-yl)pyrimidine-2,4-diamine $^1$H NMR (DMSO d$_6$, 300 MHz): δ 9.56 (s, 1H), 8.46 (bs, 1H), 8.26 (bs, 1H), 7.94 (d, 1H, J=3.3 Hz), 7.62 (bs, 1H), 7.31 (d, 1H, J=8.1 Hz), 4.41-4.29 (m, 1H), 4.16 (s, 3H), 1.69-1.60 (m, 2H), 1.48-1.34 (m, 2H), 1.08-0.878 (m, 12H); LCMS (m/z): 508 (MH$^+$).

III-142: 5-fluoro-N2-(3-fluoro-4-isopropoxy-5-(1-methyl-1H-tetrazol-5-yl)phenyl)-N4-(2,2,6,6-tetramethylpiperidin-4-yl)pyrimidine-2,4-diamine $^1$H NMR (DMSO d$_6$, 300 MHz): δ 9.42 (s, 1H), 8.06 (d, 1H), 7.88 (d, 1H), 7.49 (s, 1H), 7.28 (d, 1H), 4.42-4.32 (m, 1H), 3.96 (s, 3H), 1.65 (d, 2H), 1.15 (t, 3H), 1.07 (s, 6H), 1.00 (s, 6H), 0.89 (d, 6H); LCMS (m/z): 502 (MH$^+$).

III-143: 3-(5-Fluoro-4-(2,2,6,6-tetramethylpiperidin-4-ylamino)pyrimidin-2-ylamino)-5-(1-methyl-1H-tetrazol-5-yl)benzonitrile $^1$H NMR (DMSO d$_6$, 300 MHz): δ 9.63 (s, 1H), 8.41 (bs, 1H), 8.31 (bs, 1H), 7.94 (d, 1H, J=3.6 Hz), 7.77 (bs, 1H), 7.35 (d, 1H, J=8.1 Hz), 4.48-4.24 (m, 1H), 4.16 (s, 3H), 1.70-1.62 (m, 2H), 1.20-0.990 (m, 15H); LCMS (m/z): 451 (MH$^+$).

III-144: 3-(5-Fluoro-4-(1,2,2,6,6-pentamethylpiperidin-4-ylamino)pyrimidin-2-ylamino)-5-(1-methyl-1H-tetrazol-5-yl)benzonitrile $^1$H NMR (DMSO d$_6$, 300 MHz): δ 9.64 (s, 1H), 8.42 (bs, 1H), 8.30 (bs, 1H), 7.94 (d, 1H, J=3.6 Hz), 7.77 (bs, 1H), 7.39-7.28 (m, 1H), 4.34-4.12 (m, 1H), 4.17 (s, 3H), 2.14 (bs, 3H), 1.70-1.62 (m, 2H), 1.47-1.38 (m, 2H), 1.05-0.955 (m, 12H); LCMS (m/z): 465 (MH$^+$).

III-145: 5-Fluoro-N2-(3-(1-methyl-1H-tetrazol-5-yl)-5-(oxetan-3-yloxy)phenyl)-N4-(2,2,6,6-tetramethylpiperidin-4-yl)pyrimidine-2,4-diamine $^1$H NMR (DMSO d$_6$, 300 MHz): δ 9.32 (s, 1H), 7.88 (d, 1H, J=3.6 Hz), 7.71 (bs, 1H), 7.59 (bs, 1H), 7.26 (d, 1H, J=8.7 Hz), 6.56 (bs, 1H), 5.29 (p, 1H, J=5.4 Hz), 4.90 (t, 2H, J=6.9 Hz), 4.52 (t, 2H, J=6.9 Hz), 4.39-4.29 (m, 1H), 4.11 (s, 3H), 1.69-1.59 (m, 2H), 1.19-0.992 (m, 15H); LCMS (m/z): 498 (MH$^+$).

III-146: 5-Fluoro-N2-(3-(1-methyl-1H-tetrazol-5-yl)-5-(oxetan-3-yloxy)phenyl)-N4-(1,2,2,6,6-pentamethylpiperidin-4-yl)pyrimidine-2,4-diamine $^1$H NMR (DMSO d$_6$, 300 MHz): δ 9.32 (s, 1H), 7.88 (d, 1H, J=3.6 Hz), 7.69 (bs, 1H), 7.59 (bs, 1H), 7.28 (bs, 1H), 6.57 (bs, 1H), 5.29 (p, 1H, J=5.4 Hz), 4.92 (t, 2H, J=6.9 Hz), 4.53 (t, 2H, J=6.9 Hz), 4.39-4.28 (m, 1H), 4.11 (s, 3H), 2.14 (bs, 3H), 1.65 (bs, 2H), 1.45 (bs, 2H), 1.09-0.962 (m, 12H); LCMS (m/z): 512 (MH$^+$).

Example 14

PKC Assay

The inhibition of PKC-alpha, PKC-beta, PKC-delta, PKC epsilon and PKC-theta activity was determined via ELISA as follows: NUNC MAXISORP (#436110) or Costar High Binding (#3922) plates were coated with 0.01 mg/mL Neutravidin (Pierce #PI-31000) in 1×PBS (100 μL/well) for 18-24 hours at 4° C. When ready to be used, plates were washed with 1×PBST and then blocked with 2% BSA in 1×PBST (100 μL/well) for a minimum of 1 hour at room temperature. The reactions were conducted in a volume of 60 μL/well. When ready to begin, the plates were washed with 1×PBST to remove the 2% BSA blocking solution. Reaction solution containing the necessary buffer components as well as the appropriate concentrations of ATP and peptide substrate was then added to each well (see Table 5). Appropriate concentrations of test compound was then added—with the volume added should taking into consideration the DMSO tolerance of the kinases being about 0.2%. The reaction was then initiated by the addition of kinase—the approximate final concentration of which is listed in Table 5 (note that this will vary depending on the batch to batch variability in the activity of enzymes). After allowing the reaction to stand at room temperature for 20 minutes, the plates were then washed with 1×PBST.

TABLE 5

| Kinase | Buffer components | [ATP] (uM) | [peptide] (uM) | Time (min) | 1° and 2° antibodies | Notes |
|---|---|---|---|---|---|---|
| PKCs<br>α: ~8 ng/mL<br>β: ~16 ng/mL<br>δ: ~13 ng/mL<br>ε: ~13 ng/mL<br>θ: ~8 ng/mL | 20 mM Hepes pH 7.4<br>5 Mm MgCl$_2$<br>0.2 mM CaCl$_2$<br>1 mM DTT<br>0.05% Chaps | 1 μm | 1 μM PKC peptide (biotin-RFARKGSLRQKNV) (Invitrogen #P2760) (SEQ ID NO: 2) | 20 min | Rabbit pSer PKC substrate Ab (Cell Signaling #2261); HRP-goat a-rabbit (Jackson Immunoresearch #111-035-003) | 0.15 mg/mL DAG (Sigma #D0138)<br>0.75 mg/mL Phosphoserine (Sigma #P6641)<br>DMSO tolerance ~0.2% |

After removal of the reaction mixture from the plate and washing with 1×PBST, an antibody developing solution containing a 1:10,000 dilution of the appropriate primary and secondary antibodies (Table 5) in a 0.1% BSA solution in 1×PBST was then added to each well (100 μL/well). This was then allowed to stand at room temperature for a minimum of 1 hour. After this time, the plates were once again washed with 1×PBST. The SuperSignal ELISA Pico Chemiluminescent substrate (Pierce #PI-37069) was then added (100 μL/well) and the plate was read on a luminescence plate reader Example 15

PKC Assay

Alternatively, the inhibition of PKC activity is measured by monitoring the production of phosphorylated peptide by fluorescence polarization at different concentrations of the inhibitor. Reactions are carried out in 96-well plate format with a total volume of 20 μL containing 20 mM HEPES, pH 7.4, 5 mM $MgCl_2$, 0.2 mM $CaCl_2$, 1 mM DTT, 0.02% Brij-35, 0.1 mg/mL phosphatidylserine, 0.02 mg/mL dioleoyl-sn-glycerol and 5 μM each of ATP and the peptide substrate. Compounds are first diluted serially in DMSO and then transferred to a solution containing the above concentrations of HEPES, $MgCl_2$, $CaCl_2$, DTT, and Brij-35 to yield 5× compound solutions in 2% DMSO, which is then added to the reaction solution. Reactions are initiated by the addition of PKC at a typical concentration as described in Table 6, and then allowed to incubate at room temperature for 20 min. At the end of this time, a combination of quench (EDTA) and detection (peptide tracer and antibody) reagents is added using the protocol of Invitrogen P2748. After a 30 min. period of incubation, the amount of phosphorylated peptide generated is measured by fluorescence polarization (Ex=485 nm, Em=535 nm) using a Tecan Polarian instrument.

BD Pharmingen Catalog #555336, Anti-Human CD28, Beckman Coulter Catalog #IM1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/mL IL-2. The primary T-cells were then washed twice with PBS to remove the IL-2.

Primary T cell stimulation and IL2 ELISA: Human primary T cells (100,000 cells per well) were pre-incubated with or without test compound in Yssel's medium for 1 hr at 37° C. Cells were then stimulated by transferring them to round-bottom 96-well plates pre-coated with 1 μg/ml αCD3 and 5 μg/ml αCD28. For counter assay, cells were instead stimulated by adding 8× stock solutions of PMA and ionomycin in Yssels (for final concentrations of 0.5 ng/ml PMA and 0.1 μM ionomycin, both from Calbiochem). Cells were incubated at 37° C. for 24 hours before 100 μL supernatants were harvested for quantification of IL-2 by ELISA using Human IL-2 Duoset ELISA Kit from R and D Systems, Cat. #DY202E.

Table 7 shows the $IC_{50}$ values for compounds tested in the whole cell assay, in which "A" indicates an $IC_{50}$ in the indicated assay of less than 0.25 μM; "B" is 0.25 to 0.5 μM; "C" is 0.5 to 1 μM; and "D" indicates that the $IC_{50}$ is greater than 1 μM.

TABLE 7

| Compound | Whole Cell assay |
| --- | --- |
| I-1 | D |
| I-2 | D |
| I-3 | D |
| I-4 | B |
| I-5 | C |
| I-6 | C |
| I-7 | D |
| I-8 | D |
| I-9 | A |

TABLE 6

| Peptide substrate | SEQ ID | Enzyme source | Typical enzyme concentration |
| --- | --- | --- | --- |
| PKC theta | RFARKGSLRQKNV | Seq ID No. 1 | Upstate Biotechnologies, Temecula, CA, cat. #14-444 | 40 ng/mL |
| PKC epsilon | RFARKGSLRQKNV | Seq ID No. 1 | Upstate Biotechnologies, Temecula, CA, cat. #14-518 | 50 ng/mL |

Example 16

IL-2 ELISA, Human Primary T Cell, Anti-CD3+CD28+(Whole Cell Assay)

Human primary T cell isolation and culture: Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS: ficoll ratio and centrifuged for 30 min at 4° C. at 1750 rpm. The cells at the serum: ficoll interface were recovered and washed twice with 5 volumes of PBS. These freshly isolated human peripheral blood mononuclear cells were cultured in Yssel's medium containing 40 U/mL IL2 in a flask pre-coated with 1 μg/mL αCD3 and 5 μg/mL αCD28 (Anti-Human CD3, TABLE 7-continued

| Compound | Whole Cell assay |
| --- | --- |
| I-10 | B |
| I-11 | D |
| I-12 | C |
| I-13 | D |
| I-14 | C |
| I-15 | C |
| I-16 | D |
| I-17 | D |
| I-18 | B |
| I-19 | C |
| I-20 | A |
| I-21 | A |
| I-22 | C |
| I-23 | D |
| I-24 | C |

TABLE 7-continued

| Compound | Whole Cell assay |
| --- | --- |
| I-25 | D |
| I-26 | B |
| I-27 | A |
| I-28 | C |
| I-29 | C |
| I-30 | C |
| I-31 | A |
| I-32 | C |
| I-33 | B |
| I-34 | C |
| I-35 | C |
| I-36 | C |
| I-37 | D |
| I-38 | C |
| I-39 | D |
| I-40 | C |
| I-41 | A |
| I-42 | A |
| I-43 | D |
| I-44 | B |
| I-45 | B |
| I-46 | A |
| I-47 | C |
| I-48 | A |
| I-49 | C |
| I-50 | D |
| I-51 | C |
| I-52 | A |
| I-53 | D |
| I-54 | C |
| I-55 | B |
| I-56 | C |
| I-57 | D |
| I-58 | C |
| I-59 | D |
| I-60 | C |
| I-61 | C |
| I-62 | D |
| I-63 | B |
| I-64 | A |
| I-65 | C |
| I-66 | D |
| I-67 | D |
| I-68 | D |
| I-69 | A |
| I-70 | A |
| I-71 | B |
| I-72 | D |
| I-73 | A |
| I-74 | A |
| I-75 | C |
| I-76 | D |
| I-77 | B |
| I-78 | A |
| I-79 | A |
| I-80 | A |
| I-81 | B |
| I-82 | B |
| I-83 | D |
| I-84 | D |
| I-85 | D |
| I-86 | A |
| I-87 | C |
| I-88 | A |
| I-89 | A |
| I-90 | C |
| I-91 | B |
| I-92 | C |
| I-93 | A |
| I-94 | A |
| I-95 | B |
| I-96 | A |
| I-97 | D |
| I-98 | C |
| I-99 | D |
| I-100 | A |
| I-101 | B |
| I-102 | B |
| I-103 | C |
| I-104 | A |
| I-105 | A |
| I-106 | C |
| I-107 | B |
| I-108 | A |
| I-109 | A |
| I-110 | C |
| I-111 | D |
| I-112 | D |
| I-113 | A |
| I-114 | A |
| I-115 | C |
| I-116 | C |
| I-117 | B |
| I-118 | B |
| I-119 | B |
| I-120 | D |
| I-121 | C |
| I-122 | D |
| I-123 | A |
| I-124 | C |
| I-125 | B |
| I-126 | A |
| I-127 | B |
| I-128 | D |
| I-129 | C |
| I-130 | D |
| I-131 | C |
| I-132 | C |
| I-133 | C |
| I-134 | D |
| I-135 | C |
| I-136 | D |
| I-137 | A |
| I-138 | C |
| I-139 | A |
| I-140 | B |
| I-141 | D |
| I-142 | D |
| I-143 | D |
| I-144 | C |
| I-145 | B |
| I-146 | B |
| I-147 | A |
| I-148 | B |
| I-149 | A |
| I-150 | A |
| I-151 | C |
| II-1 | D |
| II-2 | D |
| II-3 | D |
| II-4 | D |
| II-5 | D |
| II-6 | D |
| II-7 | D |
| II-8 | D |
| II-9 | A |
| II-10 | D |
| III-1 | B |
| III-2 | D |
| III-3 | D |
| III-4 | D |
| III-5 | B |
| III-6 | B |
| III-7 | A |
| III-8 | A |
| III-9 | B |
| III-10 | B |
| III-11 | B |
| III-12 | D |
| III-13 | D |
| III-14 | D |
| III-15 | D |
| III-16 | D |
| III-17 | D |
| III-18 | A |
| III-19 | B |

TABLE 7-continued

| Compound | Whole Cell assay |
|---|---|
| III-20 | B |
| III-21 | C |
| III-22 | A |
| III-23 | B |
| III-24 | C |
| III-25 | C |
| III-26 | C |
| III-27 | B |
| III-28 | D |
| III-29 | D |
| III-32 | D |
| III-33 | D |
| III-34 | D |
| III-35 | B |
| III-36 | D |
| III-37 | A |
| III-38 | C |
| III-39 | C |
| III-40 | B |
| III-41 | A |
| III-42 | C |
| III-43 | A |
| III-44 | C |
| III-45 | B |
| III-46 | C |
| III-47 | C |
| III-48 | D |
| III-49 | D |
| III-50 | B |
| III-51 | A |
| III-52 | B |
| III-53 | C |
| III-54 | C |
| III-55 | C |
| III-56 | C |
| III-57 | D |
| III-58 | C |
| III-59 | D |
| III-60 | B |
| III-61 | D |
| III-62 | D |
| III-63 | B |
| III-64 | A |
| III-65 | D |
| III-66 | D |
| III-67 | B |
| III-68 | D |
| III-69 | D |
| III-70 | A |
| III-71 | C |
| III-72 | A |
| III-73 | C |
| III-74 | B |
| III-75 | C |
| III-76 | C |
| III-77 | D |
| III-78 | C |
| III-79 | C |
| III-80 | D |
| III-81 | C |
| III-82 | D |
| III-83 | C |
| III-84 | D |
| III-85 | D |
| III-86 | D |
| III-87 | B |
| III-88 | D |
| III-89 | B |
| III-90 | C |
| III-91 | C |
| III-92 | D |
| III-95 | A |
| III-96 | A |
| III-97 | A |
| III-98 | A |
| III-99 | A |
| III-100 | B |
| III-101 | A |
| III-102 | B |
| III-103 | B |
| III-104 | C |
| III-105 | A |
| III-106 | A |
| III-107 | C |
| III-108 | C |
| III-109 | C |
| III-110 | A |
| III-111 | A |
| III-112 | B |
| III-113 | A |
| III-114 | A |
| III-115 | A |
| III-116 | A |
| III-117 | A |
| III-118 | A |
| III-119 | A |
| III-120 | C |
| III-121 | A |
| III-122 | A |
| III-123 | A |
| III-124 | D |
| III-125 | B |
| III-126 | D |
| III-127 | A |
| III-128 | B |
| III-129 | D |
| III-130 | A |
| III-131 | A |
| III-132 | B |
| III-133 | A |
| III-134 | A |
| III-135 | A |
| III-136 | B |
| III-137 | A |
| III-138 | C |
| III-139 | A |
| III-140 | A |
| III-141 | A |
| III-142 | B |
| III-143 | C |
| III-144 | A |
| III-145 | D |
| III-146 | B |
| III-147 | A |

Example 17

Calcium Influx

HEK-FLPTREX cells are stably transfected with pcDNA5/FRT/TO+hTRPV4a, rat TRPV1-HA or rTRPA1-HA are grown in Dulbecco's Modified Eagle's Medium (DMEM) containing 10% tetracycline-free fetal bovine serum, hygromycin (50 μg/ml) and blasticidin (10 μg/ml). Cells are treated with tetracycline (0.1 g/ml, 20 h) to induce TRP expression. DRG from thoracic and lumbar spinal cord of rats or mice are minced in cold Hank's Balanced Salt Solution (HBSS) and incubated for 60 at 37° C. in DMEM containing 1 mg/ml of collagenase type IA and 0.1 mg/ml of DNAse type IV, pelleted and incubated with 0.25% trypsin for 30 min. Neurons are pelleted, suspended in DMEM containing 10% fetal bovine serum, 10% horse serum, 100 U/ml penicillin, 0.1 mg/ml streptomycin, 2 mM glutamine, dissociated by gentle trituration until the solution appears cloudy and homogeneous and plated on glass coverslips coated with PolyOnitine/laminin. Neurons are cultured for 3-4 days before the experiment.

Cells grown on coverslips or on a 96 multiwell plate are incubated in HBSS (pH 7.4) containing Ca2+ and Mg2+, 20 mM HEPES buffer, 0.1% BSA, 100 U/ml penicillin, 100 µg/ml streptomycin, with 2.5-5 µM Fura-2AM (Invitrogen) for 20-45 min at 37° C. Cells are washed and fluorescence is measured at 340 nm and 380 nm excitation and 510 nm emission in a F-2500 spectrophotometer, or in a Flexstation 3 Microplate Reader III (for the measurement of the calcium in the cell population) or using a Zeiss Axiovert microscope, an ICCD video camera and a video microscopy acquisition program (for the measurement of the calcium influx in the single neurons). Substances are injected directly into the chamber (20 ml into 2 ml, for the spectrophotometer; 20 ml in 200 ml for the Flexstation, 50 ml in 350 ml in the chamber for the single cells).

Example 18

In Vivo Hyperplasia

Mechanical pain is quantified as the number of times the hind paw is withdrawn in response to 5 applications of a 0.173 mN von Frey hair. Responses are expressed as a percentage (e.g. 3 withdrawals out of 5 are recorded as 60%) and mechanical hyperalgesia defined as increase in the percentage of withdrawal compared to basal measurement. 2) Mechanical pain is quantified using the 'up-down paradigm', determining the 50% response threshold to the von Frey filaments applied to the mid-plantar surface for 5 s or until a withdrawal response occurred. Von Frey filaments are in this range of intensities: 1.65, 2.44, 2.83, 3.22, 3.61, 3.84, 4.08.

Thermal hyperalgesia is assessed in mice using a plantar test apparatus and quantified as the latency of paw withdrawal to a radiant heat. Thermal hyperalgesia is defined as a decrease in the withdrawal latency compared to the basal measurement. After measuring basal level mice, under light halothane anesthesia (5%), are injected with testing compound into the left or right paws (5-10 µl intraplantar injection) and paw withdrawal measurements repeated at different time point. To assess PAR2 TRPV1, TRPV4 and TRPA1 mediated hyperalgesia and potentiation of TRPV-mediated responses, mice are treated with PAR2-AP for 15 min followed by capsaicin, 4αPDD or HNE. To assess the role of protein kinases, the antagonists or the corresponding vehicles are injected 20-30 minutes before the challenge with agonists. The effects induced by the different treatments are evaluated within the same rat comparing the responses recorded in the right paw (receiving for example saline, or vehicle) with the responses obtained in the left paw (receiving for example PAR2-AP or 4αPDD).

Formalin induced hyperalgesia is assessed using 5% solution of formalin administered by intradermal injection into the dorsal surface of the mouse or rat forepaw to induce a painful behavior. Pain is accessed on a four-level scale related to posture: 0, normal posture; 1, with the injected paw remaining on the ground but not supporting the animal; 2, with the injected paw clearly raised; and 3, with the injected paw being licked, nibbled, or shaken. Animals are observed and scored for behavior at 3 minutes after the injection (defined as initial phase that results from the direct stimulation of nociceptors), and then at 30-60 minutes after the injection (defined as second phase that involves a period of sensitization during which inflammatory phenomena occur). The nociceptive behavioral score for each 3-min interval is calculated as the weighted average of the number of seconds spent in each behavior. 2.5% solution of formalin is administered by intraplantar injection and thermal and mechanical pain measured as described above after 30-60 min. To assess the role of protein kinases, antagonists or their vehicles (control) are injected into the right paws 20-30 minutes before formalin. Nociceptive behavior will be scored for each rats and compared to control.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of inhibiting a protein kinase C (PKC) activity in a biological sample or a patient, which method comprises contacting the biological sample or administering to the patient a compound of formula (I):

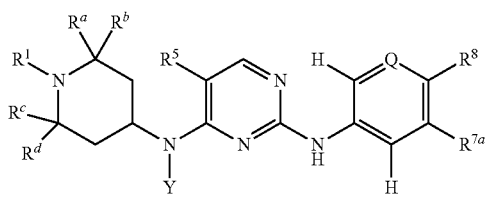

(I)

wherein
$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
Y is selected from hydrogen and alkyl;
$R^1$ is selected from hydrogen, alkyl, substituted alkyl, cycloalkyl, acyl, and oxy radical;
$R^a$ and $R^b$ are independently selected from hydrogen and alkyl;
$R^c$ and $R^d$ are independently selected from hydrogen and alkyl;
Q is $CR^{7b}$;
$R^{7a}$ is tetrazolyl or substituted tetrazolyl;
$R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;
alk, if present, is alkyl or substituted alkyl;
A is selected from aryl, cycloalkyl, heteroaryl, and heterocyclyl;
wherein the A ring can be substituted or unsubstituted;
or a salt or stereoisomer thereof.

2. The method of claim 1, wherein the inhibition of PKC results in treatment of a disease or disorder that is mediated or sustained through the activity of a PKC activity.

3. The method of claim 2, wherein the disease or disorder is associated with activation of T cells.

4. The method of claim 2, wherein the disease or disorder is a cell proliferative disorder.

5. The method of claim 2, wherein the disease or disorder is selected from hematopoietic neoplasm, lymphoid neoplasm, T cell neoplasm, T lymphoblastic leukemia, B cell neoplasm, B-lymphoblastic leukemia, Burkitt's lymphoma, myeloid neoplasm, myeloproferative disease, chronic myelogenous leukemia (CML), myelodysplastic disease, chronic myelomonocytic leukemia, myelodysplastic syndrome, and acute myeloid leukemia.

6. The method of claim 2, wherein the disease or disorder is chronic myelogenous leukemia.

7. The method of claim 1, wherein the compound is of the formula (Ia):

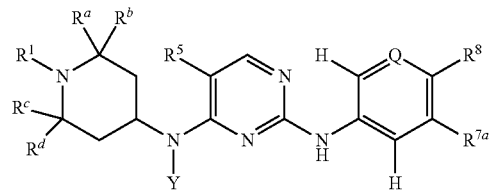

(Ia)

wherein
$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
Y is selected from hydrogen and alkyl;
$R^1$ is selected from hydrogen, alkyl, substituted alkyl, cycloalkyl, acyl, and oxy radical;
$R^a$ and $R^b$ are independently selected from hydrogen and alkyl;
$R^c$ and $R^d$ are independently selected from hydrogen and alkyl;
Q is $CR^{7b}$;
$R^{7a}$ is tetrazolyl or substituted tetrazolyl;
$R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;
wherein at least one of $R^{7b}$ and $R^8$ is —O-alk-A;
alk, if present, is alkyl or substituted alkyl;
A is selected from aryl, cycloalkyl, heteroaryl, and heterocyclyl;
wherein the A ring can be substituted or unsubstituted;
or a salt or stereoisomer thereof.

8. The method of claim 1, wherein the compound is of the formula (Ib):

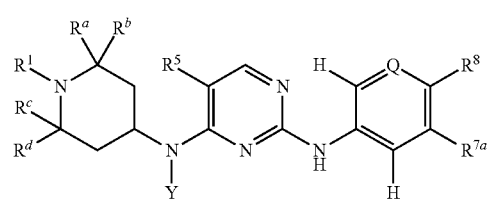

(Ib)

wherein:
R⁵ is selected from alkyl, substituted alkyl, hydroxy, alkoxy, substituted alkoxy, amino, substituted amino, cyano, fluoro, iodo, acyl, aminoacyl, and nitro;
Y is selected from hydrogen and alkyl;
R¹ is selected from hydrogen, alkyl, substituted alkyl, cycloalkyl, acyl, and oxy radical;
Rᵃ and Rᵇ are independently selected from hydrogen and alkyl;
Rᶜ and Rᵈ are independently selected from hydrogen and alkyl;
Q is CR⁷ᵇ;
R⁷ᵃ is tetrazolyl or substituted tetrazolyl;
R⁷ᵇ and R⁸ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;
wherein at least one of R⁷ᵇ and R⁸ is —O-alk-A;
alk, if present, is alkyl or substituted alkyl;
A is selected from aryl, cycloalkyl, heteroaryl, and heterocyclyl, provided that R⁸ is not 4-morpholinyl, 3-pyridinyl, 4-pyridinyl, 1-pyrrolidinyl, and 1-pyrrolyl;
wherein the A ring can be substituted or unsubstituted;
or a salt or stereoisomer thereof.

9. The method of claim 1, wherein the compound is of the formula (IIa):

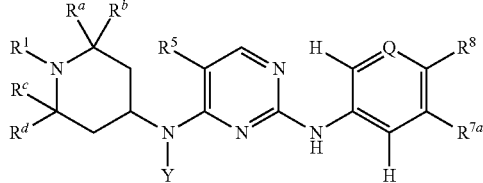

(IIa)

wherein:
R⁵ is selected from alkyl, substituted alkyl, hydroxy, alkoxy, substituted alkoxy, amino, substituted amino, cyano, fluoro, iodo, acyl, aminoacyl, and nitro;
Y is selected from hydrogen and alkyl;
R¹ is selected from hydrogen, alkyl, substituted alkyl, cycloalkyl, acyl, and oxy radical;
Rᵃ and Rᵇ are independently selected from hydrogen and alkyl;
Rᶜ and Rᵈ are independently selected from hydrogen and alkyl;
Q is CR⁷ᵇ;
R⁷ᵃ is tetrazolyl or substituted tetrazolyl;
R⁷ᵇ and R⁸ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;
wherein at least one of R⁷ᵇ and R⁸ is fluoro, difluoromethoxy, difluoromethyl, and trifluoromethyl; and alk, if present, is alkyl or substituted alkyl;
A is selected from aryl, cycloalkyl, heteroaryl, and heterocyclyl;
wherein the A ring can be substituted or unsubstituted;
or a salt or stereoisomer thereof.

10. The method of claim 1, wherein the compound is of the formula (IIb):

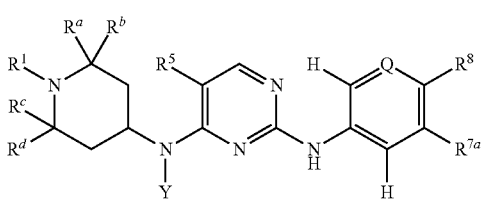

(IIb)

wherein:
R⁵ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
Y is selected from hydrogen and alkyl;
R¹ is selected from hydrogen, alkyl, substituted alkyl, cycloalkyl, acyl, and oxy radical;
Rᵃ and Rᵇ are independently selected from hydrogen and alkyl;
Rᶜ and Rᵈ are independently selected from hydrogen and alkyl;
Q is CR⁷ᵇ;
R⁷ᵃ is tetrazolyl or substituted tetrazolyl;
R⁷ᵇ and R⁸ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A; and
wherein at least one of R⁷ᵇ and R⁸ is selected from alkyl, substituted alkyl, $C_2$-$C_{10}$ alkoxy, —O-alk-A, heterocyclyl, substituted heterocyclyl, heteroaryl, and substituted heteoaryl; provided that the heterocyclyl and heteroaryl are not 1-morpholinyl, 1-piperizinyl, or 1-pyrrolidinyl;
alk, if present, is alkyl or substituted alkyl;
A is selected from aryl, cycloalkyl, heteroaryl, and heterocyclyl;
wherein the A ring can be substituted or unsubstituted;
or a salt or stereoisomer thereof.

11. The method of claim 1, wherein the compound is of the formula (III):

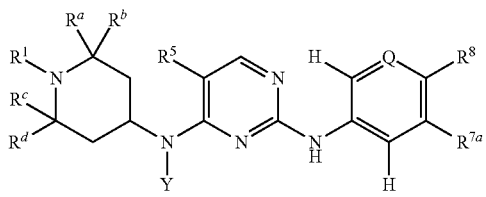

(III)

wherein:
R⁵ is selected from halogen, cyano, acyl, and aminoacyl;
Y is selected from hydrogen and alkyl;

R¹ is selected from hydrogen, alkyl, substituted alkyl, cycloalkyl, acyl, and O⁻;
Rᵃ and Rᵇ are independently selected from hydrogen and alkyl;
Rᶜ and Rᵈ are independently selected from hydrogen and alkyl;
Q is CR⁷ᵇ;
R⁷ᵃ is tetrazolyl or substituted tetrazolyl;
R⁷ᵇ and R⁸ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;
alk, if present, is alky or substituted alkyl;
A is selected from aryl, cycloalkyl, heteroaryl, and heterocyclyl;
wherein the A ring can be substituted or unsubstituted;
or a salt or stereoisomer thereof.

12. The method of claim 1, wherein the compound is of the formula (Va):

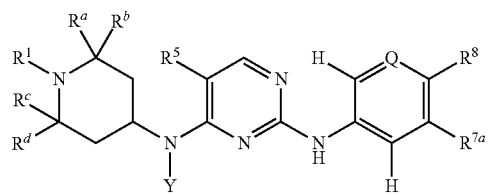

(Va)

wherein:
R⁵ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
Y is selected from hydrogen and alkyl;
R¹ is selected from hydrogen, alkyl, substituted alkyl, cycloalkyl, acyl, and oxy radical;
Rᵃ and Rᵇ are independently selected from hydrogen and alkyl;
Rᶜ and Rᵈ are independently selected from hydrogen and alkyl;
Q is CR⁷ᵇ;
R⁷ᵃ is selected from 5-tetrazolyl and substituted 5-tetrazolyl;
R⁷ᵇ and R⁸ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;
alk, if present, is alkyl or substituted alkyl;
A is selected from aryl, cycloalkyl, heteroaryl, and heterocyclyl;
wherein the A ring can be substituted or unsubstituted;
or a salt or stereoisomer thereof.

13. The method of claim 1, wherein the compound is of the formula (Vb):

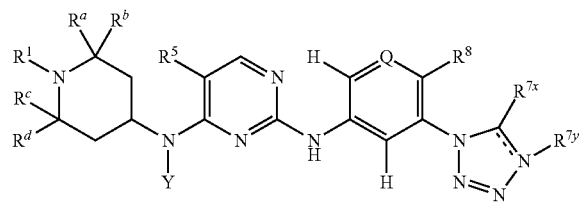

(Vb)

wherein
R⁵ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
Y is selected from hydrogen and alkyl;
R¹ is selected from hydrogen, alkyl, substituted alkyl, cycloalkyl, acyl, and oxy radical;
Rᵃ and Rᵇ are independently selected from hydrogen and alkyl;
Rᶜ and Rᵈ are independently selected from hydrogen and alkyl;
Q is CR⁷ᵇ;
R⁷ᵇ is selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;
alk, if present, is alkyl or substituted alkyl;
A is selected from aryl, cycloalkyl, heteroaryl, and heterocyclyl;
wherein the A ring can be substituted or unsubstituted;
R⁸ is selected from fluoro, trifluoromethyl, difluoromethoxy, hydroxyl, and isopropoxy;
R⁷ˣ is selected from alkyl, alkylthio, and substituted alkylthio;
R⁷ʸ is selected from hydrogen and alkyl;
the dashed line can be single bond or double bond;
or a salt or stereoisomer thereof.

14. The method of claim 1, wherein the compound is of the formula (Vc):

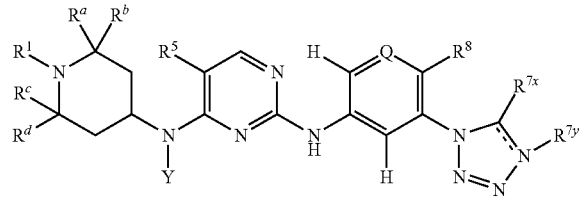

(Vc)

wherein
R⁵ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;
R¹ is selected from hydrogen, alkyl, substituted alkyl, cycloalkyl, acyl, and oxy radical;
$R^a$ and $R^b$ are independently selected from hydrogen and alkyl;
$R^c$ and $R^d$ are independently selected from hydrogen and alkyl;
Q is $CR^{7b}$;
$R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;
alk, if present, is alkyl or substituted alkyl;
A is selected from aryl, cycloalkyl, heteroaryl, and heterocyclyl;
wherein the A ring can be substituted or unsubstituted;
$R^{7x}$ is 2,2,2-trifluoroethylthio;
$R^{7y}$ is selected from hydrogen and alkyl;
the dashed line can be single bond or double bond;
or a salt or stereoisomer thereof.

15. The method of claim 1, wherein the compound is of the formula (Vd):

(Vd)

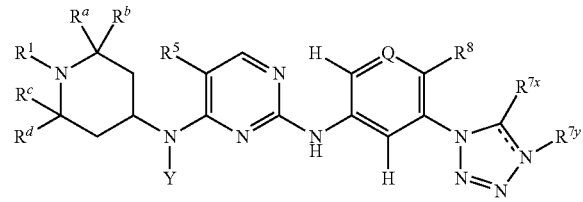

wherein
$R^5$ is —$CONH_2$ or cyano;
R¹ is selected from hydrogen, alkyl, substituted alkyl, cycloalkyl, acyl, and oxy radical;
$R^a$ and $R^b$ are independently selected from hydrogen and alkyl;
$R^c$ and $R^d$ are independently selected from hydrogen and alkyl;
Q is $CR^{7b}$;
$R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;
alk, if present, is alkyl or substituted alkyl;
A is selected from aryl, cycloalkyl, heteroaryl, and heterocyclyl;
wherein the A ring can be substituted or unsubstituted;
$R^{7x}$ is propyl;
$R^{7y}$ is selected from hydrogen and alkyl;
the dashed line can be single bond or double bond;
or a salt or stereoisomer thereof.

16. The method of claim 1, wherein the compound is of the formula (Vf):

(Vf)

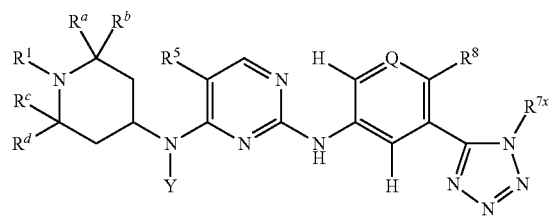

$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
Y is selected from hydrogen and alkyl;
R¹ is selected from hydrogen, alkyl, substituted alkyl, cycloalkyl, acyl, and oxy radical;
$R^a$ and $R^b$ are independently selected from hydrogen and alkyl;
$R^c$ and $R^d$ are independently selected from hydrogen and alkyl;
Q is $CR^{7b}$;
$R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;
alk, if present, is alkyl or substituted alkyl;
A is selected from aryl, cycloalkyl, heteroaryl, and heterocyclyl;
wherein the A ring can be substituted or unsubstituted;
$R^{7x}$ is selected from alkyl, substituted alkyl, cycloalkyl, and substituted cycloalkyl;
or a salt or stereoisomer thereof.

17. The method of claim 1, wherein the compound is of the formula (Vg):

(Vg)

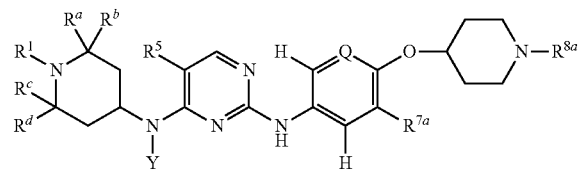

$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
Y is selected from hydrogen and alkyl;
R¹ is selected from hydrogen, alkyl, substituted alkyl, cycloalkyl, acyl, and oxy radical;
$R^a$ and $R^b$ are independently selected from hydrogen and alkyl;
$R^c$ and $R^d$ are independently selected from hydrogen and alkyl;

Q is $CR^{7b}$;

$R^{7a}$ is tetrazolyl or substituted tetrazolyl;

$R^{7b}$ is selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk, if present, is alkyl or substituted alkyl;

A is selected from aryl, cycloalkyl, heteroaryl, and heterocyclyl;

wherein the A ring can be substituted or unsubstituted;

$R^{8a}$ is selected from hydrogen, alkyl, substituted alkyl, acyl, aminoacyl, and sulfonyl;

or a salt or stereoisomer thereof.

18. The method of claim 1, wherein the compound is of the formula (Vh):

(Vh)

$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is $CR^{7b}$;

$R^{7a}$ is tetrazolyl or substituted tetrazolyl;

$R^{7b}$ is selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk, if present, is alkyl or substituted alkyl;

A is selected from aryl, cycloalkyl, heteroaryl, and heterocyclyl;

wherein the A ring can be substituted or unsubstituted;

$R^{8a}$ is selected from hydrogen, alkyl, substituted alkyl, acyl, aminoacyl, and sulfonyl;

or a salt or stereoisomer thereof.

19. The method of claim 1, wherein the compound is of the formula (Vi):

(Vi)

wherein $R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is $CR^{7b}$;

$R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, and aminosulfonyl;

wherein at least one of $R^{7b}$ and $R^8$ is cycloalkyl;

$R^{7x}$ and $R^{7y}$ are independently selected from hydrogen and alkyl;

the dashed line can be single bond or double bond;

or a salt or stereoisomer thereof.

20. The method of claim 1, wherein the compound is of the formula (Vj):

(Vj)

wherein:

$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is $CR^{7b}$;

211

R$^{7a}$ is tetrazolyl or substituted tetrazolyl;

R$^{7b}$ and R$^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

wherein at least one of R$^{7b}$ and R$^8$ is selected from cycloalkyl or —O—C$_{3-10}$ heterocyclyl group having one oxygen ring atom;

alk, if present, is alkyl or substituted alkyl;

A is selected from aryl, cycloalkyl, heteroaryl, and heterocyclyl;

wherein the A ring can be substituted or unsubstituted;

or a salt or stereoisomer thereof.

21. The method of claim 1, wherein the compound is selected from

I-9: 5-fluoro-N2-(4-fluoro-3-(5-methyl-1H-tetrazol-1-yl)phenyl)-N4-(1,2,2,6,6-pentamethylpiperidin-4-yl)pyrimidine-2,4-diamine I-10: 5-fluoro-N2-(4-fluoro-3-(5-methyl-1H-tetrazol-1-yl)phenyl)-N4-(2,2,6,6-tetramethylpiperidin-4-yl)pyrimidine-2,4-diamine I-11: N4-(1-(cyclopropylmethyl)-2,2,6,6-tetramethylpiperidin-4-yl)-5-fluoro-N2-(4-fluoro-3-(5-methyl-1H-tetrazol-1-yl)phenyl)pyrimidine-2,4-diamine I-18: 4-(2,2,6,6-tetramethylpiperidin-4-ylamino)-2-(4-fluoro-3-(5-methyl-1H-tetrazol-1-yl)phenylamino)pyrimidine-5-carbonitrile I-20: 5-fluoro-N2-(3-(5-methyl-1H-tetrazol-1-yl)-4-(trifluoromethoxy)phenyl)-N4-(1,2,2,6,6-pentamethylpiperidin-4-yl)pyrimidine-2,4-diamine I-21: 5-fluoro-N2-(3-(5-methyl-1H-tetrazol-1-yl)-4-(trifluoromethoxy)phenyl)-N4-(2,2,6,6-tetramethylpiperidin-4-yl)pyrimidine-2,4-diamine I-67: 5-aminocarbonyl-N2-[4-fluoro-3-(1H-tetrazol-1-yl)]phenyl-N4-(2,2,6,6-tetramethylpiperidin-4-yl)-2,4-pyrimidinediamine I-68: 5-aminocarbonyl-N2-[4-ethoxy-3-(5-ethyl-1H-tetrazol-1-yl)]phenyl-N4-(2,2,6,6-tetramethylpiperidin-4-yl)-2,4-pyrimidinediamine I-69: 5-fluoro-N4-(1,2,2,6,6-pentamethylpiperidin-4-yl)-N2-{3-[5-(2,2,2-trifluoroethyl)thio]-1H-tetrazol-1-yl}phenyl-2,4-pyrimidinediamine I-70: 5-fluoro-N4-(2,2,6,6-tetramethylpiperidin-4-yl)-N2-{3-[5-(2,2,2-trifluoroethyl)thio]-1H-tetrazol-1-yl}phenyl-2,4-pyrimidinediamine I-71: 5-aminocarbonyl-N4-(1,2,2,6,6-pentamethylpiperidin-4-yl)-N2-{3-[5-(2,2,2-trifluoroethyl)thio]-1H-tetrazol-1-yl}phenyl-2,4-pyrimidinediamine I-72: 5-aminocarbonyl-N4-(2,2,6,6-tetramethylpiperidin-4-yl)-N2-{3-[5-(2,2,2-trifluoroethyl)thio]-1H-tetrazol-1-yl}phenyl-2,4-pyrimidinediamine I-73: 5-cyano-N2-[4-fluoro-3-(1H-tetrazol-1-yl)]phenyl-N4-(1,2,2,6,6-pentamethylpiperidin-4-yl)-2,4-pyrimidinediamine I-74: 5-fluoro-N2-[4-methoxy-3-(5-propyl-1H-tetrazol-1-yl)]phenyl-N4-(2,2,6,6-tetramethylpiperidin-4-yl)-2,4-pyrimidinediamine I-75: 5-aminocarbonyl-N2-[4-methoxy-3-(5-propyl-1H-tetrazol-1-yl)]phenyl-N4-(1,2,2,6,6-pentamethylpiperidin-4-yl)-2,4-pyrimidinediamine

212

I-76: 5-aminocarbonyl-N2-[4-methoxy-3-(5-propyl-1H-tetrazol-1-yl)]phenyl-N4-(2,2,6,6-tetramethylpiperidin-4-yl)-2,4-pyrimidinediamine I-77: 5-cyano-N2-[4-fluoro-3-(1H-tetrazol-1-yl)]phenyl-N4-(2,2,6,6-tetramethylpiperidin-4-yl)-2,4-pyrimidinediamine I-78: 5-cyano-N4-(1,2,2,6,6-pentamethylpiperidin-4-yl)-N2-{3-[5-(2,2,2-trifluoroethyl)thio]-1H-tetrazol-1-yl}phenyl-2,4-pyrimidinediamine I-79: 5-cyano-N4-(2,2,6,6-tetramethylpiperidin-4-yl)-N2-{3-[5-(2,2,2-trifluoroethyl)thio]-1H-tetrazol-1-yl}phenyl-2,4-pyrimidinediamine I-80: 5-cyano-N2-[4-methoxy-3-(5-propyl-1H-tetrazol-1-yl)]phenyl-N4-(1,2,2,6,6-pentamethylpiperidin-4-yl)-2,4-pyrimidinediamine I-81: 5-cyano-N2-[4-methoxy-3-(5-propyl-1H-tetrazol-1-yl)]phenyl-N4-(2,2,6,6-tetramethylpiperidin-4-yl)-2,4-pyrimidinediamine I-82: N2-[4-difluoromethoxy-3-(5-ethyl-1H-tetrazol-1-yl)]phenyl-5-fluoro-N4-(2,2,6,6-tetramethylpiperidin-4-yl)-2,4-pyrimidinediamine I-83: 5-aminocarbonyl-N2-[4-difluoromethoxy-3-(5-ethyl-1H-tetrazol-1-yl)]phenyl-N4-(2,2,6,6-tetramethylpiperidin-4-yl)-2,4-pyrimidinediamine I-84: 5-cyano-N2-[4-difluoromethoxy-3-(5-ethyl-1H-tetrazol-1-yl)]phenyl-N4-(2,2,6,6-tetramethylpiperidin-4-yl)-2,4-pyrimidinediamine I-85: 5-Cyano-N4-(2,2,6,6-tetramethylpiperidin-4-yl)-N2-[3-(tetrazol-5-yl)]phenyl-2,4-pyrimidinediamine I-86: 5-Fluoro-N2-{3-[1-N-isopropyl-(tetrazol-5-yl)]}phenyl-N4-(1,2,2,6,6-pentamethylpiperidin-4-yl)-2,4-pyrimidinediamine I-87: 5-Fluoro-N2-{3-[1-N-isopropyl-(tetrazol-5-yl)]}phenyl-N4-(2,2,6,6-tetramethylpiperidin-4-yl)-2,4-pyrimidinediamine I-88: 5-Cyano-N2-{3-[1-N-isopropyl-(tetrazol-5-yl)]}phenyl-N4-(1,2,2,6,6-pentamethylpiperidin-4-yl)-2,4-pyrimidinediamine I-89: N2-{3-[1-N-Cyclopropyl-(tetrazol-5-yl)]}phenyl-5-fluoro-N4-(1,2,2,6,6-pentamethylpiperidin-4-yl)-2,4-pyrimidinediamine I-90: N2-{3-[1-N-Cyclopropyl-(tetrazol-5-yl)]}phenyl-5-fluoro-N4-(2,2,6,6-tetramethylpiperidin-4-yl)-2,4-pyrimidinediamine I-91: N2-{3-[1-N-(2-Fluoroethyl)-(tetrazol-5-yl)]}phenyl-5-fluoro-N4-(1,2,2,6,6-pentamethylpiperidin-4-yl)-2,4-pyrimidinediamine I-92: N2-{3-[1-N-(2-Fluoroethyl)-(tetrazol-5-yl)]}phenyl-5-fluoro-N4-(2,2,6,6-tetramethylpiperidin-4-yl)-2,4-pyrimidinediamine I-94: 5-Cyano-N2-{3-[1-N-cyclopropyl-(tetrazol-5-yl)]}phenyl-N4-(1,2,2,6,6-pentamethylpiperidin-4-yl)-2,4-pyrimidinediamine I-95: 5-Cyano-N2-{3-[1-N-cyclopropyl-(tetrazol-5-yl)]}phenyl-N4-(2,2,6,6-tetramethylpiperidin-4-yl)-2,4-pyrimidinediamine I-96: 5-Cyano-N2-{3-[1-N-(2-fluoroethyl)-(tetrazol-5-yl)]}phenyl-N4-(1,2,2,6,6-pentamethylpiperidin-4-yl)-2,4-pyrimidinediamine I-97: 5-Cyano-N2-{3-[1-N-(2-fluoroethyl)-(tetrazol-5-yl)]}phenyl-N4-(2,2,6,6-tetramethylpiperidin-4-yl)-2,4-pyrimidinediamine I-98: 5-Fluoro-N2-{3-[1-N-(2-morpholinoethyl)-(tetrazol-5-yl)]}phenyl-N4-(1,2,2,6,6-pentamethylpiperidin-4-yl)-2,4-pyrimidinediamine I-99: 5-Fluoro-N2-{3-[1-N-(2-morpholinoethyl)-(tetrazol-5-yl)]}phenyl-N4-(2,2,6,6-tetramethylpiperidin-4-yl)-2,4-pyrimidinediamine III-1: 5-fluoro-N2-(4-(1-isopropylpiperidin-4-yloxy)-3-(5-methyl-1H-tetrazol-1-yl)phenyl)-N4-(1,2,2,6,6-pentamethylpiperidin-4-yl)pyrimidine-2,4-diamine III-2: 5-fluoro-N2-(4-(1-isopropylpiperidin-4-yloxy)-3-(5-methyl-1H-tetrazol-1-yl)phenyl)-N4-(2,2,6,6-tetramethylpiperidin-4-yl)pyrimidine-2,4-diamine III-5: $N^2$-(3-(1H-tetrazol-1 yl)phenyl)-$N^4$-(1-cyclopropyl-2,6-dimethylpiperidin-4yl)-5-fluoropyrimidine-2,4-diamine III-6: $N^4$-(1-cyclopropyl-2,6-dimethylpiperidin-4-yl)-5-fluoro-$N^2$-(4-methyl-3-(1H-tetrazol-1-yl)phenyl)pyrimidine-2,4-diamine III-7: $N^4$-(1-cyclopropyl-2,6-dimethylpiperidin-4-yl)-5-fluoro-$N^2$-(3-methoxy-5-(1H-tetrazol-1-yl)phenyl)pyrimidine-2,4-diamine III-8: $N^4$-(1-cyclopropyl-2,6-dimethylpiperidin-4-yl)-5-fluoro-$N^2$-(3-(5-methyl-1H-tetrazol-1-yl)phenyl)pyrimidine-2,4-diamine III-9: $N^4$-(1-cyclopropyl-2,6-dimethylpiperidin-4-yl)-5-fluoro-$N^2$-(3-(5-(2,2,2-trifluoroethylthio)-1H-tetrazol-1-yl)phenyl)pyrimidine-2,4-diamine III-10: $N^4$-(1-cyclopropyl-2,6-dimethylpiperidin-4-yl)-5-fluoro-$N^2$-(3-(5-(methylthio)-1H-tetrazol-1-yl)phenyl)pyrimidine-2,4-diamine III-11: $N^4$-(1-cyclopropyl-2,6-dimethylpiperidin-4-yl)-5-fluoro-$N^2$-(4-fluoro-3-(1H-tetrazol-1-yl)phenyl)pyrimidine-2,4-diamine III-63: 5-fluoro-N2-(4-methyl-3-(1-methyl-1H-tetrazol-5-yl)phenyl)-N4-(2,2,6,6-tetramethylpiperidin-4-yl)pyrimidine-2,4-diamine III-64: 5-fluoro-N2-(4-methyl-3-(1-methyl-1H-tetrazol-5-yl)phenyl)-N4-(1,2,2,6,6-pentamethylpiperidin-4-yl)pyrimidine-2,4-diamine III-67: N2-(4-(difluoromethoxy)-3-(5-ethyl-1H-tetrazol-1-yl)phenyl)-5-fluoro-N4-(2,2,6,6-tetramethylpiperidin-4-yl)pyrimidine-2,4-diamine III-68: N2-(3-(2H-tetrazol-5-yl)phenyl)-5-fluoro-N4-(1,2,2,6,6-pentamethylpiperidin-4-yl)pyrimidine-2,4-diamine III-69: N2-(3-(2H-tetrazol-5-yl)phenyl)-5-fluoro-N4-(2,2,6,6-tetramethylpiperidin-4-yl)pyrimidine-2,4-diamine III-70: 5-fluoro-N2-(3-(1-isopropyl-1H-tetrazol-5-yl)phenyl)-N4-(1,2,2,6,6-pentamethylpiperidin-4-yl)pyrimidine-2,4-diamine III-71: 5-fluoro-N2-(3-(1-isopropyl-1H-tetrazol-5-yl)phenyl)-N4-(2,2,6,6-tetramethylpiperidin-4-yl)pyrimidine-2,4-diamine III-72: N2-(3-(1-cyclopropyl-1H-tetrazol-5-yl)phenyl)-5-fluoro-N4-(1,2,2,6,6-pentamethylpiperidin-4-yl)pyrimidine-2,4-diamine III-73: N2-(3-(1-cyclopropyl-1H-tetrazol-5-yl)phenyl)-5-fluoro-N4-(2,2,6,6-tetramethylpiperidin-4-yl)pyrimidine-2,4-diamine III-74: 5-fluoro-N2-(3-(1-(2-fluoroethyl)-1H-tetrazol-5-yl)phenyl)-N4-(1,2,2,6,6-pentamethylpiperidin-4-yl)pyrimidine-2,4-diamine III-75: 5-fluoro-N2-(3-(1-(2-fluoroethyl)-1H-tetrazol-5-yl)phenyl)-N4-(2,2,6,6-tetramethylpiperidin-4-yl)pyrimidine-2,4-diamine III-76: 5-fluoro-N2-(3-(1-(2-morpholinoethyl)-1H-tetrazol-5-yl)phenyl)-N4-(1,2,2,6,6-pentamethylpiperidin-4-yl)pyrimidine-2,4-diamine III-77: 5-fluoro-N2-(3-(1-(2-morpholinoethyl)-1H-tetrazol-5-yl)phenyl)-N4-(2,2,6,6-tetramethylpiperidin-4-yl)pyrimidine-2,4-diamine III-113: 5-fluoro-N2-(4-methyl-3-(1H-tetrazol-1-yl)phenyl)-N4-(1-trideuteromethyl-2,2,6,6-tetramethylpiperidin-4-yl)pyrimidine-2,4-diamine III-114: 5-fluoro-N2-(3-(1H-tetrazol-1-yl)phenyl)-N4-(1-trideuteromethyl-2,2,6,6-tetramethylpiperidin-4-yl)pyrimidine-2,4-diamine III-115: 5-fluoro-N2-(3-(5-methyl-1H-tetrazol-1-yl)phenyl)-N4-(1-trideuteromethyl-2,2,6,6-tetramethylpiperidin-4-yl)pyrimidine-2,4-diamine III-116: $N^2$-(3-cyclopropyl-5-(1H-tetrazol-1-yl)phenyl)-5-fluoro-$N^4$-(2,2,6,6-tetramethylpiperidin-4-yl)pyrimidine-2,4-diamine III-117: $N^2$-(3-cyclopropyl-5-(1H-tetrazol-1-yl)phenyl)-5-fluoro-$N^4$-(1,2,2,6,6-pentamethylpiperidin-4-yl)pyrimidine-2,4-diamine III-118: $N^2$-(4-cyclopropyl-3-(1H-tetrazol-1-yl)phenyl)-5-fluoro-$N^4$-(2,2,6,6-tetramethylpiperidin-4-yl)pyrimidine-2,4-diamine III-119: $N^2$-(4-cyclopropyl-3-(1H-tetrazol-1-yl)phenyl)-5-fluoro-$N^4$-(1,2,2,6,6-pentamethylpiperidin-4-yl)pyrimidine-2,4-diamine III-120: 5-fluoro-N2-(4-fluoro-3-(1-methyl-1H-tetrazol-5-yl)phenyl)-N4-(2,2,6,6-tetramethylpiperidin-4-yl)pyrimidine-2,4-diamine;

III-121: 5-fluoro-N2-(4-fluoro-3-(1-methyl-1H-tetrazol-5-yl)phenyl)-N4-(1,2,2,6,6-pentamethylpiperidin-4-yl)pyrimidine-2,4-diamine III-122: 5-fluoro-N2-(4-isopropoxy-3-(1-methyl-1H-tetrazol-5-yl)phenyl)-N4-(2,2,6,6-tetramethylpiperidin-4-yl)pyrimidine-2,4-diamine III-123: 5-fluoro-N2-(4-isopropoxy-3-(1-methyl-1H-tetrazol-5-yl)phenyl)-N4-(1,2,2,6,6-pentamethylpiperidin-4-yl)pyrimidine-2,4-diamine III-124: 5-fluoro-N2-(3-(1-methyl-1H-tetrazol-5-yl)-4-(tetrahydro-2H-pyran-4-yloxy)phenyl)-N4-(2,2,6,6-tetramethylpiperidin-4-yl)pyrimidine-2,4-diamine III-125: 5-fluoro-N2-(3-(1-methyl-1H-tetrazol-5-yl)-4-(tetrahydro-2H-pyran-4-yloxy)phenyl)-N4-(1,2,2,6,6-pentamethylpiperidin-4-yl)pyrimidine-2,4-diamine III-126: 5-fluoro-N2-(3-(1-methyl-1H-tetrazol-5-yl)-4-(oxetan-3-yloxy)phenyl)-N4-(2,2,6,6-tetramethylpiperidin-4-yl)pyrimidine-2,4-diamine III-127: 5-fluoro-N2-(3-(1-methyl-1H-tetrazol-5-yl)-4-(oxetan-3-yloxy)phenyl)-N4-(1,2,2,6,6-pentamethylpiperidin-4-yl)pyrimidine-2,4-diamine III-128: 5-fluoro-N2-(4-fluoro-3-(1-(2-methoxyethyl)-1H-tetrazol-5-yl)phenyl)-N4-(1,2,2,6,6-pentamethylpiperidin-4-yl)pyrimidine-2,4-diamine III-129: 5-fluoro-N2-(4-fluoro-3-(1-(2-methoxyethyl)-1H-tetrazol-5-yl)phenyl)-N4-(2,2,6,6-tetramethylpiperidin-4-yl)pyrimidine-2,4-diamine III-130: N2-(4-chloro-3-(1-methyl-1H-tetrazol-5-yl)phenyl)-5-fluoro-N4-(2,2,6,6-tetramethylpiperidin-4-yl)pyrimidine-2,4-diamine III-131: N2-(4-chloro-3-(1-methyl-1H-tetrazol-5-yl)phenyl)-5-fluoro-N4-(1,2,2,6,6-pentamethylpiperidin-4-yl)pyrimidine-2,4-diamine III-132: 5-fluoro-N2-(3-methyl-5-(1-methyl-1H-tetrazol-5-yl)phenyl)-N4-(2,2,6,6-tetramethylpiperidin-4-yl)pyrimidine-2,4-diamine III-133: 5-fluoro-N2-(3-methyl-5-(1-methyl-1H-tetrazol-5-yl)phenyl)-N4-(1,2,2,6,6-pentamethylpiperidin-4-yl)pyrimidine-2,4-diamine III-134: N2-(3-chloro-5-(1-methyl-1H-tetrazol-5-yl)phenyl)-5-fluoro-N4-(2,2,6,6-tetramethylpiperidin-4-yl)pyrimidine-2,4-diamine III-135: N2-(3-chloro-5-(1-methyl-1H-tetrazol-5-yl)phenyl)-5-fluoro-N4-(1,2,2,6,6-pentamethylpiperidin-4-yl)pyrimidine-2,4-diamine III-136: N2-(3,4-difluoro-5-(1-methyl-1H-tetrazol-5-yl)phenyl)-5-fluoro-N4-(2,2,6,6-tetramethylpiperidin-4-yl)pyrimidine-2,4-diamine III-137: N2-(3,4-difluoro-5-(1-methyl-1H-tetrazol-5-yl)phenyl)-5-fluoro-N4-(1,2,2,6,6-pentamethylpiperidin-4-yl)pyrimidine-2,4-diamine III-138: 5-fluoro-N2-(3-fluoro-5-(1-methyl-1H-tetrazol-5-yl)phenyl)-N4-(2,2,6,6-tetramethylpiperidin-4-yl)pyrimidine-2,4-diamine III-139: 5-fluoro-N2-(3-fluoro-5-(1-methyl-1H-tetrazol-5-yl)phenyl)-N4-(1,2,2,6,6-pentamethylpiperidin-4-yl)pyrimidine-2,4-diamine III-140: 5-fluoro-N2-(3-(1-methyl-1H-tetrazol-5-yl)-5-(trifluoromethyl)phenyl)-N4-(2,2,6,6-tetramethylpiperidin-4-yl)pyrimidine-2,4-diamine III-141: 5-fluoro-N2-(3-(1-methyl-1H-tetrazol-5-yl)-5-(trifluoromethyl)phenyl)-N4-(1,2,2,6,6-pentamethylpiperidin-4-yl)pyrimidine-2,4-diamine III-142: 5-fluoro-N2-(3-fluoro-4-isopropoxy-5-(1-methyl-1H-tetrazol-5-yl)phenyl)-N4-(2,2,6,6-tetramethylpiperidin-4-yl)pyrimidine-2,4-diamine III-143: 3-(5-fluoro-4-(2,2,6,6-tetramethylpiperidin-4-ylamino)pyrimidin-2-ylamino)-5-(1-methyl-1H-tetrazol-5-yl)benzonitrile III-144: 3-(5-fluoro-4-(1,2,2,6,6-pentamethylpiperidin-4-ylamino)pyrimidin-2-ylamino)-5-(1-methyl-1H-tetrazol-5-yl)benzonitrile III-145: 5-fluoro-N2-(3-(1-methyl-1H-tetrazol-5-yl)-5-(oxetan-3-yloxy)phenyl)-N4-(2,2,6,6-tetramethylpiperidin-4-yl)pyrimidine-2,4-diamine III-146: 5-fluoro-N2-(3-(1-methyl-1H-tetrazol-5-yl)-5-(oxetan-3-yloxy)phenyl)-N4-(1,2,2,6,6-pentamethylpiperidin-4-yl)pyrimidine-2,4-diamine III-147: N2-(3-cyclopropyl-5-(1-methyl-1H-tetrazol-5-yl)phenyl)-5-fluoro-N4-(2,2,6,6-tetramethylpiperidin-4-yl)pyrimidine-2,4-diamine III-148: N2-(4-cyclopropyl-3-(1-methyl-1H-tetrazol-5-yl)phenyl)-5-fluoro-N4-(2,2,6,6-tetramethylpiperidin-4-yl)pyrimidine-2,4-diamine or a solvate, prodrug, or a pharmaceutically acceptable salt thereof.

* * * * *

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide

<400> SEQUENCE: 1

Arg Phe Ala Arg Lys Gly Ser Leu Arg Gln Lys Asn Val
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: BLOCKED
<222> LOCATION: (1)..(1)
<223> OTHER INFORMATION: N-terminal biotinylation
```

```
<400> SEQUENCE: 2

Arg Phe Ala Arg Lys Gly Ser Leu Arg Gln Lys Asn Val
1               5                   10
```